(12) United States Patent
Ibrahim et al.

(10) Patent No.: US 7,585,859 B2
(45) Date of Patent: Sep. 8, 2009

(54) PDE4B INHIBITORS AND USES THEREFOR

(75) Inventors: Prabha N. Ibrahim, Mountain View, CA (US); Hanna Cho, Oakland, CA (US); Bruce England, Hayward, CA (US); Sam Gillette, Oakland, CA (US); Dean R. Artis, Kensington, CA (US); Rebecca Zuckerman, Alameda, CA (US); Chao Zhang, Moraga, CA (US)

(73) Assignee: Plexxikon, Inc., Berkeley, CA (US)

( * ) Notice: Subject to any disclaimer, the term of this patent is extended or adjusted under 35 U.S.C. 154(b) by 592 days.

(21) Appl. No.: 11/123,893

(22) Filed: May 6, 2005

(65) Prior Publication Data

US 2006/0041006 A1  Feb. 23, 2006

Related U.S. Application Data

(60) Provisional application No. 60/569,435, filed on May 6, 2004.

(51) Int. Cl.
*A61K 31/5377* (2006.01)
*A61K 31/4525* (2006.01)
*A61K 31/422* (2006.01)
*C07D 413/14* (2006.01)
*C07D 409/14* (2006.01)
*C07D 261/06* (2006.01)

(52) U.S. Cl. .................... 514/236.8; 514/326; 514/378; 544/137; 546/209; 548/248

(58) Field of Classification Search ................. 514/444, 514/445, 447, 448, 473, 471, 422, 423, 236.8, 514/326, 378; 549/59, 60, 63, 64, 473, 480; 548/530, 517, 248; 544/137; 546/209
See application file for complete search history.

(56) References Cited

U.S. PATENT DOCUMENTS

| | | |
|---|---|---|
| 4,150,949 A | 4/1979 | Smith |
| 4,568,649 A | 2/1986 | Bertoglio-Matte |
| 4,626,513 A | 12/1986 | Burton et al. |
| 4,861,891 A | 8/1989 | Saccomano et al. |
| 5,143,854 A | 9/1992 | Pirrung et al. |
| 5,426,039 A | 6/1995 | Wallace et al. |
| 5,434,049 A | 7/1995 | Okano et al. |
| 5,449,614 A | 9/1995 | Danos et al. |
| 5,474,935 A | 12/1995 | Chatterjee et al. |
| 5,556,752 A | 9/1996 | Lockhart et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,700,637 A | 12/1997 | Southern |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,877,007 A | 3/1999 | Housey |
| 5,922,557 A | 7/1999 | Pon |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlacsky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pederson et al. |
| 6,110,456 A | 8/2000 | During |
| 6,110,458 A | 8/2000 | Freeman et al. |
| 6,113,913 A | 9/2000 | Brough et al. |
| 6,117,681 A | 9/2000 | Salmons et al. |
| 6,178,384 B1 | 1/2001 | Kolossváry |
| 6,243,980 B1 | 6/2001 | Bronstein et al. |
| 6,258,606 B1 | 7/2001 | Kovacs |
| 6,261,776 B1 | 7/2001 | Pirrung et al. |

(Continued)

FOREIGN PATENT DOCUMENTS

EP    0154734    9/1985

(Continued)

OTHER PUBLICATIONS

Wolff et al., Burger's Medicinal Chemistry and Drug Discovery, 1994, Wiley-Interscience, Fifth Edition, vol. I: Principles and Practice, pp. 975-977.*

(Continued)

*Primary Examiner*—Kamal A Saeed
*Assistant Examiner*—Kristin Bianchi
(74) *Attorney, Agent, or Firm*—Foley & Lardner LLP

(57) ABSTRACT

Compounds active on phosphodiesterase PDE4B are provided. Also provided herewith are compositions useful for treatment of PDE4B-mediated diseases or conditions, and methods for the use thereof.

9 Claims, 5 Drawing Sheets

U.S. PATENT DOCUMENTS

| | | | |
|---|---|---|---|
| 6,277,489 | B1 | 8/2001 | Abbott et al. |
| 6,277,628 | B1 | 8/2001 | Johann et al. |
| 6,288,234 | B1 | 9/2001 | Griffin |
| 6,294,330 | B1 | 9/2001 | Michnick et al. |
| 6,500,610 | B1 | 12/2002 | Pamukcu et al. |
| 6,559,168 | B2 | 5/2003 | Marfat et al. |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0014449 | A1 | 8/2001 | Nerenberg et al. |
| 2001/0016322 | A1 | 8/2001 | Caren et al. |
| 2001/0018642 | A1 | 8/2001 | Balaban et al. |
| 2001/0019827 | A1 | 9/2001 | Dawson et al. |
| 2002/0009764 | A1 | 1/2002 | Thompson et al. |
| 2002/0165237 | A1 | 11/2002 | Fryburg et al. |
| 2003/0064374 | A1 | 4/2003 | Ait Ikhlef et al. |
| 2004/0106641 | A1 | 6/2004 | Hofgen et al. |

FOREIGN PATENT DOCUMENTS

| | | |
|---|---|---|
| EP | 0 667 345 | 8/1995 |
| EP | 1 166 785 | 1/2002 |
| WO | WO 96/17958 | 6/1996 |
| WO | WO 96/18738 | 6/1996 |
| WO | WO 97/46313 | 12/1997 |
| WO | WO 98/37078 A1 * | 8/1998 |
| WO | WO 98/45268 | 10/1998 |
| WO | WO 99/09217 | 4/1999 |
| WO | WO 99/20625 | 4/1999 |
| WO | WO 99/21845 | 5/1999 |
| WO | WO 99/51773 | 10/1999 |
| WO | WO 01/02369 | 1/2001 |
| WO | WO 2005/016924 | 2/2005 |
| WO | WO 02/062290 | 8/2006 |

OTHER PUBLICATIONS

Card et al., Structural basis for the activity of drugs that inhibit phosphodiesterases, 12:2233-2247, 2004.
Dym et al., Molecular docking of competitive phosphodiesterase inhibitors, Molecular Pharmacology, 61:20-25, 2002.
Haddad et al., Immunopharmacological potential of selective phosphodiesterase inhibition. I. Differential regulation of lipopolysaccharide-mediated proinflammatory cytokine (Interleukin-6 and tumor necrosis factor-α) Biosynthesis in alveolar epithelial cells, The Journal of Pharmacology and Experimental Therapeutics, 300:559-566, 2002.
Ho et al., Structure of the GAF domain, a ubiquitous signaling motif and a new class of cyclic GMP receptor, The EMBO Journal, 19(20):5288-5299, 2000.
Huai et al., Three-dimensional structures of PDE4D in complex with roliprams and implication on inhibitor selectivity, Structure, 11:865-873, 2003.
Manning et al., Suppression of human inflammatory cell function by subtype-selective PDE4 inhibitors correlates with inhibition of PDE4A and PDE4B, British Journal of Pharmacology, 128:1393-1398, 1999.
Rascon et al., Cloning and characterization of a cAMP-specific phosphodiesterase (TbPDE2B) from *Trypanosoma brucei*, PNAS, 99(7):4714-4719, 2002.
Sopory et al., Modeling and mutational analysis of the GAF domain of the cGMP-binding, cGMP-specific phosphodiesterase, PDE5, FEBS Letters, 539:161-166, 2003.
Tejada et al., The phosphodiesterase inhibitory selectivity and the in vitro and in vivo potency of the new PDE5 inhibitor vardenafil, International Journal of Impotence Research, 13:282-290, 2001.
Turko et al., Inhibition of cyclic GMP-binding cyclic GMP-specific phosphodiesterase (type 5) by sildenafil and related compounds, Mol Pharmacol, 56:124-130, 1999.
Abdelhamid, et. al., Reactions with Hydrazonoyl Halides. Part 21. Reinvestigation of the Reactions of Hydrazonoyl Bromides with 1,1-Dicyanothioacetanilide, *J. Chem. Res.*, 184-185 (1999).
Alfthan, "Surface plasmon resonance biosensors as a tool in antibody engineering," *Biosensors & Bioelectronics*. 13:653-63 (1998).
al-Obeidi, "Peptide and Petidomimetic Libraries" *Mol Biotechnol* 9(3):205-23 (1998).
Amersdorfer P. Marks JD., "Phage Libraries for Generation of Anti-botulinum scFv Antibodies," *Methods in Molecular Biology*, 145:219-40 (2001).
Bartlett et al., "Caveat: A Program to Facilitate the Structure-derived Design of Biologically Active Molecules," in Chemical and Biological Problems in Molecular Recognition, Roberts, S.M.; Ley, S.V.; Campbell, M.M. eds.; *Royal Society of Chemistry*: Cambridge, pp. 182-196 (1989).
Bagshaw, C.R. and Harris, D.A., "Measurement of Ligand Binding to Proteins," *Spectrophotometry and Spectrofluorometry: A Practical Approach*, Bashford, C.L. and Harris, D.A., eds.; pp. 91-114, IRL Press Ltd., Oxford, U.K., (1987).
Beavo, et al., "Multiple Cyclic Nucleotide Phosphodiesterases," *Mol. Pharmacol.*, 46:399-405 (1994).
Bell, J.E., *Spectroscopy In Biochemistry*, vol. I, pp. 155-194, CRC Press, (1981).
Berthet, et al., "The Assay of Glucagon and Epinephrine with Use of Liver Homogenates," *J. Biol. Chem.*, 229:351-361 (1957).
Blundell et al., "Knowledge-based protein modeling and design." *Eur. J. Biochem.*, 172:513-520 (1988).
Böhm, H., "On the use of LUDI to search the Fine Chemicals Director for ligands of proteins of known three-dimensional structure," *J. Comp. Aided Molec. Design* 8: 623-632 (1994).
Bolger et al., "A Family of Human Phosphodiesterases Homologous to the *dunce* Learning and Memory Gene Product of *Drosophila melanogaster* Are Potential Targets for Antidepressant Drugs," *Mol. Cell. Biol.* 13 (10), 6558-6571 (1993).
Bolger, G.B., "Molecular Biology of the Cyclic AMP-Specific Cyclic Nucleotide Phosphodiesterases: A Diverse Family of Regulatory Enzymes," *Cell Signal*, 6:851-859 (1994).
Borch, et al., "Lithium Cyanohydridoborate, a Versatile New Reagent," *J. Am. Chem. Soc.*, 91, 3996-3997 (1969).
Bowtell, D. "Options available—from start to finish—for obtaining expression data by microarray," *Nature Genetics Supp.* 21:25-32 (1999).
Brenner et al., "Encoded Combinatorial Chemistry," *Proc. Natl. Acad. Sci. USA*, 89, 5381-5383 (1992).
Brünger, A.T., "Free R value: a novel statistical quantity for assessing the accuracy of crystal structures," *Nature* 355:472-475 (1992).
Buchschacher, G.L. and Panganiban, A.T., "Human Immunodeficiency Virus Vectors for Inducible Expression of Foreign Genes," *J. Virol.* 66:2731-2739, (1992).
Burgers, et al., "Stereochemistry of Hydrolysis of Adenosine 3':5'-Cyclic Phosphorothioate by the Cyclic Phosphodiesterase from Beef Heart," *J. Biol. Chem.*, 254:9959-9961 (1979).
Butcher, et al., "Adenosine 3', 5"-Phosphate in Biological Materials," *J. Biol. Chem.*, 237:1244-1250.
Capon, et al., "Designing CD4 immunoadhesins for AIDS therapy," *Nature* 377:525-531 (1989).
Carell et al., "New promise in combinatorial chemistry: synthesis, characterization, and screening of small-molecule libraries in solution," *Chem. Biol.*, 2:171-183 (1995).
Chabala, J.C., "Solid-phase combinatorial chemistry and novel tagging methods for identifying leads," *Curr Opin Biotechnol* 6(6):633-9 (1995).
Charbonneau, H., "Structure-Function Relationships Among Cyclic Nucleotide Phosphodiesterases," *Cyclic Nucleotide Phosphodiesterases: Structure, Regulation and Drug Action*, Beavo, J., and Houslay, M.D., eds) 267-296 (1990).
Checovich, W. J., et al., "Fluorescence polarization—a new tool for cell and molecular biology," *Nature* 375:254-256 (1995).
Clark et al.,"PRO_LIGAND: An approach to de novo molecular design. 1. Application to the design of organic molecules," *J. Comp. Aided Molec. Design* 9:13 (1995).
Coe et al., "Solution-phase combinatorial chemistry," *Mol Divers*;4(1):31-38 (1999).
Colliuod et al., "Oriented and Covalent Immobilization of Target Molecules to Solid Supports: Synthesis and Application of a Light- Activatable and Thiol-Reactive Cross-Linking Reagent," *Bioconjugate Chem.* 4:528-536 (1993).

Colman, P.M., "Structure-based drug design," *Current Opinion in Struc. Biol.* 4:868-874 (1994).

Conti et al. "Cyclic AMP-specific PDE4 Phosphodiesterases as Critical Components of Cyclic AMP Signaling," *J Biol Chem.* 278(8):5493-5496 (2003).

Conti, et al., "Recent Progress in Understanding the Hormonal Regulation of Phosphodiesterases," *Endocr. Rev.*, 16:370-389 (1995).

Creighton, T., "An Empirical Approach to Protein Conformation Stability and Flexibility," *Biopolymers* 22(1):49-58 (1983).

Cwirla et al., "Peptides on phage: A vast library of peptides for identifying ligands," *Biochemistry*, 87, 6378-6382; (1990).

Dandliker, W.B., et al., "Equilibrium and Kinetic Inhibition Assays Based upon Fluorescence Polarization," *Methods in Enzymology* 74:3-28 (1981).

Degerman, et al., "Structure, Localization, and Regulation of cGMP-inhibited Phosphodiesterase (PDE3)," *J. Biol. Chem.*, 272:6823-6826 (1997).

Dobeli, et al., "Recombinant Fusion Proteins for the Industrial Production of Disulfide Bridge Containing Peptides: Purification, Oxidation without Concatamer Formation, and Selective Cleavage," *Protein Expr. Purif.* 12:404-414 (1998).

Dolle et al., "Comprehensive Survey of Combinattorial Library Synthesis: 1998," *J Comb Chem* 1(4):235-282, (1999).

Eliseev, A.V. Lehn JM., (1999) Dynamic Combinatorial Chemistry: Evolutionary Formation and Screening of Molecular Libraries, *Current Topics in Microbiology & Immunology* 243:159-72; Bolger et al., (1991) *Methods Enz.* 203:21-45.

Enjalbal C. et al., "Mass Spectrometry in Combinatorial Chemistry," *Mass Spectrometry Reviews*. 19:139-61 (2000).

Feng et al., "Stable in vivo gene transduction via a novel adenoviral/retroviral chimeric vector." *Nature Biotechnology* 15:866-870 (1997).

Fisher, et al., Isolation and Characterization of PDE9A, a Novel Human cGMP-specific Phosphodiesterase, *J. Biol. Chem.*, 273:15559-15564 (1998).

Fivash et al., BIAcore for macromolecular interaction, Current Opinion in Biotechnology, 9:97-101 (1998).

Florio, et al, Phosphorylation of the 61-kDa Calmodulin-Stimulated Cyclic Nucleotide Phosphodiesterase at Serine 120 Reduces Its Affinity for Calmodulin, *Biochemistry*, 33:8948-8954 (1994).

Francis, et al., "Zinc Interactions and Conserved Motifs of the cGMP-binding cGMP-specific Phosphodiesterase Suggest That It Is a Zinc Hydrolase," *J. Biol. Chem.*, 269:22477-22480 (1994).

Gallop et al., "Applications of Combinatorial Technologies to Drug Discovery. 1. Background and Peptide Combinatorial Libraries," *J. Med. Chem.*, 37(9):1233-1251 (1994).

Gettys, et al., "Short-term Feedback Regulation of cAMP by Accelerated Degradation in Rat Tissues." *J. Biol. Chem.* 262:333-339 (1987).

Goldberg, et al., $^{18}$O-Labeling of Guanosine Monophosphate upon Hydrolysis of Cyclic Guanosine 3':3'- Monophosphate by Phosphodiesterase, *J. Biol. Chem.*, 255:10344-10347 (1980).

Goodford, P.J., "A Computational Procedure for Determining Energetically Favorable Binding Sites on Biologically Important Macromolecules," *J. Med. Chem.* 28:849 (1985).

Goodsell and Olson, "Automated Docking of Substrates to Proteins by Simulated Annealing," *Proteins: Structure, Function, and Genetics*, 8:195 (1990).

Gordon et al., Application of Combinatorial Technologies to Drug Discovery. 2. Combinatorial Organic Synthesis, Library Screening Strategies, and Future Directions. *J. Med. Chem.*, 37, 1385-1401; (1994).

Gram H., "Phage Display in Proteolysis and Signal Transduction," Combinatorial Chemistry & High Throughput Screening, 2:19-28 (1999).

Gravert et al., Synthesis on soluble polymers: new reactions and the construction of small molecules, *Curr Opin Chem Biol* 1(1):107-13 (1997).

Greer, J., "Model Structure for the Inflammatory Protein C5a," *Science* 228:1055; (1985).

Guida, W.C., "Software for structure-based drug design," *Current Opinion in Struc. Biol.* 4: 777 (1994).

Hafner et al., "Isothermal Amplification and Multimerization of DNA by *Bst* Polymerase," *Biotechniques*, 30(4):852-6, 858, 860 passim; (2001).

Hanselman et al., "A cDNA-dependent scintillation proximity assay for quantifying apolipoprotein A-1," *J. Lipid Res.* 38:2365-2373 (1997).

Hansen et al. "Absence of Muscarinic Cholinergic Airway Responses in Mice Deficient in the Cyclic Nucleotide Phosphodiesterase PDE4D," *Proc Natl Acad Sci U S A*, 97(12):6751-6756 (2000).

Heim et al., Engineering green fluorescent protein for improved brightness longer wavelengths and fluorescence resonance energy transfer, *Curr. Biol.* 6:178-182, (1996).

Houghten et al., "Generation and use of synthetic peptide combinatorial libraries for basic research and drug discovery," *Nature*, 354:84-86 (1991).

Houghten, R.A., "Peptide libraries: criteria and trends," *Trends Genet.*, 9, 235-239 (1993).

Houghton, R.A, "Parallel Array and Mixture-Based Synthetic Combinatorial Chemistry: Tools for the Next Millenium," *Annu Rev Pharmacol Toxicol* 40:273-82 (2000).

Houslay, M.D., "Compartmentalization of Cyclic Amp Phosphodiesterases, Signalling 'Crosstalk', Desensitation and the Phosphorylation of $G_i$-2 Add Cell Specific Personalization to the Control of the Levels of the Second Messenger Cyclic Map," *Adv. Enzyme Regul.*, 35:303-338 (1995).

Hughes-Jones et al., Synthesis of Rh Fv phage-antibodies using VH and VL germline genes, *British Journal of Haematology*, 105:811-816 (1999).

Ismail, A.H., "One Pot synthesis of 1-(S-Triazolo[4,3-c] Pyrimidin-3-YL) Substituted Polyols," *Synthetic Communications*, 32(12):1791-1795, (2002).

Iwane et al., "Myosin Subfragment-1 Is Fully Equipped with Factors Essential for Motor Function," *Biophys. Biochem. Res. Comm.* 230:76-80 (1997).

Jin and Conti, "Induction of the cyclic nucleotide phosphodiesterase PDE4B is essential for LPS-activated TNF-α responses," *Proc Natl Acad Sci U S A*, 99:7628-7633 (2002).

Jin et al., "Impaired Growth and Fertility of cAMP-Specific Phosphodiesterase PDE4D-Deficient Mice," *Proc Natl Acad Sci U S A*, 96:11998-12003 (1999).

Jin et al., "Characterization of the Structure of a Low $K_m$, Rolipram-sensitive cAMP Phosphodiesterase," *J. Biol. Chem.*, 267:18929-18939 (1992).

Johann et al., "GLVR1, a Receptor for Gibbon Ape Leukemia Virus, Is Homologous to a Phosphate Permease of *Neurospora crassa* and Is Expressed at High Levels in the Brain and Thymus," *J. Virol.*, 66:1635-1640 (1992).

Johnston, M. "Gene chips: Array of hope for understanding gene regulation," *Curr. Biol.*, 8:R171-R174 (1998).

Joseph-McCarthy D., "Computational approaches to structure-based ligand design," *Pharmacology & Therapeutics*, 84:179-91 (1999).

Kahl et al., "A Multiple-Approach Scintillation Proximity Assay to Measure the Association between Ras and Raf," *Anal. Biochem.* 243:282-283, (1996).

Kanda et al."Synthesis and Structure—Activity Relationships of Potent and Orally Active Sulfonamide $ET_B$ Selective Antagonists," *Bioorganic Medicinal Chemistry*, vol. 9, No. 4, 897-907 (2001).

Kern and Hampton, Direct Hybridization of Large-Insert Genomic Clones on High-Density Gridded cDNA Filter Arrays, *Biotechniques* 23:120-124, (1997).

Khimiya, *?? Russian alphabet ?? Geterotsiklicheskikh Soedinenii*, vol. 8, 1129-1130, (1987).

Kim, H.O. and Kahn, M., A Merger of Rational Drug Design and Combinatorial Chemistry: Development and Application of Peptide Secondary Structure Mimetics, Combinatorial Chemistry & High Throughput Screening 3:167-83, (2000).

Kirkpatrick et al., Structure-based drug design: combinatorial chemistry and molecular modeling, *Combinatorial Chemistry & High Throughput Screening*. 2:211-21, (1999).

Kline et al.,"Studies by ¹H Nuclear Magnetic Resonance and Distance Geometry of the Solultion Conformation of the α-amylase Inhibitor Tendamistat," *J. Mol. Biol.* 189:377-382, (1986).

Knighton et al., "Structural Basis of the Intrasteric Regulation of Myosin Light Chain Kinases," *Science* 258:130-135, (1992).

Kolaskar and Tongaonkar, "A semi-empirical method for prediction of antigenic determinants on protein antigens," *FEBS Lett.* 276(1-2):172-174, (1990).

Kroll et al., "A Multifunctional Prokaryotic Protein Expression System: Overproduction, Affinity Purification, and Selective Detection," *DNA Cell. Biol.* 12:441-53, (1993).

Kundu et al., "Combinatorial chemistry: polymer supported synthesis of peptide and non-peptide libraries," *Progress in Drug Research*, 53:89-156, (1999).

Kunkel, T.A., "Rapid and Efficient Site-Specific Mutagenesis without Phenotypic Selection," Proc. Natl. Acad. Sci. 82:488-492, (1985).

Kuntz et al., "Structure-Based Molecular Design," *Acc. Chem. Res.* 27:117, (1994).

Kuntz et al., "A Geometric Aproach to Macromolecule-Ligand Interactions," *J. Mol. Biol.* 162: 269, (1982).

Lam et al., "A new type of synthetic peptide library for identifying ligand-binding activity," *Nature*, 354, 82-84, (1991).

Lebl et al., "One-Bead-One-Structure Combinatorial Libraries," *Biopolymers*, 37 177-198, (1995).

Lee et al., "Crystal structure of phosphodiesterase 4D and inhibitor complex," *FEBS Lett*, 530:53-58 WO 00/54759, (2002).

Liparoto, S.F. and Ciardelli, T.L., "Biosensor analysis of the interleukin-2 receptor complex," *Journal of Molecular Recognition*. 12:316-21, (1999).

Lipinski et al., "Experimental and computational approaches to estimate solubility and permeability in drug discovery and development settings," *Advanced Drug Delivery Reviews*, 23 3-25, (1997).

Lipschultz et al., "Experimental Design for Analysis of Complex Kinetics Using Surface Plasmon Resonance," *Methods*. 20(3):310-8, (2000).

Lu et al., "Oriented Immobilization of Fab' Fragments on Silica Surfaces," *Anal. Chem.* 67:83-87, (1995).

Madden et al., "Synthetic combinatorial libraries: Views on techniques and their applicaton," *Perspectives in Drug Discovery and Design*, 2:269-282, (1994).

Malmborg, A. and Borrebaeck, C.A.K., "BIAcore as a tool in antibody engineering," *Journal of Immunological Methods*. 183:7-13, (1995).

Malmqvistl, M. and Karlsson, R., "Biomolecular interaction analysis: affinity biosensor technologies for functional analysis of proteins," *Current Opinion in Chemical Biology*. 1:378-83, (1997).

Malmqvist, M., "BIACORE: an affinity biosensor system for characterization of biomolecular interactions," Biochemical Society Transactions 27:335-40, (1999).

Markiewicz et al., "Synthetic oligonucleotide combinatorial libraries and their applications," *Farmaco*. 55:174-7, (2000).

Martin, Y.C., "Computer-Assisted Rational Drug Design," *Methods Enz.* 203:587-613, (1991).

Masquelin, T. and Obrecht, D., "A new general three component solution-phase synthesis of 2-amino-1,3-thiazole and 2,4-diamino-1,3-thiazole combinatorial libraries," *Tetrahedron*, vol. 57, No. 1, 153-156, (2001).

McAllister-Lucas, et al., "An Essential Aspartic Acid at Each of Two Allosteric cGMP-binding Sites of a cGMP-specific Phosphodiesterase," *J. Biol. Chem.*, 270:30671-30679 (1995).

McCall et al., "Characterization of anti-mouse Fcγ RII single-chain Fv fragments derived from human phage display libraries," *Immunotechnology*. 4:71-87, (1998).

McCasland, G.E. and Tarbell, D.S., "Analogs of Pyridoxine. II. Synthesis of a Pyrimidine Analog," *Journal of American Chemical Society*, 68,:2393-2395, (1946).

Mekonnen, B. and Crank, G., "Friedel-Crafts Reactions of 2-Amino-4-Alkyl or aryl)oxazoles with Acid Chlorides and Acid Anjhydrides: Synthesis of 5-Acyl-2-amino-4-alkyloxazoles," *Journal of Heterocylic Chemistry*, 34(2):567-572, (1997).

McLaughlin et al., "A Low-$K_m$, Rolipram-sensitive, cAMP-specific Phosphodiesterase from Human Brain," *J. Biol. Chem.* 268 (9), 6470-6476, (1993).

McPherson, A., "Current approaches to macromolecular crystallization," John Wiley, New York; McPherson *Eur. J. Biochem.*, 189:1-23, (1990).

Meng et al., "Automated Docking with Grid-Based Energy Evaluation," *J. Compt. Chem.* 13: 505, (1992).

Merritt,A.T., "Solution Phase Combinatorial Chemistry," *Comb Chem High Throughput Screen* 1(2):57-72, (1998).

Michaeli, et al., "Isolation and Characterization of a Previously Undetected Huan cAMP Phosphodiesterase by Complementation of cAMP Phosphodiesterase-deficient *Saccaromyces cervisiae*," *J. Biol. Chem.*, 268:12925-12932, (1993).

Miller et al., "FLOG: A system to select 'quasi-flexible' ligands complementary to a receptor of known three-dimensional structure," *J. Comp. Aided Molec. Design*, 8:153, (1994).

Miranker, A. and Karplus, M., "Functionality Maps of Binding Sites: A Multiple Copy simultaneous Search Method," *Proteins: Structure, Function, and Genetics*, 11:29, (1991).

Mitra et al., "Flurescence resonalce energy transfer between blue-emitting and red-shifted excitation derivatives of the green fluorescent protein," *Gene* 173:13-17, (1996).

Nicolls et al., "Protein Folding and Association: Insights From the Interfacial and Thermodynamic Properties of Hydrocarbons," *Proteins: Structure, Function, and Genetics*, 11:281-295 (1991).

Navaza, J., "AmoRe: an Automated Package for Molecular Replacement," *Acta Cryst.*, A50:157-163, (1994).

Neidle, S. and Jenkins, T.C., "Molecular Modeling to Study DNA Intercalation by Anti-tumor Drugs" *Methods Enz.* 203:433-458, (1991).

Ng et al., "Engineering Protein—Lipid Interactions: Targeting of Histidine-Tagged Proteins to Metal Chelating Lipid Monolayers," *Langmuir*, 11:4048-4055, (1995).

Nicholls *Proteins* 11:281-296, (1994).

Nichols et al., "Development of a Scintillation Proximity Assay for Peroxisome Poliferator-Actiated Receptor γ Ligand Binding Domain," *Anal. Biochem,*.257:112-119, (1998).

O'Shannessy, D.J. and Winzor, D.J., "Interpretation of Deviations from Pseudo-First-Order Kinetic Behavior in the Characterization of Ligand Binding by Biosensor Technology," *Analytical Biochemistry*, 236:275-83, (1996).

O'Shannessy, D.J., "Determination of kinetic rate and equilibrium binding constants for macromolecular interactions: a critique of the surface plasmon resonance literature," *Current Opinions in Biotechnology*, 5:65-71, (1994).

Obernolte et al., "The cDNA of a human lymphocyte cyclic-AMP phosphodiesterase (PDE IV) reveals a multigene family." *Gene* 129 (2), 239-247 (1993).

Okada et al., "Gene therapy against an experimental glioma using adeno-associated virus vectors," *Gene Ther.*, 3:957-964, (1996).

Otwinowski, Z., "Maximum Likelihood Refinement of Heavy Atom Parameters," Daresbury, United Kingdom, 80-86, (1991).

Parker et al., "Development of High Throughput Screening Assays Using Fluorescence Polarization: Nuclear Receptor-Ligand-Binding and Kinase/Phosphatase Assays," *J Biomol Screen.*, 5:77-88, (2000).

Percival, et al., "Zinc Dependent Activation of cAMP-Specific Phosphodiesterase (PDE4A)," *Biochem. Biophys. Res. Commun.*, 241:175-180 (1997).

Perrin, D.M., Nucleic Acids for Recognition and Catalysis: Landmarks, Limitations, and Looking to the Future, *Combinatorial Chemistry & High Throughput Screening* 3:243-69, (2000).

Pflugrath et al., "Crystal Structure Determination, Refinement and the Molecular Model of the α-Amylase Inhibitor Hoe-467A," *J. Mol. Biol.*, 189:383-386; (1986).

Plunkett, M. J., and Ellman, J. A., "A Silicon-Based Linker for Traceless Solid-Phase Synthesis," *J. Org. Chem.*, 60:6006, (1995).

Poul et al., "Selection of tumor-specific internalizing human antibodies from phage libraries," Source *Journal of Molecular Biology*. 301:1149-61, (2000).

Price et al.; Summary report on the ISOBM TD-4 Workshop: Analysis of 56 Monoclonal Antibodies Against the MUC1 mucin. *Tumour Biology*, 19(Suppl 1):1-20, (1998).

Rall, T.W. and Sutherland, E.W., "Formation of a Cyclic Adenine Ribonucleotide by Tissue Particles," *J. Biol. Chem.*, 232:1065-1076 (1958).

*Remington's Pharmaceutical Sciences*, 19th ed., Mack Publishing Co., Easton, PA, vol. 2, p. 1457, (1995).

Roberts et al., "Generation of an antibody with enhanced affinity and specificity for its antigen by protein engineering," *Nature* 328:731; (1987).

Romero-Ortego et al., "Synthesis of 4-Substituted 2-Phenylaminothiazoles from Amidines. A Convenient Route to 4-Trichloromethylthiazoles," *Journal of Organic Chemistry*, 65(21):7244-7247, (2000).

Rosenfeld, M.A., "Human artificial chromosomes get real," *Nat. Genet.*, 15:333-335, (1997).

Saiki, R.K., "Amplification of Genomic DNA" in PCR Protocols, Innis et al., Eds., Academic Press, San Diego, CA, pp. 13-20, (1990).

Schneider et al., "Functional Purification of a Bacterial STP-Binding Cassette Transporter Protein (MalK) from the Cytoplasmic Fraction of an Overproducing Strain," *Protein Expr. Purif.*, 6:10-14, (1995).

Schuhmann et al., "Immobilization of Enzymes on Langmuir-Blodgett Films via a Membrane-Bound Receptor. Possible Applications for Amperometric Biosensors," *Adv. Mater.* 3:388-391, (1991).

Schummer et al., "Inexpensive Handheld Device for the construction of High-Density Nucleic Acid Arrays," *Biotechniques*, 23:1087-1092, (1997).

Schweizer, F. and Hindsgaul, O., "Combinatorial synthesis of carbohydrates," *Curr Opin Chem Biol* 3(3):291-8, (1999).

Selvin et al., "Fluorescence Resonance Energy Transfer," *Meth. Enzymol.* 246:300-345, (1995).

Sheets et al., Efficient construction of a large nonimmune phage antibody library: the production of high-affinity human single-chain antibodies to protein antigens (published erratum appears in *Proc Natl Acad Sci* USA 1999 96:795, (1998).

Sheth, et al., "Isolation and Regulation of the cGMP-Inhibited cAMP Phosphodiesterase in Human Erythroleukemia Cells," *Throm. Haemostasis*, 77:155-162 (1997).

Shiao, M. and Tarng, K., "A Convenient Synthesis of 2,4'-Dipyridine," *Heterocycles*, vol. 31, No. 4, 637-641, (1990).

Siegel et al., "Mass Spectral Analysis of a Protein Complex using Single-chain Antibodies Selected on a Peptide Target: Applications to Functional Genomics," *Journal of Molecular Biology*, 302:285-93, (2000).

Sigal et al., "A Self-Assembled Monolayer for the Binding and Study of Histidine-Tagged Proteins by Surface Plasmon Resonance," *Anal. Chem.* 68:490-497, (1996).

Smith, et al., "Necklace-Coded Polymer-Supported Combinatorial Synthesis of 2-Arylaminobenzimidazoles." *J. Comb. Chem.*, 1:368-370, (1999).

Soderling, et al., "Identification and Characterization of a Novel Family of Cyclic Nucleotide Phosphodiesterases," *J. Biol. Chem.*, 273:15553-15558, (1998).

Soderling, et al., "Cloning and Characterization of a cAMP-Specific Cyclic Nucleotide Phosphodiesterase," *Proc. Natl. Acad. Sci. U.S.A.*, 95:8991-8996 (1998).

Solinas-Toldo et al., "Matrix-Based Comparative Genomic Hyridization: Biochips to Screen for Genomic Imbalances," *Genes, Chromosomes & Cancer* 20:399-407, (1997).

Sommen, et. al., "An improved method for the synthesis of aminothiphenes precursers of theno[2,3-b]pyrrole," *Tetrahedron Lett.*, 43, 257-259, (2002).

Sonnenberg, et al., "Identification of Inhibitory and Calmodulin-binding Domains of the PDE1A1 and PDE1A2 Calmodulin-stimulated Cyclic Nucleotide Phosphodiesterases," *J. Biol. Chem.*, 270:30989-31000, (1995).

Srivastava, et al., "Effects of magnesium on cyclic GMP hydrolysis by the bovine retinal rod cyclic GMP phosphodiesterase," *Biochem. J.*, 308:653-658 (1995).

Sun, et al., "Design, Synthesis, and Evaluations of Substituted 3-[(3- or 4-Carboxyethylpyrrol-2yl)methylidenl]indolin-2-ones as Inhibitors of VEGF, FGF, and PDGF Receptor Tyrosine Kinases," *J. Med. Chem.*, 42:5120-5130, (1999).

Taylor et al., "The rapid generation of oligonucleotide-directed mutations at high frequency using phosphorothioate-modified DNA," *Nucl. Acids Res.*, 13:8764-8785, (1985).

Thompson, et al, "Regulatory Mechanisms of Particulate Cyclic Nucleotide Phosphodiesterases," *Adv. Second Messenger Phosphoprotein Res.*, 25:165-184, (1992).

Undenfriend et al., "Scintillation Proximity Assay: A Sensitive and Continuous Isotopic Method for Monitoring Ligand/Receptor and Antigen/Antibody Interactions," *Anal. Biochem.* 161:494-500, (1987).

Underwood, et al., "Comparison of Phosphodiesterase III, IV and Dual III/IV Inhibitors on Bronchospasm and Pulmonary Eosinophil Influx in Guinea Pigs," *J. Pharmacol. Exp. Ther.*, 270:250-259, (1994).

Van Regenmortel, M.H.V., "Use of Biosensors to Characterize Recombinant Proteins," *Developments in Biological Standardization.*, 83:143-51, (1994).

Vely F. et al., "BIAcore Analysis to Test Phosphopeptide-SH2 Domain Interactions," *Methods in Molecular Biology*, 121:313-21, (2000).

Wessjohann, L.A., "Synthesis of natural-product-based compound libraries," *Curr Opin Chem Biol* 4(3):303-9, (2000).

Wharam et al., "Specific detection of DNA and RNA targets using a novel isothermal nucleic acid amplification assay based on the formation of a three-way junction structure," *Nucleic Acids Res.*, 1;29(11):e54 ,1-8, (2001).

Williams, "Dissection of the Extracellular Human Interferon y Receptor α-Chain into two Immunoglobulin-like Domains. Production in an *Escherichia coli* Thioredoxin Gene Fusion Expression System and Recognition by Neutralizing Antibodies," *Biochemistry*, 34:1787-1797, (1995).

Woon et al., "Construction and Characterization of a 10-fold Genome Equivalent Rat P1-Derived Artificial Chromosome Library," *Genomics* 50:306-316, (1998).

Wüthrich, K., "Chapter 10: Three-Dimensional Protein Structures by NMR," *NMR of Proteins and Nucleic Acids*,,John Wiley and Sons, New York:176-199, Zürich, Switzerland, (1986).

Xu et al., "Atomic Structure of PDE4: Insights into Phosphodiesterase Mechanism and Specificity," *Science*, 288, 1822-1825, (2000).

Yamazaki, et al., "Enzyme Regulation and TGP Binding Protein: An Algorithm of Control That Includes Physical Displaceent of an Inhibitory Protein," *Adv. Cyclic Nucleotide Protein Phosphorylation Res.*, 16:381-392 (1984).

Yamazaki, et al., "Cyclic GMP-specific, High Affinity, Noncatalytic Binding Sites on Light-activated Phosphodiesterase," *J. Biol. Chem.*, 255:11619-11624, (1980).

Lee F-Y et al. "Synthesis of 1-benzyl-3-(5'-hydroxymethyl-2'-furyl) indazole Analogues as Novel Antiplatelet Agents" Journal of Med. Chem, Amer. Can Society, vol. 44, 3746-3749, 2001.

Ciattini, P.G. et al. "An efficient synthesis fo 3-substituted indoles by palladium-catalyzed coupling reaction of 3-tributylstannylindoles with organic triflates and halides" Tetrhedron Letters Vo. 35, No. 15, 1994 2405-2408.

PCT International Search Report, Form PCT/ISA/210 dated Nov. 6, 2006.

* cited by examiner

Figure 1.

Sequence of pET15S with multi-cloning site.

T7 promoter
AGATCTCGATCCCGCGAAATTAATACGACTCACTATAGGGGAATTGTGAGCGGATAACAATTCCCC

RBS
TCTAGAAATAATTTTGTTTAACTTTAAGAAGGAGATATACC

NdeI
ATGGGCAGCAGCCATCATCATCATCATCACAGCAGCGGCCTGGTGCCGCGCGGCAGCCATATGGGATCCGG
 M  G  S  S  H  H  H  H  H  H  S  S  G  L  V  P  R  G  S  H  M --------

StuI   SalI
AATTCAAAGGCCTACGTCGACTAGAGCCTGCAGT*CTCGAC*CATCATCATCATCATCATTAATAAAAGG*GCG*
---------------------- *

SpeI  BamHI
*AATTCCAGCACACTGGC*GGCCGTTACTAGTGGATCCGGCTGCTAACAAAGCCCGAAAGGAAGCTGAGTTGG
 IVEX-3 Primer Bpu102 I           T7 terminator
CTGCTGCCACCGCTGAGCAATAACTAGCATAACCCCTTGGGCCTCTAAACGGGTCTTGAGGGGTTTTTTG
     3'-PET Primer (SEQ ID NO:9)

Figure 2.

Nucleic acid sequences for PDE4B in pET15S pET15S sequence (PCR product; 1159 bp)
ATATACCATGGGCAGCAGCCATCATCATCATCATCACAGCAGCGGCCTGGTGCCGCGCGGCAGCCATATG

```
             ag catctcacgc tttggagtca acactgaaaa tgaagatcac
1261 ctggccaagg agctggaaga cctgaacaaa tggggtctta acatctttaa tgtggctgga
1321 tattctcaca atagacccct aacatgcatc atgtatgcta tattccagga aagagacctc
1381 ctaaagacat tcagaatctc atctgacaca tttataacct acatgatgac tttagaagac
1441 cattaccatt ctgacgtggc atatcacaac agcctgcacg ctgctgatgt agcccagtcg
1501 acccatgttc tcctttctac accagcatta gacgctgtct tcacagattt ggaaatcctg
1561 gctgccattt tgcagctgc catccatgac gttgatcatc ctggagtctc caatcagttt
1621 ctcatcaaca caaattcaga acttgctttg atgtataatg atgaatctgt gttggaaaat
1681 catcaccttg ctgtgggttt caaactgctg caagaagaac actgtgacat cttcatgaat
1741 ctcaccaaga agcagcgtca gacactcagg aagatggtta ttgacatggt gttagcaact
1801 gatatgtcta aacacatgag cctgctggca gacctgaaga caatggtaga aacgaagaaa
1861 gttacaagtt caggcgttct tctcctagac aactataccg atcgcattca ggtccttcgc
1921 aacatggtac actgtgcaga cctgagcaac cccaccaagt ccttggaatt gtatcggcaa
1981 tggacagacc gcatcatgga ggaattttc cagcagggag acaaagagcg ggagagggga
2041 atggaaatta gcccaatgtg tgataaacac acagcttctg tggaaaaatc ccaggttggt
2101 ttcatcgact acattgtcca tccattgtgg gagacatggg cagatttggt acagcctgat
2161 gctcaggaca ttctcgatac cttagaagat aacaggaact ggtatcagag catgatacct
2221 caaagtccct caccaccact ggacgagcag aacagggact gccagggtct gatggagaag
2281 tttcagtttg aactgactct cgatgaggaa gattctgaag gacctgagaa ggagggagag
2341 ggacacagct aa (NdeI site mutated)
```
CTCGACTAGAGCCTGCAGTCTCGACCATCATCATCATCATCATTAATAAAAGGGCGAATTCCAGCACACT (SEQ ID NO:10)

Figure 3.
Amino acid sequences for PDE4B in pET15S

```
MGSSHHHHHH SSGLVPRGSH MSISRFGVNT ENEDHLAKEL EDLNKWGLNI FNVAGYSHNR
PLTCIMYAIF QERDLLKTFR ISSDTFITYM MTLEDHYHSD VAYHNSLHAA DVAQSTHVLL
STPALDAVFT DLEILAAIFA AAIHDVDHPG VSNQFLINTN SELALMYNDE SVLENHHLAV
GFKLLQEEHC DIFMNLTKKQ RQTLRKMVID MVLATDMSKH MSLLADLKTM VETKKVTSSG
VLLLDNYTDR IQVLRNMVHC ADLSNPTKSL ELYRQWTDRI MEEFFQQGDK ERERGMEISP
MCDKHTASVE KSQVGFIDYI VHPLWETWAD LVQPDAQDIL DTLEDNRNWY QSMIPQSPSP
PLDEQNRDCQ GLMEKFQFEL TLDEEDSEGP EKEGEGHS
```

(SEQ ID NO:11)

Alignment of the phosphodiesterase domains of PDE4B and PDE4D (SEQ ID NO:12)
(SEQ ID NO:13)

Ribbon Diagram of PDE4B dimer

SEQUENCE LISTING

<160> NUMBER OF SEQ ID NOS: 18

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgaattcat atgagcatct cacgctttgg agtc                                34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtgctctcg agttagctgt gtccctctcc ctcc                                34

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gatatgtcta aacacatgag cctgctggc                                      29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gccagcaggc tcatgtgttt agacatatc                                        29
```

<210> SEQ ID NO 9
<211> LENGTH: 391
<212> TYPE: DNA
<213> ORGANISM: Artificial Sequence
<220> FEATURE:
<223> OTHER INFORMATION: Description of Artificial Sequence: Synthetic pET15S sequence

<400> SEQUENCE: 9

```
agatctcgat cccgcgaaat taatacgact cactataggg gaattgtgag cggataacaa       60
ttcccctcta gaaataattt tgtttaactt taagaaggag atataccatg ggcagcagcc     120
atcatcatca tcatcacagc agcggcctgg tgccgcgcgg cagccatatg ggatccggaa     180
ttcaaaggcc tacgtcgact agagcctgca gtctcgacca tcatcatcat catcattaat     240
aaaagggcga attccagcac actggcggcc gttactagtg gatccggctg ctaacaaagc     300
ccgaaaggaa gctgagttgg ctgctgccac cgctgagcaa taactagcat aacccccttgg    360
ggcctctaaa cgggtcttga ggggttttttt g                                    391
```

<210> SEQ ID NO 10
<211> LENGTH: 1134
<212> TYPE: DNA
<213> ORGANISM: Homo sapiens

<400> SEQUENCE: 10

```
agcatctcac gctttggagt caacactgaa aatgaagatc acctggccaa ggagctggaa       60
gacctgaaca aatggggtct aacatctttt aatgtggctg atattctca caatagaccc     120
ctaacatgca tcatgtatgc tatattccag gaaagagacc tcctaaagac attcagaatc     180
tcatctgaca catttataac ctacatgatg actttagaag accattacca ttctgacgtg     240
gcatatcaca acagcctgca cgctgctgat gtagcccagt cgacccatgt tctcctttct     300
acaccagcat tagacgctgt cttcacagat ttggaaatcc tggctgccat ttttgcagct     360
gccatccatg acgttgatca tcctggagtc tccaatcagt ttctcatcaa cacaaattca     420
gaacttgctt tgatgtataa tgatgaatct gtgttggaaa atcatcacct tgctgtgggt     480
ttcaaactgc tgcaagaaga acactgtgac atcttcatga atctcaccaa gaagcagcgt     540
cagacactca ggaagatggt tattgacatg gtgttagcaa ctgatatgtc taaacacatg     600
agcctgctgg cagacctgaa gacaatggta gaaacgaaga agttacaag ttcaggcgtt      660
cttctcctag acaactatac cgatcgcatt caggtccttc gcaacatggt acactgtgca     720
gacctgagca accccaccaa gtccttggaa ttgtatcggc aatggacaga ccgcatcatg     780
gaggaatttt tccagcaggg agacaaagag cgggagaggg aatgaaaat tagcccaatg      840
tgtgataaac acacagcttc tgtggaaaaa tcccaggttg gtttcatcga ctacattgtc     900
catccattgt gggagacatg ggcagatttg gtacagcctg atgctcagga cattctcgat     960
accttagaag ataacaggaa ctggtatcag agcatgatac ctcaaagtcc ctcaccacca    1020
ctggacgagc agaacaggga ctgccagggt ctgatggaga gtttcagtt tgaactgact     1080
ctcgatgagg aagattctga aggacctgag aaggagggag agggacacag ctaa          1134
```

<210> SEQ ID NO 11
<211> LENGTH: 398

```
<212> TYPE: PRT
<213> ORGANISM: Homo sapiens

<400> SEQUENCE: 11

Met Gly Ser Ser His His His His His His Ser Ser Gly Leu Val Pro
  1               5                  10                  15

Arg Gly Ser His Met Ser Ile Ser Arg Phe Gly Val Asn Thr Glu Asn
             20                  25                  30

Glu Asp His Leu Ala Lys Glu Leu Glu Asp Leu Asn Lys Trp Gly Leu
         35                  40                  45

Asn Ile Phe Asn Val Ala Gly Tyr Ser His Asn Arg Pro Leu Thr Cys
     50                  55                  60

Ile Met Tyr Ala Ile Phe Gln Glu Arg Asp Leu Leu Lys Thr Phe Arg
 65                  70                  75                  80

Ile Ser Ser Asp Thr Phe Ile Thr Tyr Met Met Thr Leu Glu Asp His
                 85                  90                  95

Tyr His Ser Asp Val Ala Tyr His Asn Ser Leu His Ala Ala Asp Val
            100                 105                 110

Ala Gln Ser Thr His Val Leu Leu Ser Thr Pro Ala Leu Asp Ala Val
        115                 120                 125

Phe Thr Asp Leu Glu Ile Leu Ala Ala Ile Phe Ala Ala Ala Ile His
    130                 135                 140

Asp Val Asp His Pro Gly Val Ser Asn Gln Phe Leu Ile Asn Thr Asn
145                 150                 155                 160

Ser Glu Leu Ala Leu Met Tyr Asn Asp Glu Ser Val Leu Glu Asn His
                165                 170                 175

His Leu Ala Val Gly Phe Lys Leu Leu Gln Glu Glu His Cys Asp Ile
            180                 185                 190

Phe Met Asn Leu Thr Lys Lys Gln Arg Gln Thr Leu Arg Lys Met Val
        195                 200                 205

Ile Asp Met Val Leu Ala Thr Asp Met Ser Lys His Met Ser Leu Leu
    210                 215                 220

Ala Asp Leu Lys Thr Met Val Glu Thr Lys Lys Val Thr Ser Ser Gly
225                 230                 235                 240

Val Leu Leu Leu Asp Asn Tyr Thr Asp Arg Ile Gln Val Leu Arg Asn
                245                 250                 255

Met Val His Cys Ala Asp Leu Ser Asn Pro Thr Lys Ser Leu Glu Leu
            260                 265                 270

Tyr Arg Gln Trp Thr Asp Arg Ile Met Glu Glu Phe Phe Gln Gln Gly
        275                 280                 285

Asp Lys Glu Arg Glu Arg Gly Met Glu Ile Ser Pro Met Cys Asp Lys
    290                 295                 300

His Thr Ala Ser Val Glu Lys Ser Gln Val Gly Phe Ile Asp Tyr Ile
305                 310                 315                 320

Val His Pro Leu Trp Glu Thr Trp Ala Asp Leu Val Gln Pro Asp Ala
                325                 330                 335

Gln Asp Ile Leu Asp Thr Leu Glu Asp Asn Arg Asn Trp Tyr Gln Ser
            340                 345                 350

Met Ile Pro Gln Ser Pro Ser Pro Leu Asp Glu Gln Asn Arg Asp
        355                 360                 365

Cys Gln Gly Leu Met Glu Lys Phe Gln Phe Glu Leu Thr Leu Asp Glu
    370                 375                 380

Glu Asp Ser Glu Gly Pro Glu Lys Glu Gly Glu Gly His Ser
385                 390                 395
```

<210> SEQ ID NO 12
<211> LENGTH: 357
<212> TYPE: PRT
<213> ORGANISM: Homo sapiens

<400> SEQUENCE: 12

Ser Ile Ser Arg Phe Gly Val Asn Thr Glu Asn Glu Asp His Leu Ala
1               5                   10                  15

Lys Glu Leu Glu Asp Leu Asn Lys Trp Gly Leu Asn Ile Phe Asn Val
            20                  25                  30

Ala Gly Tyr Ser His Asn Arg Pro Leu Thr Cys Ile Met Tyr Ala Ile
        35                  40                  45

Phe Gln Glu Arg Asp Leu Leu Lys Thr Phe Arg Ile Ser Ser Asp Thr
    50                  55                  60

Phe Ile Thr Tyr Met Met Thr Leu Glu Asp His Tyr His Ser Asp Val
65                  70                  75                  80

Ala Tyr His Asn Ser Leu His Ala Ala Asp Val Ala Gln Ser Thr His
                85                  90                  95

Val Leu Leu Ser Thr Pro Ala Leu Asp Ala Val Phe Thr Asp Leu Glu
            100                 105                 110

Ile Leu Ala Ala Ile Phe Ala Ala Ala Ile His Asp Val Asp His Pro
        115                 120                 125

Gly Val Ser Asn Gln Phe Leu Ile Asn Thr Asn Ser Glu Leu Ala Leu
    130                 135                 140

Met Tyr Asn Asp Glu Ser Val Leu Glu Asn His His Leu Ala Val Gly
145                 150                 155                 160

Phe Lys Leu Leu Gln Glu Glu His Cys Asp Ile Phe Met Asn Leu Thr
                165                 170                 175

Lys Lys Gln Arg Gln Thr Leu Arg Lys Met Val Ile Asp Met Val Leu
            180                 185                 190

Ala Thr Asp Met Ser Lys His Met Ser Leu Leu Ala Asp Leu Lys Thr
        195                 200                 205

Met Val Glu Thr Lys Lys Val Thr Ser Ser Gly Val Leu Leu Leu Asp
    210                 215                 220

Asn Tyr Thr Asp Arg Ile Gln Val Leu Arg Asn Met Val His Cys Ala
225                 230                 235                 240

Asp Leu Ser Asn Pro Thr Lys Ser Leu Glu Leu Tyr Arg Gln Trp Thr
                245                 250                 255

Asp Arg Ile Met Glu Glu Phe Phe Gln Gln Gly Asp Lys Glu Arg Glu
            260                 265                 270

Arg Gly Met Glu Ile Ser Pro Met Cys Asp Lys His Thr Ala Ser Val
        275                 280                 285

Glu Lys Ser Gln Val Gly Phe Ile Asp Tyr Ile Val His Pro Leu Trp
    290                 295                 300

Glu Thr Trp Ala Asp Leu Val Gln Pro Asp Ala Gln Asp Ile Leu Asp
305                 310                 315                 320

Thr Leu Glu Asp Asn Arg Asn Trp Tyr Gln Ser Met Ile Pro Gln Ala
                325                 330                 335

Pro Ala Pro Pro Leu Asp Glu Gln Asn Arg Asp Cys Gln Gly Leu Met
            340                 345                 350

Glu Lys Phe Gln Phe
        355

```
<210> SEQ ID NO 13
<211> LENGTH: 349
<212> TYPE: PRT
<213> ORGANISM: Homo sapiens

<400> SEQUENCE: 13

Thr Glu Gln Glu Asp Val Leu Ala Lys Glu Leu Glu Asp Val Asn Lys
 1               5                  10                  15

Trp Gly Leu His Val Phe Arg Ile Ala Glu Leu Ser Gly Asn Arg Pro
            20                  25                  30

Leu Thr Val Ile Met His Thr Ile Phe Gln Glu Arg Asp Leu Leu Lys
        35                  40                  45

Thr Phe Lys Ile Pro Val Asp Thr Leu Ile Thr Tyr Leu Met Thr Leu
     50                  55                  60

Glu Asp His Tyr His Ala Asp Val Ala Tyr His Asn Asn Ile His Ala
 65                  70                  75                  80

Ala Asp Val Val Gln Ser Thr His Val Leu Leu Ser Thr Pro Ala Leu
                 85                  90                  95

Glu Ala Val Phe Thr Asp Leu Glu Ile Leu Ala Ala Ile Phe Ala Ser
            100                 105                 110

Ala Ile His Asp Val Asp His Pro Gly Val Ser Asn Gln Phe Leu Ile
        115                 120                 125

Asn Thr Asn Ser Glu Leu Ala Leu Met Tyr Asn Asp Ser Ser Val Leu
    130                 135                 140

Glu Asn His His Leu Ala Val Gly Phe Lys Leu Leu Gln Glu Glu Asn
145                 150                 155                 160

Cys Asp Ile Phe Gln Asn Leu Thr Lys Lys Gln Arg Gln Ser Leu Arg
                165                 170                 175

Lys Met Val Ile Asp Ile Val Leu Ala Thr Asp Met Ser Lys His Met
            180                 185                 190

Asn Leu Leu Ala Asp Leu Lys Thr Met Val Glu Thr Lys Lys Val Thr
        195                 200                 205

Ser Ser Gly Val Leu Leu Leu Asp Asn Tyr Ser Asp Arg Ile Gln Val
    210                 215                 220

Leu Gln Asn Met Val His Cys Ala Asp Leu Ser Asn Pro Thr Lys Pro
225                 230                 235                 240

Leu Gln Leu Tyr Arg Gln Trp Thr Asp Arg Ile Met Glu Glu Phe Phe
                245                 250                 255

Arg Gln Gly Asp Arg Glu Arg Glu Arg Gly Met Glu Ile Ser Pro Met
            260                 265                 270

Cys Asp Lys His Asn Ala Ser Val Glu Lys Ser Gln Val Gly Phe Ile
        275                 280                 285

Asp Tyr Ile Val His Pro Leu Trp Glu Thr Trp Ala Asp Leu Val His
    290                 295                 300

Pro Asp Ala Gln Asp Ile Leu Asp Thr Leu Glu Asp Asn Arg Glu Trp
305                 310                 315                 320

Tyr Gln Ser Thr Ile Pro Gln Ser Pro Ser Pro Ala Pro Asp Asp Pro
                325                 330                 335

Glu Glu Gly Arg Gln Gly Gln Thr Glu Lys Phe Gln Phe
            340                 345

<210> SEQ ID NO 14

<400> SEQUENCE: 14

000
```

```
<210> SEQ ID NO 15

<400> SEQUENCE: 15

000

<210> SEQ ID NO 16
<211> LENGTH: 70
<212> TYPE: DNA
<213> ORGANISM: Homo sapiens

<400> SEQUENCE: 16 ataccatg ggcagcagcc atcatcatca tcatcacagc agcggcctgg tgccgcgcgg     60
cagccatatg                                                          70

<210> SEQ ID NO 17
<211> LENGTH: 70
<212> TYPE: DNA
<213> ORGANISM: Homo sapiens

<400> SEQUENCE: 17
ctcgactaga gcctgcagtc tcgaccatca tcatcatcat cattaataaa agggcgaatt   60
ccagcacact                                                          70

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 18

His His His His His His
 1               5
```

PDE4B INHIBITORS AND USES THEREFOR

CROSS-REFERENCE TO RELATED PATENT APPLICATIONS

This application claims priority under 35 U.S.C. § 119 to U.S. Provisional Application No. 60/569,435, filed May 6, 2004, which is hereby incorporated by reference in its entirety for all purposes.

FIELD OF THE INVENTION

This invention relates to the development of ligands for phosphodiesterase 4B (PDE4B) and to the use of crystal structures of PDE4B for the development of said ligands. The information provided is intended solely to assist the understanding of the reader. None of the information provided nor references cited is admitted to be prior art to the present invention. Each of the references cited is incorporated herein in its entirety and for any purpose.

BACKGROUND OF THE INVENTION

Phosphodiesterases (PDEs) were first detected by Sutherland and co-workers (Rall, et al., *J. Biol. Chem.*, 232:1065-1076 (1958), Butcher, et al., *J. Biol. Chem.*, 237:1244-1250 (1962)). The superfamily of PDEs is subdivided into two major classes, class I and class II (Charbonneau, H., *Cyclic Nucleotide Phosphodiesterases: Structure, Regulation and Drug Action*, Beavo, J., and Houslay, M.D., eds) 267-296 John Wiley & Sons, Inc., New York (1990)), which have no recognizable sequence similarity. Class I includes all known mammalian PDEs and is comprised of 11 identified families that are products of separate genes (Beavo, et al., *Mol. Pharmacol.*, 46:399-405 (1994); Conti, et al., *Endocr. Rev.*, 16:370-389 (1995); Degerman, et al., *J. Biol. Chem.*, 272: 6823-6826 (1997); Houslay, M.D., *Adv. Enzyme Regul.*, 35:303-338 (1995); Bolger, G. B., *Cell Signal*, 6:851-859 (1994); Thompson, et al, *Adv. Second Messenger Phosphoprotein Res.*, 25:165-184 (1992); Underwood, et al., *J. Pharmacol. Exp. Ther.*, 270:250-259 (1994); Michaeli, et al., *J. Biol. Chem.*, 268:12925-12932 (1993); Soderling, et al., *Proc. Natl. Acad. Sci. U.S.A.*, 95:8991-8996 (1998); Soderling, et al., *J. Biol. Chem.*, 273:15553-15558 (1998); Fisher, et al., *J. Biol. Chem.*, 273:15559-15564 (1998)). Some PDEs are highly specific for hydrolysis of cAMP (PDE4, PDE7, PDE8), some are highly cGMP-specific (PDE5, PDE6, PDE9), and some have mixed specificity (PDE1, PDE2, PDE3, PDE10).

All of the characterized mammalian PDEs are dimeric, but the importance of the dimeric structure for function in each of the PDEs is unknown. Each PDE has a conserved catalytic domain of ~270 amino acids with a high degree of conservation (25-30%) of amino acid sequence among PDE families, and which is located toward the carboxyl-terminus relative to its regulatory domain. Activators of certain PDEs appear to relieve the influence of autoinhibitory domains located within the enzyme structures (Sonnenberg, et al., *J. Biol. Chem.*, 270:30989-31000 (1995); Jin, et al., *J. Biol. Chem.*, 267: 18929-18939 (1992)).

PDEs cleave the cyclic 2'-3' nucleotide phosphodiester bond between the phosphorus and oxygen atoms at the 3'-position with inversion of configuration at the phosphorus atom (Goldberg, et al., *J. Biol. Chem.*, 255:10344-10347 (1980); Burgers, et al., *J. Biol. Chem.*, 254:9959-9961 (1979)). This apparently results from an in-line nucleophilic attack by the $OH^-$ of ionized $H_2O$. It has been proposed that metals bound in the conserved metal binding motifs within PDEs facilitate the production of the attacking $OH^-$ (Francis, et al., *J. Biol. Chem.*, 269:22477-22480 (1994)). The kinetic properties of catalysis are consistent with a random order mechanism with respect to cyclic nucleotide and the divalent cations(s) that are required for catalysis (Srivastava, et al., *Biochem. J*, 308:653-658 (1995)). The catalytic domains of all known mammalian PDEs contain two sequences ($HX_3$ $HX_n(E/D)$) arranged in tandem, each of which resembles the single $Zn^{2+}$-binding site of metalloendoproteases such as thermolysin (Francis, et al., *J. Biol. Chem.*, 269:22477-22480 (1994)). PDE5 specifically binds $Zn^{2+}$, and the catalytic activities of PDE4, PDE5, and PDE6 are supported by submicromolar concentrations of $Zn^{2+}$ (Francis, et al., *J. Biol. Chem.*, 269:22477-22480 (1994); Percival, et al., *Biochem. Biophys. Res. Commun.*, 241:175-180 (1997)). Whether each of the $Zn^{2+}$-binding motifs binds $Zn^{2+}$ independently or whether the two motifs interact to form a novel $Zn^{2+}$-binding site is not known. The catalytic mechanism for cleaving phosphodiester bonds of cyclic nucleotides by PDEs may be similar to that of certain proteases for cleaving the amide ester of peptides, but the presence of two $Zn^{2+}$ motifs arranged in tandem in PDEs is unprecedented.

The group of Sutherland and Rall (Berthet, et al., *J. Biol. Chem.*, 229:351-361 (1957)), in the late 1950s, was the first to realize that at least part of the mechanism(s) whereby caffeine enhanced the effect of glucagon, a stimulator of adenylyl cyclase, on cAMP accumulation and glycogenolysis in liver involved inhibition of cAMP PDE activity. Since that time chemists have synthesized thousands of PDE inhibitors, including the widely used 3-isobutyl-1-methylxanthine (EBMX). Many of these compounds, as well as caffeine, are non-selective and inhibit many of the PDE families. One important advance in PDE research has been the discovery/design of family-specific inhibitors such as the PDE4 inhibitor, rolipram, and the PDE5 inhibitor, sildenafil.

Precise modulation of PDE function in cells is critical for maintaining cyclic nucleotide levels within a narrow rate-limiting range of concentrations. Increases in cGMP of 2-4-fold above the basal level will usually produce a maximum physiological response. There are three general schemes by which PDEs are regulated: (a) regulation by substrate availability, such as by stimulation of PDE activity by mass action after elevation of cyclic nucleotide levels or by alteration in the rate of hydrolysis of one cyclic nucleotide because of competition by another, which can occur with any of the dual specificity PDEs (e.g. PDE1, PDE2, PDE3); (b) regulation by extracellular signals that alter intracellular signaling (e.g. phosphorylation events, $Ca^{2+}$, phosphatidic acid, inositol phosphates, protein-protein interactions, etc.) resulting, for example, in stimulation of PDE3 activity by insulin (Degerman, et al., *J. Biol. Chem.*, 272:6823-6826 (1997)), stimulation of PDE6 activity by photons through the transducin system (Yamazaki, et al., *J. Biol. Chem.*, 255:11619-11624 (1980)), which alters PDE6 interaction with this enzyme, or stimulation of PDE 1 activity by increased interaction with $Ca^{2+}$/calmodulin; (c) feedback regulation, such as by phosphorylation of PDE1, PDE3, or PDE4 catalyzed by PKA after cAmP elevation (Conti, et al., *Endocr. Rev.*, 16:370-389 (1995); Degerman, et al., *J. Biol. Chem.*, 272:6823-6826 (1997); Gettys, et al., *J. Biol. Chem.* 262:333-339 (1987); Florio, et al, *Biochemistry*, 33:8948-8954 (1994)), by allosteric cGMP binding to PDE2 to promote breakdown of cAMP or cGMP after cGMP elevation, or by modulation of PDE protein levels, such as the desensitization that occurs by increased concentrations of PDE3 or PDE4 following chronic exposure of cells to cAMP-elevating agents (Conti, et al.,

*Endocr. Rev.*, 16:370-389 (1995), Sheth, et al., *Throm. Haemostasis*, 77:155-162 (1997)) or by developmentally related changes in PDE5 content. Other factors that could influence any of the three schemes outlined above are cellular compartmentalization of PDEs (Houslay, M.D., *Adv. Enzyme Regul.*, 35:303-338 (1995)) effected by covalent modifications such as prenylation or by specific targeting sequences in the PDE primary structure and perhaps translocation of PDEs between compartments within a cell.

Within the PDE superfamily, four PDEs (PDE2, PDE5, PDE6, and PDE10) of the 10 families contain highly cGMP-specific allosteric (non-catalytic) cGMP-binding sites in addition to a catalytic site of varying substrate specificity. Each of the monomers of these dimeric cGMP-binding PDEs contains two homologous cGMP-binding sites of ~110 amino acids arranged in tandem and located in the amino-terminal portion of the protein (Charbonneau, H., *Cyclic Nucleotide Phosphodiesterases: Structure, Regulation and Drug Action*, Beavo, J., and Houslay, M.D., eds) 267-296 (1990); McAllister-Lucas, et al., *J. Biol. Chem.*, 270:30671-30679 (1995)). In PDE2, binding of the cgMP to these sites stimulates the hydrolysis of cAMP at the catalytic site (Beavo, et al., *Mol. Pharmacol.*, 46:399-405 (1994)). PDE2 hydrolyzed cGMP as well as cAMP, and cGMP hydrolysis is stimulated by cGMP binding at the allosteric sites in accordance with positively cooperative kinetics (Manganiello, et al., *Cyclic Nucleotide Phosphodiesterases: Structure, Regulation, and Drug Action*, Beavo, J., and Houslay, M.D., eds, 61-85 John Wiley & Sons, Inc., New York (1990)). This could represent a negative feedback process for regulation of tissue cGMP levels (Manganiello, et al., *Cyclic Nucleotide Phosphodiesterases: Structure, Regulation, and Drug Action*, Beavo, J., and Houslay, M.D., eds, 61-85 John Wiley & Sons, Inc., New York (1990)), which occurs in addition to the cross-talk between cyclic nucleotide pathways represented by cGMP stimulation of cAMP breakdown. Binding of cGMP to the allosteric sites of PDE6 has not been shown to affect catalysis, but this binding may modulate the interaction of PDE6 with the regulatory protein, transducin, and the inhibitory γ subunit of PDE6 (Yamazaki, et al., *Adv. Cyclic Nucleotide Protein Phosphorylation Res.*, 16:381-392 (1984)).

The PDE4 subfamily is comprised of 4 members: PDE4A (SEQ ID NO:14), PDE4B (SEQ ID NO:12), PDE4C (SEQ ID NO: 15), and PDE4D (SEQ ID NO:13) (Conti et al. (2003) *J Biol. Chem.* 278:5493-5496). The PDE4 enzymes display a preference for cAMP over cGMP as a substrate. These enzymes possess N-terminal regulatory domains that presumably mediate dimerization, which results in optimally regulated PDE activity. In addition, activity is regulated via cAMP-dependent protein kinase phosphorylation sites in this upstream regulatory domain. These enzymes are also rather ubiquitously expressed, but importantly in lymphocytes.

Inhibitors of the PDE4 enzymes have proposed utility in the treatment of inflammatory diseases. Knockout of PDE4B results in viable mice (Jin and Conti (2002) *Proc Natl Acad Sci USA*, 99, 7628-7633), while knockout of PDE4D results in reduced viability (Jin et al. (1999) *Proc Natl Acad Sci USA*, 96, 11998-12003). The PDE4D knockout genotype can be rescued by breeding onto other background mouse strains. Airway epithelial cells from these PDE4D knockout embryos display greatly reduced hypersensitivity to adrenergic agonists, suggesting PDE4D as a therapeutic target in airway inflammatory diseases (Hansen et al. (2000) *Proc Natl Acad Sci USA*, 97, 6751-6756). PDE4B-knockout mice have few symptoms and normal airway hypersensitivity.

By contrast, monocytes from the PDE4B knockout mice exhibit a reduced response to LPS (Jin and Conti (2002) *Proc Natl Acad Sci USA*, 99, 7628-7633). This suggests that a PDE4B compound with selectivity versus PDE4D could exhibit anti-inflammatory activity with reduced side-effects.

Crystal structures of PDE4B (Xu et al. (2000) *Science*, 288, 1822-1825) and PDE4D (Lee et al. (2002) *FEBS Lett*, 530, 53-58) have been reported in the literature. The PDE4B structure was solved without ligand present in the active site, so information about active site properties was limited to determination of two metal ion sites (presumably zinc and magnesium). A binding mode for cAMP was proposed based on computational modeling. Accordingly, there is need in the art for more potent and specific inhibitors and modulators of PDE4B and methods for designing them.

SUMMARY OF THE INVENTION

The present invention relates to compounds active on PDE4B, and the use of structural information about PDE4B to design additional PDE4B modulators. In particular, the invention is directed to compounds of Formula I, Formula II, and Formula III as described below. Thus, the invention provides compounds that can be used for therapeutic methods involving modulation of PDE4B, as well as providing molecular scaffolds for developing additional modulators of PDE4B and other PDEs.

The compounds of Formula I have the following structure:

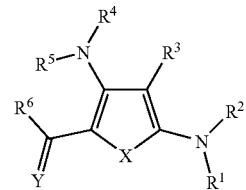

Formula I where:

$X$ is O, S, or $NR^7$;

Y and Z are independently O or S;

$R^1, R^2, R^4, R^5, R^7, R^9$ and $R^{10}$ are independently hydrogen, acyl, optionally substituted lower alkyl, optionally substituted lower alkenyl, optionally substituted lower alkynyl, optionally substituted cycloalkyl, optionally substituted heterocycle, optionally substituted heterocycloalkyl, optionally substituted aryl, optionally substituted aralkyl, optionally substituted heteroaryl or optionally substituted heteroaralkyl and $R^1$ and $R^2$, or $R^4$ and $R^5$, or $R^9$ and $R^{10}$, or $R^2$ and $R^3$ can independently combine to form a heterocycle or optionally substituted heterocycle;

$R^3$ is cyano, nitro, —$C(Z)R^8$, $S(O_2)NR^9R^{10}$, $S(O_2)R^{11}$, or optionally substituted lower alkyl;

$R^6$ and $R^8$ are independently hydroxy, alkoxy, thioalkoxy, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, or optionally substituted heterocycle;

$R^{11}$ is independently hydroxy, alkoxy, thioalkoxy, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl. The invention comprises all salts, prodrugs, and isomers of compounds of the invention.

In certain embodiments, X is S, $R^1$ is H or optionally substituted lower alkyl, $R^2$ is or includes a cyclic group such as phenyl, methoxyphenyl, and benzyl.

In certain embodiments X is S; alternatively, X is O; or alternatively X is $NR^7$. In particular embodiments for each of X as S, X as O, and X as $NR^7$, Y is O; Y is S; $R^3$ is cyano; $R^3$ is $C(Z)R^8$; $R^3$ is $S(O_2)NR^9R^{10}$; $R^3$ is $S(O_2)R^{11}$, $R^3$ is $C(O)NH_2$, or $R^3$ is lower alkyl.

In certain embodiments, $R^2$ is or includes an optionally substituted cyclic group, e.g., a carbocyclic or heterocyclic group, which can be an aromatic group. Examples include cyclopentyl, cyclohexyl, phenyl, pyrrolyl, pyridinyl; in further related embodiments of each of the just mentioned selections for $R^2$ is H; $R^2$ is lower alkyl. In further embodiments, for each of the just mentioned selections for $R^2$, $R^3$ is carbonitrile or a carboxylic acid alkyl ester, e.g., carboxylic acid ethyl ester (such as shown in compound 33).

In certain embodiments, $R^6$ is

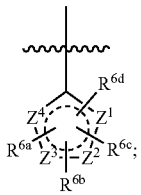

$Z^1$, $Z^2$, $Z^3$, and $Z^4$ are independently selected from the group consisting of —O—, —S—, —$CR^{6a}$—, —$CR^{6b}$—, —$CR^{6c}$—, and —$NR^{6d}$—,
wherein:
at least one of $Z^1$, $Z^2$, $Z^3$, and Z4 is a heteroatom, where $Z^1$, $Z^2$, $Z^3$, and $Z^4$ are selected to produce a stable compound;
$R^{6a}$, $R^{6b}$ and $R^{6c}$ are independently selected from the group consisting of hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound; or
$R^{6a}$, $R^{6b}$, and $R^{6c}$ can, in combination with the five-membered ring comprising $Z^1$, $Z^2$, $Z^3$, and $Z^4$, combine to form an optionally substituted fused heterocyclic ring system;
$R^{6d}$ is optionally present, and when present is selected from the group consisting of hydrogen, optionally substituted lower alkyl, optionally substituted aryl, optionally substituted heterocycle, optionally substituted heteroaryl, acyl, sulfonyl, amido, thioamido, and sulfonamido;
provided, however, that
when $R^6$ is thiophen-2-yl, then $R^1$ and $R^2$ are not selected from the group consisting of phenyl, lower alkyl, and lower alkenyl; and when $R^6$ is furan-2-yl, then $R^1$ and $R^2$ are not selected from the group consisting of optionally substituted phenyl and optionally substituted phenylalkyl.

In a further embodiment $R^1$ is selected from the group consisting of optionally substituted lower alkyl, optionally substituted lower alkenyl, optionally substituted lower alkynyl, acyl, optionally substituted cycloalkyl, optionally substituted heterocycle, optionally substituted heterocycloalkyl, optionally substituted aryl, optionally substituted aralkyl, optionally substituted heteroaryl, and optionally substituted heteroaralkyl; and $R^2$, $R^4$ and $R^5$ are hydrogen.

In a further embodiment, optionally substituted heterocycle is optionally substituted cycloheteroalkyl, such as an optionally substituted pyrrolidine or piperidine.

In certain embodiments, $R^6$ is selected from the group consisting of

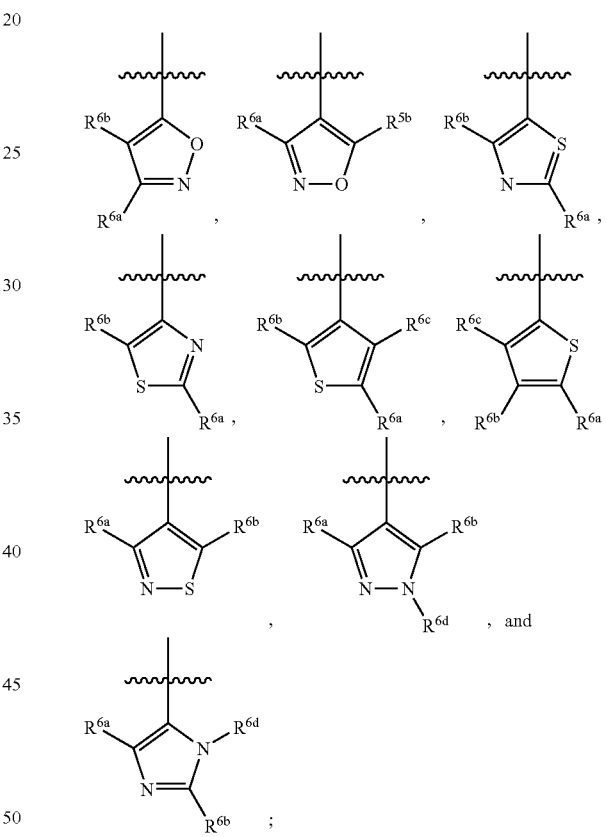

$R^{6a}$, $R^{6b}$, and $R^{6c}$ are independently selected from the group consisting of hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound; and $R^{6d}$ is selected from the group consisting of hydrogen, optionally substituted lower alkyl, optionally substituted aryl, optionally substituted heterocycle, optionally substituted heteroaryl, acyl, sulfonyl, amido, thioamido, and sulfonamido;

provided, however, that when $R^6$ is thiophene-2-yl, then $R^{6a}$ is not hydrogen or halo.

In a further embodiment, $R^{6a}$ is selected from the group consisting of halo, optionally substituted lower alkyl, alkoxy, alkylthio, alkynyl, amino, amido, carboxyl, hydroxy, aryl, substituted aryl, aryloxy, optionally substituted heterocycle, optionally substituted heteroaryl, nitro, cyano, thiol, sulfonamide.

In a further embodiment $R^6$ is selected from the group consisting of

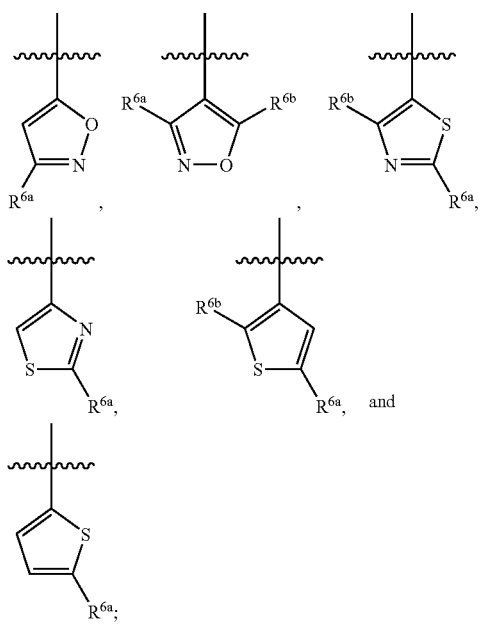

and $R^{6a}$ and $R^{6b}$ are independently selected from the group consisting of hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound;

provided, however, that when $R^6$ is thiophene-2-yl, then $R^{6a}$ is not hydrogen or halo.

In certain embodiments compounds of Formula I have the structure

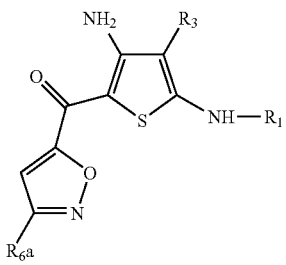

wherein:

$R^1$ is selected from the group consisting of hydrogen, acyl, optionally substituted lower alkyl, optionally substituted lower alkenyl, optionally substituted lower alkynyl, optionally substituted cycloalkyl, optionally substituted heterocycle, optionally substituted heterocycloalkyl, optionally substituted aryl, optionally substituted aralkyl, optionally substituted heteroaryl and optionally substituted heteroaralkyl;

$R^3$ is selected from the group consisting of cyano, nitro, —C(Z)R$^8$, —S(O$_2$)NR$^9$R$^{10}$, —S(O$_2$)R$^{11}$, and optionally substituted lower alkyl; and $R^{6a}$ is selected from the group consisting of hydrogen, halo, hydroxy, alkoxy, alkylthio, alkylsulfinyl, alkylsulfonyl, acyloxy, optionally substituted aryl, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound.

In certain embodiments of any of the above compounds, $R^3$ is selected from the group consisting of cyano, C(O)NH2 and optionally substituted lower alkyl.

In certain embodiments of any of the above compounds, at least one of $R^1$ and $R^2$ is selected from the group consisting of optionally substituted cycloalkyl, optionally substituted heterocycle, and optionally substituted heterocycloalkyl. Where in further embodiments, optionally substituted heterocycle is optionally substituted cycloheteroalkyl. Embodiments of the above formulas include all salt, prodrugs, and isomers thereof.

Likewise, compounds of Formula II have the following structure:

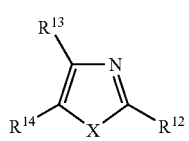

Formula II where

X=S, O, NR$^{15}$;

$R^{12}$ is hydrogen, OR$^{16}$, SR$^{16}$, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl or optionally substituted heteroaralkyl;

$R^{13}$ is $OR^{16}$, $SR^{16}$, or optionally substituted amine;

$R^{14}$ is $OR^{16}$, $SR^{16}$, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, $C(Z)R^{19}$, $C(Z)NR^{20}R^{21}$, $S(O_2)NR^{20}R^{21}$, or $S(O_2)R^{22}$;

$R^{15}$ is hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, $C(Z)R^{19}$, $C(Z)NR^{20}R^{21}$, $S(O_2)NR^{20}R^{21}$, or $S(O_2)R^{22}$;

$R^{16}$ is optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, or $C(Z)R^{19}$;

$R^{19}$ is hydroxy, alkoxy, thioalkoxy, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl;

$R^{20}$ and $R^{21}$ are independently hydrogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, or they may combine to form a 5-7 membered carbocyclic or heterocyclic ring;

$R^{22}$ is hydroxy, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, or optionally substituted heteroaralkyl;

Z is O or S.

In particular embodiments of compounds of Formula II, X is S, $R^{12}$ is secondary amine, preferably with an optionally substituted aryl or heteroaryl group, $R^{13}$ is $—NH_2$, $R^{14}$ is $—C(O)$-aryl or $C(O)$-heteroaryl, where the aryl or heteroaryl group is optionally substituted. In further embodiments, the aryl or heteroaryl group in $R^{12}$ is mono or di-substituted, e.g., with halo (e.g., fluoro or chloro) or halo substituted lower alkyl, where a substitution is preferably at the para position for a 6-membered ring. In further embodiments, the aryl or heteroaryl is mono or di-substituted, preferably with halo or halo substituted lower alkyl, preferably including a substitution at the para position for a 6-membered ring.

In further embodiments of Formula II, $R^{14}$ is $C(O)R^{19}$;

$R^{19}$ is optionally substituted cycloalkyl; and $R^{12}$ is selected from the group consisting of optionally substituted arylamine, optionally substituted heteroarylamine, and optionally substituted cycloalkyl, provided, however, that where when $R^{12}$ is phenylamine, $R^{19}$ is not cyclopropyl.

In further embodiments of compounds of Formula II $R^{14}$ is $C(O)R^{19}$;

$R^{19}$ is optionally substituted aryl, optionally substituted heteroaryl, or optionally substituted cycloalkyl; and $R^{12}$ is optionally substituted cycloalkylamine
wherein when $R^{12}$ is cyclohexylamine, then $R^{19}$ is not optionally substituted phenyl.

In certain embodiments, compounds of Formula II have the structure

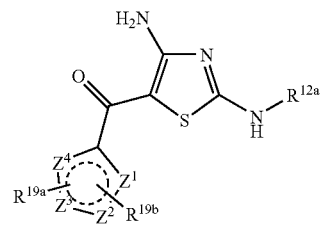

wherein:

$Z^1$, $Z^2$, $Z^3$, and $Z^4$ are independently selected from the group consisting of —O—, —S—, —$CR^{19a}$—, —$CR^{19b}$—, —$CR^{19c}$—, and —$NR^{19d}$—, wherein:

at least one of $Z^1$, $Z^2$, $Z^3$, and $Z^4$ is a heteroatom where $Z^1$, $Z^2$, $Z^3$, and $Z^4$ are selected to produce a stable compound;

$R^{12a}$ is selected from the group consisting of hydrogen, optionally substituted lower alkyl, optionally substituted cycloalkyl, optionally substituted aryl provided, however, that sulfonamide may not substitute aryl, optionally substituted heteroaryl, acyl, and sulfonyl; and $R^{19a}$, $R^{19b}$ and $R^{19c}$ are independently selected from the group consisting of hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound;

wherein at least one of $R^{19a}$, $R^{19b}$ and $R^{19c}$ is optionally substituted aryl, optionally substituted heteroaryl, or carboxyl; or $R^{19a}$, $R^{19b}$ and $R^{19c}$ can, in combination with the five-membered ring comprising $Z^1$, $Z^2$, $Z^3$, and $Z^4$, combine to form an optionally substituted fused heterocyclic ring system; and $R^{19d}$ is optionally present, and when present is selected from the group consisting of hydrogen, optionally substituted lower alkyl, optionally substituted aryl, optionally substituted heterocycle, optionally substituted heteroaryl, acyl, sulfonyl, amido, thioamido, and sulfonamido.

In a further embodiment, $R^{12a}$ is selected from the group consisting of optionally substituted cycloalkyl, optionally substituted aryl, and optionally substituted heteroaryl, wherein aryl may not be substituted with acyl, amine, and sulfonylamido.

In certain embodiments, compounds of Formula II have the structure

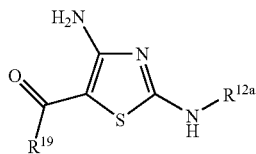

wherein:

$R^{19}$ is selected from the group consisting of

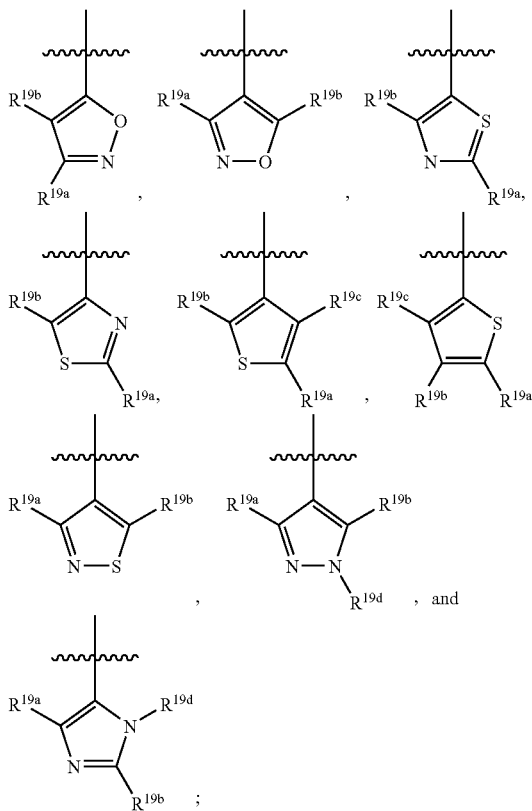

$R^{19a}$, $R^{19b}$, and $R^{19c}$ are independently hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound; and $R^{19d}$ is optionally present, and when present is hydrogen, optionally substituted lower alkyl, optionally substituted aryl, optionally substituted heterocycle, optionally substituted heteroaryl, acyl, sulfonyl, amido, thioamido, and sulfonamido.

In a further embodiment $R^{19}$ is selected from the group consisting of

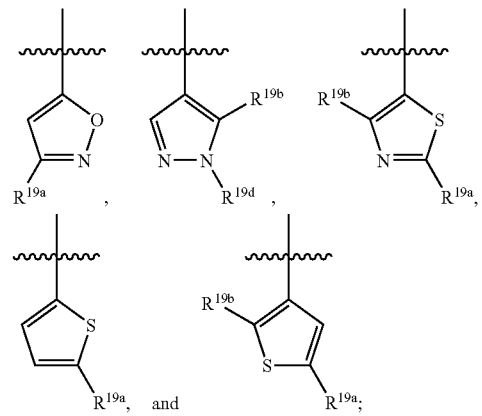

$R^{19a}$ is independently hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound;

$R^{19b}$ is selected from the group consisting of hydrogen and lower alkyl; and $R^{19d}$ is optionally present, and when present is hydrogen, optionally substituted lower alkyl, optionally substituted aryl, optionally substituted heterocycle, optionally substituted heteroaryl, acyl, sulfonyl, amido, thioamido, and sulfonamido.

In further embodiments of the above structures, $R^{19a}$ is selected from halo, optionally substituted lower alkyl, alkoxy, alkylthio, alkynyl, amino, amido, carboxyl, hydroxy, optionally substituted aryl, aryloxy, optionally substituted heterocycle, optionally substituted heteroaryl, nitro, cyano, thiol, and sulfonamido, attached at any available point to produce a stable compound.

In certain embodiments compounds of Formula II have the structure

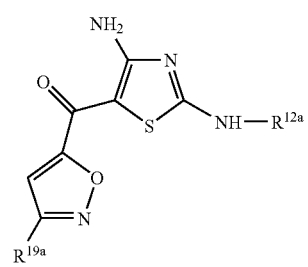

wherein
  $R^{12a}$ is selected from the group consisting of hydrogen, optionally substituted lower alkyl, optionally substituted cycloalkyl, optionally substituted aryl, optionally substituted heteroaryl, acyl, and sulfonyl; and
  $R^{19a}$ is selected from the group consisting of hydrogen, halo, hydroxy, alkoxy, alkylthio, alkylsulfinyl, alkylsulfonyl, acyloxy, optionally substituted aryl, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound;

In certain embodiments, compounds of Formula II have the structure

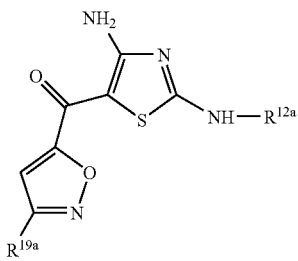

wherein
  $R^{12a}$ is selected from the group consisting of hydrogen, optionally substituted lower alkyl, optionally substituted cycloalkyl, optionally substituted aryl, optionally substituted heteroaryl, acyl, and sulfonyl; and
  $R^{19a}$ is selected from the group consisting of alkoxy, amino, carboxyl, optionally substituted aryl, and optionally substituted heteroaryl.

In certain embodiments, compounds of Formula II have the structure

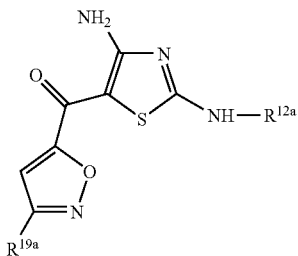

wherein
  $R^{12a}$ is selected from the group consisting optionally substituted lower alkyl, optionally substituted cycloalkyl, and optionally substituted aryl; and
  $R^{19a}$ is selected from the group consisting of alkoxy, amino, carboxyl, optionally substituted aryl, and optionally substituted heteroaryl.

In certain embodiments, compounds of Formula II have the structure

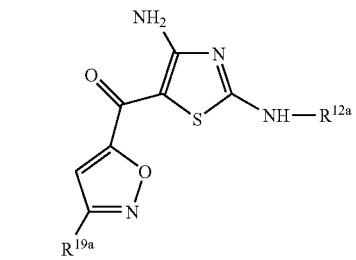

wherein
  $R^{12a}$ is selected from the group consisting of lower alkyl, cycloalkyl, and optionally substituted aryl; and
  $R^{19a}$ is selected from the group consisting of alkoxy, amino, carboxyl, optionally substituted aryl, and optionally substituted heteroaryl.

In certain embodiments, compounds of Formula II have the structure

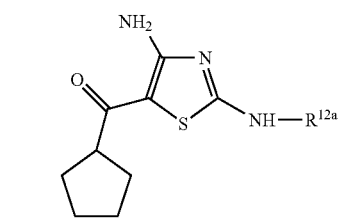

wherein
  $R^{12a}$ is selected from the group consisting of hydrogen, optionally substituted lower alkyl, optionally substituted cycloalkyl, optionally substituted aryl provided, however, that sulfonamide may not substitute aryl, optionally substituted heteroaryl, acyl, and sulfonyl.

In a further embodiment, $R^{12a}$ is optionally substituted aryl.

In a further embodiment, $R^{12a}$ is optionally substituted phenyl.

Embodiments of the above formulas include all salt, prodrugs, and isomers thereof.

Compounds of Formula III have the following structure:

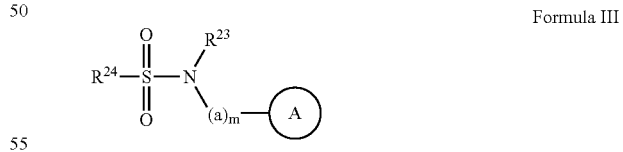

Formula III wherein
  A is a carbocyclic or heterocyclic structure having 3-14 ring atoms, which may be aryl or heteroaryl, joined to N by a bond or a set of linked atoms, a, where m is 0-3;
  $R^{23}$ is hydrogen, optionally substituted lower alkyl, optionally substituted cycloalkyl, optionally substituted heteroalkyl, optionally substituted heterocycloalkyl, optionally substituted aryl, optionally substituted aralkyl, optionally substituted heteroaryl, and optionally substituted heteroaralkyl, or it can combine with A and/or $(a)_m$ to form a 5-7 membered optionally substituted carbocyclic or heterocyclic ring systems, or an optionally substituted aryl or heteroaryl group;

$R^{24}$ is optionally substituted lower alkyl, optionally substituted cycloalkyl, optionally substituted heteroalkyl, optionally substituted heterocycloalkyl, optionally substituted aryl, optionally substituted aralkyl, optionally substituted heteroaryl, and optionally substituted heteroaralkyl.

In certain embodiments, a substitution on $R^{24}$ is optionally substituted lower alkyl, optionally substituted lower alkenyl, optionally substituted lower alkynyl, optionally substituted cycloalkyl, optionally substituted heteroalkyl, optionally substituted heterocycloalkyl, optionally substituted aryl, optionally substituted aralkyl, optionally substituted heteroaryl, and optionally substituted heteroaralkyl, with the option that it can be attached to $R^{24}$ through a carbon or oxygen or sulfur or optionally substituted nitrogen.

In certain embodiments of compounds of Formula III, $R^{24}$ is an optionally substituted thiophene ring; $R^{24}$ is an optionally substituted phenyl ring; $R^{24}$ is an optionally substituted carbocyclic ring; $R^{24}$ is an optionally substituted heterocyclic ring; $R^{24}$ is an optionally substituted aryl group; $R^{24}$ is an optionally substituted heteroaryl group; $R^{24}$ is a thiophene ring substituted with a 5- or 6-membered carbocyclic ring (which itself may be substituted); $R^{24}$ is a thiophene ring substituted with a 5- or 6-membered heterocyclic ring (which itself may be substituted); $R^{24}$ is a thiophene ring substituted with an optionally substituted pyrimidine ring; $R^{24}$ is a phenyl group substituted with an alkyl ester group; $R^{24}$ is a phenyl group substituted with an alkoxy group.

In certain embodiments, for each of the selections of $R^{24}$ described above, A is an optionally substituted carbocyclic group; alternatively, A is an optionally substituted heterocyclic group; alternatively, A is an optionally substituted aryl group; alternatively, A is an optionally substituted heteroaryl group; alternatively, A is an optionally substituted indole group; alternatively, A is an optionally substituted phenyl group; or alternatively, A is an optionally substituted quinoline group.

In certain embodiments, for each of the selections of A described above, $R^{23}$ is H; $R^{23}$ is alkyl; $R^{23}$ is methyl; $R^{23}$ is ethyl; $R^{23}$ is propyl; $R^{23}$ is an optionally substituted carbocyclic group; $R^{23}$ is an optionally substituted heterocyclic group; or, $R^{23}$ is an optionally substituted phenyl group.

In some embodiments, $(a)_m$ includes an S; $(a)_m$ includes an O; $(a)_m$ includes an N; $(a)_m$ is a carbon chain; $(a)_m$ is an alkylene chain; $(a)_m$ is a chain —S-alkylene-; or $(a)_m$ is a chain —O-alkylene-.

For $(a)_m$ and $(b)_m$, the number of linked atoms is the minimum number of atoms linking the maximal identifiable moiety A with N, or the maximal identifiable moiety B with S as shown in Formula IIIa, respectively.

In certain embodiments, a compound of Formula III, $R^{24}$ is not —Ar-substituted isopropyl and —$(a)_m$-A is not aryl or arylalkyl. In certain embodiments, —$(a)_m$-A is not Ar-substituted isopropyl. In certain embodiments, a compound of Formula III is not a compound as described in Li et al., PCT/US00/06611, WO 00/54759, which is incorporated herein by reference.

In certain embodiments of compounds of Formula III, the compounds have the structure of Formula IIIa:

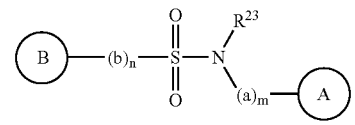

Formula IIIa where
m=0-3 atoms;
n=0-3 atoms;
A=cyclic group; and
B=cyclic group.

In certain embodiments, compounds of Formula III have the structure

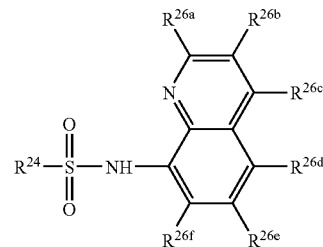

wherein:
$R^{26a}$, $R^{26b}$, $R^{26c}$, $R^{26d}$, $R^{26e}$, and $R^{26f}$ are independently selected from the group consisting of hydrogen, halo, lower alkyl, and alkoxy. And $R^{24}$ is as defined above.

In a further embodiment $R^{24}$ is selected from the group consisting of aryl optionally substituted with optionally substituted heterocycloalkyl, optionally substituted arylamino, optionally substituted heteroarylamino, optionally substituted arylsulfonyl, and —RNHC(O)R', wherein:
R is alkylene, and
R' is optionally substituted alkyl, optionally substituted aryl, or optionally substituted heteroaryl; or
$R^{24}$ is optionally substituted heteroaryl,
provided, however, that $R^{24}$ is not tetrazole or a triazolopyrimidine ring.

In certain embodiments, compounds of Formula III have the structure

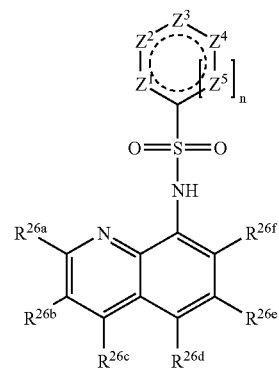

wherein:

n is 0 or 1; and $Z^1$, $Z^2$, $Z^3$, $Z^4$, and $Z^5$ are independently selected from the group consisting of —O—, —S—, —$CR^{24a}$—, —$CR^{24b}$—, —$CR^{24c}$, —$CR^{24d}$—, and —$NR^{24e}$—, wherein:

$Z^1$, $Z^2$, $Z^3$, $Z^4$, and $Z^5$ are selected to form a stable compound;

$R^{24a}$, $R^{24b}$, $R^{24c}$, and $R^{24d}$ are independently selected from the group consisting of hydrogen, halo, hydroxy, alkoxy, alkylthio, alkylsulfinyl, alkylsulfonyl, acyloxy, optionally substituted aryl, , amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound; and $R^{24e}$ is optionally present, and when present is hydrogen, optionally substituted lower alkyl, optionally substituted aryl, optionally substituted heterocycle, optionally substituted heteroaryl, acyl, sulfonyl, amido, thioamido, or sulfonamido.

In a further embodiment, the ring comprising Z1-Z4 is phenyl, thiophenyl, or furanyl. Embodiments of the above formulas include all salt, prodrugs, and isomers thereof.

In connection with the compounds of Formulas I, II, and III the following definitions apply.

"Halo" and "halogen" refer to all halogens, that is, chloro (Cl), fluoro (F), bromo (Br), or iodo (I).

"Hydroxyl" and "hydroxy" refer to the group —OH.

"Thiol" and "mercapto" refer to the group —SH.

"Alkyl" refers to an alkane-derived radical containing from 1 to 20, preferably 1 to 15, carbon atoms. Alkyl includes straight chain alkyl, branched alkyl and cycloalkyl. Straight chain or branched alkyl groups contain from 1-15, preferably 1 to 8, more preferably 1-6, yet more preferably 1-4 and most preferably 1-2, carbon atoms, such as methyl, ethyl, propyl, isopropyl, butyl, t-butyl, and the like. Alkyl also includes straight chain or branched alkyl groups that contain or are interrupted by one or more cycloalkyl portions. Examples of this include, but are not limited to, 4-(isopropyl)-cyclohexylethyl or 2-methyl-cyclopropylpentyl. The alkyl group is attached at any available point to produce a stable compound.

A "substituted alkyl" is an alkyl group independently substituted with 1 or more, e.g., 1, 2, or 3, groups or substituents such as halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, oxo, or the like attached at any available point to produce a stable compound.

"Lower alkyl" refers to an alkyl group having 1-6 carbon atoms.

A "substituted lower alkyl" is a lower alkyl which is substituted with 1 or more, e.g., 1, 2, or 3, groups or substituents as defined in [0079] attached at any available point to produce a stable compound.

"Cycloalkyl" refers to a monocyclic, bicyclic or tricyclic ring system of 3-8, more preferably 3-6, ring members per ring, such as cyclopropyl, cyclopentyl, cyclohexyl, adamantyl, and the like.

A "substituted cycloalkyl" is a cycloalkyl which is independently substituted with 1 or more, e.g., 1, 2, or 3, groups or substitutents as defined in [0079], optionally substituted alkyl, optionally substituted alkenyl, or optionally substituted alkynyl, attached at any available point to produce a stable compound.

"Alkylene" refers to a divalent alkane-derived radical containing 1-20, preferably 1-15, carbon atoms, from which two hydrogen atoms are taken from the same carbon atom or from different carbon atoms. Examples of alkylene include, but are not limited to, methylene —$CH_2$—, ethylene —$CH_2CH_2$—, and the like.

A "substituted alkylene" is an alkylene which is independently substituted with 1 or more, e.g., 1, 2, or 3, groups or substitutents as defined in [0079] attached at any available point to produce a stable compound.

A "lower alkylene" is an alkylene containing 1-6 carbon atoms.

A "substituted lower alkylene" is a lower alkylene which is independently substituted with 1 or more, e.g., 1, 2, or 3, groups or substitutents as defined in [0079] attached at any available point to produce a stable compound.

"Alkenyl" refers to a straight chain, branched, or cyclic hydrocarbon containing 2-20, preferably 2-17, more preferably 2-10, even more preferably 2-8, most preferably 2-4, carbon atoms, and which contains at least one, preferably 1-3, more preferably 1-2, and most preferably one, carbon to carbon double bond. In the case of a cycloalkyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include, but are not limited to, ethenyl, propenyl, isopropenyl, butenyl, cyclohexenyl, cyclohexenylalkyl, and the like.

A "substituted alkenyl" is an alkenyl which is independently substituted with 1 to more, e.g., 1, 2, or 3, groups or substituents as defined in [0079], attached at any available point to produce a stable compound.

"Alkynyl" refers to a straight chain or branched hydrocarbon containing 2-20, preferably 2-17, more preferably 2-10, even more preferably 2-8, most preferably 2-4, carbon atoms, and which contains at least one, preferably one, carbon to carbon triple bond. Examples of alkynyl groups include, but are not limited to, ethynyl, propynyl, butynyl, and the like.

A "substituted alkynyl" is an alkynyl which is independently substituted with 1 to more, e.g., 1, 2, or 3, groups or substituents as defined in [0079], attached at any available point to produce a stable compound.

"Alkyl alkenyl" refers to the group —$R^a$—$CR^b$=$CR^cR^d$, wherein $R^a$ is lower alkylene, or substituted lower alkylene, $R^b$, $R^c$, and $R^d$ are independently hydrogen, halogen, lower alkyl, substituted lower alkyl, acyl, aryl, substituted aryl, hetaryl, or substituted hetaryl.

"Alkyl alkynyl" refers to the group —$R^aC$≡$CR^e$ where $R^a$ is lower alkyllene or substituted lower alkylene, and $R^e$ is hydrogen, lower alkyl, substituted lower alkyl, acyl, aryl, substituted aryl, hetaryl, or substituted hetaryl.

"Alkoxy" denotes the group —OR$^f$, where R$^f$ is lower alkyl, substituted lower alkyl, acyl, aryl, substituted aryl, aralkyl, substituted aralkyl, heteroalkyl, substituted heteroalkyl, heteroarylalkyl, substituted heteroarylalkyl, heteroaryl, substituted heteroaryl, cycloalkyl, substituted cycloalkyl, cycloheteroalkyl, or substituted cycloheteroalkyl.

"Alkylthio" or "thioalkoxy" refers to the group —S—R, where R is lower alkyl, substituted lower alkyl, acyl, aryl, substituted aryl, aralkyl, substituted aralkyl, heteroalkyl, substituted heteroalkyl, heteroarylalkyl, substituted heteroarylalkyl, heteroaryl, substituted heteroaryl, cycloalkyl, substituted cycloalkyl, cycloheteroalkyl, or substituted cycloheteroalkyl.

"Sulfinyl" denotes the group —S(O)—.

"Sulfonyl" denotes the group —S(O)$_2$—.

"Alkylsulfinyl" denotes the group —S(O)—R$^y$, where R$^y$ is optionally substituted lower alkyl, optionally substituted aryl, or optionally substituted aralkyl.

"Alkylsulfonyl" denotes the group —S(O)$_2$-R$^y$, where R$^y$ is optionally substituted lower alkyl, optionally substituted aryl, or optionally substituted aralkyl.

"Aminosulfonyl" denotes the group —S(O)$_2$—NHR$^u$, where R$^u$ is a bond, hydrogen or optionally substituted lower alkyl.

"Alkylaminosulfonyl" denotes the group —S(O)$_2$—NR$^v$R$^w$, where R$^v$ is hydrogen or optionally substituted lower alkyl, and R$^w$ is optionally substituted lower alkyl.

"Arylaminosulfonyl" denotes the group group —S(O)$_2$—NR$^v$R$^x$, where R$^v$ is hydrogen or optionally substituted lower alkyl, and R$^x$ is optionally substituted aryl, or optionally substituted aralkyl.

"Heteroarylaminosulfonyl" denotes the group group —S(O)$_2$—NR$^v$R$^z$, where R$^v$ is hydrogen or optionally substituted lower alkyl, and R$^z$ is optionally substituted heteroaryl, or optionally substituted heteroaralkyl.

"Acyl" denotes the group —C(O)R$^h$, where R$^h$ is hydrogen, lower alkyl, substituted lower alkyl, aryl, substituted aryl, heteroaryl, substituted heteroaryl, and the like.

"Acyloxy" denotes the group —OC(O)R$^h$, where R$^h$ is hydrogen, lower alkyl, substituted lower alkyl, aryl, substituted aryl, heteroaryl, substituted heteroaryl, and the like.

"Aryloxy" denotes the group —OAr, where Ar is an aryl, substituted aryl, heteroaryl, or substituted heteroaryl group.

"Heteroaryloxy" denotes groups —OHet, wherein Het is an optionally substituted heteroaryl group.

"Amino" or "substituted amine" denotes the group —NR$^i$R$^j$, wherein R$^i$ and R$^j$ are independently hydrogen, lower alkyl, substituted lower alkyl, aryl, substituted aryl, hetaryl, substituted heteroaryl, acyl or sulfonyl. Further, N, R$^i$ and R$^j$ may combine to form an optionally substituted heterocycle.

"Amido" denotes the group —C(O)NR$^k$R$^l$, wherein R$^k$ and R$^l$ are independently hydrogen, lower alkyl, substituted lower alkyl, cycloalkyl, substituted cycloalkyl, aryl, substituted aryl, hetaryl, or substituted heteroaryl. Further, N, R$^k$ and R$^l$ may combine to form an optionally substituted heterocycle.

"Thioamido" denotes the group —C(S)NR$^k$R$^l$, wherein R$^k$ and R$^l$ are independently hydrogen, lower alkyl, substituted lower alkyl, cycloalkyl, substituted cycloalkyl, aryl, substituted aryl, hetaryl, or substituted heteroaryl.

"Sulfonamido" and "sulfonamide" and "sulfamido" denote the group —S(O)$_2$NR$^k$R$^l$, wherein R$^k$ and R$^l$ are independently hydrogen, lower alkyl, substituted lower alkyl, cycloalkyl, substituted cycloalkyl, aryl, substituted aryl, hetaryl, or substituted heteroaryl.

"Amidino" denotes the group —C(=NR$^m$)NR$^n$R$^o$, wherein R$^m$, R$^n$, and R$^o$ are independently hydrogen or optionally substituted lower alkyl.

"Sulfonylamino" denotes the group —NR$^q$S(O)$_2$—, wherein R$^q$ is hydrogen or optionally substituted lower alkyl.

"Alkylsulfonylamino" denotes the group —NR$^q$S(O)$_2$R$^p$, wherein R$^p$ is optionally substituted alkyl, and R$^q$ is hydrogen or lower alkyl.

"Arylsulfonylamino" denotes the group —NR$^q$S(O)$_2$R$^s$, wherein R$^s$ is optionally substituted aryl, and R$^q$ is hydrogen or lower alkyl.

"Heteroarylsulfonylamino" denotes the group —NR$^q$S(O)$_2$R$^t$, wherein R$^t$ is optionally substituted heteroaryl, and R$^q$ is hydrogen or lower alkyl.

"Alkylcarbonylamino" denotes the group —NR$^q$C(O)$_2$R$^p$, wherein R$^p$ is optionally substituted alkyl, and R$^q$ is hydrogen or lower alkyl.

"Arylcarbonylamino" denotes the group —NR$^q$C(O)$_2$R$^s$, wherein R$^s$ is optionally substituted aryl, and R$^q$ is hydrogen or lower alkyl.

"Heteroarylcarbonylamino" denotes the group —NR$^q$C(O)$_2$R$^t$, wherein R$^t$ is optionally substituted aryl, and R$^q$ is hydrogen or lower alkyl.

"Carboxyl" denotes the group —C(O)OR$^r$, wherein R$^r$ is hydrogen, lower alkyl, substituted lower alkyl, aryl, substituted aryl, hetaryl, or substituted hetaryl.

"Aryl" means phenyl or naphthyl optionally fused with a cycloalkyl of preferably 5-7, more preferably 5-6, ring members.

A "substituted aryl" is an aryl which is independently substituted with 1 or more, e.g., 1, 2, or 3, groups or substituents as defined in [0079], optionally substituted alkyl, optionally substituted alkenyl, optionally substituted alkynyl, optionally substituted heterocycle, or optionally substituted heteroaryl, attached at any available point to produce a stable compound.

"Carbocycle" means a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

"Heterocycle" means a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having 1 or more, e.g., 1, heteroatom such as N, O or S, within the ring or within one of more of the multiple condensed rings.

A "substituted heterocycle" is a heterocycle substituted with 1 or more, e.g., 1, 2, or 3, substituents as defined in [0079], optionally substituted alkyl, optionally substituted alkenyl, or optionally substituted alkynyl, attached at any available point to produce a stable compound.

"Oxo" refers to an oxygen substituent double bonded to the attached carbon.

"Heteroaryl" and "hetaryl" refer to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like.

"Substituted heteroaryl" and "substituted hetaryl" refer to a heteroaryl which is independently substituted with 1 or more, e.g., 1, 2, or 3, groups or substituents as defined in [0079], optionally substituted alkyl, optionally substituted alkenyl, or optionally substituted alkynyl, attached at any available point to produce a stable compound.

"Heterocyclyl" means a non-aromatic cycloalkyl group having from 5 to 10 atoms in which from 1 to 3 carbon atoms in the ring are replaced by heteroatoms, such as O, S or N, and are optionally benzo fused or fused heteroaryl of 5-6 ring members and/or are optionally substituted as in the case of cycloalkyl. Heterocycyl is also intended to include oxidized S or N, such as sulfinyl, sulfonyl and N-oxide of a tertiary ring nitrogen. The point of attachment is at a carbon or nitrogen atom. Examples of heterocyclyl groups are tetrahydrofuranyl, dihydropyridinyl, piperidinyl, pyrrolidinyl, piperazinyl, dihydrobenzofuryl, dihydroindolyl, and the like.

A "substituted hetercyclyl" is a heterocyclyl which is independently substituted with 1 or more, e.g., 1, 2, or 3, groups or substituents as defined in [0079], optionally substituted alkyl, optionally substituted alkenyl, or optionally substituted alkynyl, attached at any available point to produce a stable compound.

"Aralkyl" refers to the group —R—Ar where Ar is an aryl group and R is lower alkylene or substituted lower alkylene group. The aryl functionality of aralkyl can optionally be unsubstituted or substituted with, e.g., halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

"Heteroalkyl" and "heterocycloalkyl" refer to the group —R-Het where Het is a heterocycle group and R is a lower alkylene or substituted lower alkylene group. Heteroalkyl groups can optionally be unsubstituted or substituted with e.g., halogen, lower alkyl, alkoxy, alkylthio, acetylene, amino, amido, carboxyl, aryl, aryloxy, heterocycle, substituted heterocycle, hetaryl, substituted hetaryl, nitro, cyano, thiol, sulfamido, and the like.

"Heteroarylalkyl" and "heteroaralkyl" refer to the group —R-HetAr where HetAr is an heteroaryl group and R lower alkylene or substituted lower alkylene. Heteroarylalkyl and heteroaralkyl groups can optionally be unsubstituted or substituted with, e.g., halogen, lower alkyl, substituted lower alkyl, alkoxy, alkylthio, acetylene, aryl, aryloxy, heterocycle, substituted heterocycle, hetaryl, substituted hetaryl, nitro, cyano, thiol, sulfamido, and the like.

"Cycloheteroalkyl" refers to a cycloalkyl group wherein one or more of the ring carbon atoms is replaced with a heteroatom (e.g., N, O, S or P).

A "substituted cycloheteroalkyl" is a cycloheteroalkyl group which is independently substituted with 1 or more, e.g., 1, 2, or 3, groups or substituents as defined in [0079] or optionally substituted alkyl, attached at any available point to produce a stable compound.

"Alkyl cycloalkyl" means the group —R-cycloalk where cycloalk is a cycloalkyl group, and R is a lower alkylene or substituted lower alkylene. Cycloalkyl functionalities of alkyl cycloalkyl groups can optionally be unsubstituted or substituted with e.g. halogen, lower alkyl, alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

"Alkyl cycloheteroalkyl" means the group —R-cycloheteroalk where cycloheteroalk is a cycloheteroalkyl group, and R is a lower alkylene or substituted lower alkylene. Cycloheteroalkyl functionalities of alkyl cycloheteroalkyl groups can optionally be unsubstituted or substituted with e.g. halogen, lower alkyl, alkoxy, alkylthio, amino, amido, carboxyl, acetylene, hydroxyl, aryl, aryloxy, heterocycle, substituted heterocycle, heteroaryl, substituted heteroaryl, nitro, cyano, thiol, sulfamido, and the like.

Thus, in a first aspect, the invention relates to novel compounds of Formula I or II or Formula III as described herein. Unless otherwise specified, a reference to a particular compound includes all isomeric forms, including racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein in a known manner. Note that, as discussed below in the context of isomers, where unsaturation permits isomers, e.g., cis- and trans, E- and Z-, etc., and combinations thereof, a reference to one isomer is to be considered a reference to all such isomers, unless otherwise specified. Unless otherwise specified, a reference to a particular compound also includes ionic, salt, solvate (e.g., hydrate), protected forms, and prodrugs thereof, for example, as discussed below.

An additional aspect of this invention relates to pharmaceutical formulations, that include a therapeutically effective amount of a compound of Formula I or II or III (or a compound within a sub-group of compounds within any of those generic formulas) and at least one pharmaceutically acceptable carrier or excipient.

In particular embodiments, the composition includes a plurality of different pharmacalogically active compounds, which can be a plurality of compounds of Formula I and/or II and/or III, and can also include other compounds in combination with one or more compounds of Formula I and/or II and/or III.

A related aspect of this invention relates to pharmaceutical compositions that include a compound of Formula I or Formula II or Formula III and at least one pharmaceutically acceptable carrier, excipient, or diluent. The composition can include a plurality of different pharmacalogically active compounds.

In another related aspect, compounds of Formula I or Formula II or Formula III can be used in the preparation of a medicament for the treatment of a PDE4B-mediated disease or condition.

In another aspect, the invention relates to a method of treating or prophylaxis of a disease or condition in a mammal, by administering to the mammal a therapeutically effective amount of a compound of Formula I or Formula II or Formula III, a prodrug of such compound, or a pharmaceutically acceptable salt of such compound or prodrug. The compound can be administered alone or can be administered as part of a composition. The term "prodrug," as used herein, refers to a compound which, when metabolised, yields the desired active compound. Typically, the prodrug is inactive, or less active than the active compound, but may provide advantageous handling, administration, or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

Thus, in a further aspect, the invention relates to methods for treating a PDEB4-mediated disease or condition in an animal patient, e.g., a mammal such as a human, e.g., a disease or condition characterized by abnormal PDE4B activity. The method involves administering an effective amount of a compound of Formula I or Formula II or Formula III, or a composition comprising a compound of Formula I or Formula II or Formula III to a patient in need thereof. An "effective amount" of a compound or composition, as used herein, includes within its meaning a non-toxic but sufficient amount of the particular compound or composition to which it is referring to provide the desired therapeutic effect.

As used herein, the term PDE4B-mediated disease or condition refers to a disease or condition in which the biological function of PDE4B affects the development and/or course of the disease or condition, and/or in which modulation of PDE4B alters the development, course, and/or symptoms.

In aspects and embodiments involving treatment or prophylaxis of a disease or condition, the disease or condition is for example, without limitation, an acute or chronic pulmonary disease such as obstructive diseases (e.g. asthma, chronic obstructive pulmonary disease (COPD), cystic fibrosis), interstitial lung diseases (e.g. idiopathic pulmonary fibrosis, sarcoidosis), vascular lung diseases (e.g. pulmonary hypertension), bronchitis, allergic bronchitis, and emphysema. Additional diseases or conditions contemplated for treatment by embodiments of the present invention include for example, without limitation, CNS diseases such as Alzheimer's disease, Parkinson's disease and Huntington's chorea; inflammatory autoimmune diseases such as multiple sclerosis, rheumatoid arthritis and Crohn's disease as well as other inflammatory disorders, such as cerebral ischemia, inflammatory bowel disease, and ulcerative colitis; bone disease, such as osteoporosis, osteopetrosis, and Paget's disease; cancers, such as diffuse large-cell B cell lymphoma, chronic lymphocytic leukemia, acute lymphoblastic leukemia; Severe Acute Respiratory Syndrome; and pre-term labor.

The identification of compounds of Formula I, Formula II, and Formula III active on PDE4B also provides a method for identifying or developing additional compounds active on PDE4B, e.g., improved modulators, by determining whether any of a plurality of test compounds of Formula I or Formula II or Formula III active on PDE4B provides an improvement in one or more desired pharmacologic properties relative to a reference compound active on PDE4B, and selecting a compound if any, that has an improvement in the desired pharmacologic property, thereby providing an improved modulator.

In particular aspects of modulator development, the desired pharmacologic property is serum half-life longer than 2 hr or longer than 4 hr or longer than 8 hr, aqeous solubility, oral bioavailability more than 10%, oral bioavailability more than 20%.

Also in particular aspects of modulator development, the reference compound is a compound of Formula I or Formula II or Formula III. The process can be repeated multiple times, i.e., multiple rounds of preparation of derivatives and/or selection of additional related compounds and evaluation of such further derivatives of related compounds, e.g., 1, 2, 3, 4, 5, 6, 7, 8, 9, 10 or more additional rounds.

In additional aspects, structural information about PDE4B is utilized for a variety of purposes, e.g., the design of modulators of PDE4B activity. Additionally, the present invention provides methods of using structural information about PDE4B in conjunction with compounds, such as Formula I or Formula II or Formula III or a molecular scaffold or scaffold core of Formula I or Formula II or Formula III, in the design of modulators of PDE4B activity. In addition, structural information about one or more other PDEs can be utilized, e.g., PDE5A, PDE4D, in the design of modulators of PDE4B activity.

The invention also provides a method for developing ligands which bind to a PDE4B. The method includes identifying as molecular scaffolds one or more compounds that bind to a binding site of the PDE; determining the orientation of at least one molecular scaffold in co-crystals with the PDE; identifying chemical structures of one or more of the molecular scaffolds, that, when modified, alter the binding affinity or binding specificity or both between the molecular scaffold and the PDE; and synthesizing a ligand in which one or more of the chemical structures of the molecular scaffold is modified to provide a ligand that binds to the PDE with altered binding affinity or binding specificity or both. Such a scaffold can, for example, be a compound of Formula I or Formula II or Formula III, or include the core of Formula I or Formula II or Formula III.

The terms "PDE4B phosphodiesterase" and "PDE4B" mean an enzymatically active phosphodiesterase that contains a portion with greater than 90% amino acid sequence identity to amino acid residues 152-528 (S152-S528) with reference to GenBank polypeptide sequence JC1519 of native PDE4B (SEQ ID NO:1), for a maximal alignment over an equal length segment; or that contains a portion with greater than 90% amino acid sequence identity to at least 200 contiguous amino acids from amino acid residues 152-528 of JC1519 of native PDE4B that retains binding to natural PDE4B ligand. Preferably the sequence identity is at least 95, 97, 98, 99, or even 100%. Preferably the specified level of sequence identity is over a sequence at least 300 contiguous amino acid residues in length. The sequence represented by amino acid residues 152-528 of JC1519 is also available as S324 to S700 of NP_002591 (encoded by NM_002600, SEQ ID NO:2), S309 to S685 of AAB96381 (SEQ ID NO:3), and S194 to S570 of AAA35643 (SEQ ID NO:4). Therefore, amino acid residues identified in one of the listed sequences can also be expressed as the matching amino acid residue in any other of the listed sequences or other matching sequence.

The term "PDE4B phosphodiesterase domain" refers to a reduced length PDE4B (i.e., shorter than a full-length PDE4B by at least 100 amino acids) that includes the phosphodiesterase catalytic region in PDE4B. Highly preferably for use in this invention, the phosphodiesterase domain retains phosphodiesterase activity, preferably at least 50% the level of phosphodiesterase activity as compared to the native PDE4B, more preferably at least 60, 70, 80, 90, or 100% of the native activity.

As used herein, the terms "ligand" and "modulator" are used equivalently to refer to a compound that up-regulates or down-regulates the activity of a target biomolecule, e.g., an enzyme such as a kinase or phosphodiesterase. Generally a ligand or modulator will be a small molecule, where "small molecule" refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined for a particular biological system or therapeutic use. In terms of the development of ligands from scaffolds, a ligand is a derivative of a scaffold.

As used herein, the term "modulating" or "modulate" refers to an effect of altering a biological activity, especially a biological activity associated with a particular biomolecule such as PDE4B. For example, an agonist or antagonist of a particular biomolecule modulates the activity of that biomolecule, e.g., an enzyme.

In the context of binding compounds, molecular scaffolds, and ligands, the term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound for another compound, having structural features maintained in the derivative compound. Often but not always, a parent compound has a simpler chemical structure than the derivative.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand. The term "target molecule" embraces proteins which bind ligands, e.g., phosphodiesterases, including PDE4B.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($k_d$) of 1 mM or less. A binding compound can bind with "low affinity", "very low affinity", "extremely low affinity", "moderate affinity", "moderately high affinity", or "high affinity" as described herein.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of PDE4B, other phosphodiesterases (e.g., PDE4D) or even other type of enzymes. In particular embodiments, the greater specificity is at least 2, 3, 4, 5, 8, 10, 50, 100, 200, 400, 500, or 1000-fold greater specificity.

As used in connection with binding of a compound with a target, the term "interact" indicates that the distance from a bound compound to a particular amino acid residue will be 5.0 angstroms or less. In particular embodiments, the distance from the compound to the particular amino acid residue is 4.5 angstroms or less, 4.0 angstroms or less, or 3.5 angstroms or less. Such distances can be determined, for example, using co-crystallography, or estimated using computer fitting of a compound in an active site.

Reference to particular amino acid residues in PDE4B by polypeptide residue number is defined by the numbering corresponding to NCBI protein sequence accession number JC1519, as described, for example, in McLaughlin et al., *J. Biol. Chem.* 268 (9), 6470-6476 (1993); Obernolte et al., *Gene* 129 (2), 239-247 (1993); and Bolger et al., *Mol. Cell. Biol.* 13 (10), 6558-6571 (1993). As indicated above, alternate numbering from other matching PDE4B sequences can also be used.

In a related aspect, the invention provides a method for developing ligands specific for PDE4B, where the method involves determining whether a derivative of a compound that binds to a plurality of phosphodiesterases has greater specificity for the particular phosphodiesterase than the parent compound with respect to other phosphodiesterases.

As used herein in connection with binding compounds or ligands, the term "specific for PDE4B phosphodiesterase", "specific for PDE4B" and terms of like import mean that a particular compound binds to PDE4B to a statistically greater extent than to other phosphodiesterases that may be present in a particular organism. Also, where biological activity other than binding is indicated, the term "specific for PDE4B" indicates that a particular compound has greater biological activity associated with binding PDE4B than to other phosphodiesterases. Preferably, the specificity is also with respect to other biomolecules (not limited to phosphodiesterases) that may be present from an organism.

In another aspect, the invention provides a method for obtaining improved ligands which bind PDE4B. The method contemplates identifying a compound that binds to that particular PDE, determining whether that compound interacts with one or more conserved active site residues, and determining whether a derivative of that compound binds to that PDE with greater affinity or greater specificity or both than the parent binding compound. Binding with greater affinity or greater specificity or both than the parent compound indicates that the derivative is an improved ligand. This process can also be carried out in successive rounds of selection and derivatization and/or with multiple parent compounds to provide a compound or compounds with improved ligand characteristics. Likewise, the derivative compounds can be tested and selected to give high selectivity for that PDE, or to give cross-reactivity to a particular set of targets, for example to a subset of phosphodiesterases that includes PDE4B and/or PDE4D. In particular embodiments, known PDE4B inhibitors can be used, and derivatives with greater affinity and/or greater specificity can be developed, preferably using PDE4B and/or PDE4D structure information; greater specificity for PDE4B relative to PDE4D is developed.

By "molecular scaffold" or "scaffold" is meant a simple target binding molecule to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group including, but not limited to, those recited in this application. Molecular scaffolds bind to at least one target molecule, preferably to a plurality of molecules in a protein family, and the target molecule can preferably be a enzyme, receptor, or other protein. Preferred characteristics of a scaffold can include binding at a target molecule binding site such that one or more substituents on the scaffold are situated in binding pockets in the target molecule binding site; having chemically tractable structures that can be chemically modified, particularly by synthetic reactions, so that a combinatorial library can be easily constructed; having chemical positions where moieties can be attached that do not interfere with binding of the scaffold to a protein binding site, such that the scaffold or library members can be modified to form ligands, to achieve additional desirable characteristics, e.g., enabling the ligand to be actively transported into cells and/or to specific organs, or enabling the ligand to be attached to a chromatography column for additional analysis. Thus, a molecular scaffold is an identified target binding molecule prior to modification to improve binding affinity and/or specificity, or other pharmacalogic properties.

The term "scaffold core" refers to the underlying chemical structure of a molecular scaffold onto which various substituents can be attached. Thus, for a number of scaffold molecules of a particular chemical class, the scaffold core is common to all the scaffold molecules. In many cases, the scaffold core includes one or more ring structures.

For Formula I, the scaffold core includes the 5-membered ring, the two amino group nitrogens, and the —C=Y group; particular Formula I scaffold cores are described by each selection of X in each combination with each selection of Y.

For Formula II, the scaffold core includes the 5-membered ring with $R^{13}$ and $R^{14}$. Particular Formula II scaffold cores are described by each selection for X, in each combination with each selection of O, S, or N for the $R^{13}$ atom attached to the 5-membered ring, in each combination with each selection of O, S, N, C for the $R^{14}$ atom attached to the 5-membered ring.

For Formula III, the scaffold core includes the sulfonamide moiety; in certain embodiments, a scaffold core includes the sulfonamide moiety with the sulfur attached to a five-membered ring, e.g., a thiophene ring (for exampled linked to a C adjacent to the ring sulfur).

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket can often be a particular shape, indentation, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation", in reference to a binding compound bound to a target molecule is meant the spatial relationship of the binding compound (which can be defined by reference to at least some of its consitituent atoms) to the binding pocket and/or atoms of the target molecule at least partially defining the binding pocket.

In the context of target molecules in this invention, the term "crystal" refers to a regular assemblage of a target molecule of a type suitable for X-ray crystallography. That is, the assemblage produces an X-ray diffraction pattern when illuminated with a beam of X-rays. Thus, a crystal is distinguished from an agglomeration or other complex of target molecule that does not give a diffraction pattern.

By "co-crystal" is meant a complex of the compound, molecular scaffold, or ligand bound non-covalently to the target molecule and present in a crystal form appropriate for analysis by X-ray or protein crystallography. In preferred embodiments the target molecule-ligand complex can be a protein-ligand complex.

The phrase "alter the binding affinity or binding specificity" refers to changing the binding constant of a first compound for another, or changing the level of binding of a first compound for a second compound as compared to the level of binding of the first compound for third compounds, respectively. For example, the binding specificity of a compound for a particular protein is increased if the relative level of binding to that particular protein is increased as compared to binding of the compound to unrelated proteins.

As used herein in connection with test compounds, binding compounds, and modulators (ligands), the term "synthesizing" and like terms means chemical synthesis from one or more precursor materials.

The phrase "chemical structure of the molecular scaffold is modified" means that a derivative molecule has a chemical structure that differs from that of the molecular scaffold but still contains common core chemical structural features. The phrase does not necessarily mean that the molecular scaffold is used as a precursor in the synthesis of the derivative.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

By a "set" of compounds is meant a collection of compounds. The compounds may or may not be structurally related.

In another aspect, structural information about PDE4B can also be used to assist in determining a structure for another phosphodiesterase by creating a homology model from an electronic representation of a PDE4B structure.

Typically creating such a homology model involves identifying conserved amino acid residues between the known PDE having known structures, e.g., PDE4B, and the other phosphodiesterase of interest; transferring the atomic coordinates of a plurality of conserved amino acids in the known structure to the corresponding amino acids of the other phosphodiesterase to provide a rough structure of that phosphodiesterase; and constructing structures representing the remainder of the other phosphodiesterase using electronic representations of the structures of the remaining amino acid residues in the other phosphodiesterase. In particular, for PDE4B, coordinates from Table 1 of U.S. Provisional Application No. 60/569,435, filed May 6, 2004, which is hereby incorporated by reference in its entirety for all purposes, can be used. Conserved residues in a binding site can be used.

To assist in developing other portions of the phosphodiesterase structure, the homology model can also utilize, or be fitted with, low resolution x-ray diffraction data from one or more crystals of the phosphodiesterase, e.g., to assist in linking conserved residues and/or to better specify coordinates for terminal portions of a polypeptide.

The PDE4B structural information used can be for a variety of different variants, including full-length wild type, naturally-occurring variants (e.g., allelic variants and splice variants), truncated variants of wild type or naturally-occurring variants, and mutants of full-length or truncated wild-type or naturally-occurring variants (that can be mutated at one or more sites). For example, in order to provide a PDE4B structure closer to a variety of other phosphodiesterase structures, a mutated PDE4B that includes a mutation to a conserved residue in a binding site can be used.

In another aspect, the invention provides a crystalline form of PDE4B, which may be a reduced length PDE4B such as a phosphodiesterase domain. The crystalline form can contain one or more heavy metal atoms, for example, atoms useful for X-ray crystallography. The crystalline form can also include a binding compound in a co-crystal, e.g., a binding compound that interacts with one more more conserved active site residues in the PDE, or any two, any three, any four, any five, any six of those residues, and can, for example, be a known PDE inhibitor. Such PDE crystals can be in various environments, e.g., in a crystallography plate, mounted for X-ray crystallography, and/or in an X-ray beam. The PDE may be of various forms, e.g., a wild-type, variant, truncated, and/or mutated form as described herein.

The invention further relates to co-crystals of PDE4B, which may be a reduced length PDE, e.g., a phosphodiesterase domain, and a PDE4B binding compound. Advantageously, such co-crystals are of sufficient size and quality to allow structural determination of the PDE to at least 3 Angstroms, 2.5 Angstroms, 2.0 Angstroms, 1.8 Angstroms, 1.7 Angstroms, 1.5 Angstroms, 1.4 Angstroms, 1.3 Angstroms, or 1.2 Angstroms. The co-crystals can, for example, be in a crystallography plate, be mounted for X-ray crystallography and/or in an X-ray beam. Such co-crystals are beneficial, for example, for obtaining structural information concerning interaction between the PDE and binding compounds.

In particular embodiments, the binding compound includes the core structure of Formula I, Formula II, or Formula III.

PDE4B binding compounds can include compounds that interact with at least one of the conserved active site residues in the PDE, or any 2, 3, 4, 5, or 6 of those residues. Exemplary compounds that bind to PDE4B include compounds described in references cited herein.

Likewise, in additional aspects, methods for obtaining PDE4B crystals and co-crystals are provided. In one aspect of the present invention there is provided a method for obtaining a crystal of PDE4B phosphodiesterase domain, said method comprising subjecting PDE4B protein at 5-20 mg/ml, e.g., 8-12 mg/ml, to crystallization conditions substantially equivalent to 30% PEG 400, 0.2M $MgCl_2$, 0.1M Tris pH 8.5, 1 mM binding compound, at 4° C.; or 20% PEG 3000, 0.2M $Ca(OAc)_2$, 0.1M Tris pH 7.0, 1 mM binding compound, 15.9 mg/ml protein at 4° C.; or 1.8M-2.0M ammonium sulphate, 0.1 M CAPS pH 10.0-10.5, 0.2M Lithium sulphate.

Crystallization conditions can be initially identified using a screening kit, such as a Hampton Research (Riverside, Calif.) screening kit 1. Conditions resulting in crystals can be selected and crystallization conditions optimized based on the demonstrated crystallization conditions. To assist in subsequent crystallography, the PDE can be seleno-methionine labeled. Also, as indicated above, the PDE may be any of various forms, e.g., truncated to provide a phosphodiesterase domain, which can be selected to be of various lengths.

In another aspect, provision of compounds active on PDE4B (such as compounds developed using methods described herein) also provides a method for modulating the PDE activity by contacting the PDE with a compound that binds to the PDE and interacts with one more conserved active site residues. The compound is preferably provided at a level sufficient to modulate the activity of the PDE by at least 10%, more preferably at least 20%, 30%, 40%, or 50%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM.

The term "PDE4B activity" refers to a biological activity of PDE4B, particularly including phosphodiesterase activity.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In a related aspect, the invention provides a method for treating a patient suffering from a disease or condition characterized by abnormal PDE4B phosphodiesterase activity. The invention method involves administering to the patient an effective amount of a compound identified by a method as described herein.

Specific diseases or disorders which might be treated or prevented include those described in the Detailed Description herein, and in the references cited therein.

As crystals of PDE4B have been developed and analyzed, and binding modes determined, another aspect of the present invention relates to an electronic representation of these PDEs (which may be a reduced length PDE), for example, an electronic representation containing atomic coordinate representations for PDE4B corresponding to the coordinates listed for PDE4B in Table 1 of U.S. Provisional Application No. 60/569,435, filed May 6, 2004, which is hereby incorporated by reference in its entirety for all purposes, or a schematic representation such as one showing secondary structure and/or chain folding, and may also show conserved active site residues. The PDE may be wild type, an allelic variant, a mutant form, or a modified form, e.g., as described herein.

The electronic representation can also be modified by replacing electronic representations of particular residues with electronic representations of other residues. Thus, for example, an electronic representation containing atomic coordinate representations corresponding to the coordinates for PDE4B listed in Table 1, 2, 3, or 4 of U.S. Provisional Application No. 60/569,435, filed May 6, 2004, which is hereby incorporated by reference in its entirety for all purposes, can be modified by the replacement of coordinates for a particular conserved residue in a binding site by a different amino acid. Following a modification or modifications, the representation of the overall structure can be adjusted to allow for the known interactions that would be affected by the modification or modifications. In most cases, a modification involving more than one residue will be performed in an iterative manner.

In addition, an electronic representation of a PDE4B binding compound or a test compound in the binding site can be included, e.g., a non-hydrolyzable cAMP analog or a compound including the core structure of sildenafil.

Likewise, in a related aspect, the invention relates to an electronic representation of a portion of PDE4B, which can be a binding site (which can be an active site) or phosphodiesterase domain, for example, PDE4B residues 152-528 of JC1519, or other phosphodiesterase domain described herein. A binding site or phosphodiesterase domain can be represented in various ways, e.g., as representations of atomic coordinates of residues around the binding site and/or as a binding site surface contour, and can include representations of the binding character of particular residues at the binding site, e.g., conserved residues. The binding site preferably includes no more than 1 heavy metal atom; a binding compound or test compound such as a compound including the core structure of Formula I, Formula II, or Formula III may be present in the binding site; the binding site may be of a wild type, variant, mutant form, or modified form of PDE4B; the electronic representation includes representations coordinates of conserved residues as for example given in Table 1, 2, 3, or 4 of U.S. Provisional Application No. 60/569,435, filed May 6, 2004, which is hereby incorporated by reference in its entirety for all purposes.

In yet another aspect, the structural and sequence information of PDE4B can be used in a homology model for another PDE. It is helpful if high resolution structural information for PDE4B is used for such a model, e.g., at least 1.7, 1.5, 1.4, 1.3, or 1.2 Angstrom resolution.

In still another aspect, the invention provides an electronic representation of a modified PDE4B crystal structure, that includes an electronic representation of the atomic coordinates of a modified PDE4B based on the atomic coordinates of Table 1, 2, 3, and/or 4 of U.S. Provisional Application No. 60/569,435, filed May 6, 2004, which is hereby incorporated by reference in its entirety for all purposes. In an exemplary embodiment, atomic coordinates can be modified by the replacement of atomic coordinates for a conserved residue with atomic coordinates for a different amino acid. Modifications can include substitutions, deletions (e.g., C-terminal and/or N-terminal detections), insertions (internal, C-terminal, and/or N-terminal) and/or side chain modifications.

In another aspect, the PDE4B structural information provides a method for developing useful biological agents based on PDE4B, by analyzing a PDE4B structure to identify at least one sub-structure for forming the biological agent. Such sub-structures can include epitopes for antibody formation, and the method includes developing antibodies against the epitopes, e.g., by injecting an epitope presenting composition in a mammal such as a rabbit, guinea pig, pig, goat, or horse. The sub-structure can also include a mutation site at which mutation is expected to or is known to alter the activity of the PDE4B, and the method includes creating a mutation at that site. Still further, the sub-structure can include an attachment point for attaching a separate moiety, for example, a peptide, a polypeptide, a solid phase material (e.g., beads, gels, chromatographic media, slides, chips, plates, and well surfaces), a linker, and a label (e.g., a direct label such as a fluorophore or an indirect label, such as biotin or other member of a specific binding pair). The method can include attaching the separate moiety.

In another aspect, the invention provides a method for identifying potential PDE4B binding compounds by fitting at least one electronic representation of a compound in an electronic representation of the PDE binding site. The representation of the binding site may be part of an electronic representation of a larger portion(s) or all of a PDE molecule or may be a representation of only the catalytic domain or of the binding site or active site. The electronic representation may be as described above or otherwise described herein. For PDE4B the electronic representation includes representations of coordinates according to Table 1, 2, 3, or 4 of U.S. Provisional Application No. 60/569,435, filed May 6, 2004, which is hereby incorporated by reference in its entirety for all purposes, in particular residues with coordinates differing significantly from the previously proposed PDE4B structure.

In particular embodiments, the method involves fitting a computer representation of a compound from a computer database with a computer representation of the active site of the PDE, and involves removing a computer representation of a compound complexed with the PDE molecule and identifying compounds that best fit the active site based on favorable geometric fit and energetically favorable complementary interactions as potential binding compounds. In particular embodiments, the compound is a known PDE4B inhibitor, e.g., as described in a reference cited herein, or a derivative thereof.

In other embodiments, the method involves modifying a computer representation of a compound complexed with the PDE molecule, by the deletion or addition or both of one or more chemical groups; fitting a computer representation of a compound from a computer database with a computer representation of the active site of the PDE molecule; and identifying compounds that best fit the active site based on favorable geometric fit and energetically favorable complementary interactions as potential binding compounds.

In still other embodiments, the method involves removing a computer representation of a compound complexed with the PDE, and searching a database for compounds having structural similarity to the complexed compound using a compound searching computer program or replacing portions of the complexed compound with similar chemical structures using a compound construction computer program.

Fitting a compound can include determining whether a compound will interact with one or more conserved active site residues for the PDE. Compounds selected for fitting or that are complexed with the PDE can, for example, be a known PDE4B inhibitor compound, or a compound including the core structure of such compound.

In another aspect, the invention relates to a method for attaching a PDE4B binding compound to an attachment component, as well as a method for indentifying attachment sites on a PDE4B binding compound. The method involves identifying energetically allowed sites for attachment of an attachment component for the binding compound bound to a binding site of PDE4B; and attaching the compound or a derivative thereof to the attachment component at the energetically allowed site. "Energetically allowed sites" are regions of the molecule with the property that any free energy change associated with the presence of the attached component should not destablize the binding of the compound to the phosphodiesterase to an extent that will disrupt the binding.

Attachment components can include, for example, linkers (including traceless linkers) for attachment to a solid phase or to another molecule or other moiety. Such attachment can be formed by synthesizing the compound or derivative on the linker attached to a solid phase medium e.g., in a combinatorial synthesis in a plurality of compound. Likewise, the attachment to a solid phase medium can provide an affinity medium (e.g., for affinity chromatography).

The attachment component can also include a label, which can be a directly detectable label such as a fluorophore, or an indirectly detectable such as a member of a specific binding pair, e.g., biotin.

The ability to identify energetically allowed sites on a PDE4B binding compound, also, in a related aspect, provides modified binding compounds that have linkers attached, preferably at an energetically allowed site for binding of the modified compound to PDE4B. The linker can be attached to an attachment component as described above.

Another aspect of the present invention relates to a modified PDE4B polypeptide that includes a modification that makes the modified PDE4B more similar than native PDE4B to another phosphodiesterase, and can also include other mutations or other modifications. In various embodiments, the polypeptide includes a full-length PDE4B polypeptide, includes a modified PDE4B binding site, includes at least 20, 30, 40, 50, 60, 70, or 80 contiguous amino acid residues derived from PDE4B including a conserved site.

Still another aspect of the invention relates to a method for developing a ligand for a phosphodiesterase that includes conserved residues matching any one, 2, 3, 4, 5, or 6 of conserved PDE4B active site residues respectively, by determining whether a compound binds to the phosphodiesterase and interacts with such active site residues in a PDE4B crystal or a PDE4B binding model having coordinates as in Table 1, 2, 3, and/or 4 of U.S. Provisional Application No. 60/569,435, filed May 6, 2004, which is hereby incorporated by reference in its entirety for all purposes. The method can also include determining whether the compound modulates the activity of the phosphodiesterase. Preferably the phosphodiesterase has at least 50, 55, 60, or 70% identity over an equal length phosphodiesterase domain segment.

In particular embodiments, the determining includes computer fitting the compound in a binding site of the phosphodiesterase and/or the method includes forming a co-crystal of the phosphodiesterase and the compound. Such co-crystals can be used for determining the binding orientation of the compound with the phosphodiesterase and/or provide structural information on the phosphodiesterase, e.g., on the binding site and interacting amino acid residues. Such binding orientation and/or other structural information can be accomplished using X-ray crystallography.

The invention also provides compounds that bind to and/or modulate (e.g., inhibit) PDE4B phosphodiesterase activity e.g., compounds identified by the methods described herein. Accordingly, in aspects and embodiments involving PDE4B binding compounds, molecular scaffolds, and ligands or modulators, the compound is a weak binding compound; a moderate binding compound; a strong binding compound; the compound interacts with one or more conserved active site residues in the PDE; the compound is a small molecule; the compound binds to a plurality of different phosphodiesterases (e.g., at least 2, 3, 4, 5, 7, 10, or more different phosphodiesterases). In particular, the invention relates to compounds identified or selected.

In yet another embodiment, the present invention relates to a method for identifying a compound having selectivity between PDE4B and PDE4D by utilizing particular differential sites. The method involves analyzing whether a compound differentially interacts in PDE4B and PDE4D in at least one of the differential sites, where a differential interaction is indicative of such selectivity. The "differential sites" are identified from crystal structure comparison and represent sites with different chemical properties, e.g., charge density, atomic placement, degree of hydration, and the like, observed in a comparison between the compared structures.

In particular embodiments, the analyzing includes fitting an electronic representation of the compound in electronic representations of binding sites of PDE4B and PDE4D, and determining whether the compound differentially interacts based on said fitting; the method involves selecting an initial compound that binds to both PDE4B and PDE4D, fitting an electronic representation of the initial compound in electronic representations of binding sites of PDE4B and PDE4D, modifying the electronic representation of the initial compound with at least one moiety that interacts with at least differentials site, and determining whether the modified compound differentially binds to PDE4B and PDE4D; the modified compound binds differentially to a greater extent than does the initial compound; the method also includes assaying a compound that differentially interacts for differential activity on PDE4B and PDE4D; the initial compound includes the sildenafil scaffold structure; the initial compound includes the sildenafil core.

In the various aspects described above that involve atomic coordinates for PDE4B in connection with binding compounds, the coordinates are provided by X-ray crystallographic structures made by the methods described herein. Those coordinates can then be adjusted using conventional modeling methods to fit compounds having structures different from sildenafil, and can thus be used for development of PDE4B modulators different from currently described PDE4B modulators. PDE4B crystal coordinates provided by the methods described herein can be used instead of the previously described PDE4B crystal coordinates.

Additional aspects and embodiments will be apparent from the following Detailed Description and from the claims.

BRIEF DESCRIPTION OF THE FIGURES

FIG. 1 provides nucleic acid sequence for pET15S (SEQ ID NO: 9) with multi-cloning site. Protein sequence disclosed as residues 1-21 of SEQ ID NO: 11.

FIG. 2 provides nucleic acid sequences for PDE4B phosphodiesterase domain as used in the work described herein. Figure discloses SEQ ID NOS: 16, 10 and 17, respectively, in order of appearance.

FIG. 3 provides amino acid sequences for PDE4B phosphodiesterase domain as used in the work described herein (SEQ ID NO: 11).

DETAILED DESCRIPTION OF THE PREFERRED EMBODIMENTS

Figure 4:
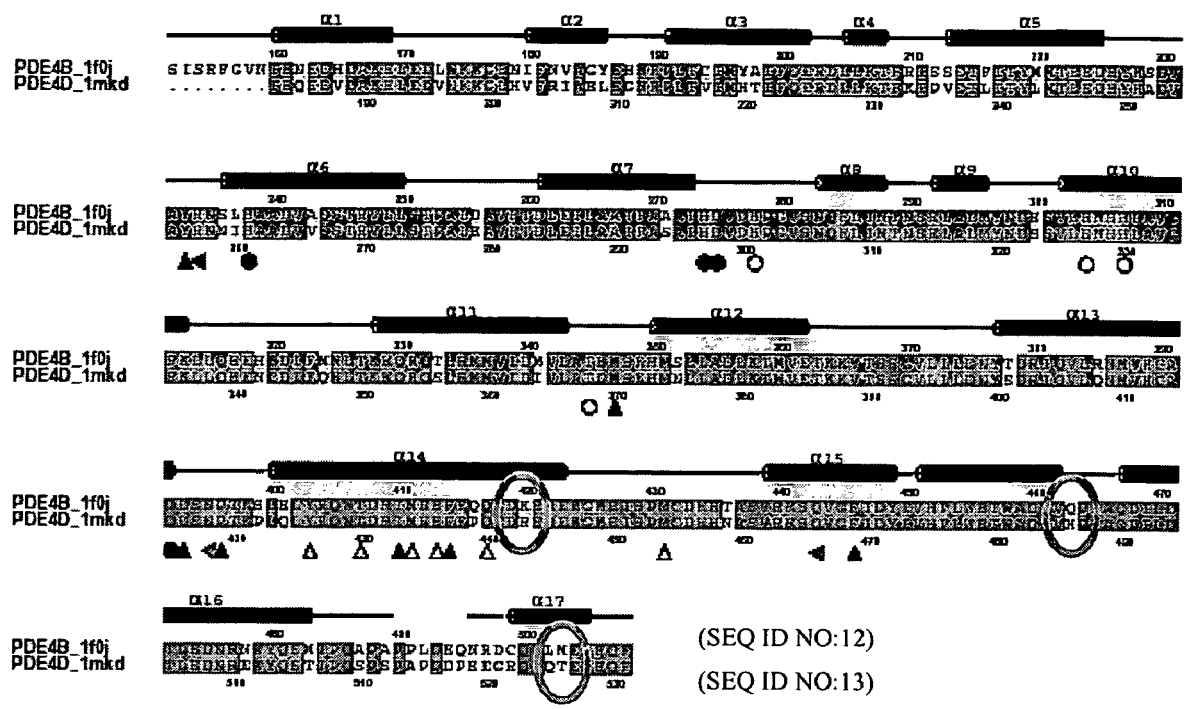
FIG. 4 shows the alignment of the phosphodiesterase domains of PDE4B (SEQ ID NO: 12) and PDE4D (SEQ ID NO: 13), with 3 regions that can be exploited for designing selective ligands circled.
Figure 5:
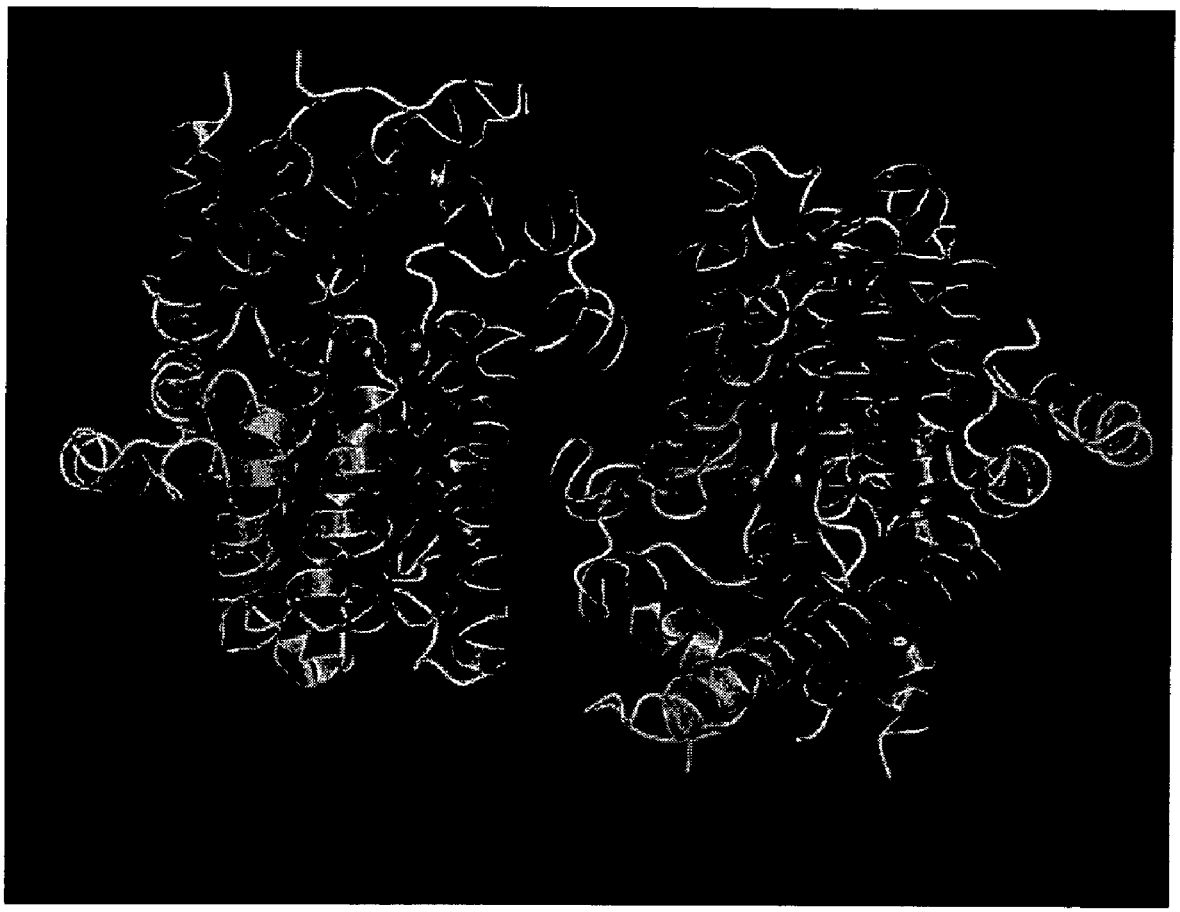
FIG. 5 shows a ribbon diagram schematic representation of PDE4B phosphodiesterase domain.

Exemplary compounds of Formula I are presented in Table 1A. Table 1B presents exemplary activity data for compounds of Formula I. Table 1C presents additional exemplary compounds of the invention.

Exemplary compounds of Formula II are presented in Table 2A. Table 2B shows exemplary activity data for compounds of Formula II.

Table 3A shows exemplary compounds and activity data for compounds of Formula III. Table 3B presents additional exemplary compounds of the invention.

Systematic chemical names provided in Tables 1A, 2A, and 3A, were automatically generated by the AutoNom 2000 add-in feature of the ISIS program (Elsevier MDL, San Leandro, Calif.). To the extent that the graphical depiction of a chemical species and the systematic nomenclature ascribed to said chemical species differ, the graphical depiction represents the intended chemical structure.

I. General

The present invention relates to compounds of Formula I, Formula II, and Formula III that are inhibitors of PDE4B, and the use of PDE4B phosphodiesterase structures, structural information, and related compositions for developing improved compounds with those structures that modulate PDE4B phosphodiesterase activity.

A number of patent publications have concerned PDE4 inhibitors and their use. Most such publications have focused on PDE4D. For example, Marfat et al., U.S. Pat. No. 6,559,168 describes PDE4 inhibitors, especially PDE4D inhibitors, and cites additional patent publications that describe additional PDE4 inhibitors. Such additional publications include Marfat et al., WO 98/45268; Saccoomano et al., U.S. Pat. No. 4,861,891; Pon, U.S. Pat. No. 5,922,557; and Eggleston, WO 99/20625.

Ait Ikhlef et al., U.S. Patent Publ. 20030064374, application Ser. No. 10/983,754 describes compounds active on PDE4B and their use in treatment of neurotoxicity, including treatment in neurodegenerative diseases such as Alzheimers' disease, Parkinson's disease, multiple sclerosis, Huntington's chorea, and cerebral ischemia.

Exemplary Diseases Associated with PDE4B.

Modulation of PDE4B has been correlated with treatment of a number of different diseases and conditions. For example, Ait Ikhlef et al., U.S. Patent Publ. 20030064374, application Ser. No. 10/983,754 describes compounds active on PDE4B and their use in treatment of neurotoxicity, including treatment in neurodegenerative diseases such as Alzheimers' disease, Parkinson's disease, multiple sclerosis, Huntington's chorea, and cerebral ischemia.

Thus, PDE4B modulators can be used for treatment or prophylaxis of such conditions correlated with PDE4 and in particular PDE4B. Additional conditions that can be treated include, without limitation, an acute or chronic pulmonary disease such as obstructive diseases (e.g. asthma, chronic obstructive pulmonary disease (COPD), cystic fibrosis), interstitial lung diseases (e.g. idiopathic pulmonary fibrosis, sarcoidosis), vascular lung diseases (e.g. pulmonary hypertension), bronchitis, allergic bronchitis, and emphysema. Additional diseases or conditions contemplated for treatment by embodiments of the present invention include for example, without limitation, CNS diseases such as Alzheimer's disease, Parkinson's disease and Huntington's chorea; inflammatory autoimmune diseases such as multiple sclerosis, rheumatoid arthritis and Crohn's disease as well as other inflammatory disorders, such as cerebral ischemia, inflammatory bowel disease, and ulcerative colitis; bone disease, such as osteoporosis, osteopetrosis, and Paget's disease; cancers, such as diffuse large-cell B cell lymphoma, chronic lymphocytic leukemia, acute lymphoblastic leukemia; Severe Acute Respiratory Syndrome; and pre-term labor.

II. Crystalline PDE4B

Crystalline PDE4B includes native crystals, phosphodiesterase domain crystals, derivative crystals and co-crystals. The native crystals generally comprise substantially pure polypeptides corresponding to PDE4B in crystalline form. PDE4B phosphodiesterase domain crystals generally comprise substantially pure PDE4B phosphodiesterase domain in crystalline form. In connection with the development of inhibitors of PDE4B phosphodiesterase function, it is advantageous to use PDE4B phosphodiesterase domain respectively for structural determination, because use of the reduced sequence simplifies structure determination. To be useful for this purpose, the phosphodiesterase domain should be active and/or retain native-type binding, thus indicating that the phosphodiesterase domain takes on substantially normal 3D structure.

It is to be understood that the crystalline phosphodiesterases and phosphodiesterase domains of the invention are not limited to naturally occurring or native phosphodiesterase. Indeed, the crystals of the invention include crystals of mutants of native phosphodiesterases. Mutants of native phosphodiesterases are obtained by replacing at least one amino acid residue in a native phosphodiesterase with a different amino acid residue, or by adding or deleting amino acid residues within the native polypeptide or at the N- or C-terminus of the native polypeptide, and have substantially the same three-dimensional structure as the native phosphodiesterase from which the mutant is derived.

By having substantially the same three-dimensional structure is meant having a set of atomic structure coordinates that have a root-mean-square deviation of less than or equal to about 2 Å when superimposed with the atomic structure coordinates of the native phosphodiesterase from which the mutant is derived when at least about 50% to 100% of the Cα atoms of the native phosphodiesterase domain are included in the superposition.

Amino acid substitutions, deletions and additions which do not significantly interfere with the three-dimensional structure of the phosphodiesterase will depend, in part, on the region of the phosphodiesterase where the substitution, addition or deletion occurs. In highly variable regions of the molecule, non-conservative substitutions as well as conservative substitutions may be tolerated without significantly disrupting the three-dimensional, structure of the molecule. In highly conserved regions, or regions containing significant secondary structure, conservative amino acid substitutions are preferred. Such conserved and variable regions can be identified by sequence alignment of PDE4B with other phosphodiesterases.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

For phosphodiesterases obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native phosphodiesterase in order to provide convenient cloning sites in cDNA encoding the polypeptide, to aid in purification of the polypeptide, and for crystallization of the polypeptide. Such substitutions, deletions and/or additions which do not substantially alter the three dimensional structure of the native phosphodiesterase domain will be apparent to those of ordinary skill in the art.

It should be noted that the mutants contemplated herein need not all exhibit phosphodiesterase activity. Indeed, amino acid substitutions, additions or deletions that interfere with the phosphodiesterase activity but which do not significantly alter the three-dimensional structure of the domain are specifically contemplated by the invention. Such crystalline polypeptides, or the atomic structure coordinates obtained therefrom, can be used to identify compounds that bind to the native domain. These compounds can affect the activity of the native domain.

The derivative crystals of the invention can comprise a crystalline phosphodiesterase polypeptide in covalent association with one or more heavy metal atoms. The polypeptide may correspond to a native or a mutated phosphodiesterase.

Heavy metal atoms useful for providing derivative crystals include, by way of example and not limitation, gold, mercury, selenium, etc.

The co-crystals of the invention generally comprise a crystalline phosphodiesterase domain polypeptide in association with one or more compounds. The association may be covalent or non-covalent. Such compounds include, but are not limited to, cofactors, substrates, substrate analogues, inhibitors, allosteric effectors, etc.

III. Three Dimensional Structure Determination Using X-ray Crystallography

X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated aqueous solution of that protein. The process of X-ray crystallography can include the following steps:
 (a) synthesizing and isolating (or otherwise obtaining) a polypeptide;
 (b) growing a crystal from an aqueous solution comprising the polypeptide with or without a modulator; and
 (c) collecting X-ray diffraction patterns from the crystals, determining unit cell dimensions and symmetry, determining electron density, fitting the amino acid sequence of the polypeptide to the electron density, and refining the structure.

Production of Polypeptides

The native and mutated phosphodiesterase polypeptides described herein may be chemically synthesized in whole or part using techniques that are well-known in the art (see, e.g., Creighton (1983) *Biopolymers* 22(1):49-58).

Alternatively, methods which are well known to those skilled in the art can be used to construct expression vectors containing the native or mutated phosphodiesterase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the phosphodiesterase coding sequence. These include but are not limited to microorganisms such as bacteria transformed with recombinant bacteriophage DNA, plasmid DNA or cosmid DNA expression vectors containing the phosphodiesterase domain coding sequence; yeast transformed with recombinant yeast expression vectors containing the phosphodiesterase domain coding sequence; insect cell systems infected with recombinant virus expression vectors (e.g., baculovirus) containing the phosphodiesterase domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the phosphodiesterase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage $\lambda$, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the phosphodiesterase domain DNA, SV4O-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

Crystal Growth

Crystals are grown from an aqueous solution containing the purified and concentrated polypeptide by a variety of techniques. These techniques include batch, liquid, bridge, dialysis, vapor diffusion, and hanging drop methods. McPherson (1982) John Wiley, New York; McPherson (1990) *Eur. J. Biochem.* 189:1-23; Webber (1991) *Adv. Protein Chem.* 41:1-36, incorporated by reference herein in their entireties, including all figures, tables, and drawings.

The native crystals of the invention are, in general, grown by adding precipitants to the concentrated solution of the polypeptide. The precipitants are added at a concentration just below that necessary to precipitate the protein. Water is removed by controlled evaporation to produce precipitating conditions, which are maintained until crystal growth ceases.

For crystals of the invention, exemplary crystallization conditions are described in the Examples. Those of ordinary skill in the art will recognize that the exemplary crystallization conditions can be varied. Such variations may be used alone or in combination. In addition, other crystallization conditions may be found, e.g., by using crystallization screening plates to identify such other conditions. Those alternate conditions can then be optimized if needed to provide larger or better quality crystals.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or $KAu(CN)_2$ for about 2 hr to about 72 hr provides derivative crystals suitable for use as isomorphous replacements in determining the X-ray crystal structure.

Co-crystals of the invention can be obtained by soaking a native crystal in mother liquor containing compound that binds the phosphodiesterase, or can be obtained by co-crystallizing the phosphodiesterase polypeptide in the presence of a binding compound.

Generally, co-crystallization of phosphodiesterase and binding compound can be accomplished using conditions identified for crystallizing the corresponding phosphodiesterase without binding compound. It is advantageous if a plurality of different crystallization conditions have been identified for the phosphodiesterase, and these can be tested to determine which condition gives the best co-crystals. It may also be beneficial to optimize the conditions for co-crystallization. Alternatively, new crystallization conditions can be determined for obtaining co-crystals, e.g., by screening for crystallization and then optimizing those conditions. Exemplary co-crystallization conditions are provided in the Examples.

Determining Unit Cell Dimensions and the Three Dimensional Structure of a Polypeptide or Polypeptide Complex Once the crystal is grown, it can be placed in a glass capillary tube or other mounting device and mounted onto a holding device connected to an X-ray generator and an X-ray detection device. Collection of X-ray diffraction patterns are well documented by those in the art. See, e.g., Ducruix and Geige, (1992), IRL Press, Oxford, England, and references cited therein. A beam of X-rays enters the crystal and then diffracts from the crystal. An X-ray detection device can be utilized to record the diffraction patterns emanating from the crystal. Although the X-ray detection device on older models of these instruments is a piece of film, modern instruments digitally record X-ray diffraction scattering. X-ray sources can be of various types, but advantageously, a high intensity source is used, e.g., a synchrotron beam source.

Methods for obtaining the three dimensional structure of the crystalline form of a peptide molecule or molecule complex are well known in the art. See, e.g., Ducruix and Geige, (1992), IRL Press, Oxford, England, and references cited therein. The following are steps in the process of determining the three dimensional structure of a molecule or complex from X-ray diffraction data.

After the X-ray diffraction patterns are collected from the crystal, the unit cell dimensions and orientation in the crystal can be determined. They can be determined from the spacing between the diffraction emissions as well as the patterns made from these emissions. The unit cell dimensions are characterized in three dimensions in units of Angstroms (one $Å=10^{-10}$ meters) and by angles at each vertices. The symmetry of the unit cell in the crystals is also characterized at this stage. The symmetry of the unit cell in the crystal simplifies the complexity of the collected data by identifying repeating patterns. Application of the symmetry and dimensions of the unit cell is described below.

Each diffraction pattern emission is characterized as a vector and the data collected at this stage of the method determines the amplitude of each vector. The phases of the vectors can be determined using multiple techniques. In one method, heavy atoms can be soaked into a crystal, a method called isomorphous replacement, and the phases of the vectors can be determined by using these heavy atoms as reference points in the X-ray analysis. (Otwinowski, (1991), Daresbury, United Kingdom, 80-86). The isomorphous replacement method usually utilizes more than one heavy atom derivative.

In another method, the amplitudes and phases of vectors from a crystalline polypeptide with an already determined structure can be applied to the amplitudes of the vectors from a crystalline polypeptide of unknown structure and consequently determine the phases of these vectors. This second method is known as molecular replacement and the protein structure which is used as a reference must have a closely related structure to the protein of interest. (Naraza (1994) *Proteins* 11:281-296). Thus, the vector information from a phosphodiesterase of known structure, such as those reported herein, are useful for the molecular replacement analysis of another phosphodiesterase with unknown structure.

Once the phases of the vectors describing the unit cell of a crystal are determined, the vector amplitudes and phases, unit cell dimensions, and unit cell symmetry can be used as terms in a Fourier transform function. The Fourier transform function calculates the electron density in the unit cell from these measurements. The electron density that describes one of the molecules or one of the molecule complexes in the unit cell can be referred to as an electron density map. The amino acid structures of the sequence or the molecular structures of compounds complexed with the crystalline polypeptide may then be fitted to the electron density using a variety of computer programs. This step of the process is sometimes referred to as model building and can be accomplished by using computer programs such as Turbo/FRODO or "O". (Jones (1985) *Methods in Enzymology* 115:157-171).

A theoretical electron density map can then be calculated from the amino acid structures fit to the experimentally determined electron density. The theoretical and experimental electron density maps can be compared to one another and the agreement between these two maps can be described by a parameter called an R-factor. A low value for an R-factor describes a high degree of overlapping electron density between a theoretical and experimental electron density map.

The R-factor is then minimized by using computer programs that refine the theoretical electron density map. A computer program such as X-PLOR can be used for model refinement by those skilled in the art. (Brünger (1992) *Nature* 355:472-475.) Refinement may be achieved in an iterative process. A first step can entail altering the conformation of atoms defined in an electron density map. The conformations of the atoms can be altered by simulating a rise in temperature, which will increase the vibrational frequency of the bonds and modify positions of atoms in the structure. At a particular point in the atomic perturbation process, a force field, which typically defines interactions between atoms in terms of allowed bond angles and bond lengths, Van der Waals interactions, hydrogen bonds, ionic interactions, and hydrophobic interactions, can be applied to the system of atoms. Favorable interactions may be described in terms of free energy and the atoms can be moved over many iterations until a free energy minimum is achieved. The refinement process can be iterated until the R-factor reaches a minimum value.

The three dimensional structure of the molecule or molecule complex is described by atoms that fit the theoretical electron density characterized by a minimum R-value. As is well known in the art, a file can then be created for the three dimensional structure that defines each atom by coordinates in three dimensions.

IV. Structures of PDE4B

High-resolution three-dimensional structures and atomic structure coordinates of crystalline PDE4B phosphodiesterase domain and PDE4B phosphodiesterase domain co-complexed with exemplary binding compounds are described. The methods used to obtain the structure coordinates are provided in the examples. The atomic structure coordinates of crystalline PDE4B phosphodiesterase domain are listed in Table 1 of U.S. Provisional Application No. 60/569,435, filed May 6, 2004, which is hereby incorporated by reference in its entirety for all purposes. Co-crystal coordinates can be used in the same way, e.g., in the various aspects described herein, as coordinates for the protein by itself, but can be advantageous because such co-crystals demonstrate or confirm the binding mode of binding compound, and can also include shifts of protein atoms in response to the presence of the binding compound.

Those having skill in the art will recognize that atomic structure coordinates as determined by X-ray crystallography are not without error. Thus, it is to be understood that generally any set of structure coordinates obtained for crystals of PDE, whether native crystals, phosphodiesterase domain crystals, derivative crystals or co-crystals, that have a root mean square deviation ("r.m.s.d.") of less than or equal to about 1.5 Å when superimposed, using backbone atoms (N, $C_\alpha$, C and O), on a subject structure are considered to be identical with the subject structure when at least about 50% to 100% of the backbone atoms of the crystallized protein are included in the superposition.

V. Uses of the Crystals and Atomic Structure Coordinates

The crystals of the invention, and particularly the atomic structure coordinates obtained therefrom, have a wide variety of uses. For example, the crystals described herein can be used as a starting point in any of the methods of use for phosphodiesterases known in the art or later developed. Such methods of use include, for example, identifying molecules that bind to the native or mutated catalytic domain of phosphodiesterases. The crystals and structure coordinates are particularly useful for identifying ligands that modulate phosphodiesterase activity as an approach towards developing new therapeutic agents. In particular, the crystals and structural information are useful in methods for ligand development utilizing molecular scaffolds.

The structure coordinates described herein can be used as phasing models for determining the crystal structures of additional phosphodiesterases, as well as the structures of co-crystals of such phosphodiesterases with ligands such as inhibitors, agonists, antagonists, and other molecules. The structure coordinates, as well as models of the three-dimensional structures obtained therefrom, can also be used to aid the elucidation of solution-based structures of native or mutated phosphodiesterases, such as those obtained via NMR.

VI. Electronic Representations of Phosphodiesterase Structures

Structural information of phosphodiesterases or portions of phosphodiesterases (e.g., phosphodiesterase active sites) can be represented in many different ways. Particularly useful are electronic representations, as such representations allow rapid and convenient data manipulations and structural modifications. Electronic representations can be embedded in many different storage or memory media, frequently computer readable media. Examples include without limitations, computer random access memory (RAM), floppy disk, magnetic hard drive, magnetic tape (analog or digital), compact disk (CD), optical disk, CD-ROM, memory card, digital video disk (DVD), and others. The storage medium can be separate or part of a computer system. Such a computer system may be a dedicated, special purpose, or embedded system, such as a computer system that forms part of an X-ray crystallography system, or may be a general purpose computer (which may have data connection with other equipment such as a sensor device in an X-ray crystallographic system. In many cases, the information provided by such electronic representations can also be represented physically or visually in two or three dimensions, e.g., on paper, as a visual display (e.g., on a computer monitor as a two dimensional or pseudo-three dimensional image) or as a three dimensional physical model. Such physical representations can also be used, alone or in connection with electronic representations. Exemplary useful representations include, but are not limited to, the following:

Atomic Coordinate Representation

One type of representation is a list or table of atomic coordinates representing positions of particular atoms in a molecular structure, portions of a structure, or complex (e.g., a co-crystal). Such a representation may also include additional information, for example, information about occupancy of particular coordinates. One such atomic coordinate representation contains the coordinate information of Table 1 of U.S. Provisional Application No. 60/569,435, filed May 6, 2004, which is hereby incorporated by reference in its entirety for all purposes, in electronic form.

Energy Surface or Surface of Interaction Representation

Another representation is an energy surface representation, e.g., of an active site or other binding site, representing an energy surface for electronic and steric interactions. Such a representation may also include other features. An example is the inclusion of representation of a particular amino acid residue(s) or group(s) on a particular amino acid residue(s), e.g., a residue or group that can participate in H-bonding or ionic interaction. Such energy surface representations can be readily generated from atomic coordinate representations using any of a variety of available computer programs.

Structural Representation

Still another representation is a structural representation, i.e., a physical representation or an electronic representation of such a physical representation. Such a structural representation includes representations of relative positions of particular features of a molecule or complex, often with linkage between structural features. For example, a structure can be represented in which all atoms are linked; atoms other than hydrogen are linked; backbone atoms, with or without representation of sidechain atoms that could participate in significant electronic interaction, are linked; among others. However, not all features need to be linked. For example, for structural representations of portions of a molecule or complex, structural features significant for that feature may be represented (e.g., atoms of amino acid residues that can have significant binding interation with a ligand at a binding site. Those amino acid residues may not be linked with each other.

A structural representation can also be a schematic representation. For example, a schematic representation can represent secondary and/or tertiary structure in a schematic manner. Within such a schematic representation of a polypeptide, a particular amino acid residue(s) or group(s) on a residue(s) can be included, e.g., conserved residues in a binding site, and/or residue(s) or group(s) that may interact with binding compounds. Electronic structural representations can be generated, for example, from atomic coordinate information using computer programs designed for that function and/or by constructing an electronic representation with manual input based on interpretation of another form of structural information. Physical representations can be created, for example, by printing an image of a computer-generated image or by constructing a 3D model.

VII. Structure Determination for Phosphodiesterases with Unknown Structure Using Structural Coordinates Structural coordinates, such as those set forth in Table 1 of U.S. Provisional Application No. 60/569,435, filed May 6, 2004, which is hereby incorporated by reference in its entirety for all purposes, can be used to determine the three dimensional structures of phosphodiesterases with unknown structure. The methods described below can apply structural coordinates of a polypeptide with known structure to another data set, such as an amino acid sequence, X-ray crystallographic diffraction data, or nuclear magnetic resonance (NMR) data. Preferred embodiments of the invention relate to determining the three dimensional structures of modified phosphodiesterases, other native phosphodiesterases, and related polypeptides.

Structures Using Amino Acid Homology

Homology modeling is a method of applying structural coordinates of a polypeptide of known structure to the amino acid sequence of a polypeptide of unknown structure. This method is accomplished using a computer representation of the three dimensional structure of a polypeptide or polypeptide complex, the computer representation of amino acid sequences of the polypeptides with known and unknown structures, and standard computer representations of the structures of amino acids. Homology modeling generally involves (a) aligning the amino acid sequences of the polypeptides with and without known structure; (b) transferring the coordinates of the conserved amino acids in the known structure to the corresponding amino acids of the polypeptide of unknown structure; refining the subsequent three dimensional structure; and (d) constructing structures of the rest of the polypeptide. One skilled in the art recognizes that conserved amino acids between two proteins can be determined from the sequence alignment step in step (a).

The above method is well known to those skilled in the art. (Greer (1985) Science 228:1055; Blundell et al. A(1988) Eur. J. Biochem. 172:513. An exemplary computer program that can be utilized for homology modeling by those skilled in the art is the Homology module in the Insight II modeling package distributed by Accelerys Inc.

Alignment of the amino acid sequence is accomplished by first placing the computer representation of the amino acid sequence of a polypeptide with known structure above the amino acid sequence of the polypeptide of unknown structure. Amino acids in the sequences are then compared and groups of amino acids that are homologous (e.g., amino acid side chains that are similar in chemical nature—aliphatic, aromatic, polar, or charged) are grouped together. This method will detect conserved regions of the polypeptides and account for amino acid insertions or deletions. Such alignment and/or can also be performed fully electronically using sequence alignment and analyses software.

Once the amino acid sequences of the polypeptides with known and unknown structures are aligned, the structures of the conserved amino acids in the computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions are to be assigned manually by either using standard peptide geometries or molecular simulation techniques, such as molecular dynamics. The final step in the process is accomplished by refining the entire structure using molecular dynamics and/or energy minimization. The homology modeling method is well known to those skilled in the art and has been practiced using different protein molecules. For example, the three dimensional structure of the polypeptide corresponding to the catalytic domain of a serine/threonine protein kinase, myosin light chain protein kinase, was homology modeled from the cAMP-dependent protein kinase catalytic subunit. (Knighton et al. (1992) Science 258:130-135.)

Structures Using Molecular Replacement

Molecular replacement is a method of applying the X-ray diffraction data of a polypeptide of known structure to the X-ray diffraction data of a polypeptide of unknown sequence. This method can be utilized to define the phases describing the X-ray diffraction data of a polypeptide of unknown structure when only the amplitudes are known. X-PLOR is a commonly utilized computer software package used for molecular replacement. Brunger (1992) Nature 355:472-475. AMORE is another program used for molecular replacement. Navaza (1994) Acta Crystallogr. A50:157-163. Preferably, the resulting structure does not exhibit a root-mean-square deviation of more than 3 Å.

A goal of molecular replacement is to align the positions of atoms in the unit cell by matching electron diffraction data from two crystals. A program such as X-PLOR can involve four steps. A first step can be to determine the number of molecules in the unit cell and define the angles between them. A second step can involve rotating the diffraction data to define the orientation of the molecules in the unit cell. A third step can be to translate the electron density in three dimensions to correctly position the molecules in the unit cell. Once the amplitudes and phases of the X-ray diffraction data is determined, an R-factor can be calculated by comparing electron diffraction maps calculated experimentally from the reference data set and calculated from the new data set. An R-factor between 30-50% indicates that the orientations of the atoms in the unit cell are reasonably determined by this method. A fourth step in the process can be to decrease the R-factor to roughly 20% by refining the new electron density map using iterative refinement techniques described herein and known to those or ordinary skill in the art.

Structures Using NMR Data

Structural coordinates of a polypeptide or polypeptide complex derived from X-ray crystallographic techniques can be applied towards the elucidation of three dimensional structures of polypeptides from nuclear magnetic resonance (NMR) data. This method is used by those skilled in the art. (Wuthrich, (1986), John Wiley and Sons, New York:176-199; Pflugrath et al. (1986) J. Mol. Biol. 189:383-386; Kline et al. (1986) J. Mol. Biol. 189:377-382.) While the secondary structure of a polypeptide is often readily determined by utilizing two-dimensional NMR data, the spatial connections between individual pieces of secondary structure are not as readily determinable. The coordinates defining a three-dimensional structure of a polypeptide derived from X-ray crystallographic techniques can guide the NMR spectroscopist to an understanding of these spatial interactions between secondary structural elements in a polypeptide of related structure.

The knowledge of spatial interactions between secondary structural elements can greatly simplify Nuclear Overhauser Effect (NOE) data from two-dimensional NMR experiments. Additionally, applying the crystallographic coordinates after the determination of secondary structure by NMR techniques only simplifies the assignment of NOEs relating to particular amino acids in the polypeptide sequence and does not greatly bias the NMR analysis of polypeptide structure. Conversely, using the crystallographic coordinates to simplify NOE data while determining secondary structure of the polypeptide would bias the NMR analysis of protein structure.

VIII. Structure-Based Design of Modulators of Phosphodiesterase Function Utilizing Structural Coordinates Structure-based modulator design and identification methods are powerful techniques that can involve searches of computer databases containing a wide variety of potential modulators and chemical functional groups. The computerized design and identification of modulators is useful as the computer databases contain more compounds than the chemical libraries, often by an order of magnitude. For reviews of structure-based drug design and identification (see Kuntz et al. (1994), *Acc. Chem. Res.* 27:117; Guida (1994) *Current Opinion in Struc. Biol.* 4: 777; Colman (1994) *Current Opinion in Struc. Biol.* 4: 868).

The three dimensional structure of a polypeptide defined by structural coordinates can be utilized by these design methods, for example, the structural coordinates of Table 1 of U.S. Provisional Application No. 60/569,435, filed May 6, 2004, which is hereby incorporated by reference in its entirety for all purposes. In addition, the three dimensional structures of phosphodiesterases determined by the homology, molecular replacement, and NMR techniques described herein can also be applied to modulator design and identification methods.

For identifying modulators, structural information for a native phosphodiesterase, in particular, structural information for the active site of the phosphodiesterase, can be used. However, it may be advantageous to utilize structural information from one or more co-crystals of the phosphodiesterase with one or more binding compounds. It can also be advantageous if the binding compound has a structural core in common with test compounds.

Design by Searching Molecular Data Bases

One method of rational design searches for modulators by docking the computer representations of compounds from a database of molecules. Publicly available databases include, for example:

a) ACD from Molecular Designs Limited
b) NCI from National Cancer Institute
c) CCDC from Cambridge Crystallographic Data Center
d) CAST from Chemical Abstract Service
e) Derwent from Derwent Information Limited
f) Maybridge from Maybridge Chemical Company LTD
g) Aldrich from Aldrich Chemical Company
h) Directory of Natural Products from Chapman & Hall One such data base (ACD distributed by Molecular Designs Limited Information Systems) contains compounds that are synthetically derived or are natural products. Methods available to those skilled in the art can convert a data set represented in two dimensions to one represented in three dimensions. These methods are enabled by such computer programs as CONCORD from Tripos Associates or DE-Converter from Molecular Simulations Limited.

Multiple methods of structure-based modulator design are known to those in the art. (Kuntz et al., (1982), *J. Mol. Biol.* 162: 269; Kuntz et aZ., (1994), *Acc. Chern. Res.* 27: 117; Meng et al., (1992), *J. Compt. Chem.* 13: 505; Bohm, (1994), *J. Comp. Aided Molec. Design* 8: 623.)

A computer program widely utilized by those skilled in the art of rational modulator design is DOCK from the University of California in San Francisco. The general methods utilized by this computer program and programs like it are described in three applications below. More detailed information regarding some of these techniques can be found in the Accelerys User Guide, 1995. A typical computer program used for this purpose can perform a processes comprising the following steps or functions:

(a) remove the existing compound from the protein;
(b) dock the structure of another compound into the active-site using the computer program (such as DOCK) or by interactively moving the compound into the active-site;
(c) characterize the space between the compound and the active-site atoms;
(d) search libraries for molecular fragments which (i) can fit into the empty space between the compound and the active-site, and (ii) can be linked to the compound; and
(e) link the fragments found above to the compound and evaluate the new modified compound.

Part (c) refers to characterizing the geometry and the complementary interactions formed between the atoms of the active site and the compounds. A favorable geometric fit is attained when a significant surface area is shared between the compound and active-site atoms without forming unfavorable steric interactions. One skilled in the art would note that the method can be performed by skipping parts (d) and (e) and screening a database of many compounds.

Structure-based design and identification of modulators of phosphodiesterase function can be used in conjunction with assay screening. As large computer databases of compounds (around 10,000 compounds) can be searched in a matter of hours or even less, the computer-based method can narrow the compounds tested as potential modulators of phosphodiesterase function in biochemical or cellular assays.

The above descriptions of structure-based modulator design are not all encompassing and other methods are reported in the literature and can be used, e.g.:

(1) CAVEAT: Bartlett et al.,(1989), in Chemical and Biological Problems in Molecular Recognition, Roberts, S. M.; Ley, S. V.; Campbell, M. M. eds.; *Royal Society of Chemistry*: Cambridge, pp. 182-196.
(2) FLOG: Miller et al., (1994), *J. Comp. Aided Molec. Design* 8:153.
(3) PRO Modulator: Clark et al., (1995), *J. Comp. Aided Molec. Design* 9:13.
(4) MCSS: Miranker and Karplus, (1991), *Proteins: Structure, Function, and Genetics* 11:29.
(5) AUTODOCK: Goodsell and Olson, (1990), *Proteins: Structure, Function, and Genetics* 8:195.
(6) GRID: Goodford, (1985), *J. Med. Chem.* 28:849.

Design by Modifying Compounds in Complex with PDE4B

Another way of identifying compounds as potential modulators is to modify an existing modulator in the polypeptide active site. For example, the computer representation of modulators can be modified within the computer representation of a PDE4B active site. Detailed instructions for this technique can be found, for example, in the Accelerys User Manual, 1995 in LUDI. The computer representation of the modulator is typically modified by the deletion of a chemical group or groups or by the addition of a chemical group or groups.

Upon each modification to the compound, the atoms of the modified compound and active site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

Design by Modifying the Structure of Compounds that Bind PDE4B

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound that has been removed from the active site of the three dimensional structure of a compound-phosphodiesterase complex. Operating the program on such a compound is preferable since it is in a biologically active conformation.

A modulator construction computer program is a computer program that may be used to replace computer representations of chemical groups in a compound complexed with a phosphodiesterase or other biomolecule with groups from a computer database. A modulator searching computer program is a computer program that may be used to search computer representations of compounds from a computer data base that have similar three dimensional structures and similar chemical groups as compound bound to a particular biomolecule.

A typical program can operate by using the following general steps:
(a) map the compounds by chemical features such as by hydrogen bond donors or acceptors, hydrophobic/lipophilic sites, positively ionizable sites, or negatively ionizable sites;
(b) add geometric constraints to the mapped features; and
(c) search databases with the model generated in (b).

Those skilled in the art also recognize that not all of the possible chemical features of the compound need be present in the model of (b). One can use any subset of the model to generate different models for data base searches.

Modulator Design Using Molecular Scaffolds

The present invention can also advantageously utilize methods for designing compounds, designated as molecular scaffolds, that can act broadly across families of molecules and/or for using a molecular scaffold to design ligands that target individual or multiple members of those families. Such design using molecular scaffolds is described in Hirth and Milburn, U.S. patent application Ser. No. 10/377,268, which is incorporated herein by reference in its entirety. Such design and development using molecular scaffolds is described, in part, below.

In preferred embodiments, the molecules can be proteins and a set of chemical compounds can be assembled that have properties such that they are 1) chemically designed to act on certain protein families and/or 2) behave more like molecular scaffolds, meaning that they have chemical substructures that make them specific for binding to one or more proteins in a family of interest. Alternatively, molecular scaffolds can be designed that are preferentially active on an individual target molecule.

Useful chemical properties of molecular scaffolds can include one or more of the following characteristics, but are not limited thereto: an average molecular weight below about 350 daltons, or between from about 150 to about 350 daltons, or from about 150 to about 300 daltons; having a clogP below 3; a number of rotatable bonds of less than 4; a number of hydrogen bond donors and acceptors below 5 or below 4; a polar surface area of less than 50 Å$^2$; binding at protein binding sites in an orientation so that chemical substituents from a combinatorial library that are attached to the scaffold can be projected into pockets in the protein binding site; and possessing chemically tractable structures at its substituent attachment points that can be modified, thereby enabling rapid library construction.

By "clog P" is meant the calculated log P of a compound, "P" referring to the partition coefficient between octanol and water.

The term "Molecular Polar Surface Area (PSA)" refers to the sum of surface contributions of polar atoms (usually oxygens, nitrogens and attached hydrogens) in a molecule. The polar surface area has been shown to correlate well with drug transport properties, such as intestinal absorption, or blood-brain barrier penetration.

Additional useful chemical properties of distinct compounds for inclusion in a combinatorial library include the ability to attach chemical moieties to the compound that will not interfere with binding of the compound to at least one protein of interest, and that will impart desirable properties to the library members, for example, causing the library members to be actively transported to cells and/or organs of interest, or the ability to attach to a device such as a chromatography column (e.g., a streptavidin column through a molecule such as biotin) for uses such as tissue and proteomics profiling purposes.

A person of ordinary skill in the art will realize other properties that can be desirable for the scaffold or library members to have depending on the particular requirements of the use, and that compounds with these properties can also be sought and identified in like manner. Methods of selecting compounds for assay are known to those of ordinary skill in the art, for example, methods and compounds described in U.S. Pat. Nos. 6,288,234, 6,090,912, 5,840,485, each of which is hereby incorporated by reference in its entirety, including all charts and drawings.

In various embodiments, the present invention provides methods of designing ligands that bind to a plurality of members of a molecular family, where the ligands contain a common molecular scaffold. Thus, a compound set can be assayed for binding to a plurality of members of a molecular family, e.g., a protein family. One or more compounds that bind to a plurality of family members can be identified as molecular scaffolds. When the orientation of the scaffold at the binding site of the target molecules has been determined and chemically tractable structures have been identified, a set of ligands can be synthesized starting with one or a few molecular scaffolds to arrive at a plurality of ligands, wherein each ligand binds to a separate target molecule of the molecular family with altered or changed binding affinity or binding specificity relative to the scaffold. Thus, a plurality of drug lead molecules can be designed to preferentially target individual members of a molecular family based on the same molecular scaffold, and act on them in a specific manner.

IX. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. The assays of the present invention can also include assaying compounds for low affinity binding to the target molecule. A large variety of assays indicative of binding are known for different target types and can be used for this invention. Compounds that act broadly across protein families are not likely to have a high affinity against individual targets, due to the broad nature of their binding. Thus, assays described herein allow for the identification of compounds that bind with low affinity, very low affinity, and extremely low affinity. Therefore, potency (or binding affinity) is not the primary, nor even the most important, indicia of identification of a potentially useful binding compound. Rather, even those compounds that bind with low affinity, very low affinity, or extremely low affinity can be considered as molecular scaffolds that can continue to the next phase of the ligand design process.

By binding with "low affinity" is meant binding to the target molecule with a dissociation constant ($k_d$) of greater than 1 µM under standard conditions. By binding with "very low affinity" is meant binding with a $k_d$ of above about 100

μM under standard conditions. By binding with "extremely low affinity" is meant binding at a $k_d$ of above about 1 mM under standard conditions. By "moderate affinity" is meant binding with a $k_d$ of from about 200 nM to about 1 μM under standard conditions. By "moderately high affinity" is meant binding at a $k_d$ of from about 1 nM to about 200 nM. By binding at "high affinity" is meant binding at a $k_d$ of below about 1 nM under standard conditions. For example, low affinity binding can occur because of a poorer fit into the binding site of the target molecule or because of a smaller number of non-covalent bonds, or weaker covalent bonds present to cause binding of the scaffold or ligand to the binding site of the target molecule relative to instances where higher affinity binding occurs. The standard conditions for binding are at pH 7.2 at 37° C. for one hour. For example, 100 μl/well can be used in HEPES 50 mM buffer at pH 7.2, NaCl 15 mM, ATP 2 μM, and bovine serum albumin 1 ug/well, 37° C. for one hour.

Binding compounds can also be characterized by their effect on the activity of the target molecule. Thus, a "low activity" compound has an inhibitory concentration ($IC_{50}$) or excitation concentration ($EC_{50}$) of greater than 1 μM under standard conditions. By "very low activity" is meant an $IC_{50}$ or $EC_{50}$ of above 100 μM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 μM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

To design or discover scaffolds that act broadly across protein families, proteins of interest can be assayed against a compound collection or set. The assays can preferably be enzymatic or binding assays. In some embodiments it may be desirable to enhance the solubility of the compounds being screened and then analyze all compounds that show activity in the assay, including those that bind with low affinity or produce a signal with greater than about three times the standard deviation of the background signal. The assays can be any suitable assay such as, for example, binding assays that measure the binding affinity between two binding partners.

Various types of screening assays that can be useful in the practice of the present invention are known in the art, such as those described in U.S. Pat. Nos. 5,763,198, 5,747,276, 5,877,007, 6,243,980, 6,294,330, and 6,294,330, each of which is hereby incorporated by reference in its entirety, including all charts and drawings.

In various embodiments of the assays at least one compound, at least about 5%, at least about 10%, at least about 15%, at least about 20%, or at least about 25% of the compounds can bind with low affinity. In general, up to about 20% of the compounds can show activity in the screening assay and these compounds can then be analyzed directly with high-throughput co-crystallography, computational analysis to group the compounds into classes with common structural properties (e.g., structural core and/or shape and polarity characteristics), and the identification of common chemical structures between compounds that show activity.

The person of ordinary skill in the art will realize that decisions can be based on criteria that are appropriate for the needs of the particular situation, and that the decisions can be made by computer software programs. Classes can be created containing almost any number of scaffolds, and the criteria selected can be based on increasingly exacting criteria until an arbitrary number of scaffolds is arrived at for each class that is deemed to be advantageous.

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, *Methods in Molecular Biology.* 121: 313-21; Liparoto et al., (1999) Biosensor analysis of the interleukin-2 receptor complex, *Journal of Molecular Recognition.* 12:316-21; Lipschultz et al., (2000) Experimental design for analysis of complex kinetics using surface plasmon resonance, *Methods.* 20(3):310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, *Biosensors & Bioelectronics.* 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology.* 1:378-83; O'Shannessy et al., (1996) Interpretation of deviations from pseudo-first-order kinetic behavior in the characterization of ligand binding by biosensor technology, *Analytical Biochemistry.* 236:275-83; Malmborg et al., (1995) BIAcore as a tool in antibody engineering, *Journal of Immunological Methods.* 183:7-13; Van Regenmortel, (1994) Use of biosensors to characterize recombinant proteins, *Developments in Biological Standardization.* 83:143-51; and O'Shannessy, (1994) Determination of kinetic rate and equilibrium binding constants for macromolecular interactions: a critique of the surface plasmon resonance literature, *Current Opinions in Biotechnology.* 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owicki et al., (1997), Application of Fluorescence Polarization Assays in High-Throughput Screening, *Genetic Engineering News*, 17:27.

FP is particularly desirable since its readout is independent of the emission intensity (Checovich, W. J., et al., (1995) *Nature* 375:254-256; Dandliker, W. B., et al., (1981) *Methods in Enzymology* 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY®

FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multiwell plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a FMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 (SEQ ID NO: 18) or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

Assay Compounds and Molecular Scaffolds

Preferred characteristics of a scaffold include being of low molecular weight (e.g., less than 350 Da, or from about 100 to about 350 daltons, or from about 150 to about 300 daltons). Preferably clog P of a scaffold is from −1 to 8, more preferably less than 6, 5, or 4, most preferably less than 3. In particular embodiments the clogP is in a range −1 to an upper limit of 2, 3, 4, 5, 6, or 8; or is in a range of 0 to an upper limit of 2, 3, 4, 5, 6, or 8. Preferably the number of rotatable bonds is less than 5, more preferably less than 4. Preferably the number of hydrogen bond donors and acceptors is below 6, more preferably below 5. An additional criterion that can be useful is a polar surface area of less than 5. Guidance that can be useful in identifying criteria for a particular application can be found in Lipinski et al., (1997) Advanced Drug Delivery Reviews 23 3-25, which is hereby incorporated by reference in its entirety.

A scaffold may preferably bind to a given protein binding site in a configuration that causes substituent moieties of the scaffold to be situated in pockets of the protein binding site. Also, possessing chemically tractable groups that can be chemically modified, particularly through synthetic reactions, to easily create a combinatorial library can be a preferred characteristic of the scaffold. Also preferred can be having positions on the scaffold to which other moieties can be attached, which do not interfere with binding of the scaffold to the protein(s) of interest but do cause the scaffold to achieve a desirable property, for example, active transport of the scaffold to cells and/or organs, enabling the scaffold to be attached to a chromatographic column to facilitate analysis, or another desirable property. A molecular scaffold can bind to a target molecule with any affinity, such as binding at high affinity, moderate affinity, low affinity, very low affinity, or extremely low affinity.

Thus, the above criteria can be utilized to select many compounds for testing that have the desired attributes. Many compounds having the criteria described are available in the commercial market, and may be selected for assaying depending on the specific needs to which the methods are to be applied.

A "compound library" or "library" is a collection of different compounds having different chemical structures. A compound library is screenable, that is, the compound library members therein may be subject to screening assays. In preferred embodiments, the library members can have a molecular weight of from about 100 to about 350 daltons, or from about 150 to about 350 daltons. Examples of libraries are provided above.

Libraries of the present invention can contain at least one compound than binds to the target molecule at low affinity. Libraries of candidate compounds can be assayed by many different assays, such as those described above, e.g., a fluorescence polarization assay. Libraries may consist of chemically synthesized peptides, peptidomimetics, or arrays of combinatorial chemicals that are large or small, focused or nonfocused. By "focused" it is meant that the collection of compounds is prepared using the structure of previously characterized compounds and/or pharmacophores.

Compound libraries may contain molecules isolated from natural sources, artificially synthesized molecules, or molecules synthesized, isolated, or otherwise prepared in such a manner so as to have one or more moieties variable, e.g., moieties that are independently isolated or randomly synthesized. Types of molecules in compound libraries include but are not limited to organic compounds, polypeptides and nucleic acids as those terms are used herein, and derivatives, conjugates and mixtures thereof.

Compound libraries of the invention may be purchased on the commercial market or prepared or obtained by any means including, but not limited to, combinatorial chemistry techniques, fermentation methods, plant and cellular extraction procedures and the like (see, e.g., Cwirla et al., (1990) *Biochemistry*, 87, 6378-6382; Houghten et al., (1991) *Nature*, 354, 84-86; Lam et al., (1991) *Nature*, 354, 82-84; Brenner et al., (1992) *Proc. Natl. Acad. Sci. USA*, 89, 5381-5383; R. A. Houghten, (1993) *Trends Genet.*, 9, 235-239; E. R. Felder, (1994) *Chimia*, 48, 512-541; Gallop et al., (1994) *J. Med. Chem.*, 37, 1233-1251; Gordon et al., (1994) *J. Med. Chem.*, 37, 1385-1401; Carell et al., (1995) *Chem. Biol.*, 3, 171-183; Madden et al., *Perspectives in Drug Discovery and Design* 2, 269-282; Lebl et al., (1995) *Biopolymers*, 37 177-198); small molecules assembled around a shared molecular structure; collections of chemicals that have been assembled by various commercial and noncommercial groups, natural products; extracts of marine organisms, fungi, bacteria, and plants.

Preferred libraries can be prepared in a homogenous reaction mixture, and separation of unreacted reagents from members of the library is not required prior to screening. Although many combinatorial chemistry approaches are based on solid state chemistry, liquid phase combinatorial chemistry is capable of generating libraries (Sun CM., (1999) Recent advances in liquid-phase combinatorial chemistry, *Combinatorial Chemistry & High Throughput Screening*. 2:299-318).

Libraries of a variety of types of molecules are prepared in order to obtain members therefrom having one or more preselected attributes that can be prepared by a variety of techniques, including but not limited to parallel array synthesis (Houghton, (2000) *Annu Rev Pharmacol Toxicol* 40:273-82, Parallel array and mixture-based synthetic combinatorial chemistry; solution-phase combinatorial chemistry (Merritt, (1998) *Comb Chem High Throughput Screen* 1(2):57-72, Solution phase combinatorial chemistry, Coe et al., (1998-99) *Mol Divers;* 4(1):31-8, Solution-phase combinatorial chemistry, Sun, (1999) *Comb Chem High Throughput Screen* 2(6): 299-318, Recent advances in liquid-phase combinatorial chemistry); synthesis on soluble polymer (Gravert et al., (1997) *Curr Opin Chem Biol* 1(1):107-13, Synthesis on soluble polymers: new reactions and the construction of small molecules); and the like. See, e.g., Dolle et al., (1999) *J Comb Chem* 1(4):235-82, Comprehensive survey of cominatorial library synthesis: 1998. Freidinger RM., (1999) Nonpeptidic ligands for peptide and protein receptors, Current Opinion in Chemical Biology; and Kundu et al., *Prog Drug Res;*53:89-156, Combinatorial chemistry: polymer supported synthesis of peptide and non-peptide libraries). Compounds may be clinically tagged for ease of identification (Chabala, (1995) *Curr Opin Biotechnol* 6(6):633-9, Solid-phase combinatorial chemistry and novel tagging methods for identifying leads).

The combinatorial synthesis of carbohydrates and libraries containing oligosaccharides have been described (Schweizer et al., (1999) *Curr Opin Chem Biol* 3(3):291-8, Combinatorial synthesis of carbohydrates). The synthesis of naturalproduct based compound libraries has been described (Wessjohann, (2000) *Curr Opin Chem Biol* 4(3):303-9, Synthesis of natural-product based compound libraries).

Libraries of nucleic acids are prepared by various techniques, including by way of non-limiting example the ones described herein, for the isolation of aptamers. Libraries that include oligonucleotides and polyaminooligonucleotides (Markiewicz et al., (2000) Synthetic oligonucleotide combinatorial libraries and their applications, *Farmaco*. 55:174-7) displayed on streptavidin magnetic beads are known. Nucleic acid libraries are known that can be coupled to parallel sampling and be deconvoluted without complex procedures such as automated mass spectrometry (Enjalbal C. Martinez J. Aubagnac J L, (2000) Mass spectrometry in combinatorial chemistry, *Mass Spectrometry Reviews*. 19:139-61) and parallel tagging. (Perrin DM., Nucleic acids for recognition and catalysis: landmarks, limitations, and looking to the future, *Combinatorial Chemistry & High Throughput Screening* 3:243-69).

Peptidomimetics are identified using combinatorial chemistry and solid phase synthesis (Kim HO. Kahn M., (2000) A merger of rational drug design and combinatorial chemistry: development and application of peptide secondary structure mimetics, Combinatorial Chemistry & High Throughput Screening 3:167-83; al-Obeidi, (1998) *Mol Biotechnol* 9(3): 205-23, Peptide and peptidomimetric libraries. Molecular diversity and drug design). The synthesis may be entirely random or based in part on a known polypeptide.

Polypeptide libraries can be prepared according to various techniques. In brief, phage display techniques can be used to produce polypeptide ligands (Gram H., (1999) Phage display in proteolysis and signal transduction, Combinatorial Chemistry & High Throughput Screening. 2:19-28) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Large libraries of individual variants of human single chain Fv antibodies have been produced. See, e.g., Siegel R W. Allen B. Pavlik P. Marks J D. Bradbury A., (2000) Mass spectral analysis of a protein complex using single-chain antibodies selected on a peptide target: applications to functional genomics, *Journal of Molecular Biology* 302:285-93; Poul M A. Becerril B. Nielsen U B. Morisson P. Marks J D.,(2000) Selection of tumor-specific internalizing human antibodies from phage libraries. Source *Journal of Molecular Biology*. 301:1149-61; Amersdorfer P. Marks JD., (2001) Phage libraries for generation of anti-botulinum scFv antibodies, *Methods in Molecular Biology*. 145:219-40; Hughes-Jones N C. Bye J M. Gorick B D. Marks J D. Ouwehand W H., (1999) Synthesis of Rh Fv phage-antibodies using VH and VL germline genes, *British Journal of Haematology*. 105: 811-6; McCall A M. Amoroso A R. Sautes C. Marks J D. Weiner L M., (1998) Characterization of anti-mouse Fc gamma RII single-chain Fv fragments derived from human phage display libraries, *Immunotechnology*. 4:71-87; Sheets M D. Amersdorfer P. Finnern R. Sargent P. Lindquist E. Schier R. Hemingsen G. Wong C. Gerhart J C. Marks J D. Lindquist E., (1998) Efficient construction of a large nonimmune phage antibody library: the production of high-affinity human single-chain antibodies to protein antigens (published erratum appears in *Proc Natl Acad Sci USA* 1999 96:795), *Proc Natl Acad Sci USA* 95:6157-62).

Focused or smart chemical and pharmacophore libraries can be designed with the help of sophisticated strategies involving computational chemistry (e.g., Kundu B. Khare S K. Rastogi S K., (1999) Combinatorial chemistry: polymer supported synthesis of peptide and non-peptide libraries, *Progress in Drug Research* 53:89-156) and the use of structure-based ligands using database searching and docking, de novo drug design and estimation of ligand binding affinities (Joseph-McCarthy D., (1999) Computational approaches to structure-based ligand design, *Pharmacology & Therapeutics* 84:179-91; Kirkpatrick D L. Watson S. Ulhaq S., (1999) Structure-based drug design: combinatorial chemistry and molecular modeling, *Combinatorial Chemistry & High Throughput Screening.* 2:211-21; Eliseev A V. Lehn J M., (1999) Dynamic combinatorial chemistry: evolutionary formation and screening of molecular libraries, *Current Topics in Microbiology & Immunology* 243:159-72; Bolger et al., (1991) *Methods Enz.* 203:21-45; Martin, (1991) *Methods Enz.* 203:587-613; Neidle et al., (1991) *Methods Enz.* 203: 433-458; U.S. Pat. No. 6,178,384).

X. Crystallography

After binding compounds have been determined, the orientation of compound bound to target is determined. Preferably this determination involves crystallography on co-crystals of molecular scaffold compounds with target. Most protein crystallographic platforms can preferably be designed to analyze up to about 500 co-complexes of compounds, ligands, or molecular scaffolds bound to protein targets due to the physical parameters of the instruments and convenience of operation. If the number of scaffolds that have binding activity exceeds a number convenient for the application of crystallography methods, the scaffolds can be placed into groups based on having at least one common chemical structure or other desirable characteristics, and representative compounds can be selected from one or more of the classes. Classes can be made with increasingly exacting criteria until a desired number of classes (e.g., 500) is obtained. The classes can be based on chemical structure similarities between molecular scaffolds in the class, e.g., all possess a pyrrole ring, benzene ring, or other chemical feature. Likewise, classes can be based on shape characteristics, e.g., space-filling characteristics.

The co-crystallography analysis can be performed by co-complexing each scaffold with its target at concentrations of the scaffold that showed activity in the screening assay. This co-complexing can be accomplished with the use of low percentage organic solvents with the target molecule and then concentrating the target with each of the scaffolds. In preferred embodiments these solvents are less than 5% organic solvent such as dimethyl sulfoxide (DMSO), ethanol, methanol, or ethylene glycol in water or another aqueous solvent. Each scaffold complexed to the target molecule can then be screened with a suitable number of crystallization screening conditions at both 4 and 20 degrees. In preferred embodiments, about 96 crystallization screening conditions can be performed in order to obtain sufficient information about the co-complexation and crystallization conditions, and the orientation of the scaffold at the binding site of the target molecule. Crystal structures can then be analyzed to determine how the bound scaffold is oriented physically within the binding site or within one or more binding pockets of the molecular family member.

It is desirable to determine the atomic coordinates of the compounds bound to the target proteins in order to determine which is a most suitable scaffold for the protein family. X-ray crystallographic analysis is therefore most preferable for determining the atomic coordinates. Those compounds selected can be further tested with the application of medicinal chemistry. Compounds can be selected for medicinal chemistry testing based on their binding position in the target molecule. For example, when the compound binds at a binding site, the compound's binding position in the binding site of the target molecule can be considered with respect to the chemistry that can be performed on chemically tractable structures or sub-structures of the compound, and how such modifications on the compound might interact with structures or sub-structures on the binding site of the target. Thus, one can explore the binding site of the target and the chemistry of the scaffold in order to make decisions on how to modify the scaffold to arrive at a ligand with higher potency and/or selectivity. This process allows for more direct design of ligands, by utilizing structural and chemical information obtained directly from the co-complex, thereby enabling one to more efficiently and quickly design lead compounds that are likely to lead to beneficial drug products. In various embodiments it may be desirable to perform co-crystallography on all scaffolds that bind, or only those that bind with a particular affinity, for example, only those that bind with high affinity, moderate affinity, low affinity, very low affinity, or extremely low affinity. It may also be advantageous to perform co-crystallography on a selection of scaffolds that bind with any combination of affinities.

Standard X-ray protein diffraction studies such as by using a Rigaku RU-200® (Rigaku, Tokyo, Japan) with an X-ray imaging plate detector or a synchrotron beam-line can be performed on co-crystals and the diffraction data measured on a standard X-ray detector, such as a CCD detector or an X-ray imaging plate detector.

Performing X-ray crystallography on about 200 co-crystals should generally lead to about 50 co-crystals structures, which should provide about 10 scaffolds for validation in chemistry, which should finally result in about 5 selective leads for target molecules.

Virtual Assays

Commercially available software that generates three-dimensional graphical representations of the complexed target and compound from a set of coordinates provided can be used to illustrate and study how a compound is oriented when bound to a target. (e.g., QUANTA®, Accelerys, San Diego, Calif.). Thus, the existence of binding pockets at the binding site of the targets can be particularly useful in the present invention. These binding pockets are revealed by the crystallographic structure determination and show the precise chemical interactions involved in binding the compound to the binding site of the target. The person of ordinary skill will realize that the illustrations can also be used to decide where chemical groups might be added, substituted, modified, or deleted from the scaffold to enhance binding or another desirable effect, by considering where unoccupied space is located in the complex and which chemical substructures might have suitable size and/or charge characteristics to fill it. The person of ordinary skill will also realize that regions within the binding site can be flexible and its properties can change as a result of scaffold binding, and that chemical groups can be specifically targeted to those regions to achieve a desired effect. Specific locations on the molecular scaffold can be considered with reference to where a suitable chemical substructure can be attached and in which conformation, and which site has the most advantageous chemistry available.

An understanding of the forces that bind the compounds to the target proteins reveals which compounds can most advantageously be used as scaffolds, and which properties can most effectively be manipulated in the design of ligands. The person of ordinary skill will realize that steric, ionic, hydrogen bond, and other forces can be considered for their contribution to the maintenance or enhancement of the target-compound complex. Additional data can be obtained with automated computational methods, such as docking and/or Free Energy Perturbations (FEP), to account for other energetic effects such as desolvation penalties. The compounds selected can be used to generate information about the chemical interactions with the target or for elucidating chemical modifications that can enhance selectivity of binding of the compound.

Computer models, such as homology models (i.e., based on a known, experimentally derived structure) can be constructed using data from the co-crystal structures. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

Additives that promote co-crystallization can of course be included in the target molecule formulation in order to enhance the formation of co-crystals. In the case of proteins or enzymes, the scaffold to be tested can be added to the protein formulation, which is preferably present at a concentration of approximately 1 mg/ml. The formulation can also contain between 0%-10% (v/v) organic solvent, e.g. DMSO, methanol, ethanol, propane diol, or 1,3 dimethyl propane diol (MPD) or some combination of those organic solvents. Compounds are preferably solubilized in the organic solvent at a concentration of about 10 mM and added to the protein sample at a concentration of about 100 mM. The protein-compound complex is then concentrated to a final concentration of protein of from about 5 to about 20 mg/ml. The complexation and concentration steps can conveniently be performed using a 96-well formatted concentration apparatus (e.g., Amicon Inc., Piscataway, N.J.). Buffers and other reagents present in the formulation being crystallized can contain other components that promote crystallization or are compatible with crystallization conditions, such as DTT, propane diol, glycerol.

The crystallization experiment can be set-up by placing small aliquots of the concentrated protein-compound complex (1 μl) in a 96 well format and sampling under 96 crystallization conditions. (Other screening formats can also be used, e.g., plates with greater than 96 wells.) Crystals can typically be obtained using standard crystallization protocols that can involve the 96 well crystallization plate being placed at different temperatures. Co-crystallization varying factors other than temperature can also be considered for each protein-compound complex if desirable. For example, atmospheric pressure, the presence or absence of light or oxygen, a change in gravity, and many other variables can all be tested. The person of ordinary skill in the art will realize other variables that can advantageously be varied and considered.

Ligand Design and Preparation

The design and preparation of ligands can be performed with or without structural and/or co-crystallization data by considering the chemical structures in common between the active scaffolds of a set. In this process structure-activity hypotheses can be formed and those chemical structures found to be present in a substantial number of the scaffolds, including those that bind with low affinity, can be presumed to have some effect on the binding of the scaffold. This binding can be presumed to induce a desired biochemical effect when it occurs in a biological system (e.g., a treated mammal). New or modified scaffolds or combinatorial libraries derived from scaffolds can be tested to disprove the maximum number of binding and/or structure-activity hypotheses. The remaining hypotheses can then be used to design ligands that achieve a desired binding and biochemical effect.

But in many cases it will be preferred to have co-crystallography data for consideration of how to modify the scaffold to achieve the desired binding effect (e.g., binding at higher affinity or with higher selectivity). Using the case of proteins and enzymes, co-crystallography data shows the binding pocket of the protein with the molecular scaffold bound to the binding site, and it will be apparent that a modification can be made to a chemically tractable group on the scaffold. For example, a small volume of space at a protein binding site or pocket might be filled by modifying the scaffold to include a small chemical group that fills the volume. Filling the void volume can be expected to result in a greater binding affinity, or the loss of undesirable binding to another member of the protein family. Similarly, the co-crystallography data may show that deletion of a chemical group on the scaffold may decrease a hindrance to binding and result in greater binding affinity or specificity.

It can be desirable to take advantage of the presence of a charged chemical group located at the binding site or pocket of the protein. For example, a positively charged group can be complemented with a negatively charged group introduced on the molecular scaffold. This can be expected to increase binding affinity or binding specificity, thereby resulting in a more desirable ligand. In many cases, regions of protein binding sites or pockets are known to vary from one family member to another based on the amino acid differences in those regions. Chemical additions in such regions can result in the creation or elimination of certain interactions (e.g., hydrophobic, electrostatic, or entropic) that allow a compound to be more specific for one protein target over another or to bind with greater affinity, thereby enabling one to synthesize a compound with greater selectivity or affinity for a particular family member. Additionally, certain regions can contain amino acids that are known to be more flexible than others. This often occurs in amino acids contained in loops connecting elements of the secondary structure of the protein, such as alpha helices or beta strands. Additions of chemical moieties can also be directed to these flexible regions in order to increase the likelihood of a specific interaction occurring between the protein target of interest and the compound. Virtual screening methods can also be conducted in silico to assess the effect of chemical additions, subtractions, modifications, and/or substitutions on compounds with respect to members of a protein family or class.

The addition, subtraction, or modification of a chemical structure or sub-structure to a scaffold can be performed with any suitable chemical moiety. For example the following moieties, which are provided by way of example and are not intended to be limiting, can be utilized: hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbamylthio, cyclohexyl, pyridyl, piperidinyl, alkylamino, amino, nitro, mercapto, cyano, hydroxyl, a halogen atom, halomethyl, an oxygen atom (e.g., forming a ketone or N-oxide) or a sulphur atom (e.g., forming a thiol, thione, di-alkylsulfoxide or sulfone) are all examples of moieties that can be utilized.

Additional examples of structures or sub-structures that may be utilized are an aryl optionally substituted with one, two, or three substituents independently selected from the group consisting of alkyl, alkoxy, halogen, trihalomethyl, carboxylate, carboxamide, nitro, and ester moieties; an amine of formula $-NX_2X_3$, where $X_2$ and $X_3$ are independently selected from the group consisting of hydrogen, saturated or unsaturated alkyl, and homocyclic or heterocyclic ring moieties; halogen or trihalomethyl; a ketone of formula $-COX_4$, where $X_4$ is selected from the group consisting of alkyl and homocyclic or heterocyclic ring moieties; a carboxylic acid of formula $-(X_5)_n COOH$ or ester of formula $(X_6)_n COOX_7$, where $X_5$, $X_6$, and $X_7$ and are independently selected from the group consisting of alkyl and homocyclic or heterocyclic ring moieties and where n is 0 or 1; an alcohol of formula $(X_8)_n OH$ or an alkoxy moiety of formula $-(X_8)_n OX_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; an amide of formula $NHCOX_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; $SO_2$, $NX_{11}X_{12}$, where $X_{11}$ and $X_{12}$ are selected from the group consisting of hydrogen, alkyl, and homocyclic or heterocyclic ring moieties; a homocyclic or heterocyclic ring moiety optionally substituted with one, two, or three substituents independently selected from the group consisting of alkyl, alkoxy, halogen, trihalomethyl, carboxylate, carboxamide, nitro, and ester moieties; an aldehyde of formula $-CHO$; a sulfone of formula $-SO_2X_{13}$, where $X_{13}$ is selected from the group consisting of saturated or unsaturated alkyl and homocyclic or heterocyclic ring moieties; and a nitro of formula $-NO_2$.

Identification of Attachment Sites on Molecular Scaffolds and Ligands

In addition to the identification and development of ligands for phosphodiesterases and other enzymes, determination of the orientation of a molecular scaffold or other binding compound in a binding site allows identification of energetically allowed sites for attachment of the binding molecule to another component. For such sites, any free energy change associated with the presence of the attached component should not destablize the binding of the compound to the phosphodiesterase to an extent that will disrupt the binding. Preferably, the binding energy with the attachment should be at least 4 kcal/mol., more preferably at least 6, 8, 10, 12, 15, or 20 kcal/mol. Preferably, the presence of the attachment at the particular site reduces binding energy by no more than 3, 4, 5, 8, 10, 12, or 15 kcal/mol.

In many cases, suitable attachment sites will be those that are exposed to solvent when the binding compound is bound in the binding site. In some cases, attachment sites can be used that will result in small displacements of a portion of the enzyme without an excessive energetic cost. Exposed sites can be identified in various ways. For example, exposed sites can be identified using a graphic display or 3-dimensional model. In a grahic display, such as a computer display, an image of a compound bound in a binding site can be visually inspected to reveal atoms or groups on the compound that are exposed to solvent and oriented such that attachment at such atom or group would not preclude binding of the enzyme and binding compound. Energetic costs of attachment can be calculated based on changes or distortions that would be caused by the attachment as well as entropic changes.

Many different types of components can be attached. Persons with skill are familiar with the chemistries used for various attachments. Examples of components that can be attached include, without limitation: solid phase components such as beads, plates, chips, and wells; a direct or indirect label; a linker, which may be a traceless linker; among others. Such linkers can themselves be attached to other components, e.g., to solid phase media, labels, and/or binding moieties.

The binding energy of a compound and the effects on binding energy for attaching the molecule to another component can be calculated approximately using any of a variety of available software or by manual calculation. An example is the following:

Calculations were performed to estimate binding energies of different organic molecules to two Kinases: PIM-1 and CDK2. The organic molecules considered included Staurosporine, identified compounds that bind to PDE5A, and several linkers.

Calculated binding energies between protein-ligand complexes were obtained using the FlexX score (an implementation of the Bohm scoring function) within the Tripos software suite. The form for that equation is shown in the equation below:

$$\Delta G\text{bind} = \Delta G\text{tr} + \Delta G\text{hb} + \Delta G\text{ion} + \Delta G\text{lipo} + \Delta G\text{arom} + \Delta G\text{rot}$$

where: $\Delta G\text{tr}$ is a constant term that accounts for the overall loss of rotational and translational entropy of the lignand, $\Delta G\text{hb}$ accounts for hydrogen bonds formed between the ligand and protein, $\Delta G\text{ion}$ accounts for the ionic interactions between the ligand and protein, $\Delta G\text{lipo}$ accounts for the lipophilic interaction that corresponds to the protein-ligand contact surface, $\Delta G\text{arom}$ accounts for interactions between aromatic rings in the protein and ligand, and $\Delta G\text{rot}$ accounts for the entropic penalty of restricting rotatable bonds in the ligand upon binding.

This method estimates the free energy that a lead compound should have to a target protein for which there is a crystal structure, and it accounts for the entropic penalty of flexible linkers. It can therefore be used to estimate the free energy penalty incurred by attaching linkers to molecules being screened and the binding energy that a lead compound should have in order to overcome the free energy penalty of the linker. The method does not account for solvation and the entropic penalty is likely overestimated for cases where the linker is bound to a solid phase through another binding complex, such as a biotin:streptavidin complex.

Co-crystals were aligned by superimposing residues of PIM-1 with corresponding residues in CDK2. The PIM-1 structure used for these calculations was a co-crystal of PIM-1 with a binding compound. The CDK2:Staurosporine co-crystal used was from the Brookhaven database file 1aq1. Hydrogen atoms were added to the proteins and atomic charges were assigned using the AMBER95 parameters within Sybyl. Modifications to the compounds described were made within the Sybyl modeling suite from Tripos.

These calculations indicate that the calculated binding energy for compounds that bind strongly to a given target (such as Staurosporine:CDK2) can be lower than −25 kcal/mol, while the calculated binding affinity for a good scaffold or an unoptimized binding compound can be in the range of −15 to −20. The free energy penalty for attachment to a linker such as the ethylene glycol or hexatriene is estimated as typically being in the range of +5 to +15 kcal/mol.

Linkers

Linkers suitable for use in the invention can be of many different types. Linkers can be selected for particular applications based on factors such as linker chemistry compatible for attachment to a binding compound and to another component utilized in the particular application. Additional factors can include, without limitation, linker length, linker stability, and ability to remove the linker at an appropriate time. Exemplary linkers include, but are not limited to, hexyl, hexatrienyl, ethylene glycol, and peptide linkers. Traceless linkers can also be used, e.g., as described in Plunkett, M. J., and Ellman, J. A., (1995), *J. Org. Chem.*, 60:6006.

Typical functional groups, that are utilized to link binding compound(s), include, but are not limited to, carboxylic acid, amine, hydroxyl, and thiol. (Examples can be found in Solid-supported combinatorial and parallel synthesis of small molecular weight compound libraries; (1998) Tetrahedron organic chemistry series Vol. 17; Pergamon; p85).

Labels

As indicated above, labels can also be attached to a binding compound or to a linker attached to a binding compound. Such attachment may be direct (attached directly to the binding compound) or indirect (attached to a component that is directly or indirectly attached to the binding compound). Such labels allow detection of the compound either directly or indirectly. Attachement of labels can be performed using conventional chemistries. Labels can include, for example, fluorescent labels, radiolabels, light scattering particles, light absorbent particles, magnetic particles, enzymes, and specific binding agents (e.g., biotin or an antibody target moiety).

Solid Phase Media

Additional examples of components that can be attached directly or indirectly to a binding compound include various solid phase media. Similar to attachment of linkers and labels, attachment to solid phase media can be performed using conventional chemistries. Such solid phase media can include, for example, small components such as beads, nano-particles, and fibers (e.g., in suspension or in a gel or chromatographic matrix). Likewise, solid phase media can include larger objects such as plates, chips, slides, and tubes. In many cases, the binding compound will be attached in only a portion of such an objects, e.g., in a spot or other local element on a generally flat surface or in a well or portion of a well.

Identification of Biological Agents

The possession of structural information about a protein also provides for the identification of useful biological agents, such as epitpose for development of antibodies, identification of mutation sites expected to affect activity, and identification of attachment sites allowing attachment of the protein to materials such as labels, linkers, peptides, and solid phase media.

Antibodies (Abs) finds multiple applications in a variety of areas including biotechnology, medicine and diagnosis, and indeed they are one of the most powerful tools for life science research. Abs directed against protein antigens can recognize either linear or native three-dimensional (3D) epitopes. The obtention of Abs that recognize 3D epitopes require the use of whole native protein (or of a portion that assumes a native conformation) as immunogens. Unfortunately, this not always a choice due to various technical reasons: for example the native protein is just not available, the protein is toxic, or its is desirable to utilize a high density antigen presentation. In such cases, immunization with peptides is the alternative. Of course, Abs generated in this manner will recognize linear epitopes, and they might or might not recognize the source native protein, but yet they will be useful for standard laboratory applications such as western blots. The selection of peptides to use as immunogens can be accomplished by following particular selection rules and/or use of epitope prediction software.

Though methods to predict antigenic peptides are not infallible, there are several rules that can be followed to determine what peptide fragments from a protein are likely to be antigenic. These rules are also dictated to increase the likelihood that an Ab to a particular peptide will recognize the native protein.

1. Antigenic peptides should be located in solvent accessible regions and contain both hydrophobic and hydrophilic residues.

For proteins of known 3D structure, solvent accessibility can be determined using a variety of programs such as DSSP, NACESS, or WHATIF, among others.

If the 3D structure is not known, use any of the following web servers to predict accessibilities: PHD, JPRED, PredAcc (c) ACCpro 2. Preferably select peptides lying in long loops connecting Secondary Structure (SS) motifs, avoiding peptides located in helical regions. This will increase the odds that the Ab recognizes the native protein. Such peptides can, for example, be identified from a crystal structure or crystal structure-based homology model.

For protein with known 3D coordinates, SS can be obtained from the sequence link of the relevant entry at the Brookhaven data bank. The PDBsum server also offer SS analysis of pdb records.

When no structure is available secondary structure predictions can be obtained from any of the following servers: PHD, JPRED, PSI—PRED, NNSP, etc 3. When possible, choose peptides that are in the N- and C-terminal region of the protein. Because the N- and C-terminal regions of proteins are usually solvent accessible and unstructured, Abs against those regions are also likely to recognize the native protein.

4. For cell surface glycoproteins, eliminate from initial peptides those containing consesus sites for N-glycosilation.

N-glycosilation sites can be detected using Scanprosite, or NetNGlyc

In addition, several methods based on various physiochemical properties of experimental determined epitopes (flexibility, hydrophibility, accessibility) have been published for the prediction of antigenic determinants and can be used. The antigenic index and Preditop are example.

A desirable method for the prediction of antigenic determinants is that of Kolaskar and Tongaonkar, which is based on the occurrence of amino acid residues in experimentally determined epitopes. (Kolaskar and Tongaonkar (1990) A semi-empirical method for prediction of antigenic determinants on protein antigens. *FEBBS Lett.* 276(1-2):172-174.) The prediction algorithm works as follows:

1. Calculate the average propensity for each overlapping 7-mer and assign the result to the central residue (i+3) of the 7-mer.

2. Calculate the average for the whole protein.
3. (a) If the average for the whole protein is above 1.0 then all residues having average propensity above 1.0 are potentially antigenic.
3. (b) If the average for the whole protein is below 1.0 then all residues having above the average for the whole protein are potentially antigenic.
4. Find 8-mers where all residues are selected by step 3 above (6-mers in the original paper)

The Kolaskar and Tongaonkar method is also available from the GCG package, and it runs using the command egcg.

Crystal structures also allow identification of residues at which mutation is likely to alter the activity of the protein. Such residues include, for example, residues that interact with susbtrate, conserved active site residues, and residues that are in a region of ordered secondary structure of involved in tertiary interactions. The mutations that are likely to affect activity will vary for different molecular contexts. Mutations in an active site that will affect activity are typically substitutions or deletions that eliminate a charge-charge or hydrogen bonding interaction, or introduce a steric interference. Mutations in secondary structure regions or molecular interaction regions that are likely to affect activity include, for example, substitutions that alter the hydrophobicity/hydrophilicity of a region, or that introduce a sufficient strain in a region near or including the active site so that critical residue (s) in the active site are displaced. Such substitutions and/or deletions and/or insertions are recognized, and the predicted structural and/or energetic effects of mutations can be calculated using conventional software.

XI. Phosphodiesterase Activity Assays

A number of different assays for phosphodiesterase activity can be utilized for assaying for active modulators and/or determining specificity of a modulator for a particular phosphodiesterase or group or phosphodiesterases. In addition to the assay mentioned in the Examples below, one of ordinary skill in the art will know of other assays that can be utilized and can modify an assay for a particular application. For example, numerous papers concerning PDEs described assays that can be used. For example, useful assays are described in Fryburg et al., U.S. Patent Application Publication 2002/0165237, Thompson et al., U.S. Patent Application Publication 2002/0009764, Pamukcu et al., U.S. patent application Ser. No. 09/046,739, and Pamukcu et al., U.S. Pat. No. 6,500,610.

An assay for phosphodiesterase activity that can be used for PDE4B, can be performed according to the following procedure using purified PDE4B using the procedure described in the Examples.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

XII. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of phosphodiesterase function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry, Reactions, Mechanisms and Structure*, New York, McGraw Hill. Thus, the techniques useful to synthesize a potential modulator of phosphodiesterase function identified by computer-based methods are readily available to those skilled in the art of organic chemical synthesis.

XIII. Administration

The methods and compounds will typically be used in therapy for human patients. However, they may also be used to treat similar or identical diseases in other vertebrates such as other primates, sports animals, and pets such as horses, dogs and cats.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in Remington's Pharmaceutical Sciences, $18^{th}$ ed., Mack Publishing Co., Easton, Pa., 1990 (hereby incorporated by reference herein).

Compounds can be formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, $19^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Carriers or excipients can be used to produce pharmaceutical compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, inhalant, or transdermal. Oral administration is preferred. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross—linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/ orsubcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, transdermal, or inhalant means. For transmucosal, transdermal, or inhalant administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

For inhalants, compounds of the invention may be formulated as dry powder or a suitable solution, suspension, or aerosol. Powders and solutions may be formulated with suitable additives known in the art. For example, powders may include a suitable powder base such as lacatose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

It is understood that use in combination includes delivery of compounds of the invention and one or more other inhaled therapeutics together in any formulation, including formulations where the two compounds are chemically linked such that they maintain their therapeutic activity when administered. Combination use includes administration of co-formulations or formulations of chemically joined compounds, or co-administration of the compounds in separate formulations. Separate formulations may be co-administered by delivery from the same inhalant device, or can be co-administered from separate inhalant devices, where co-administration in this case means administered within a short time of each other. Co-formulations of a compound of the invention and one or more additional inhaled therapies includes preparation of the materials together such that they can be administered by one inhalant device, including the separate compounds combined in one formulation, or compounds that are modified such that they are chemically joined, yet still maintain their biological activity.

The amounts of various compound to be administered can be determined by standard procedures taking into account factors such as the compound $IC_{50}$, the biological half-life of the compound, the age, size, and weight of the patient, and the disorder associated with the patient. The importance of these and other factors are well known to those of ordinary skill in the art. Generally, a dose will be between about 0.01 and 50 mg/kg, preferably 0.1 and 20 mg/kg of the patient being treated. Multiple doses may be used.

XIV. Manipulation of PDE4B

As the full-length coding sequence and amino acid sequence of PDE4B from various mammals including human is known, cloning, construction of recombinant PDE4B, production and purification of recombinant protein, introduction of PDE4B into other organisms, and other molecular biological manipulations of PDE4B are readily performed.

Techniques for the manipulation of nucleic acids, such as, e.g., subcloning, labeling probes (e.g., random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., *Nucleic Acids Res.* 2001 Jun 1;29(11):E54-E54; Hafner et al., *Biotechniques* 2001 April;30(4):852-6, 858, 860 passim; Zhong et al., *Biotechniques* 2001 April;30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids of the invention can also be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus, Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

The nucleic acids can be administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng (1997) *Nature Biotechnology* 15:866-870). Such viral genomes may be modified by recombinant DNA techniques to include the nucleic acids of the invention; and may be further engineered to be replication deficient, conditionally replicating or replication competent. In alternative aspects, vectors are derived from the adenoviral (e.g., replication incompetent vectors derived from the human adenovirus genome, see, e.g., U.S. Pat. Nos. 6,096, 718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to fusion proteins, and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif.* 12:404-414). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) *DNA Cell. Biol.* 12:441-53.

The nucleic acids and polypeptides of the invention can be bound to a solid support, e.g., for use in screening and diagnostic methods. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g., utilizing single reactive thiol groups of cysteine residues (see, e.g., Colliuod (1993) *Bioconjugate Chem.* 4:528-536) or non-covalently but specifically (e.g., via immobilized antibodies (see, e.g., Schuhmann (1991) *Adv. Mater.* 3:388-391; Lu (1995) *Anal. Chem.* 67:83-87; the biotin/strepavidin system (see, e.g., Iwane (1997) *Biophys. Biochem. Res.* Comm. 230:76-80); metal chelating, e.g., Langmuir-Blodgett films (see, e.g., Ng (1995) *Langmuir* 11:4048-55); metal-chelating self-assembled monolayers (see, e.g., Sigal (1996) *Anal. Chem.* 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the crosslinking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SLAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyldithio)propionate (SPDP) (Pierce Chemicals, Rockford, Ill.).

Antibodies can also be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) *Nature* 377:525-531 (1989).

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) *Curr. Biol.* 8:R171-R174; Schummer (1997) *Biotechniques* 23:1087-1092; Kern (1997) *Biotechniques* 23:120-124; Solinas-Toldo (1997) *Genes, Chromosomes & Cancer* 20:399-407; Bowtell (1999) *Nature Genetics Supp.* 21:25-32. See also published U.S. patent applications Nos. 20010018642; 20010019827; 20010016322; 20010014449; 20010014448; 20010012537; 20010008765.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 µg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y, pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 µM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples involved in the present invention are described below. In most cases, alternative techniques can be used. The examples are intended to be illustrative and are not limiting or restrictive to the scope of the invention. Additional compounds were synthesized following the methods described below, substituting appropriate materials readily known or available to one skilled in the art. These compounds are shown along with mass spectroscopy data and in some cases biological data in Tables 3, 4 and 5.

Example 1

Synthesis of Compounds of Formula I:

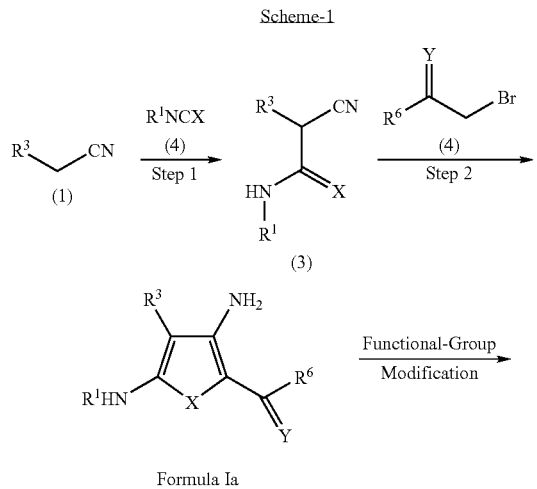

Formula Ia

-continued

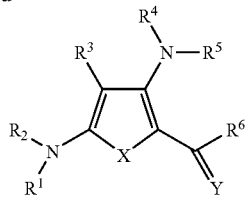

Formula I

The tetra-substituted thiophene compounds represented by Formula I can be prepared as shown in Scheme-1 (Abdelhamid, et. al., *J. Chem. Res.*, 1999, 184-185 and references therein).

Step-1 Preparation of Formula (3)

The compound of formula (3) can be prepared by reacting compound of formula (2), where $R^1$=alkyl, heteroalkyl, heteroaryl or aryl (e.g. phenylisothiocyanate), with a nitrile of formula (1) in an inert solvent (e.g. DMF), in the presence of a base (e.g. $K_2CO_3$), typically at ambient temperature for 12-36 hours. When the reaction is substantially complete, the product of formula (3) is isolated by conventional means, for example, distillation.

Step-2 Preparation of Formula Ia

The compound of formula Ia can be prepared conventionally by reacting compound of formula (3) with a compound of formula (4) a basic medium, (e.g. $K_2CO_3$/DMF), at ambient temperature for several hours. When the reaction is substantially complete, the product of formula Ia can be isolated by conventional means (e.g. reverse phase HPLC) (Smith, et. al., *J. Comb. Chem.*, 1999, 1, 368-370; and references therein).

Preparation of Formula I

The compound of formula I can be prepared by employing common amine alkylation chemistry (e.g. Borch reduction) (Borch, et al., *J. Am. Chem. Soc.*, 1969, 91, 3996-3997).

Example 2

Synthesis of the Compounds of Formula Ib:

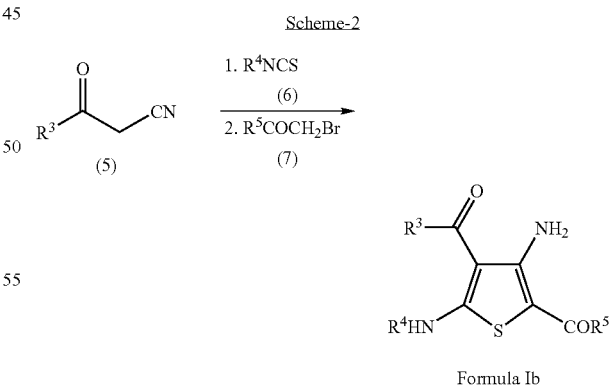

Formula Ib

The tetra-substituted thiophenes represented by Formula Ib can be prepared as shown in Scheme-2 following the procedure of Abdelhamid, et. al. as described in *J. Chem. Res.*, 1999,184-185.

Step-1 Preparation of Formula Ib

The compound of formula Ib can be prepared conventionally by reaction of a β-cyano-carbonyl compound of formula (5), where $R^3$=alkyl, heteroalkyl, heteroaryl, N(H)R, OR, or aryl (e.g. 2-cyanoacetamide), with an isothiocyanate of formula (6) where $R^4$=alkyl, aryl, heteroalkyl or heteroaryl (e.g. methylisothiocyanate) in an inert solvent (e.g. DMF), in the presence of a base (e.g. $K_2CO_3$), typically run at ambient temperature for several hours. When the reaction is substantially complete, β-halo-carbonyl compound of formula (7) can be added to the reaction mixture and run for several hours at ambient temperature. The product can be isolated by conventional means (e.g. reverse phase HPLC). Smith, et. al., *J. Comb. Chem.*, 1999, 1, 368-370).

Example 3

Synthesis of the Compounds of Formula Ib:

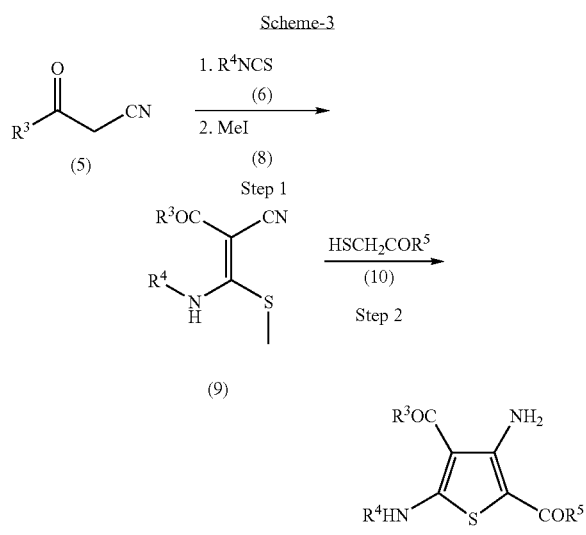

The tetra-substituted thiophene represented by Formula Ib can be prepared as shown in Scheme 3 (Sommen, et. al., *Tetrahedron Lett.*, 2002, 43, 257-259).

Step-1 Preparation of Formula (9)

The compound of formula (9) can be prepared conventionally by reaction of a β-cyano-carbonyl compound of formula (5), where $R^3$=alkyl, heteroalkyl, heteroaryl, NR, OR, or aryl (e.g. 2-cyanoacetamide), with an isothiocyanate of formula (6) where $R^4$=alkyl, aryl, heteroalkyl or heteroaryl (e.g. methylisothiocyanate) in an inert solvent (e.g. DMF), in the presence of a base (e.g. $K_2CO_3$), typically run at ambient temperature for several hours. When the reaction is substantially complete, iodomethane (formula 8) is added to the reaction mixture and stirred for several hours at ambient temperature. When the reaction is substantially complete, the product of formula (9) is isolated by conventional means (e.g. reverse phase HPLC; Smith, et. al., *J. Comb. Chem.*, 1999, 1, 368-370).

Step-2 Preparation of Formula Ib

The compound of formula Ib is prepared conventionally by reaction of compounds of formula (9) with a thioglycolate of formula (10) where $R^5$=alkyl, aryl, heteroalkyl, heteroaryl, OR, or NR. (e.g. ethyl thioglycolate) in an inert solvent (e.g. EtOH), in the presence of a base (e.g. $K_2CO_3$), typically run at ambient temperature for several hours. When the reaction is substantially complete, the product of formula Ib is isolated by conventional means (e.g. reverse phase HPLC). Smith, et. al., *J. Comb. Chem.*, 1999, 1, 368-370; and references therein.

Example 4

Synthesis of the Compounds of Formula Ic:

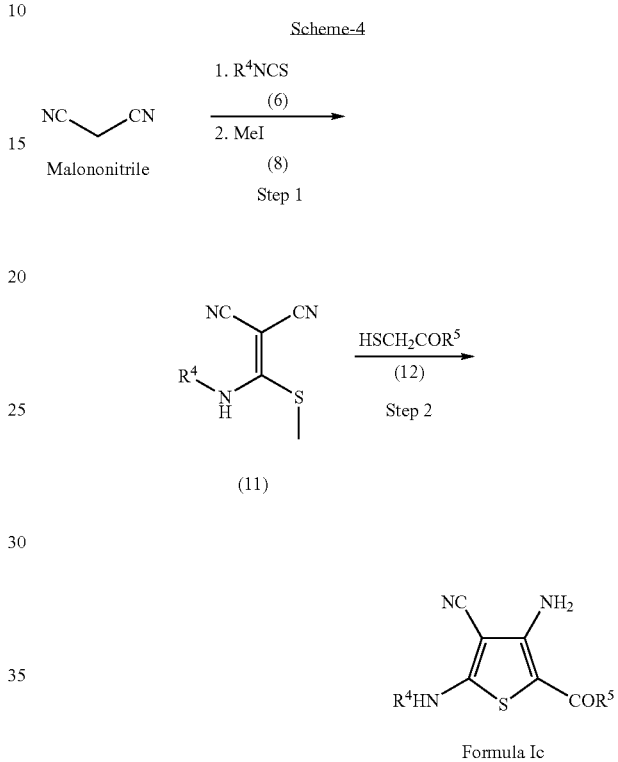

The tetra-substituted thiophene represented by Formula Ic can be prepared as shown in Scheme-4 (Sommen, et. al., *Tetrahedron Lett.*, 2002, 43, 257-259).

Step-1 Preparation of Formula (11)

The compound of formula (11) can be prepared conventionally by reaction of malononitrile, with an isothiocyanate of formula (6) where $R^4$=alkyl, aryl, heteroalkyl or heteroaryl (e.g. methylisothiocyanate) in an inert solvent (e.g. DMF), in the presence of a base (e.g. $K_2CO_3$), typically run at ambient temperature for several hours. When the reaction is substantially complete, iodomethane (formula 8) can be added to the reaction mixture and stirred for several hours at ambient temperature. The product of formula (11) can be isolated by conventional means (e.g. reverse phase HPLC; Smith, et. al., *J. Comb. Chem.*, 1999, 1, 368-370).

Step- Preparation of Formula Ic

The compound of Formula Ic can be prepared conventionally by reaction of compounds of formula (11) with a thioglycolate of formula (12) where $R^5$=alkyl, aryl, heteroalkyl, heteroaryl, OR, or NR. (e.g. ethyl thioglycolate) in an inert solvent (e.g. EtOH), in the presence of a base (e.g. $K_2CO_3$), typically run at ambient temperature for several hours. When the reaction is substantially complete, the product of formula Ic is isolated by conventional means (e.g. reverse phase HPLC; Smith, et. al., *J. Comb. Chem.*, 1999, 1, 368-370).

Example 5

Synthesis of the Compounds of Formula Ic:

Scheme-5

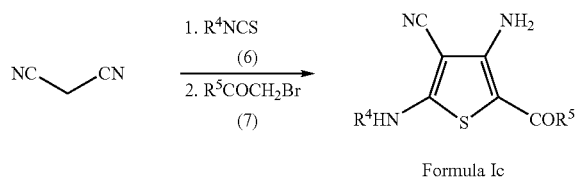

Formula Ic

The tetra-substituted thiophene represented by Formula Ic was prepared as shown in Scheme-2 following the procedure of Abdelhamid, et. al. as described in *J. Chem. Res.*, 1999, 184-185.

Step-1 Preparation of Formula Ic

The compound of formula Ic was prepared by reaction of malononitrile with an isothiocyanate of formula (6) where $R^4$=alkyl, aryl, heteroalkyl or heteroaryl (e.g. methylisothiocyanate) in an inert solvent (e.g. DMF), in the presence of a base (e.g. $K_2CO_3$), run at ambient temperature for several hours. When the reaction was substantially complete, β-halocarbonyl compound of formula (7) was added to the reaction mixture and run for several hours at ambient temperature. The product was isolated by crystallization.

Example 6

Synthesis of compounds of Formula Ia (where X=O or $NR^4$; $R^1$=alkyl, aryl, or heteroaryl; $R^2$=substituted amine, ether, or nitrile; $R^3$=alkyl, aryl, or heteroaryl):

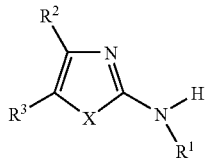

Formula IIa

Step-1 Preparation of Formula (14)

Compound of formula (14) can be prepared by bubbling hydrogen chloride gas into the solution of compound of formula (13) in ethanol, typically at 0° C. for 1 h and stirred at room temperature for 16 hours. Compound of formula (14) can be obtained by following the standard work-up procedure, typically evaporate the solvent. (*Journal of American Chemical Society*, Vol. 68, 2393-2395, 1946 and references therein)

Step-2 Preparation of Formula (16)

Compound of formula (16) can be prepared conventionally by mixing compound of formula (14) and thiocarbonyl reagent (15, e.g. 1,1'-thiocarbonyldiimidazole) in an inert solvent (e.g. THF). The mixture can be stirred until all the starting material is gone. The product of formula (16) can be isolated by conventional means (e.g. column chromatography).

Step-3 Preparation of Formula (17)

Compound of formula (17) can be prepared by mixing compound of formula (16) and primary alkyl or arylamine in an inert solvent (e.g. acetonitrile). The resulting mixture can be heated if necessary. Compound of formula (17) can be obtained after the work-up procedure as described in *Khimiya Geterotsiklicheskikh Soedinenii*, Vol. 8, 1129-1130, 1987.

Step-4 Preparation of Formula (18)

Compound of formula (18) can be prepared by stirring compound of formula (17) in an aqueous hydrochloric solution till the starting material is gone. This mixture can be heated as necessary. The inert solvent (e.g. ethyl acetate) can be added, and it can be dried over anhydrous salt (e.g. magnesium sulfate). After all solvent can be evaporized, the residue can be dissolved in an inert solvent (e.g. chloroform). To a resulting solution, phosphorus trichloride can be added and stirred. Compound of formula (18) can be obtained after the work-up procedure as indicated in the reference papers, *Synthetic Communications*, Vol. 32, No. 12, 1791-1795, 2002; *Heterocycles*, Vol. 31, No. 4, 637-641, 1990 and references therein.

Step-5 Preparation of Formula (19)

Compound of formula (19) can be prepared by mixing crude compound of formula (18) with alcohol or primary alkyl or aryl amine. The mixture can be heated as necessary. Compound of formula (19) can be obtained after the work-up

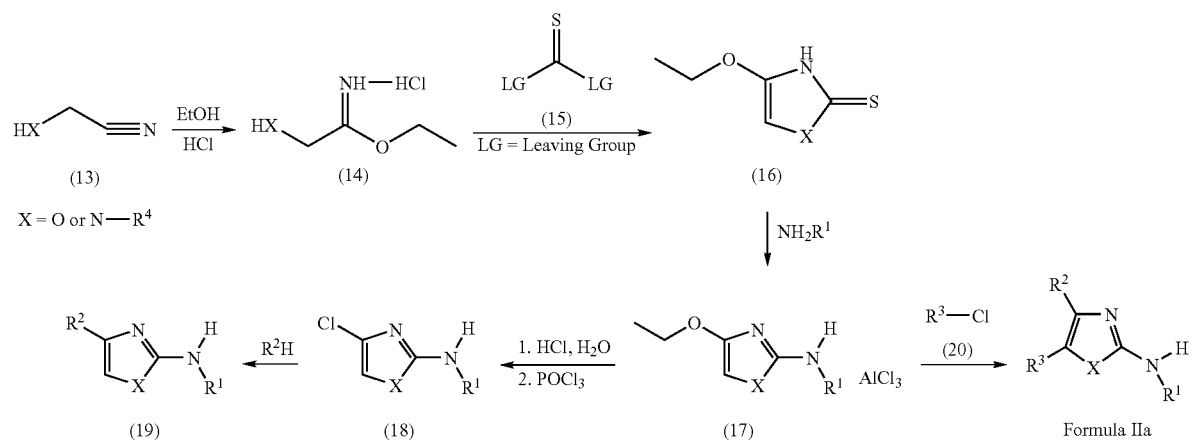

Scheme-6 procedure as indicated in the reference paper, *Bioorganic Medicinal chemistry*, Vol. 9, No. 4, 897-907, 2001 and references therein.

Step-6 Preparation of Formula IIa

Compound of formula IIa can be prepared by mixing compound of formula (19) in an inert solvent (e.g. methylene chloride) with aluminum chloride, and compound of formula (20) can be added to the mixture. Compound of formula (19) can be obtained after the work-up procedure as described in *Journal of Heterocylic Chemistry*, Vol. 34, No. 2, 567-572, 1997, and references therein.

Example 7

Synthesis of compounds of Formula IIb (where $R^1$=alkyl, aryl, or heteroaryl; $R^2$=alkyl, aryl, heteroaryl, amino, substituted amine, or ether; $R^3$=alkyl, aryl, or heteroaryl):

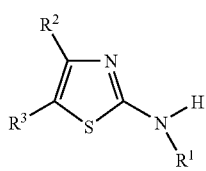

Formula IIb

Step-1 Preparation of Formula (23)

Compound of formula (23) can be prepared by mixing compound of formula (21) in an inert solvent (e.g. THF) with aqueous base (e.g. NaOH) and compound of formula (22) at 0° C. Compound of formula (23) can be obtained after the work-up procedure as described in *Tetrahedron*, Vol. 57, No. 1, 153-156, 2001 and *Journal of Organic Chemistry*, Vol. 65, No. 21, 7244-7247, 2000.

Step-2 Preparation of Formula (25)

Compound of formula (25) can be prepared by mixing compound of formula (23) in an inert solvent (e.g. toluene) with a base (e.g. triethyl amine), and can be added compound of formula (24) typically at room temperature. When the reaction is substantially complete, compound of formula (25) can be obtained after the work-up procedure as described in *Tetrahedron*, Vol. 57, No. 1, 153-156, 2001 and *Journal of Organic Chemistry*, Vol. 65, No. 21, 7244-7247, 2000.

Step-3 Preparation of Formula (IIb)

Compound of formula (IIb) can be prepared by mixing compound of formula (25) in an inert solvent (e.g. toluene) under a nitrogen atmosphere and can be heated at reflux temperature. When the reaction is substantially complete, compound of formula (IIb) can be obtained after the work-up Scheme -7

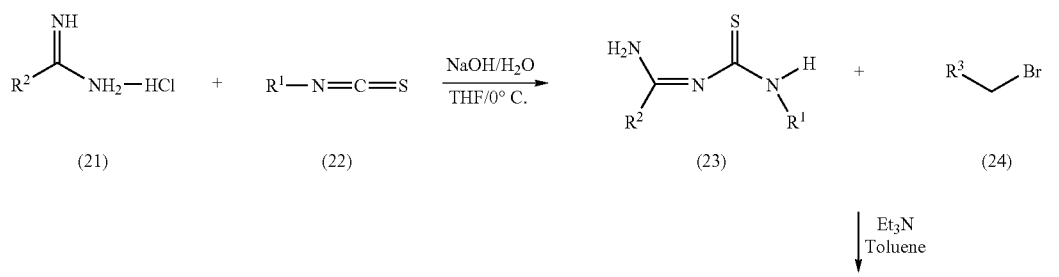

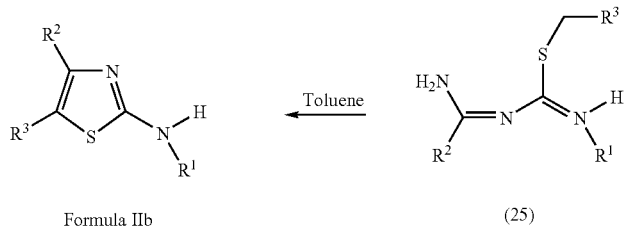

procedure as described in *Tetrahedron*, Vol. 57, No. 1, 153-156, 2001 and *Journal of Organic Chemistry*, Vol. 65, No. 21, 7244-7247, 2000.

Example 8

Synthesis of Compound 2-25 (Table 2A)

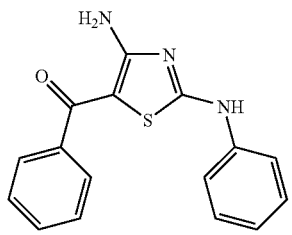

Compound 2-25

Exemplary compound 2-25 within Formula II, (4-amino-2-phenylamino-thiazol-5-yl)-phenyl-methanone, can be prepared according to Scheme 8 as follows:

anate (Compound 28, 655 μL, 5.47 mmol). The resulting solution was stirred at 0° C. for one hour and at room temperature for another hour. It was then diluted with ethyl acetate (40 mL) and water (10 mL), and two layers were separated. The organic phase was washed with brine and dried over anhydrous sodium sulfate and evaporated. The solid residue was washed with mixture of dichloromethane and hexane to obtain compound 29 as a white solid (1.28 g, 3.78 mmol).

Step-2 Preparation of Formula (31)

To a solution of thiocarbamoylamidine (Compound 29, 122 mg, 0.363 mmol) in tetrahydrofuran (1.5 mL) under a nitrogen atmosphere was added triethylamine (56 μL) and followed by 2-bromoacetophenone (30, 72 mg, 0.363 mmol) at room temperature. The reaction mixture was stirred for five hours, and then diluted with ethyl acetate (20 mL). The resulting mixture was washed with brine and dried over anhydrous sodium sulfate and evaporated to obtain Compound 31.

Step-3 Preparation of Formula (2-25)

A solution of S-alkylated compound (Compound 31, 0.363 mmol) and 1,8-diazabicyclo[5.4.0]undec-7-ene (DBU, 54 μL) in toluene (10 mL) was heated at reflux temperature under a nitrogen atmosphere for two hours. The resulting solution was cooled to room temperature and diluted with ethyl acetate

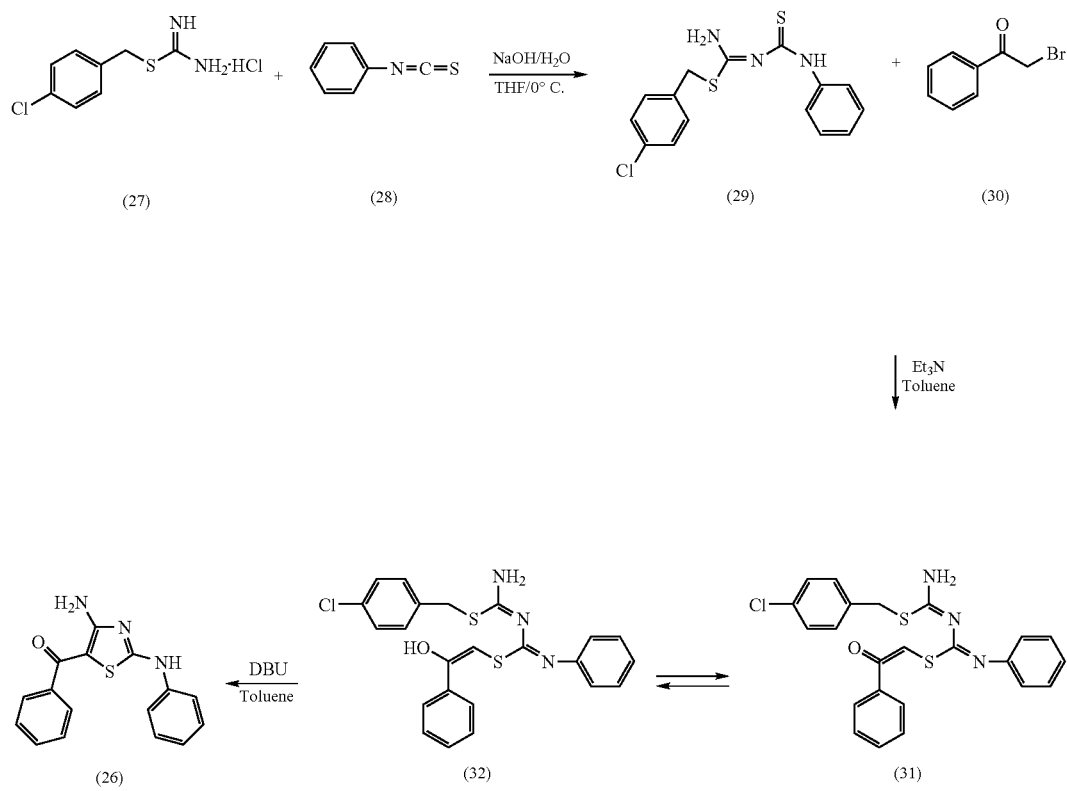

Step-1 Preparation of Formula (29)

To a suspension of 2-(4-chlorobenzyl)-2-thiopseudourea hydrochloride (Compound 27, 1.24 g, 5.21 mmol) in tetrahydrofuran (21 mL) was added aqueous sodium hydroxide (1.00 M, 5.5 mL) dropwise at 0° C. followed by phenyl isothiocy- (20 mL). It was then washed with water and saturated ammonium chloride solution. The organic phase was dried over anhydrous sodium sulfate, evaporated, and purified by column chromatography (Ethyl acetate/Hexane=2/3) to obtained Compound 2-25 as a white solid; (M+H): 296.

Example 9

Synthesis of Compounds of Formula IIc (where $R^1$=alkyl, aryl, or heteroaryl; $R^3$=alkyl, aryl, or heteroaryl):

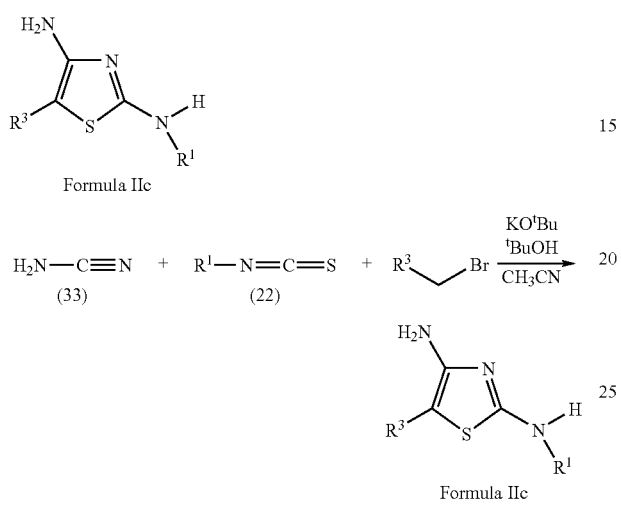

Formula IIc

Step-1 Preparation of Formula (IIc)

Compound of formula (IIc) can be prepared by dissolving compound of formula (33) and compound of formula (22) in an inert solvent (e.g. $CH_3CN$) and adding potassium tert-butoxide in warm tert-butyl alcohol. After stirring for 30 minutes, typically at room temperature, compound of formula (24) in an inert solvent (e.g. $CH_3CN$) is added. The resulting solution is stirred at room temperature or heated (typically 80° C.) for 3-10 h. The reaction is quenched with water and the product is isolated by filtration (Chong, W. et al., WO9921845).

Example 10

Synthesis of Compound 2-33 (Table 2A)

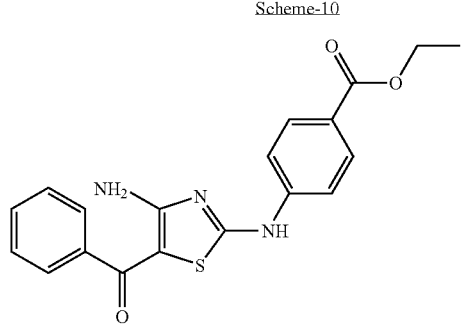

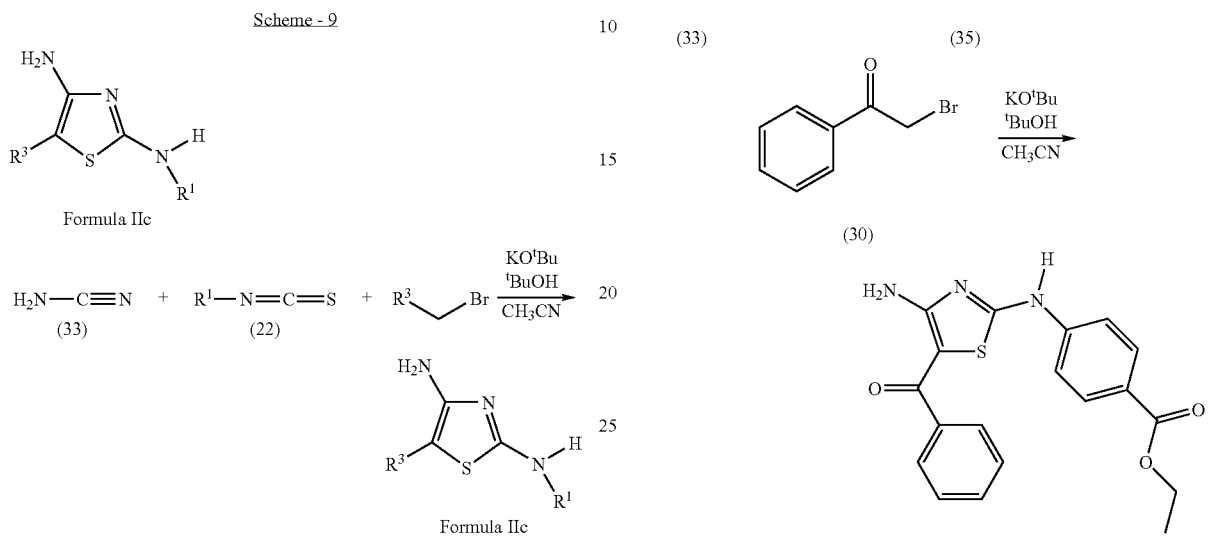

Compound (34)

Step-1 Preparation of Compound 4-(4-Amino-5-benzoyl-thiazol-2-ylamino)-benzoic acid ethyl ester (Compound 2-33, Table 2A)

Cyanamide (compound 33, 0.0467 g, 1.1 mmol) and 4-ethoxycarbonylphenyl isothiocyanate (compound 35, 0.211 g, 1.0 mmol) were dissolved in acetonitrile (10.0 mL) and stirred at room temperature. A solution of potassium tert-butoxide (0.130 g, 1.1 mmol) in a mixture of warm tert-butyl alcohol (10.0 mL) and acetonitrile (1 mL) was added. The resulting solution was stirred for 30 minutes at room temp. 2-Bromoacetophenone (compound 30, 0.203 g, 1.0 mmol) in acetonitrile (2 mL) was added at room temperature and the resulting mixture was stirred for 2 hours at room temperature. The reaction was quenched with water (100 mL) and the precipitated solid was filtered, washed with water and diethyl ether. Compound 2-33 was obtained as a yellow solid (298 mg; M+H=368.1).

Example 11

Synthesis of Compounds of Formula III

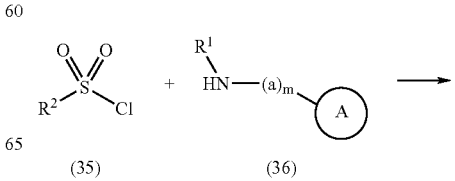

-continued

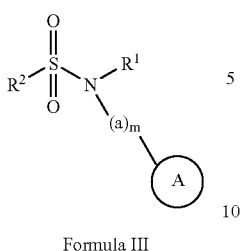

Formula III

Compounds of formula III are prepared by adding sulfonyl chloride of formula (35) to a solution of the amine of formula (36) in base (e.g., pyridine) and stirred at room temperature, typically for 16 h, followed by work up by standard procedures, evaporation of the solvent and purification.

Example 12

Synthesis of 5-(2-Methylsulfanyl-pyrimidin-4-yl)-thiophene-2-sulfonic acid quinolin-8-ylamide (Compound 3-16 in Table 3A).

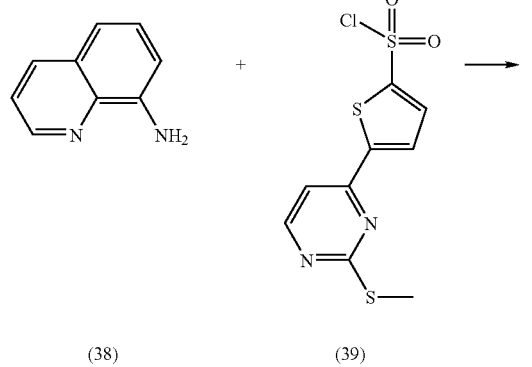

8-Quinolinamine (compound (38), 0.0998 g, 0.692 mmol) and thiophenesulfonylchloride (0.212 g, 0.692 mmol) were dissolved in Pyridine (10.0 mL, 0.124 mol). 4-Dimethylaminopyridine (0.010 g, 0.082 mmol) was added, and the resulting solution was stirred over night at room temperature. All solvents were removed and the product was purified by biotage column using 10-30% ethyl acetate hexane as solvent. The purified product was obtained as a yellow solid (M+1=415.4).

Example 13

Synthesis of Compound 1-29 (Table 1A)

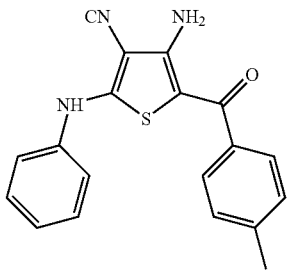

Preparation of 4-Amino-5-(4-methyl-benzoyl)-2-phenylamino-thiophene-3-carbonitrile (Compound 1-29, Table 1A)

Malononitrile (0.661 g, 0.0100 mol) was dissolved in N,N-dimethylformamide (50 mL, 0.6 mol) and was stirred under an atmosphere of Argon. Potassium carbonate (1.52 g, 0.0110 mol) was added and was stirred for 30 minutes. Isothiocyanatobenzene (1.49 g, 0.0110 mol) was added and the reaction mixture was stirred for 2 hours. 2-Bromo-1-(4-methylphenyl)-ethanone, (2.34 g, 0.0110 mol) was added and the reaction mixture was allowed to stir overnight. The resultant dark red solution was diluted with 150 mL ethyl acetate and washed successively with 100 mL each of 1/2 saturated NaHCO$_3$ solution, 1N LiCl (2×) and 1N Na$_2$S$_2$O$_3$. The combined aqueous layers were discarded and the organic layer was dried, filtered, and evaporated to collect 1.46 g of the desired product as pale yellow-orange crystals. MS(ESI) [M+H$^+$]$^+$=334.2.

Example 14

Synthesis of Compound 1-30 (Table 1A)

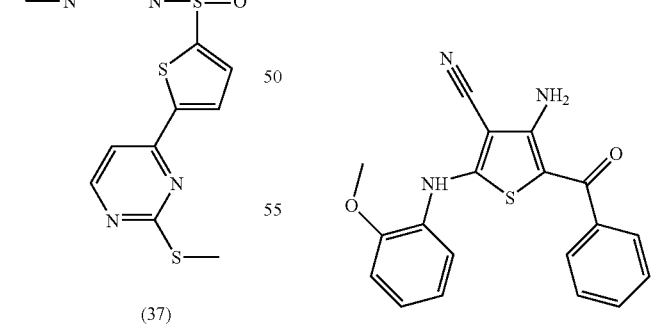

Preparation of 4-Amino-5-(benzoyl)-2-(2-methoxyphenyl)amino-thiophene-3-carbonitrile (Compound 1-30, Table 1 A)

4-Amino-5-(benzoyl)-2-(2-methoxyphenyl)amino-thiophene-3-carbonitrile was prepared as described in Example 13 substituting isothiocyanatobenzene and 2-bromo-1-(4-methylphenyl)-ethanone with 2-methoxyphenylisothiocyante and 2-bromoacetophenone respectively to provide compound 1-30. MS(ESI) [M+H$^+$]$^+$=350.11.

Example 15

Synthesis of Compound 1-32 (Table 1A)

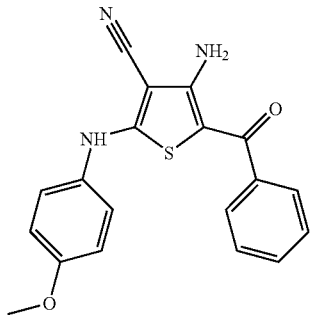

Preparation of 4-Amino-5-benzoyl-2-(4-methoxy-phenylamino)-thiophene-3-carbonitrile (Compound 1-32, Table 1A)

4-Amino-5-benzoyl-2-(4-methoxy-phenylamino)-thiophene-3-carbonitrile was prepared as described in Example 13 substituting isothiocyanatobenzene and 2-bromo-1-(4-methylphenyl)-ethanone with 4-methoxyphenylisothiocyante and 2-bromoacetophenone respectively to provide compound 1-32. MS(ESI) [M+H$^+$]$^+$=350.14.

Example 16

Synthesis of Compound 1-33 (Table 1A)

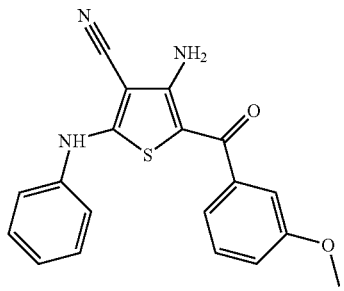

Preparation of 4-Amino-5-(3'-methoxybenzoyl-2-phenylamino-thiophene-3-carbonitrile, (Compound 1-33, Table 1A)

4-Amino-5-(3'-methoxybenzoyl-2-phenylamino-thiophene-3-carbonitrile, was prepared as described in Example 13 substituting 2-bromo-1-(4-methylphenyl)-ethanone, with 2-bromo-1-(3-methoxyphenyl)-ethanone, to provide compound 1-33. MS(ESI) [M+H$^+$]$^+$=350.14.

Example 17

Synthesis of compound 1-143 (Table 1A)

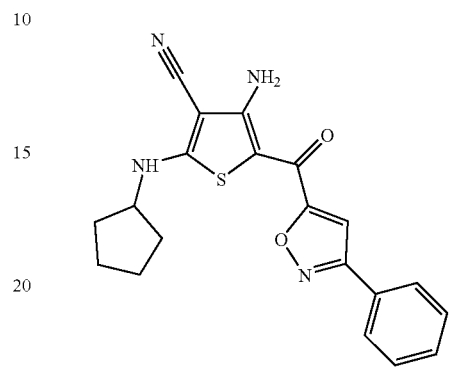

Preparation of 4-Amino-2-cyclopentylamino-5-(3-phenyl-isoxazole-5-carbonyl)-thiophene-3-carbonitrile, (Compound 1-143, Table 1A)

4-Amino-2-cyclopentylamino-5-(3-phenyl-isoxazole-5-carbonyl)-thiophene-3-carbonitrile, was prepared as described in Example 13 substituting isothiocyanatobenzene and 2-bromo-1-(4-methylphenyl)-ethanone with cyclopentaneisothiocyanate and 2-bromo-1-(3-phenyl-isoxazol-5-yl)-ethanone respectively to provide compound 1-143. MS(ESI) [M+H$^+$]$^+$=378.99.

Example 18

Synthesis of Compound 1-28 (Table 1A)

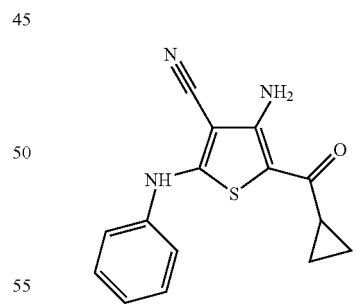

Preparation of 4-Amino-5-cyclopropanecarbonyl-2-phenylamino-thiophene-3-carbonitrile, (Compound 1-28, Table 1A)

4-Amino-5-cyclopropanecarbonyl-2-phenylamino-thiophene-3-carbonitrile, was prepared as described in Example 13 substituting, 2-bromo-1-(4-methylphenyl)-ethanone, with 2-Bromo-1-cyclopropyl-ethanone to provide compound 1-28. ¹H NMR (DMSO-d6) 10.49 (s, 1H), 7.62 (bs, 2H), 7.45 (s, 4H), 7.24 (m, 1H), 1.79 (m, 1H), 0.87 (m, 2H), 0.82 (m, 2H).

Example 19

Synthesis of Compound 1-173 (Table 1A)

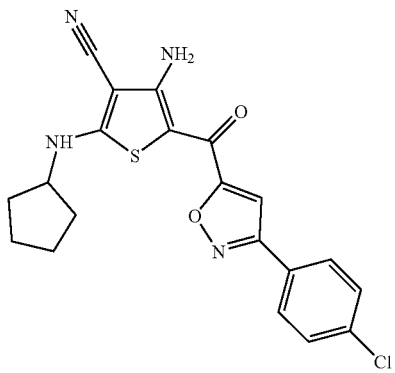

Preparation of 4-Amino-5-((4-chlorophen-3-yl)isoxazol-5-yl)carbonyl-2-cyclopentylamino-thiophene-3-carbonitrile, (Compound 1-173, Table 1A)

4-Amino-5-((4-chlorophen-3-yl)isoxazol-5-yl)carbonyl-2-cyclopentylamino-thiophene-3-carbonitrile was prepared as described in Example 13 substituting isothiocyanatobenzene and 2-bromo-1-(4-methylphenyl)-ethanone with cyclopentaneisothiocyanate and 5-bromoacetyl-3-(4-chlorophenyl)isoxazole respectively to provide compound 1-173. MS(ESI) [M−H⁺]⁻=411.0.

Example 20

Synthesis Compound 1-172 (Table 1A)

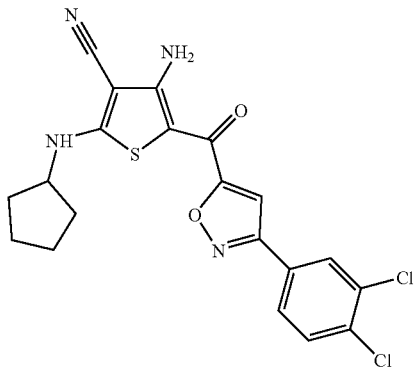

Preparation of 4-Amino-5-((3,4-dichlorophen-3-yl)isoxazol-5-yl)carbonyl-2-cyclopentylamino-thiophene-3-carbonitrile, (Compound 1-173, Table 1A)

4-Amino-5-((3,4-dichlorophen-3-yl)isoxazol-5-yl)carbonyl-2-cyclopentylamino-thiophene-3-carbonitrile was pre-pared as described in Example 13 substituting isothiocyanatobenzene and 2-bromo-1-(4-methylphenyl)-ethanone with cyclopentaneisothiocyanate and 5-bromoacetyl-3-(3,4-dichlorophenyl)isoxazole respectively to provide compound 1-172. MS(ESI) [M+H⁺]⁺=448.9.

Example 21

Synthesis of Compound 1-179 (Table 1A)

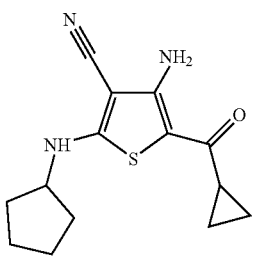

Preparation of 4-Amino-2-cyclopentylamino-5-cyclopropanecarbonyl-thiophene-3-carbonitrile, (Compound 1-179, Table 1A)

4-Amino-2-cyclopentylamino-5-cyclopropanecarbonyl-thiophene-3-carbonitrile was prepared as described in Example 13 substituting isothiocyanatobenzene and 2-bromo-1-(4-methylphenyl)-ethanone with cyclopentaneisothiocyanate and 2-bromo-1-cyclopropyl-ethanone respectively to provide 1-179; MS(ESI) [M+H⁺]⁺: 276.13.

Example 22

Synthesis of Compound 1-192 (Table 1A)

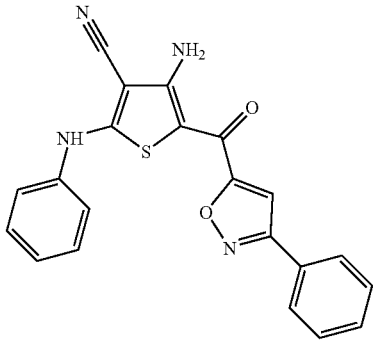

Preparation of 4-Amino-5-(phen-3-yl)isoxazol-5-yl)carbonyl-2-phenylamino-thiophene-3-carbonitrile, (Compound 1-192, Table 1A)

4-Amino-5-(phen-3-yl)isoxazol-5-yl)carbonyl-2-phenylamino-thiophene-3-carbonitrile was prepared as described in Example 13 substituting 2-bromo-1-(4-methylphenyl)- ethanone with 2-bromo-1-(3-phenyl-isoxazol-5-yl)-ethanone to provide compound 1-192. MS(ESI) [M−H⁺]⁻ =385.05

Example 23

Prophetic Synthesis of Compound-P1

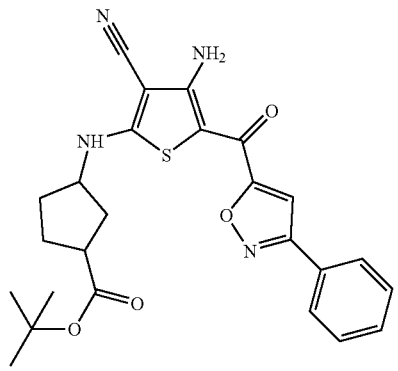

Preparation of 3-[4-amino-3-cyano-5-(3-phenyl-isoxazole-5-carbonyl)-thiophen-2-ylamino]-pyrrolidine-1-carboxylic acid tert-butyl ester, (Compound 1-P1)

3-[4-Amino-3-cyano-5-(3-phenyl-isoxazole-5-carbonyl)-thiophen-2-ylamino]-pyrrolidine-1-carboxylic acid tert-butyl ester, can be prepared as described in Example 13 substituting isothiocyanatobenzene and 2-bromo-1-(4-methylphenyl)-ethanone with 3-isothiocyanato-pyrrolidine-1-carboxylic acid tert-butyl ester and 2-bromo-1-(3-phenyl-isoxazol-5-yl)-ethanone respectively to provide compound 1-P1.

Example 24

Prophetic synthesis of Compound 1-P2

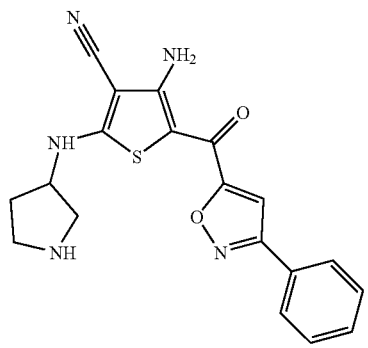

Preparation of 4-Amino-5-(3-phenyl-isoxazole-5-carbonyl)-2-(pyrrolidin-3-ylamino)-thiophene-3-carbonitrile, (Compound 1-P2)

4-Amino-5-(3-phenyl-isoxazole-5-carbonyl)-2-(pyrrolidin-3-ylamino)-thiophene-3-carbonitrile can be prepared by treating 3-[4-amino-3-cyano-5-(3-phenyl-isoxazole-5-carbonyl)-thiophen-2-ylamino]-pyrrolidine-1-carboxylic acid tert-butyl ester (Compound 1-P1) with a strong acid (e.g. trifluoroacetic acid, sulfuric acid, HCl or the like) and subjecting the reaction mixture to aqueous work up (e.g. neutralizing with aqueous base and extracting the product with an organic solvent) to isolate the product, compound 1-P2.

Example 25

Prophetic synthesis of Compound 1-P3

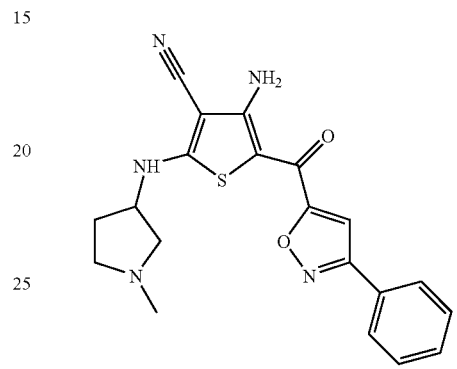

Peparation of 4-Amino-2-(1-methyl-pyrrolidin-3-ylamino)-5-(3-phenyl-isoxazole-5-carbonyl)-thiophene-3-carbonitrile, (Compound 1-P3)

4-Amino-2-(1-methyl-pyrrolidin-3-ylamino)-5-(3-phenyl-isoxazole-5-carbonyl)-thiophene-3-carbonitrile, can be prepared by treating 4-amino-5-(3-phenyl-isoxazole-5-carbonyl)-2-(pyrrolidin-3-ylamino)-thiophene-3-carbonitrile (Compound 1-P2) with methyl iodide, dimethylsulfate or suitable alkylating agent under basic conditions and subjecting the reaction mixture to standard aqueous work up (e.g. addition of water and extracting the product with an organic solvent) to isolate the product, compound 1-P3.

Example 26

Prophetic synthesis of Compound 1-P4

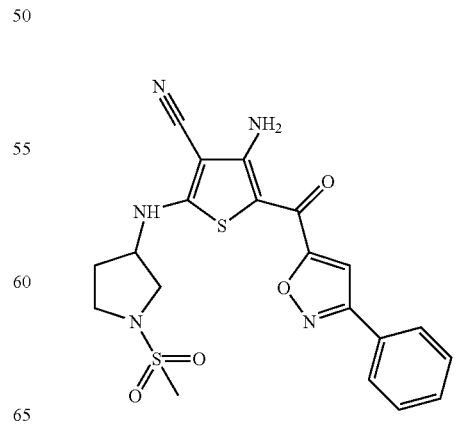

Preparation of 4-Amino-2-(1-methanesulfonyl-pyrrolidin-3-ylamino)-5-(3-phenyl-isoxazole-5-carbonyl)-thiophene-3-carbonitrile, (Compound 1-P4)

4-Amino-2-(1-methanesulfonyl-pyrrolidin-3-ylamino)-5-(3-phenyl-isoxazole-5-carbonyl)-thiophene-3-carbonitrile can be prepared by treating 4-amino-5-(3-phenyl-isoxazole-5-carbonyl)-2-(pyrrolidin-3-ylamino)-thiophene-3-carbonitrile (compound 1-P2) with methanesulfonyl chloride under basic conditions and subjecting the reaction mixture to standard aqueous work up (e.g. addition of water and extracting the product with an organic solvent) to isolate the product, compound 1-P4.

Example 27

Prophetic synthesis of Compound 1-P5

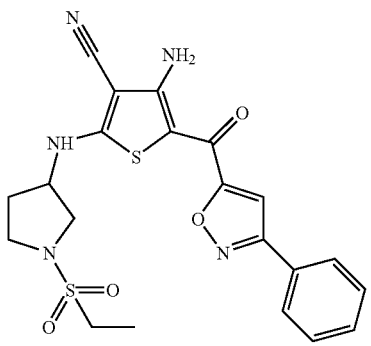

Preparation of 4-Amino-2-(1-ethanesulfonyl-pyrrolidin-3-ylamino)-5-(3-phenyl-isoxazole-5-carbonyl)-thiophene-3-carbonitrile, (Compound 1-P5)

4-Amino-2-(1-ethanesulfonyl-pyrrolidin-3-ylamino)-5-(3-phenyl-isoxazole-5-carbonyl)-thiophene-3-carbonitrile, can be prepared by treating 4-amino-5-(3-phenyl-isoxazole-5-carbonyl)-2-(pyrrolidin-3-ylamino)-thiophene-3-carbonitrile (compound 1-P2) with ethanesulfonyl chloride under basic conditions and subjecting the reaction mixture to standard aqueous work up (e.g. addition of water and extracting the product with an organic solvent) to isolate the product, compound 1-P5.

Example 28

Prophetic Synthesis of Compound 1-P6

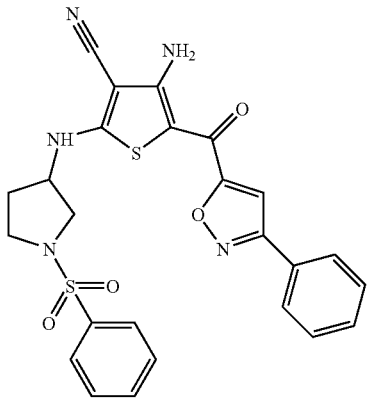

Preparation of 4-Amino-2-(1-benzenesulfonyl-pyrrolidin-3-ylamino)-5-(3-phenyl-isoxazole-5-carbonyl)-thiophene-3-carbonitrile, (Compound 1-P6)

4-Amino-2-(1-benzenesulfonyl-pyrrolidin-3-ylamino)-5-(3-phenyl-isoxazole-5-carbonyl)-thiophene-3-carbonitrile, can be prepared by treating 4-amino-5-(3-phenyl-isoxazole-5-carbonyl)-2-(pyrrolidin-3-ylamino)-thiophene-3-carbonitrile (compound 1-P2) with benzenesulfonyl chloride under basic conditions and subjecting the reaction mixture to standard aqueous work up (e.g. addition of water and extracting the product with an organic solvent) to isolate the product, compound 1-P6.

Example 29

Synthesis of Compound 1-251 (Table 1A)

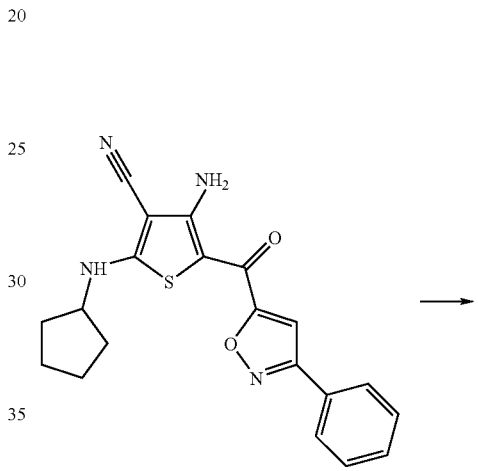

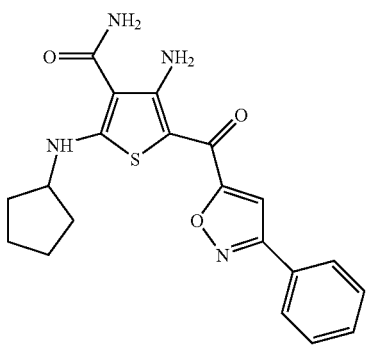

Preparation of 4-amino-5-[3-phenyl isoxazole-5-carbonyl]-2-cyclopentylamino thiophene-3-carboxylic acid amide, (Compound 1-251, Table 1A)

4-Amino-5-(phen-3-yl)isoxazol-5-yl)carbonyl-2-cyclopentylamino-thiophene-3-carbonitrile (Compound 1-143) (40 mg, 0.0001 mol) was slowly dissolved by conc. sulfuric acid (1 mL, 0.02 mol). The reaction mixture was stirred at room temperature for 45 min. Ice was added and the mixture was diluted with water (4 mL) followed by the addition of saturated potassium carbonate solution to neutralize the acid.

The product was extracted with ethyl acetate and purified by preparative TLC to provide compound 1-251. MS(ESI) [M+H$^+$]$^+$=397.2.

Example 30

Synthesis of Compound 1-236 (Table 1A)

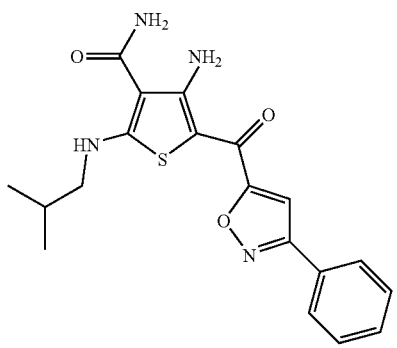

Preparation of 4-amino-5-[3-phenyl isoxazole-5-carbonyl]-2-isobutylamino thiophene-3-carboxylic acid amide, (Compound 1-236, Table 1A)

4-amino-5-[3-phenyl isoxazole-5-carbonyl]-2-isobutylamino thiophene-3-carboxylic acid amide was prepared as described in Example 29 replacing 4-amino-5-(phen-3-yl)isoxazle-5-yl)carbonyl-2-cyclopentylamino-thiophene-3-carbonitrile with 4-amino-5-(phen-3-yl)isoxazol-5-yl)carbonyl-2-isobutylamino-thiophene-3-carbonitrile, (compound 1-209, Table 1A) to provide compound 1-236. MS(ESI) [M+H$^+$]$^+$=385.2

Example 31

Synthesis of Compound 1-253 (Table 1A)

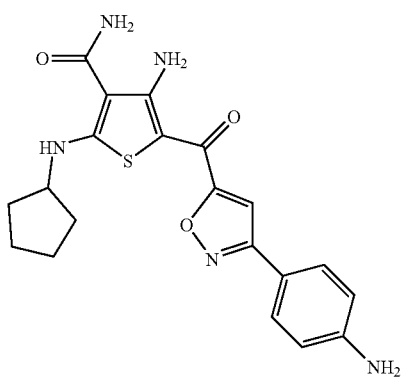

Step 1: Preparation 4-Amino-5-[3-(4-nitro-phenyl)-isoxazole-5-carbonyl]-2-cyclopentylamino-thiophene-3-carbonitrile (Compound 1-220, Table 1A)

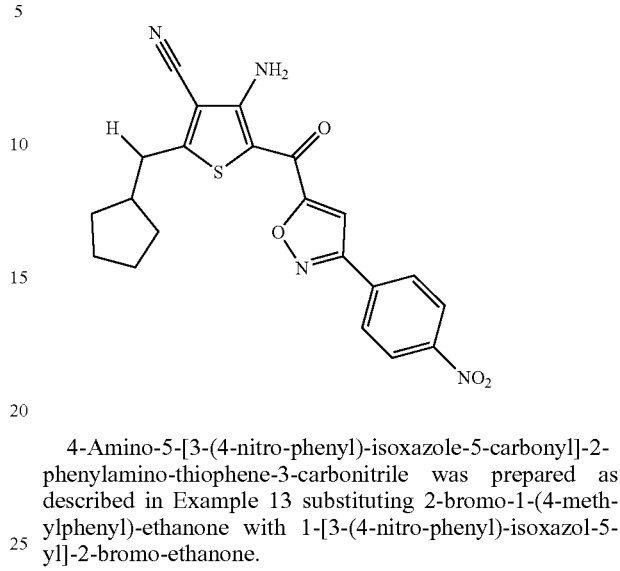

4-Amino-5-[3-(4-nitro-phenyl)-isoxazole-5-carbonyl]-2-phenylamino-thiophene-3-carbonitrile was prepared as described in Example 13 substituting 2-bromo-1-(4-methylphenyl)-ethanone with 1-[3-(4-nitro-phenyl)-isoxazol-5-yl]-2-bromo-ethanone.

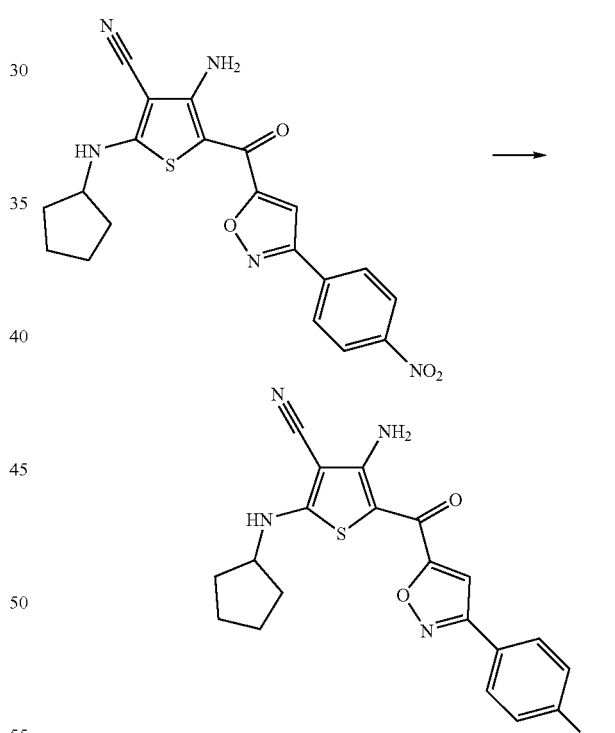

Step 2: Preparation of 4-Amino-5-[3-(4-amino-phenyl)-isoxazole-5-carbonyl]-2-cyclopentylamino-thiophene-3-carbonitrile (Compound 1-250, Table 1A)

4-Amino-5-[3-(4-nitro-phenyl)-isoxazole-5-carbonyl]-2-cyclopentylamino-thiophene-3-carbonitrile (Compound 1-220, 20 mg, 0.05 mmol) was slowly dissolved in methanol (3 mL). Palladium (10% on calcium carbonate) (5 mg, 0.02 mmol) was added. The reaction vessel was charged with an atmosphere of hydrogen gas and was agitated over night. The reaction mixture was filtered and concentrated under reduced pressure to provide compound 1-250, which was used without further purification.

Step 3: Preparation of 4-amino-5-[3-(4-aminophenyl) isoxazole-5-carbonyl]-2-cyclopentylamino thiophene-3-carboxylic acid amide, (Compound 1-253, Table 1A)

4-Amino-5-[3-(4-aminophenyl) isoxazole-5-carbonyl]-2-cyclopentylamino thiophene-3-carboxylic acid amide was prepared using the same protocol as described in Example 29 substituting 4-amino-5-(phen-3-yl)isoxazol-5-yl)carbonyl-2-cyclopentylamino-thiophene-3-carbonitrile with 4 amino-5-(4-amino-phen-3-yl)isoxazle-5-yl)carbonyl-2-cyclopentylamino-thiophene-3-carbonitrile (compound 1-250) to provide compound 1-253. MS(ESI) [M+H$^+$]$^+$=412.41.

Example 32

Synthesis of Compound 1-254 (Table 1A)

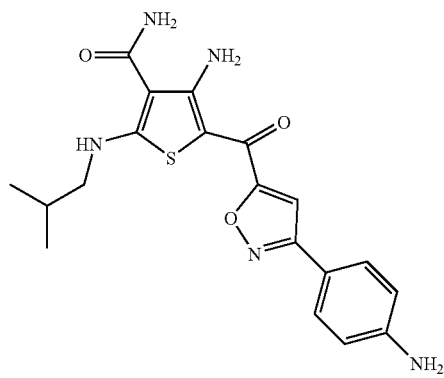

Step 1: Preparation 4-Amino-5-[3-(4-nitro-phenyl)-isoxazole-5-carbonyl]-2-isobutylamino-thiophene-3-carbonitrile

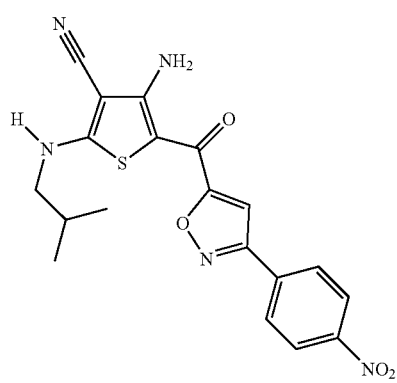

4-Amino-5-[3-(4-nitro-phenyl)-isoxazole-5-carbonyl]-2-isobutylamino-thiophene-3-carbonitrile was prepared as described in Example 13 substituting isothiocyanatobenzene and 2-bromo-1-(4-methylphenyl)-ethanone with isobutyl-isothiocyanate and 1-[3-(4-nitro-phenyl)-isoxazol-5-yl]-2-bromo-ethanone.

Step 2: Preparation of 4-Amino-5-[3-(4-amino-phenyl)-isoxazole-5-carbonyl]-2-isobutylamino-thiophene-3-carbonitrile

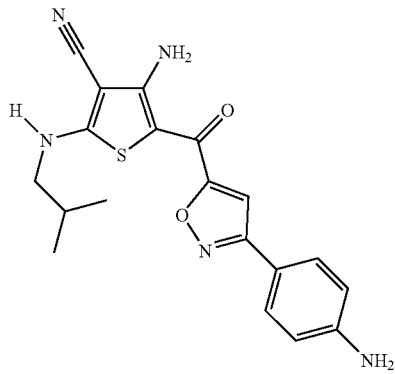

4-Amino-5-[3-(4-amino-phenyl)-isoxazole-5-carbonyl]-2-isobutylamino-thiophene-3-carbonitrile was prepared as described in Example 31 step 2, substituting 4-Amino-5-[3-(4-nitro-phenyl)-isoxazole-5-carbonyl]-2-cyclopentylaino-thiophene-3-carbonitrile with 4-Amino-5-[3-(4-nitro-phenyl)-isoxazole-5-carbonyl]-2-isobutylamino-thiophene-3-carbonitrile.

Step 3: Preparation of 4-amino-5-[3-(4-aminophenyl) isoxazole-5-carbonyl]-2-isobutylamino thiophene-3-carboxylic acid amide (compound 1-254, Table 1A)

4-Amino-5-[3-(4-aminophenyl) isoxazole-5-carbonyl]-2-isobutylamino thiophene-3-carboxylic acid amide was prepared as described in Example 29 substituting 4-amino-5-(phen-3-yl)isoxazol-0.5-yl)carbonyl-2-cyclopentylamino-thiophene-3-carbonitrile with 4-amino-5-(4-amino-phen-3-yl)isoxazol-5-yl)carbonyl-2-isobutylamino-thiophene-3-carbonitrile to provide Compound 1-254. MS(ESI) [M+H$^+$]$^+$=400.44.

Example 33

Prophetic synthesis of Compound 1-P7

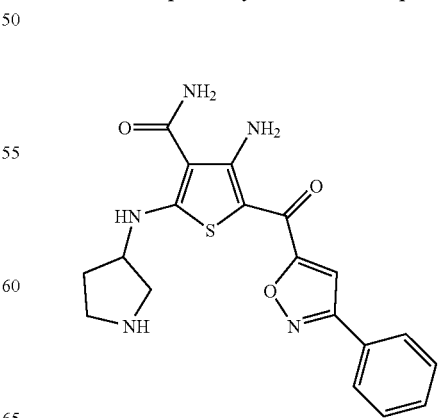

Preparation of 4-Amino-5-(3-phenyl-isoxazole-5-carbonyl)-2-(pyrrolidin-3-ylamino)-thiophene-3-carboxylic acid amide 4-Amino-5-(3-phenyl-isoxazole-5-carbonyl)-2-(pyrrolidin-3-ylamino)-thiophene-3-carboxylic acid amide can be prepared as described in Example 29 substituting 4-amino-5-(phen-3-yl)isoxazol-5-yl)carbonyl-2-cyclopentylamino-thiophene-3-carbonitrile with 3-[4-amino-3-cyano-5-(3-phenyl-isoxazole-5-carbonyl)-thiophen-2-ylamino]-pyrrolidine-1-carboxylic acid tert-butyl ester (Compound 1-P1).

Example 34

Prophetic synthesis of Compound 1-P8

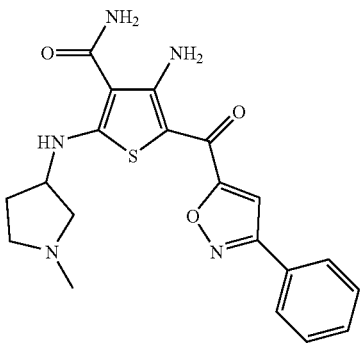

Preparation of 4-Amino-2-(1-methyl-pyrrolidin-3-ylamino)-5-(3-phenyl-isoxazole-5-carbonyl)-thiophene-3-carboxylic acid amide 4-Amino-2-(1-methyl-pyrrolidin-3-ylamino)-5-(3-phenyl-isoxazole-5-carbonyl)-thiophene-3-carboxylic acid amide can be prepared as described in Example 25 substituting 4-Amino-5-(3-phenyl-isoxazole-5-carbonyl)-2-(pyrrolidin-3-ylamino)-thiophene-3-carbonitrile with 4-Amino-5-(3-phenyl-isoxazole-5-carbonyl)-2-(pyrrolidin-3-ylamino)-thiophene-3-carboxylic acid amide (Compound 1-P7).

Example 35

Prophetic synthesis of Compound 1-P9

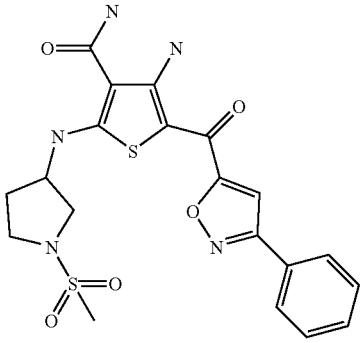

Preparation of 4-amino-2-(1-methanesulfonyl-pyrrolidin-3-ylamino)-5-(3-phenyl-isoxazole-5-carbonyl)-thiophene-3-carboxylic acid amide 4-Amino-2-(1-methanesulfonyl-pyrrolidin-3-ylamino)-5-(3-phenyl-isoxazole-5-carbonyl)-thiophene-3-carboxylic acid amide can be prepared as described in Example 26 substituting 4-Amino-5-(3-phenyl-isoxazole-5-carbonyl)-2-(pyrrolidin-3-ylamino)-thiophene-3-carbonitrile with 4-Amino-5-(3-phenyl-isoxazole-5-carbonyl)-2-(pyrrolidin-3-ylamino)-thiophene-3-carboxylic acid amide (Compound 1-P7).

Example 36

Prophetic synthesis of Compound 1-P10

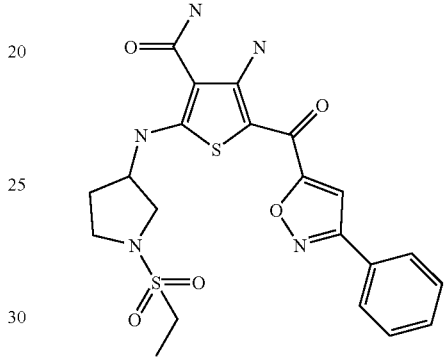

Preparation of 4-Amino-2-(1-ethanesulfonyl-pyrrolidin-3-ylamino)-5-(3-phenyl-isoxazole-5-carbonyl)-thiophene-3-carboxylic acid amide 4-Amino-2-(1-ethanesulfonyl-pyrrolidin-3-ylamino)-5-(3-phenyl-isoxazole-5-carbonyl)-thiophene-3-carboxylic acid amide can be prepared using the same protocol as described in Example 27 substituting 4-amino-5-(3-phenyl-isoxazole-5-carbonyl)-2-(pyrrolidin-3-ylamino)-thiophene-3-carbonitrile with 4-Amino-5-(3-phenyl-isoxazole-5-carbonyl)-2-(pyrrolidin-3-ylamino)-thiophene-3-carboxylic acid amide (Compound 1-P7).

Example 37

Prophetic synthesis of Compound 1-P11

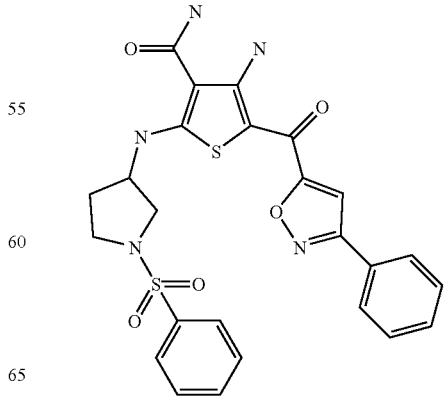

Preparation of 4-amino-2-(1-benzenesulfonyl-pyrrolidin-3-ylamino)-5-(3-phenyl-isoxazole-5-carbonyl)-thiophene-3-carboxylic acid amide 4-Amino-2-(1-benzenesulfonyl-pyrrolidin-3-ylamino)-5-(3-phenyl-isoxazole-5-carbonyl)-thiophene-3-carboxylic acid amide can be prepared as described in Example 28 by substituting 4-amino-5-(3-phenyl-isoxazole-5-carbonyl)-2-(pyrrolidin-3-ylamino)-thiophene-3-carbonitrile with 4-Amino-5-(3-phenyl-isoxazole-5-carbonyl)-2-(pyrrolidin-3-ylamino)-thiophene-3-carboxylic acid amide (Compound 1-P7).

Example 38

Synthesis of Compound 2-30 (Table 2A)

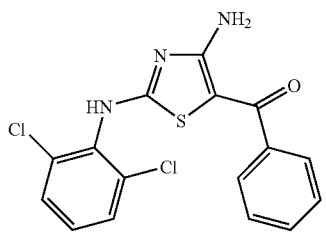

Preparation of 2-(2,6-dichlorophenyl)amino-4-amino-5-benzoylthiazole (Compound 2-30, Table 2A)

Cyanamide (0.0701 g, 0.00165 mol) and 2,6-dichlorophenyl isothiocyanate (0.312 g, 0.00150 mol) were dissolved in Acetonitrile (15.0 mL, 0.287 mol). In another vessel, Potassium tert-Butoxide (0.195 g, 0.00165 mol) was dissolved in warm tert-Butyl alcohol (15.0 mL, 0.157 mol) and the contents of this vessel were added to the first vessel. The resulting solution was stirred for 30 minutes at room temp. 2-Bromoacetophenone (0.305 g, 0.00150 mol) was added and the resulting mixture was stirred for 2 hours. 100 mL of water was added, and the resultant solid was filtered out. The solids were washed with water and diethyl ether to provide compound 2-30 as a yellow solid. MS(ESI) [M+H$^+$]$^+$=365.1

Example 39

Synthesis of Compound 2-33 (Table 2A)

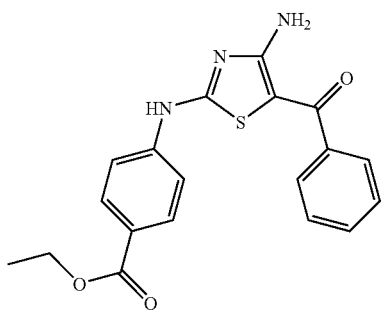

Preparation of 2-(4-ethoxycarbonylphenyl)amino-4-amino-5-benzoylthiazole(Compound 2-33, Table 2A)

2-(4-ethoxycarbonylphenyl)amino-4-amino-5-benzoylthiazole was prepared as described in Example 38 substituting 2,6-dichlorophenyl isothiocyanate with 4-Ethoxycarbonyl phenylisothiocyanate to provide compound 2-33. MS(ESI) [M−H$^+$]$^-$=366.1

Example 40

Synthesis of Compound 2-1 (Table 2A)

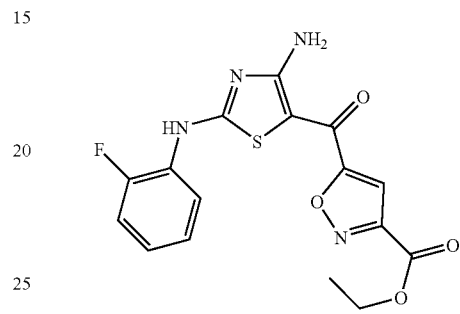

Preparation of 5-[4-Amino-2-(2-fluoro-phenylamino)-thiazole-5-carbonyl]-isoxazole-3-carboxylic acid ethyl ester(Compound 2-1, Table 2A)

5-[4-Amino-2-(2-fluoro-phenylamino)-thiazole-5-carbonyl]-isoxazole-3-carboxylic acid ethyl ester was prepared as described in Example 38 substituting 2,6-dichlorophenyl isothiocyanate and bromoacetophenone with 2-fluorophenyl isothiocyante and 5-(2-Bromo-acetyl)-isoxazole-3-carboxylic acid ethyl ester respecively to provide compound 2-1. MS(ESI) [M+H$^+$]$^+$=377.1

Example 41

Synthesis of Compound 2-9 (Table 2A)

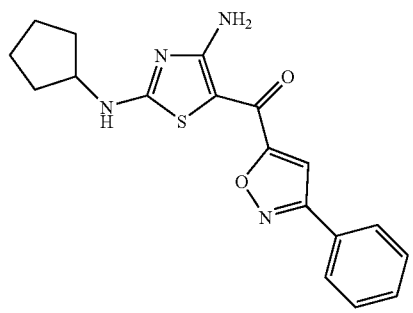

Preparation of (4-Amino-2-cyclopentylamino-thiazol-5-yl)-(3-phenyl-isoxazol-5-yl)-methanone (Compound 2-9)

(4-Amino-2-cyclopentylamino-thiazol-5-yl)-(3-phenyl-isoxazol-5-yl)-methanone was prepared as described in Example 38 substituting 2,6-dichlorophenyl isothiocyanate and bromoacetophenone with cyclopentyl isothiocyante and 2-Bromo-1-(3-phenyl-isoxazol-5-yl)-ethanone respecively to provide compound 2-9. MS(ESI) [M+H$^+$]$^+$=355.1

Example 42

Synthesis of Compound 2-16 (Table 2A)

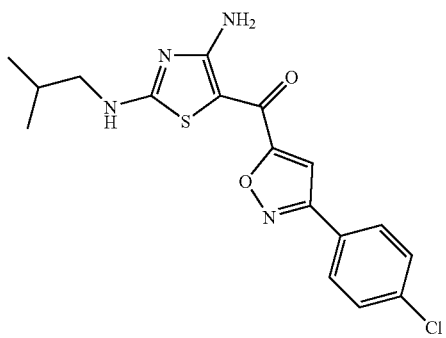

Preparation of 4-amino-2-isobutylamino-thiazol-5-yl-[3-(4-chlorophenyl)-isoxazol-5-yl]-methanone (Compound 2-16)

4-amino-2-isobutylamino-thiazol-5-yl-[3-(4-chlorophenyl)-isoxazol-5-yl]-methanone was prepared as described in Example 38 substituting 2,6-dichlorophenyl isothiocyanate and bromoacetophenone with isobutyl isothiocyante and 2-Bromo-1-(3-(4-chlorophenyl-isoxazol-5-yl)-ethanone respecively to provide compound 2-16. MS(ESI) [M+H$^+$]$^+$=377.01

Example 43

Synthesis of Compound 1-240 (Table 1A)

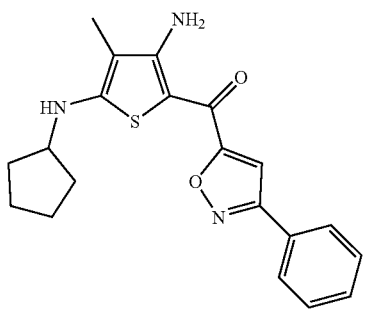

Preparation of (3-Amino-5-cyclopentylamino-4-methyl-thiophen-2-yl)-(3-phenyl-isoxazol-5-yl)-methanone (Compound 1-240, Table 1A).

Lithium hexamethyldisilazide (214 mg, 0.00124 mol) was dissolved in 5 ml of tetrahydrofuran under an atmosphere of Nitrogen. At −78 Celsius, Propanenitrile (0.0659 g, 0.00118 mol) was added. After 30 minutes, Isothiocyanato-cyclopentane (0.164 mL, 0.00130 mol) was added at −40 Celsius. After 1 hour, the reaction mixture was warmed to room temperature and was stirred for 2 hours. The reaction mixture was chilled to −78 Celsius and lithium hexamethyldisilazide (0.214 g, 0.00124 mol) in tetrahydrofuran was added. After 30 minutes, 2-Bromo-1-(3-phenyl-isoxazol-5-yl)-ethanone (0.378 g, 0.00142 mol) was added at −40 Celsius. The resulting reaction mixture was gradually warmed to room temperature and allowed to stir overnight. The reaction was quenched with the addition of saturated NH$_4$Cl solution and was extracted with ethyl acetate. The organic layer was washed with brine and dried over anhydrous sodium sulfate. The reaction mixture was concentrated under reduced pressure and purified by silica gel chromatography to provide compound 1-240. MS(ESI) [M+H$^+$]$^+$=368.1

Example 44

Synthesis of Compound 1-243 (Table 1A)

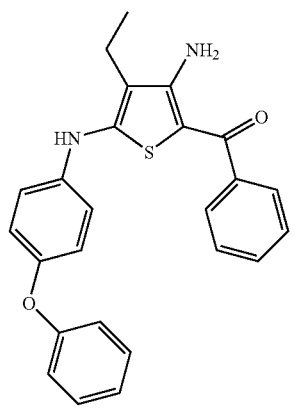

Preparation of [3-Amino-4-ethyl-5-(4-phenoxy-phenylamino)-thiophen-2-yl]-phenyl-methanone

[3-Amino-4-ethyl-5-(4-phenoxy-phenylamino)-thiophen-2-yl]-phenyl-methanone was prepared as described in Example 43 substituting Propanenitrile, Isothiocyanato-cyclopentane and 2-Bromo-1-(3-phenyl-isoxazol-5-yl)-ethanone with butanenitrile, 4-phenoxyphenylisothiocyanate and 2-Bromo-1-phenyl-ethanone respectively to provide compound 1-243. MS(ESI) [M+H$^+$]$^+$=415.0

Example 45

Synthesis of 4-(2-Methylsulfanyl-quinazolin-4-yl amino)-N-quinolin-8-yl-benzenesulfonamide (Compound 3-62, Table 3A)

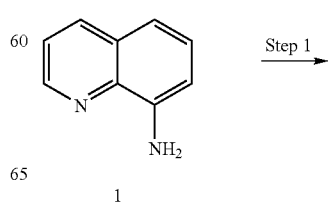

1

-continued

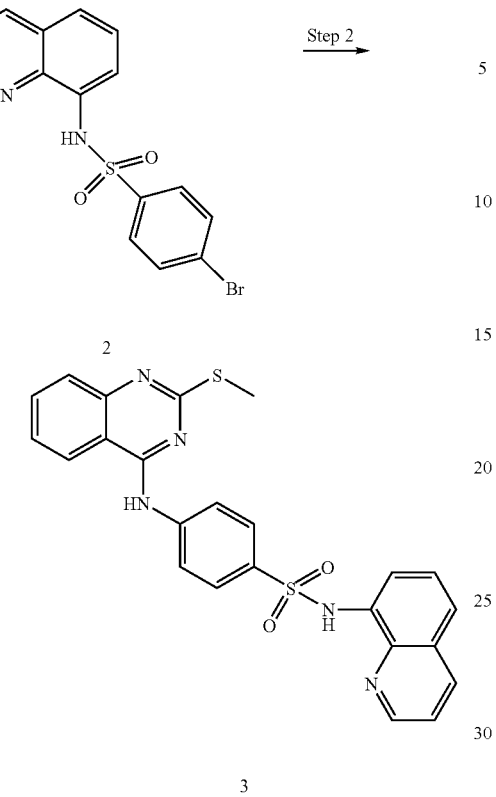

Step-1-Preparation of 4-Bromo-N-quinolin-8-yl-benzenesulfonamide 2

To a solution of 4-bromobenzene sulfonylchloride (1.10 g, 4.32 mmol) in pyridine (5 mL) was added 8-quinolinamine (1, 623 mg, 4.32 mmol) and the reaction mixture was stirred overnight at 25° C. Ethyl acetate was added to the reaction mixture and the organic layer was washed with saturated sodium carbonate (X 3), dried over magnesium sulfate, filtered and concentration under reduced pressure to afford a light brown solid (2, 1.57 g, 3.80 mmol). MS(ESI) [M+H$^+$]$^+$ =363.1; 365.1 (1:1)

Step-2-Preparation of 4-(2-Methylsulfanyl-quinazolin-4-yl amino)-N-quinolin-8-yl-benzenesulfonamide 3

To a stirring solution of (4-bromo-N-quinolin-8-yl-benzenesulfonamide (2, 111 mg, 0.307 mmol) in 1,4-Dioxane (2 mL) was added 2-methylsulfanyl-quinazolin-4-yl-amine (165 mg, 0.863 mmol), cesium carbonate (140 mg, 0.429 mmol), tris(dibenzylideneacetone)dipalladium(0) (9.6 mg, 0.010 mmol), and xanthphos (6.4 mg, 0.011 mmol). The reaction mixture was heated in a high pressure tube at 150° C. for overnight, cooled and filtrated over a bed of Celite. Ethyl acetate was added to the resulting filtrate and the solution was washed with saturated sodium carbonate, dried over magnesium sulfate, filtered, and concentrated under reduced pressure. The crude material was purified using preparative HPLC (5-95% acetonitrile:water with 1.5% formic acid) to afford compound 3-62 as a white solid (52 mg, 0.110 mmol). MS(ESI) [M+H$^+$]$^+$=474.2

Example 46

Synthesis of 3-(2-methylsulfanyl-quinazolin-4-yl amino)-N-quinolin-8-yl-benzenesulfonamide (Compound 3-63, Table 3A)

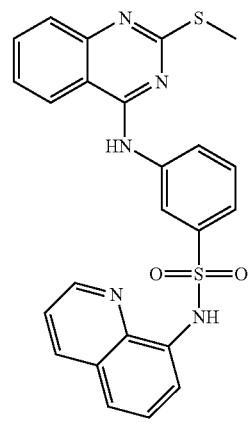

3-(2-Methylsulfanyl-quinazolin-4-yl amino)-N-quinolin-8-yl-benzenesulfonamide 4 was prepared using the same protocol as described in Example 45, substituting 4-bromobenzene sulfonylchloride with 3-bromobenzene sulfonylchloride; MS(ESI)[M+H$^+$]$^+$:474.2

Example 47

Synthesis of 3-(Pyrimidin-4-ylamino)-N-quinolin-8-yl-benzenesulfonamide (Compound 3-61, Table 3A)

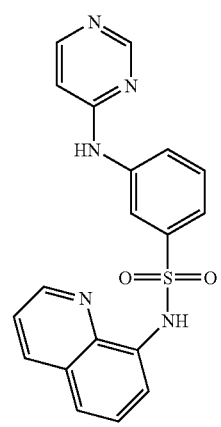

3-(Pyrimidin-4-ylamino)-N-quinolin-8-yl-benzenesulfonamide 5 was prepared using the same protocol as described in Example 45, substituting 4-bromobenzene sulfonylchloride with 3-bromobenzene sulfonylchloride and 2-methylsulfanyl-quinazolin-4-yl-amine with 4-aminopyrimidine. MS(ESI) [M+H$^+$]$^+$=378.0.

Example 48

Cloning of PDE4B Phosphodiesterase Domain

PDE4B cDNA sequence was amplified from a Human Brain, hippocampus QUICK-Clone cDNA library (Clontech, #7169-1) by PCR using the following primers:

```
                                        (SEQ ID NO:5)
PDE4B-S:
5'-CCGAATT CATATG AGCATCTCACGCTTTGGAGTC-3'

(SEQ ID NO:6)
PDE4B-A:
5'-TGTGCT CTCGAG TTA GCTGTGTCCCTCTCCCTCC-3'
```

An internal NdeI site was then engineered out by site directed mutagenesis using the following primers:

```
PDE4B-NDE1:
5'-GATATGTCTAAACACATGAGCCTGCTGGC-3'  (SEQ ID NO:7)

PDE4B-NDE2:
5'-GCCAGCAGGCTCATGTGTTTAGACATATC-3'  (SEQ ID NO:8)
```

The resulting PCR fragment was digested with NdeI and SalI and subcloned into the pET15S vector.

In this expression plasmid, residues 152-528 of PDE4B (NCBI sequence JC1519, SEQ ID NO:1) are in frame with an N-terminal His-tag followed by a thrombin cleavage site.

The sequence of pET15S, with multi-cloning site is shown in FIG. 1.

pETI 15S vector is derived from pET15b vector (Novagen) for bacterial expression to produce the proteins with N-terminal His6 (SEQ ID NO: 18). This vector was modified by replacement of NdeI-BamHI fragment to others to create a SalI site and stop codon (TAG). Vector size is 5814 bp. Insertion can be performed using NdeI-SalI site. The nucleic acid and amino acid sequences for the PDE4B phosphodiesterase domain utilized are provided in FIGS. 2-3.

Example 49

Purification of PDE4B

PDE4B is purified from *E. coli* cells [BL21(DE3)Codon Plus(RIL) (Novagen)] grown in Terrific broth that has been supplemented with 0.2 mM Zinc Acetate and 1 mM MgCl2 and induced for 16-20 h with 1 mM IPTG at 22° C. The centrifuged bacterial pellet (typically 200-250 g from 16 L) is suspended in lysis buffer (0.1M potassium phosphate buffer, pH 8.0, 10% glycerol, 1 mM PMSF). 100 ug/ml of lysozyme is added to the lysate and the cells are lysed in a Cell Disruptor (MicroFluidics). The cell extract is clarified at 5000 rpm in a Sorvall SA6000 rotor for 1 h, and the supernatant is recentrifuged for another hour at 17000 rpm in a Sorvall SA 600 rotor. 5 mM imidazole (pH 8.0) is added to the clarified supernatant and 2 ml of cobalt beads (50% slurry) is added to each 35 ml of extract. The beads are mixed at 4 C for 3-4 h on a Nutator and the beads are recovered by centrifugation at 4000 rpm for 3 min. The pelleted beads are washed several times with lysis buffer and the beads are packed on a BioRad disposable column. The bound protein is eluted with 3-4 column volumes of 0.1M imidazole followed by 0.25M imidazole, both prepared in lysis buffer. The protein eluted from the cobalt beads is concentrated on Centriprep-10 membranes (Amicon) and separated on a Pharmacia Superdex 200 column (26/60) in low salt buffer (25 mM Tris-HCl, pH 8.0, 150 mM NaCl, 14 mM beta-mercaptoethanol). At this stage the PDE proteins are treated with thrombin for 16-20 hours at room temperature. The PDE proteins are further purified by anion exchange chromatography on a Pharmacia Source Q column (10/10) in 20 mM Tris-HCl pH 8 and 14 mM beta-mercaptoethanol using a NaCl gradient in an AKTA-FPLC (Pharmacia).

Example 50

Crystallization of PDE4B Phosphodiesterase Domain

Crystals of PDE4B were grown in 30% PEG 400, 0.2M $MgCl_2$, 0.1M Tris pH 8.5, 1 mM Cmpd 1-2, 15.9 mg/ml protein at 4° C., using an Intelliplate (Robbins Scientific, Hampton) by mixing one microliter of protein with one microliter of precipitant. Data was collected to 1.4 Å.

Additionally, PDE4B crystals were grown in 20% PEG 3000, 0.2M $Ca(OAc)_2$, 0.1M Tris pH 7.0, 1 mM Cmpd 1-2, 15.9 mg/ml protein at 4° C., using an Intelliplate (Robbins Scientific, Hampton) by mixing one microliter of protein with one microliter of precipitant. Data was collected to 1.7 Å.

Example 51

Structure Determination of PDE4B

The structure of PDE4B was solved using molecular replacement, using the previously deposited coordinates for PDE4B. The atomic coordinates for the PDE4B structure determined are provided in Table 1 and coordinates for co-crystal structures are provided in Tables 2, 3, and 4, all of U.S. Provisional Application No. 60/569,435, filed May 6, 2004, which is hereby incorporated by reference in its entirety for all purposes.

Furthermore, using the methods of crystallization and crystallography described herein, co-crystals and/or co-crystal structures in combination with PDE4B and/or PDE4D have been obtained for a plurality of compounds such as, without limitation, Cmpds 2-23, 2-24, 2-25, 2-26, 3-16, 2-30, 2-89, 2-34, 2-93, 1-191, 2-98, 2-100, 2-51, 2-80, 2-6,2-82, 2-80, 2-54, 1-219, 1-250, 1-242, 3-63, and 1-249; see Tables 3A, 4A, and 5A for compound structures.

Example 52

PDE Binding Assays

Binding assays can be performed in a variety of ways, including a variety of ways known in the art. For example, as indicated above, binding assays can be performed using fluorescence resonance energy transfer (FRET) format, or using an AlphaScreen Alternatively, any method which can measure binding of a ligand to the cAMP-binding site can be used. For example, a fluorescent ligand can be used. When bound to PDE4B, the emitted fluorescence is polarized. Once displaced by inhibitor binding, the polarization decreases.

Determination of IC50 for compounds by competitive binding assays. (Note that $K_1$ is the dissociation constant for inhibitor binding; $K_D$ is the dissociation constant for substrate binding.) For this system, the IC50, inhibitor binding constant and substrate binding constant can be interrelated according to the following formula:

When using radiolabeled substrate $$K_I = \frac{IC_{50}}{1 + [L^*]/K_D},$$

the $IC_{50} \sim K_1$ when there is a small amount of labeled substrate.

Example 53

PDE Activity Assay

As an exemplary phosphodiesterase assay, the effect of potential modulators phosphodiesterase activity of PDE4B, PDE5A, and other PDEs was measured in the following assay format:

Reagents
  Assay Buffer
  50 mM Tris, 7.5
  8.3 mM MgCl$_2$
  1.7 mM EGTA
  0.01% BSA
  Store @ 4 degrees
  RNA binding YSi SPA beads
  Beads are 100 mg/ml in water. Dilute to 5 mg/ml in 18 mM Zn using 1M ZnAcetate/ZnSO$_4$ solution(3:1) and water. Store @ 4 degrees.

| Low control compounds | Concentration of 20X DMSO Stock |
|---|---|
| PDE1B: 8-methoxymethyl IBMX | 20 mM |
| PDE2A: EHNA | 10 mM |
| PDE3B: Milrinone | 2 mM |
| PDE4D: Rolipram | 10 mM |
| PDE5A: Zaprinast | 10 mM |
| PDE7B: IBMX | 40 mM |
| PDE10A: Dipyridamole | 4 mM |

Enzyme concentrations (2× final concentration. Diluted in assay buffer)
  PDE1B 50 ng/ml
  PDE2A 50 ng/ml
  PDE3B 10 ng/ml
  PDE4D 5 ng/ml
  PDE5A 20 ng/ml
  PDE7B 25 ng/ml
  PDE 10A 5 ng/ml)
  Radioligands
  [$^3$H] cAMP (Amersham TRK559). Dilute 2000× in assay buffer.
  [$^3$H] cGMP (Amersham TRK392). For PDE5A assay only. Dilute 2000× in assay buffer.
  Protocol
  Make assay plates from 2 mM, 96 well master plates by transferring 1 ul of compound to 384 well plate using BiomekFx. Final concentration of compounds will be ~100 µM. Duplicate assay plates are prepared from each master plate so that compounds are assayed in duplicate.
  To column 23 of the assay plate add 1 ul of 20× DMSO stock of appropriate control compound. These will be the low controls.
  Columns 1 and 2 of Chembridge library assay plates and columns 21 and 22 of the Maybridge library assay plates have 1 ul DMSO. These are the high controls.

Using BiomekFx, pipet 10 µl of radioligand into each assay well, then, using the same tips, pipet 10 µl of enzyme into each well.
  Seal assay plate with transparent cover. Centrifuge briefly @11000 RPM, them mix on plate shaker for 10 s.
  Incubate @ 30° for 30 min.
  Using BiomekFx, add 10 µl of bead mixture to each assay well. Mix beads thoroughly in reservoir immediately prior to each assay plate addition.
  Re-seal plate with fresh transparent cover. Mix on plate shaker for 10 s, then centrifuge for 1 min. @ 1000 RPM.
  Place plates in counting racks. Let stand for ≧30 min, then count on Wallac TriLux using program 8.
  Analyze data as % inhibition of enzyme activity. Average of high controls=0% inhibition. Average of low controls=100% inhibition.

Example 54

PDE4 IC$_{50}$ Determinations

IC$_{50}$s were determined by Scintillation Proximity Assay (SPA). The principle of the assay is based on the fact that cAMP, the PDE4 substrate, binds weakly to Yittrium Silicate SPA beads, whereas AMP, the product of PDE4 hydrolysis binds strongly. Thus, the extent of PDE4 hydrolysis of a sample of [$^3$H]cAMP can be measured because only the [$^3$H]AMP produced by PDE4 hydrolysis will bind to the SPA beads and produce a scintillation signal.
  PDE4 enzymes used for IC$_{50}$ assays were:
  PDE4B: The catalytic domain of human PDE4B from S152-S528 with an N- terminal His6 tag (SEQ ID NO: 18) and thrombin cleavage site, expressed in E. coli and purified by metal ion affinity chromatography. Enzyme was stored in 50% glycerol at −20°.
  PDE4D: The catalytic domain of human PDE4B from S3 16-V692 with an N- terminal His6 tag (SEQ ID NO: 18) and thrombin cleavage site, expressed in E. coli and purified by metal ion affinity chromatography. Enzyme was stored in 50% glycerol at −20°.
  PDE4B2: The full-length human PDE4B2 isozyme with an N-terminal His6 tag (SEQ ID NO: 18) and TEV cleavage site expressed in baculovirus infected insect cells. The enzyme was not purified from the cell lysates, so enzyme concentrations were not determined. Enzyme was stored in 50% glycerol at −20°.
  PDE4D5: The full-length human PDE4D5 isozyme with an N-terminal His6 tag (SEQ ID NO: 18) and TEV cleavage site expressed in baculovirus infected insect cells. The enzyme was not purified from the cell lysates, so enzyme concentrations were not determined. Enzyme was stored in 50% glycerol at −20°.
  IC$_{50}$ procedure
  Compounds tested (see Tables 3B, 4B and 5A for compounds and results) were 3-fold serially diluted 11 times in DMSO from a starting concentration of 4 mM or 40 µM, depending on compound potency. 1 µl of each dilution was transferred into duplicate wells of a white polystyrene 384-well assay plate (Coming #3705). In addition to the compound dilutions, each assay plate contained control wells with 1 µl of DMSO (to define 0% enzyme inhibition) or 1 µl of 200 µM roflumilast (to define 100% enzyme inhibition). Using a Beckman FX robot, 10 µl of [$^3$H] cAMP (Amersham TRK559) at 2 mCi/ml in assay buffer (50 mM Tris, pH 7.5; 8.3 mM MgCl; 1.7 mM EGTA; 0.01% BSA) was transferred to each assay well. Next, 10 µl of PDE4 enzyme in assay buffer was added and the plates were shaken for 30 s. at 1000 rpm to start the cAMP hydrolysis reaction. The concentrations of enzyme used were: PDE4B, 80 ng/ml; PDE4D, 4 ng/ml; PDE4B2, 2.5 µl of 50% glycerol stock/ml; PDE4D5 0.083 µl of 50% glycerol stock/ml. Assay plates were covered and incubated for 30 min. at 30°. Reactions were stopped by robotic addition of 10 µl of 5 mg/ml SPA beads (Amersham RPNQ0013) in 18 mM $ZnSO_4$. The assay plates were covered with clear plastic film, centrifuged for 1 min. at 1000 RPM to settle the SPA beads, and counted using a Wallac TriLux scintillation counter. $IC_{50}$'s were calculated from the raw assay data by non-linear regression curve fitting using the Assay Explorer software package from MDL.

Example 55

TNF alpha production by stimulation with LPS in whole blood cultures

Compounds were assayed to generate $IC_{50}$ numbers as described in Example 54, using the following assay protocol (see Tables 3B and 4B for compounds and results).
Protocol
1) Obtained 20 mM DMSO aliquots of desired concentrations of compounds (see Tables 3B and 4B for compounds tested and results). Placed 2 µl/well compound in DMSO in the top row of the dilution plate. Added 98 µl of RPMI 1640 media w/2.5% heat inactivated FBS.
2) Made the same media with 2% DMSO in it. Added 60 µl/well to well to make compound titration. Took 30 µl of top row and did a 1:3 dilution down the plate. In column 11 added 4 wells of 50 µM roflumilast and piclamilast. In column 12 added 2% DMSO media.
3) Transfered 20 µl/well into assay plates in duplicate.
4) Obtained human Buffy coat.
5) Diluted blood with 7 volumes of RPMI 1640 media with 1% P/S and 2.5% heat inactivated FBS (a 1:8 dilution)
6) Added 160 µl/well of diluted blood to the assay plates.
7) Incubated for 1 hour at 37 degrees 5% CO2
8) Diluted LPS (which was already diluted to 1 mg/ml in PBS, 20 µl aliquots frozen −20 C.) to 10× desired final concentration to make a 1000 fold dilution (final concentration should be 100 ng/ml).
9) After 1 hour incubation added 20 µl/well of LPS to plates. A non-LPS treated background was also prepared. Samples were put on the shaker for a one minute 900 rpm.
10) Incubated for 4 hours in incubator.
11) After incubation, put on the shaker for a one minute 900 rpm and spun plate at 100 g for 10 minutes, Decel 5.
12) Carefully pipetted the top 75 µl supernatant into a new plate. Samples were frozen as needed.

Biosource hu-TNF ALPHA ELISA
REAGENTS USED
DPBS 10x: VWR45000-428 (dilute 1:10 with Millipore Water)
TWEEN 20: FISHER BP337-500
CAPTURE AND DETECTION ANTIBODIES: R&D DY510E
STREP-HRP: Biosource part SNN4004X
COLOR REAGENTS: R&D DY994
STOP SOLUTION: from chemistry, or R&D DY999
1) Thawed samples to RT as needed.
2) Added 50 µl Incubation buffer/well.
3) Added 50 µl blood samples +50 µl Diluent buffer
4) Incubated 2 hours at room temp.
5) Washed the plate 4× with 300 µl/well wash buffer with microfill. Wash buffer was DPBS with 0.05% Tween pH 7.2-7.4
6) Added 100 µl biotinylated anti-TNFalpha
7) Incubateed 1 hours at room temp.
8) Washed the plate 4× with 300 µl/well wash buffer with microfill. Wash buffer was DPBS with 0.05% Tween pH 7.2-7.4
9) Added 100 µl Streptavidin-HRP working solution
10) Incubated for 30 minutes at room temp.
11) Washed the plate 4× with 300 µl/well wash buffer with microfill. Wash buffer was DPBS with 0.05% Tween pH 7.2-7.4
12) Added 100 µl Chromagen
13) Incubated in the dark for 30 minutes until the blue color developed satisfactorily.
14) Added 100 µl/well stop solution (2 N $H_2SO_4$).
15) Read plate on WallacVictor at 450 nm for 0.1 sec/well Example 56

Rat Inhibition Studies

All studies were done with male rats CD (SD) IGS BR (Crl) (Charles River, France), which were grouped in to 5 animal groups. Compound doses were as indicated in Tables 3B and 4B, dosing at 100 mg/kg po unless indicated otherwise in the Table.

At the end of the acclimatization period, the non-fasted rats were weighed, individually identified on the tail with a permanent marker and administered by oral (po) or interperitoneal (ip) route with either vehicle, reference or test compound in a volume of 10 mL/kg adapted to the body weight. The animals were gathered in groups of 5 animals in a polystyrene labeled cage with sawdust covered floors. 2-hours after vehicle, reference or test substance administration, rats received an intravenous (iv) injection of 0.1 mg/kg LPS in a volume of 1 mL/kg of body weight. 2 h after LPS challenge (or as indicated in Tables 3B and 4B), blood samples were collected into tubes without anticoagulant by retro-orbital puncture under gas (isoflurane) anesthesia. Samples were allowed to clot at room temperature for 5 to 10 min then put on ice until there were prepared by centrifugation (6000×g for 3 min at 4° C.) and stored at −20° C. until use. TNFα levels were measured in serum samples in duplicate by ELISA technique according to the manufacturer's procedure (Rat TNFα kit Quantikine M (RTA00, R&D System, France)). Data are reported as percent decrease in observed TNFα levels versus TNFa levels observed for vehicle dosed animal groups.

Example 57

Site-directed Mutagenesis of PDE4B

Mutagenesis of PDE4B can be carried out according to the following procedure as described in Molecular Biology: Current Innovations and Future Trends. Eds. A. M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps:

(i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of *E. coli* is Dam-methylated at the sequence 5-GATC-3); (iv) using Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl2; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94 C, 2 min at 50 C and 2 min at 72° C.; followed by 5-10 cycles of 1 min at 94° C., 2 min at 54 C and 1 min at 72° C.

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent *E. coli* (step 4).

In addition to the PCR-based site-directed mutagenesis described above, other methods are available. Examples include those described in Kunkel (1985) Proc. Natl. Acad. Sci. 82:488-492; Eckstein et al. (1985) Nucl. Acids Res. 13:8764-8785; and using the GeneEditor™ Site-Directed Mutageneis Sytem from Promega.

TABLE 1A

Exemplary compounds of Formula I

| Cmpd number | Structure | Name | M + H |
|---|---|---|---|
| 1-1 | 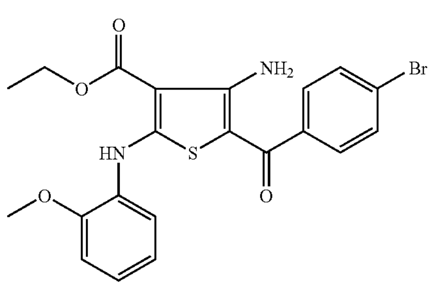 | 4-Amino-5-(4-bromo-benzoyl)-2-(2-methoxy-phenylamino)-thiophene-3-carboxylic acid ethyl ester | N/A |
| 1-2 | 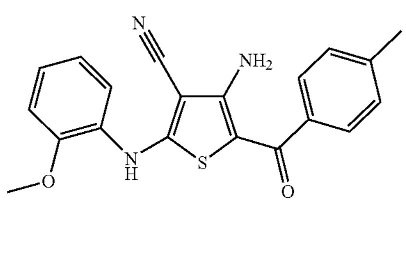 | 4-Amino-2-(2-methoxy-phenylamino)-5-(4-methyl-benzoyl)-thiophene-3-carbonitrile | N/A |

TABLE 1A-continued

Exemplary compounds of Formula I

| Cmpd number | Structure | Name | M + H |
|---|---|---|---|
| 1-3 | 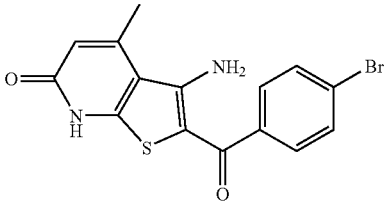 | 3-Amino-2-(4-bromo-benzoyl)-4-methyl-7H-thieno[2,3-b]pyridin-6-one | N/A |
| 1-4 | 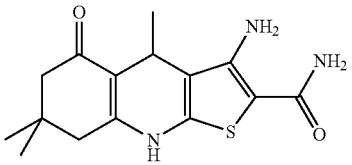 | 3-Amino-4,7,7-trimethyl-5-oxo-4,5,6,7,8,9-hexahydro-thieno[2,3-b]quinoline-2-carboxylic acid amide | N/A |
| 1-5 | 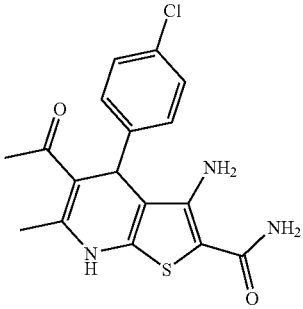 | 5-Acetyl-3-amino-4-(4-chloro-phenyl)-6-methyl-4,7-dihydro-thieno[2,3-b]pyridine-2-carboxylic acid amide | N/A |
| 1-6 | 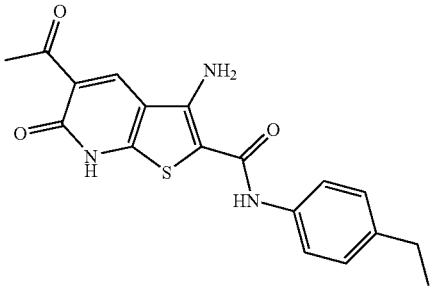 | 3-Amino-2-(4-ethyl-phenylcarbamoyl)-6-oxo-6,7-dihydro-thieno[2.3-b]pyridine-5-carboxylic acid | N/A |
| 1-7 | 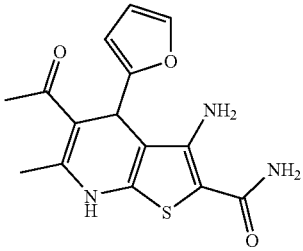 | 5-Acetyl-3-amino-4-furan-2-yl-6-methyl-4,7-dihydro-thieno[2,3-b]pyridine-2-carboxylic acid amide | N/A |

TABLE 1A-continued

Exemplary compounds of Formula I

| Cmpd number | Structure | Name | M + H |
|---|---|---|---|
| 1-8 | 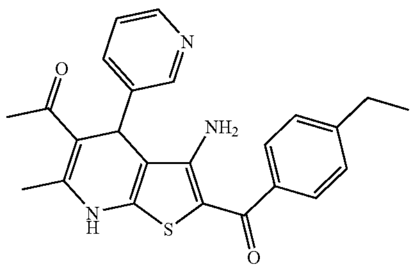 | 1-[3-Amino-2-(4-ethyl-benzoyl)-6-methyl-4-pyridin-3-yl-4,7-dihydro-thieno[2,3-b]pyridin-5-yl]-ethanone | N/A |
| 1-9 | 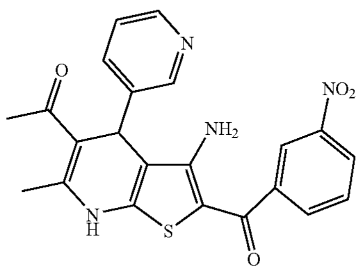 | 1-[3-Amino-6-methyl-2-(3-nitro-benzoyl)-4-pyridin-3-yl-4,7-dihydro-thieno[2,3-b]pyridin-5-yl]-ethanone | N/A |
| 1-10 | 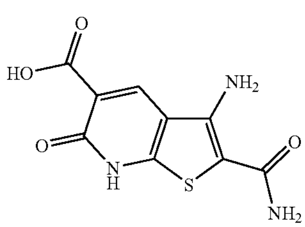 | 3-Amino-2-carbamoyl-6-oxo-6,7-dihydro-thieno[2,3-b]pyridine-5-carboxylic acid | N/A |
| 1-11 | 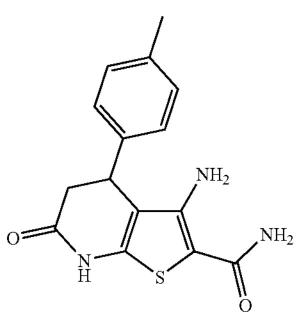 | 3-Amino-6-oxo-4-p-tolyl-4,5,6,7-tetrahydro-thieno[2,3-b]pyridine-2-carboxylic acid amide | N/A |
| 1-12 | 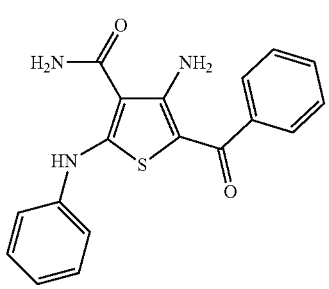 | 4-Amino-5-benzoyl-2-phenylamino-thiophene-3-carboxylic acid amide | N/A |

TABLE 1A-continued

Exemplary compounds of Formula I

| Cmpd number | Structure | Name | M + H |
|---|---|---|---|
| 1-13 | 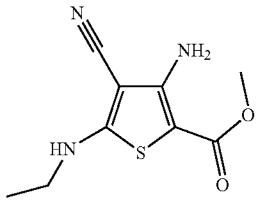 | 3-Amino-4-cyano-5-ethylamino-thiophene-2-carboxylic acid methyl ester | N/A |
| 1-14 | 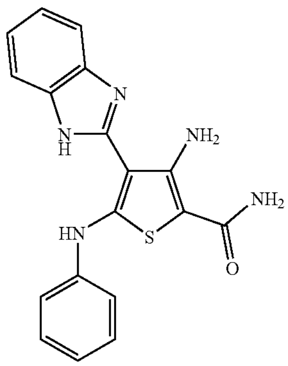 | 3-Amino-4-(1H-benzoimidazol-2-yl)-5-phenylamino-thiophene-2-carboxylic acid amide | N/A |
| 1-15 | 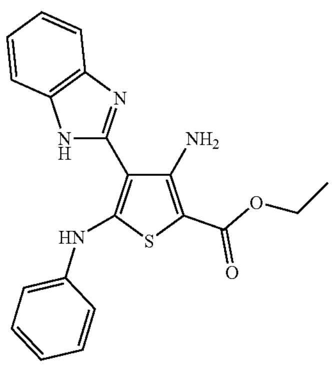 | 3-Amino-4-(1H-benzoimidazol-2-yl)-5-phenylamino-thiophene-2-carboxylic acid ethyl ester | N/A |
| 1-16 | 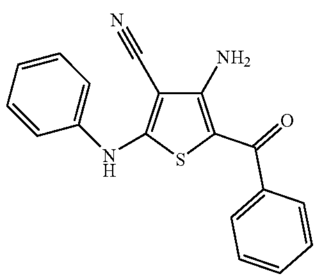 | 4-Amino-5-benzoyl-2-phenylamino-thiophene-3-carbonitrile | N/A |
| 1-17 | 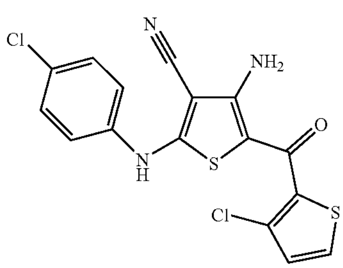 | 4-Amino-2-(4-chloro-phenylamino)-5-(3-chloro-thiophene-2-carbonyl)-thiophene-3-carbonitrile | N/A |

TABLE 1A-continued

Exemplary compounds of Formula I

| Cmpd number | Structure | Name | M + H |
|---|---|---|---|
| 1-18 | 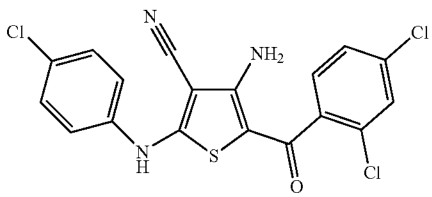 | 4-Amino-2-(4-chloro-phenylamino)-5-(2,4-dichloro-benzoyl)-thiophene-3-carbonitrile | N/A |
| 1-19 | 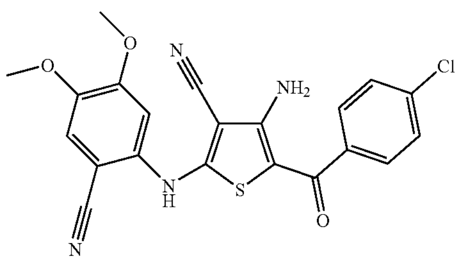 | 4-Amino-5-(4-chloro-benzoyl)-2-(2-cyano-4,5-dimethoxy-phenylamino)-thiophene-3-carbonitrile | N/A |
| 1-20 | 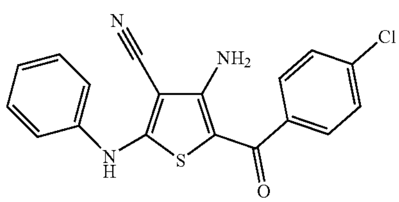 | 4-Amino-5-(4-chloro-benzoyl)-2-phenylamino-thiophene-3-carbonitrile | N/A |
| 1-21 | 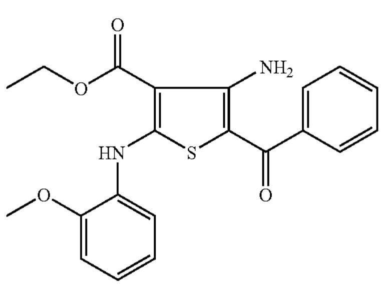 | 4-Amino-5-benzoyl-2-(2-methoxy-phenylamino)-thiophene-3-carboxylic acid ethyl ester | N/A |
| 1-22 | 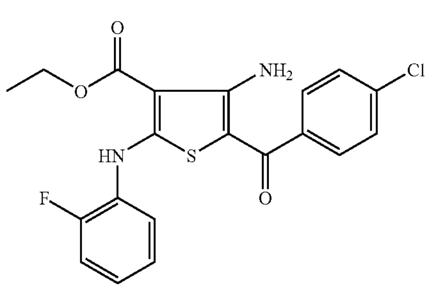 | 4-Amino-5-(4-chloro-benzoyl)-2-(2-fluoro-phenylamino)-thiophene-3-carboxylic acid ethyl ester | N/A |

TABLE 1A-continued

Exemplary compounds of Formula I

| Cmpd number | Structure | Name | M + H |
|---|---|---|---|
| 1-23 | 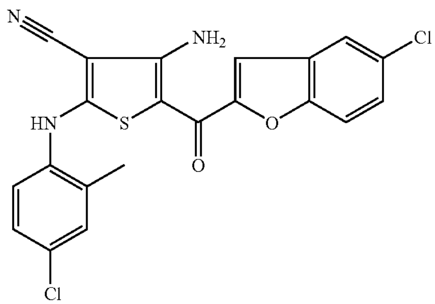 | 4-Amino-5-(5-chloro-benzofuran-2-carbonyl)-2-(4-chloro-2-methyl-phenylamino)-thiophene-3-carbonitrile | N/A |
| 1-24 | 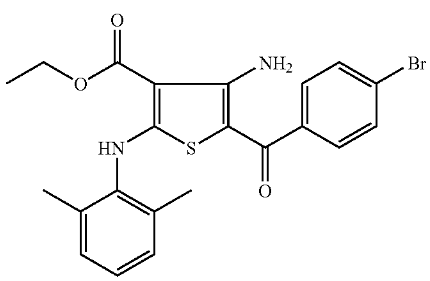 | 4-Amino-5-(4-bromo-benzoyl)-2-(2,6-dimethyl-phenylamino)-thiophene-3-carboxylic acid ethyl ester | N/A |
| 1-25 | 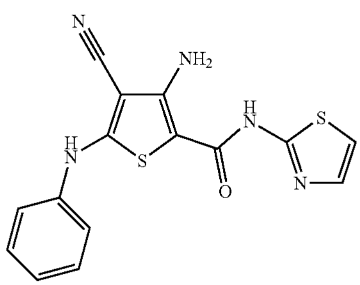 | 3-Amino-4-cyano-5-phenylamino-thiophene-2-carboxylic acid thiazol-2-yl amide | N/A |
| 1-26 | 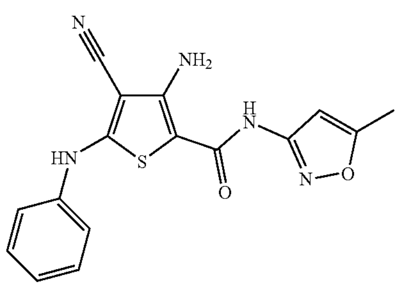 | 3-Amino-4-cyano-5-phenylamino-thiophene-2-carboxylic acid (5-methyl-isoxazol-3-yl)-amide | N/A |
| 1-27 | 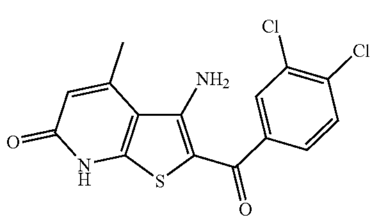 | 3-Amino-2-(3,4-dichloro-benzoyl)-4-methyl-7H-thioeno[2,3-b]pyridin-6-one | N/A |

TABLE 1A-continued
Exemplary compounds of Formula I
| Cmpd number | Structure | Name | M + H |
|---|---|---|---|
| 1-28 | 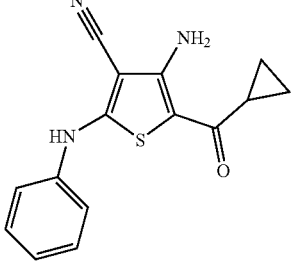 | 4-Amino-5-cyclopropanecarbonyl-2-phenylamino-thiophene-3-carbonitrile | N/A |
| 1-29 | 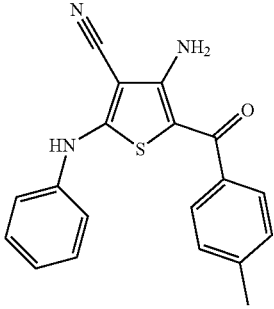 | 4-Amino-5-(4-methyl-benzoyl)-2-phenylamino-thiophene-3-carbonitrile | 334.2 |
| 1-30 | 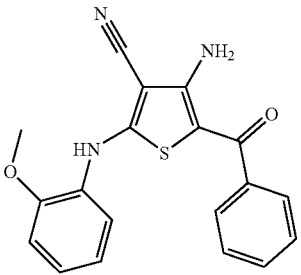 | 4-Amino-5-benzoyl-2-(2-methoxy-phenylamino)-thiophene-3-carbonitrile | 350.11 |
| 1-31 | 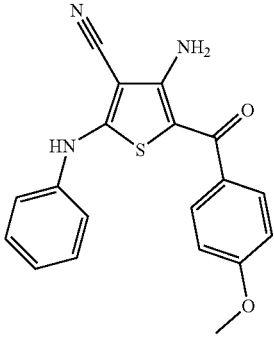 | 4-Amino-5-(4-methoxy-benzoyl)-2-phenylamino)-thiophene-3-carbonitrile | 350.1 |

TABLE 1A-continued

Exemplary compounds of Formula I

| Cmpd number | Structure | Name | M + H |
|---|---|---|---|
| 1-32 | 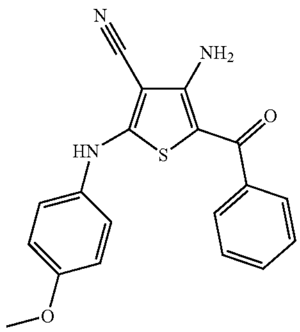 | 4-Amino-5-benzoyl-2-(4-methoxy-phenylamino)-thiophene-3-carbonitrile | 350.14 |
| 1-33 | 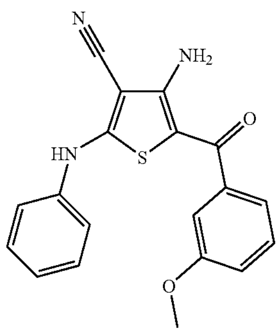 | 4-Amino-5-(3-methoxy-benzoyl)-2-phenylamino-thiophene-3-carbonitrile | 350.1 |
| 1-34 | 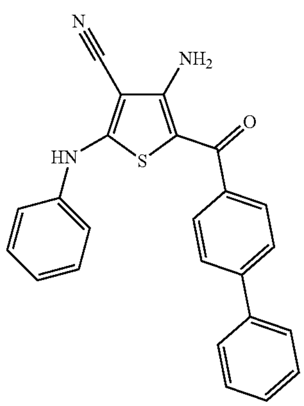 | 4-Amino-5-(biphenyl-4-carbonyl)-2-phenylamino-thiophene-3-carbontrile | N/A |
| 1-35 | 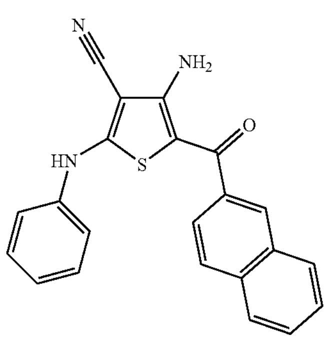 | 4-Amino-5-(naphthalene-2-carbonyl)-2-phenylamino-thiophene-3-carbonitrile | N/A |

TABLE 1A-continued

Exemplary compounds of Formula I

| Cmpd number | Structure | Name | M + H |
|---|---|---|---|
| 1-36 | 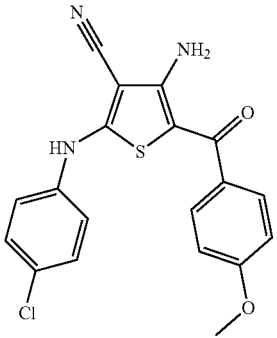 | 4-Amino-2-(4-chloro-phenylamino)-5-(4-methoxy-benzoyl)-thiophene-3-carbonitrile | 384.05 |
| 1-37 | 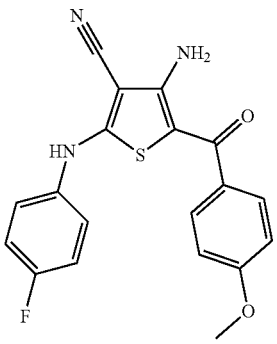 | 4-Amino-2-(4-fluoro-phenylamino)-5-(4-methoxy-benzoyl)-thiophene-3-carbonitrile | 368.12 |
| 1-38 | 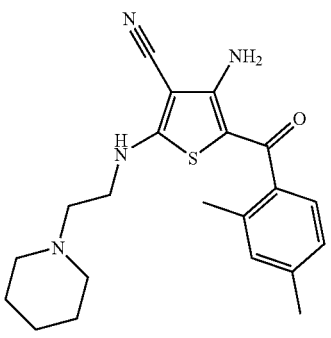 | 4-Amino-5-(2,4-dimethyl-benzoyl)-2-(2-piperidin-1-yl-ethylamino)-thiophene-3-carbonitrile | 383.1 |
| 1-39 | 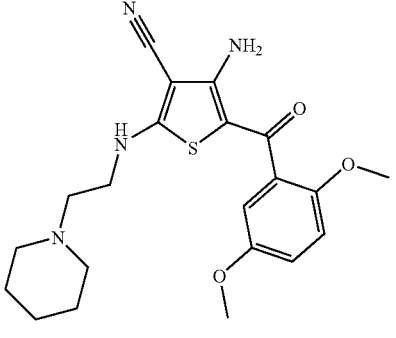 | 4-Amino-5-(2,5-dimethoxy-benzoyl)-2-(2-piperidin-1-yl-ethylamino)-thiophene-3-carbonitrile | 415.5 |

TABLE 1A-continued

Exemplary compounds of Formula I

| Cmpd number | Structure | Name | M + H |
|---|---|---|---|
| 1-40 | 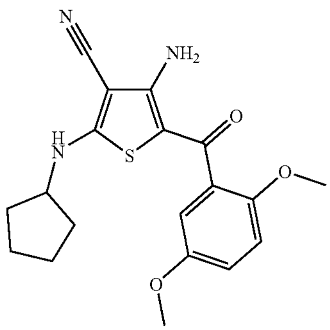 | 4-Amino-5-cyclopentylamino-5-(2,5-dimethoxy-benzoyl)-thiophene-3-carbonitrile | 372.3 |
| 1-41 | 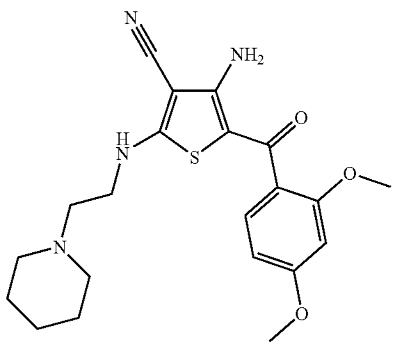 | 4-Amino-5-(2,4-dimethoxy-benzoyl)-2-(2-piperidin-1-yl-ethylamino)-thiophene-3-carbonitrile | N/A |
| 1-42 | 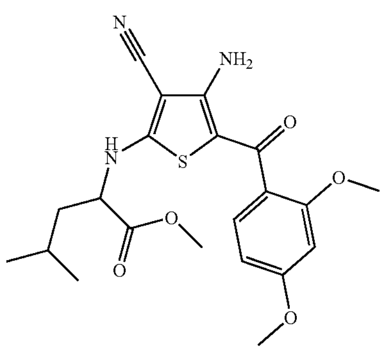 | 2-[4-Amino-3-cyano-5-(2,4-dimethoxy-benzoyl)-thiophen-2-ylamino]-4-methyl-pentanoic acid methyl ester | 432.3 |
| 1-43 | 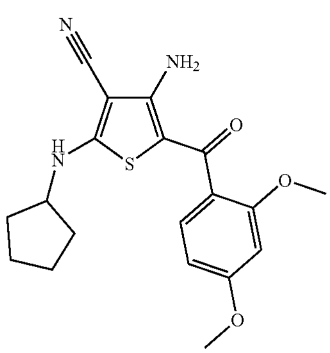 | 4-Amino-2-cyclopentylamino-5-(2,4-dimethoxy-benzoyl)-thiophene-3-carbonitrile | 371.9 |

TABLE 1A-continued

Exemplary compounds of Formula I

| Cmpd number | Structure | Name | M + H |
|---|---|---|---|
| 1-44 | 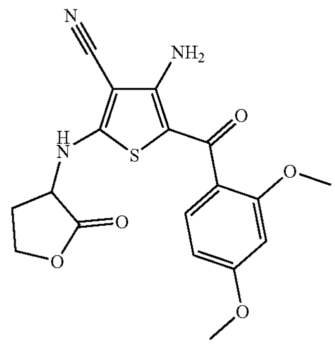 | 4-Amino-5-(2,4-dimethoxy-benzoyl)-2-(2-oxo-tetrahydro-furan-3-ylamino)-thiophene-3-carbonitrile | 388.3 |
| 1-45 | 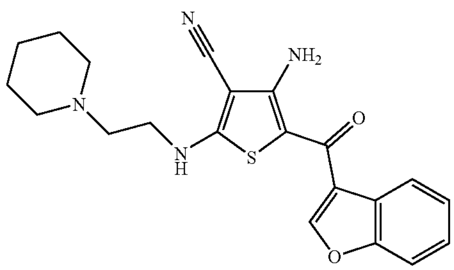 | 4-Amino-5-(benzofuran-3-carbonyl)-2-(2-piperidin-1-yl-ethylamino)-thiophene-3-carbonitrile | 395.1 |
| 1-46 | 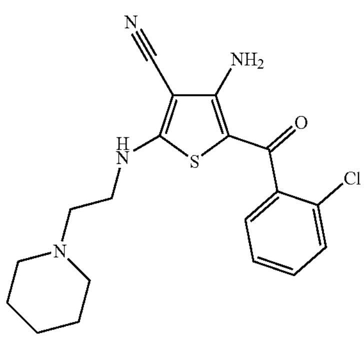 | 4-Amino-5-(2-chloro-benzoyl)-2-(2-piperidin-1-yl-ethylamino)-thiophene-3-carbonitrile | 389.1 |
| 1-47 | 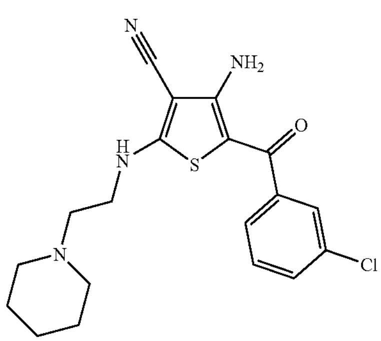 | 4-Amino-5-(3-chloro-benzoyl)-2-(2-piperidin-1-yl-ethylamino)-thiophene-3-carbonitrile | 389.5 |

TABLE 1A-continued

Exemplary compounds of Formula I

| Cmpd number | Structure | Name | M + H |
|---|---|---|---|
| 1-48 | 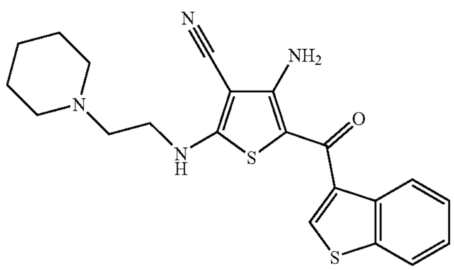 | 4-Amino-5-(benzo[b]thiophene-3-carbonyl)-2-(2-piperidin-1-yl-ethylamino)-thiophene-3-carbonitrile | 411.1 |
| 1-49 | 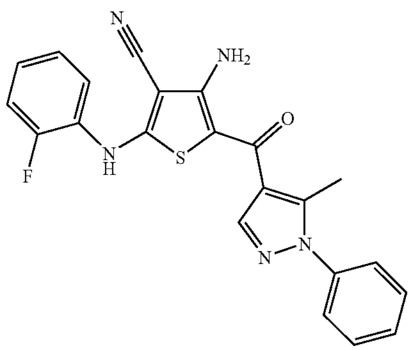 | 4-Amino-2-(2-fluoro-phenylamino)-5-(5-methyl-1-phenyl-1H-pyrazole-4-carbonyl)-thiophene-3-carbonitrile | 418.3 |
| 1-50 | 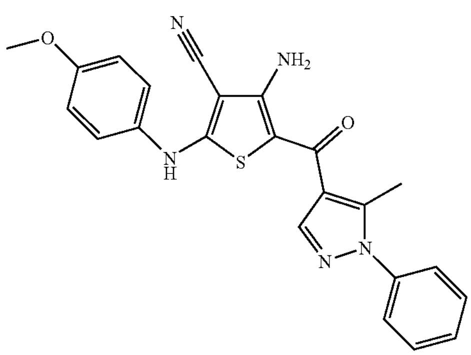 | 4-Amino-2-(4-methoxy-phenylamino)-5-(5-methyl-1-phenyl-1H-pyrazole-4-carbonyl)-thiophene-3-carbonitrile | 430.3 |
| 1-51 | 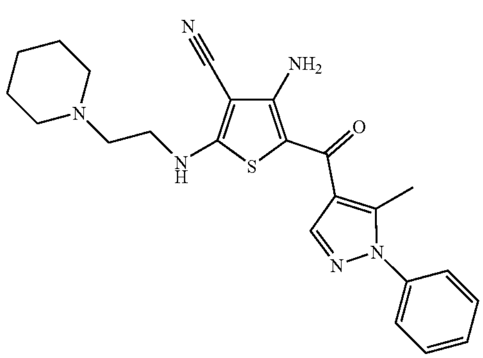 | 4-Amino-5-(5-methyl-1-phenyl-1H-pyrazole-4-carbonyl)-2-(2-piperidin-1-yl-ethylamino)-thiophene-3-carbonitrile | 435.1 |

TABLE 1A-continued

Exemplary compounds of Formula I

| Cmpd number | Structure | Name | M + H |
|---|---|---|---|
| 1-52 | 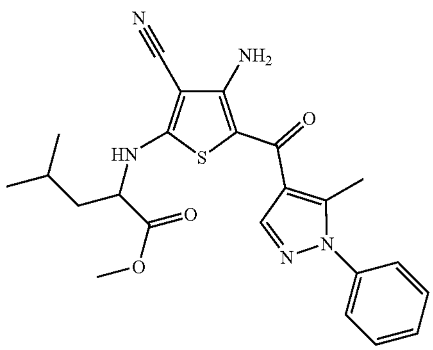 | 2-[4-Amino-3-cyano-5-(5-methyl-1-phenyl-1H-pyrazole-4-carbonyl)-thiophen-2-ylamino]-4-methyl-pentanoic acid methyl ester | 452.3 |
| 1-53 | 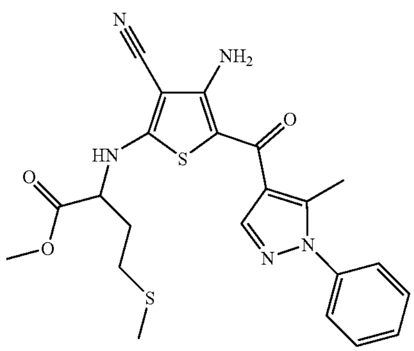 | 2-[4-Amino-3-cyano-5-(5-methyl-1-phenyl-1H-pyrazole-4-carbonyl)-thiophen-2-ylamino]-4-methylsulfanyl-butyric acid methyl ester | 470.3 |
| 1-54 | 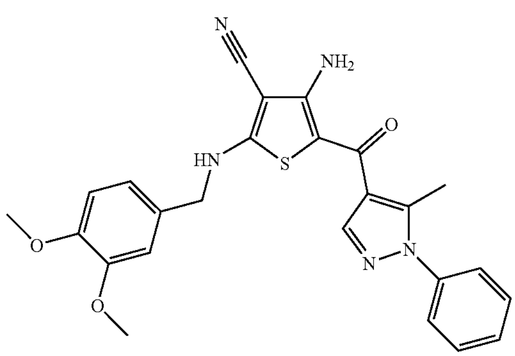 | 4-Amino-2-(3,4-dimethoxy-benzylamino)-5-(5-methyl-1-phenyl-1H-pyrazole-4-carbonyl)-thiophene-3-carbonitrile | 474.3 |
| 1-55 | 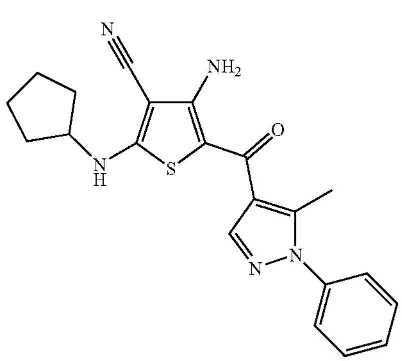 | 4-Amino-2-cyclopentylamino-5-(5-methyl-1-phenyl-1H-pyrazole-4-carbonyl)-thiophene-3-carbonitrile | 392.3 |

TABLE 1A-continued

Exemplary compounds of Formula I

| Cmpd number | Structure | Name | M + H |
|---|---|---|---|
| 1-56 | 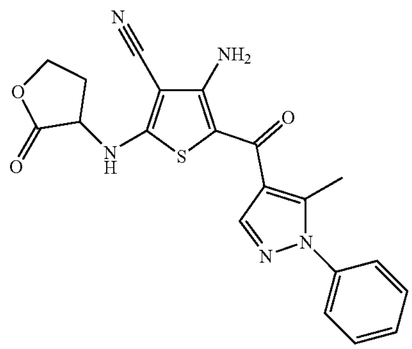 | 4-Amino-5-(5-methyl-1-phenyl-1H-pyrazole-4-carbonyl)-2-(2-oxo-tetrahydro-furan-3-ylamino)-thiophene-3-carbonitrile | 408.3 |
| 1-57 | 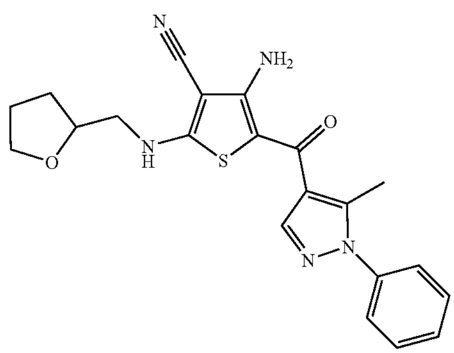 | 4-Amino-5-(5-methyl-1-phenyl-1H-pyrazole-4-carbonyl)-2-[(tetrahydro-furan-2-ylmethyl)-amino]-thiophene-3-carbonitrile | 408.3 |
| 1-58 | 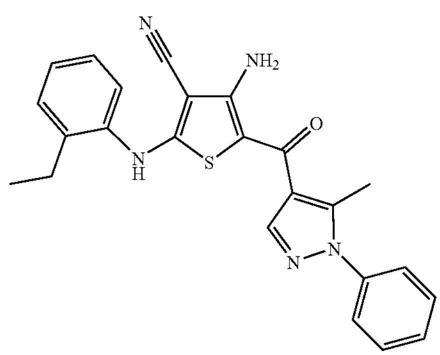 | 4-Amino-2-(2-ethyl-phenylamino)-5-(5-methyl-1-phenyl-1H-pyrazole-4-carbonyl)-thiophene-3-carbonitrile | 428.3 |
| 1-59 | 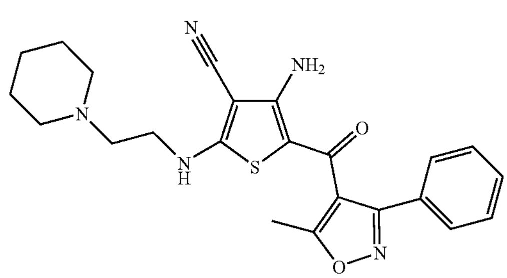 | 4-Amino-5-(5-methyl-3-phenyl-isoxazole-4-carbonyl)-2-(2-piperidin-1-yl-ethylamino)-thiophene-3-carbonitrile | 436.3 |

TABLE 1A-continued

Exemplary compounds of Formula I

| Cmpd number | Structure | Name | M + H |
|---|---|---|---|
| 1-60 | 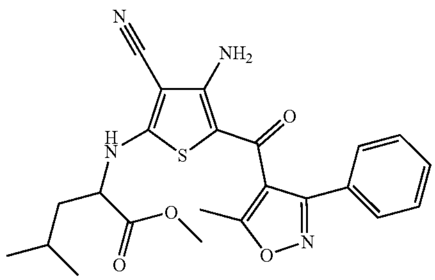 | 2-[4-Amino-3-cyano-5-(5-methyl-3-phenyl-isoxazole-4-carbonyl)-thiophen-2-ylamino]-4-methyl-pentanoic acid methyl ester | 453.1 |
| 1-61 | 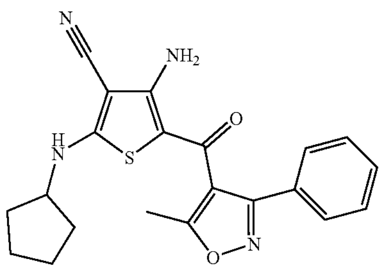 | 4-Amino-2-cyclopentylamino-5-(5-methyl-3-phenyl-isoxazole-4-carbonyl)-thiophene-3-carbonitrile | 393.1 |
| 1-62 | 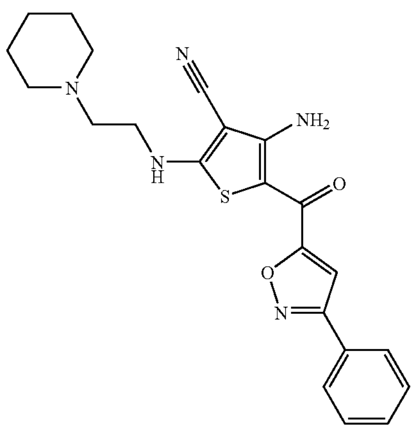 | 4-Amino-5-(3-phenyl-isoxazole-5-carbonyl)-2-(2-piperidin-1-yl-ethylamino)-thiophene-3-carbonitrile | 421.9 |
| 1-63 | 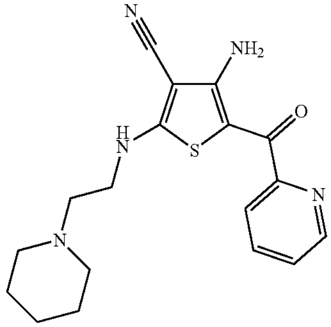 | 4-Amino-2-(2-piperidin-1-yl-ethylamino)-5-(pyridine-2-carbonyl)-thiophene-3-carbonitrile | 356.3 |

TABLE 1A-continued

Exemplary compounds of Formula I

| Cmpd number | Structure | Name | M + H |
|---|---|---|---|
| 1-64 | 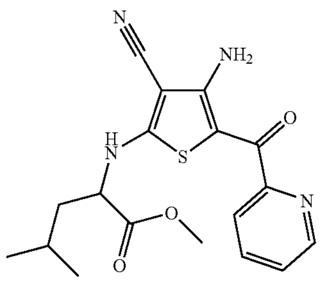 | 2-[4-Amino-3-cyano-5-(pyridine-2-carbonyl)-thiophen-2-ylamino]-4-methyl-pentanoic acid methyl ester | 373.1 |
| 1-65 | 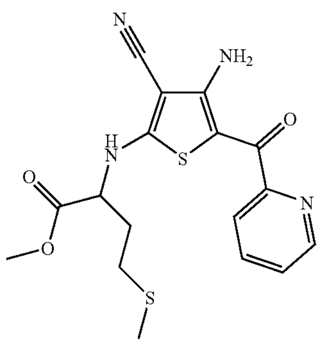 | 2-[4-Amino-3-cyano-5-(pyridine-2-carbonyl)-thiophen-2ylamino]-4-methylsulfanyl-butyric acid methyl ester | 391.1 |
| 1-66 | 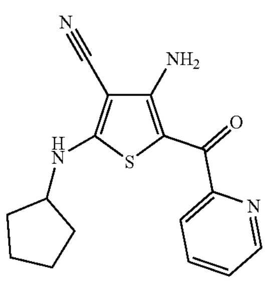 | 4-Amino-2-cyclopentylamino-5-(pyridine-2-carbonyl)-thiophene-3-carbontrile | 313.1 |
| 1-67 | 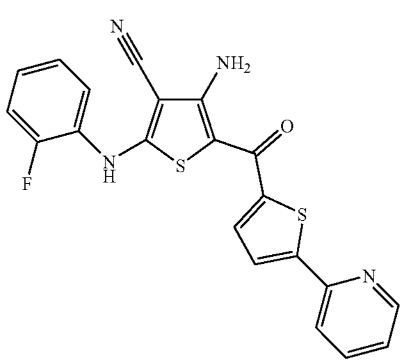 | 4-Amino-2-(2-fluoro-phenylamino)-5-(5-pyridin-2-yl-thiophene-2-carbonyl)-thiophene-3-carbonitrile | 421.1 |

TABLE 1A-continued

Exemplary compounds of Formula I

| Cmpd number | Structure | Name | M + H |
|---|---|---|---|
| 1-68 | 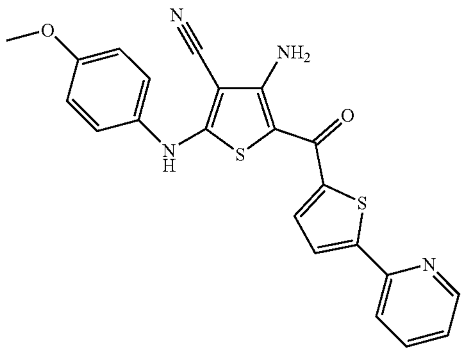 | 4-Amino-2-(4-methoxy-phenylamino)-5-(5-pyridin-2-yl-thiophene-2-carbonyl)-thiophene-3-carbonitrile | 433.1 |
| 1-69 | 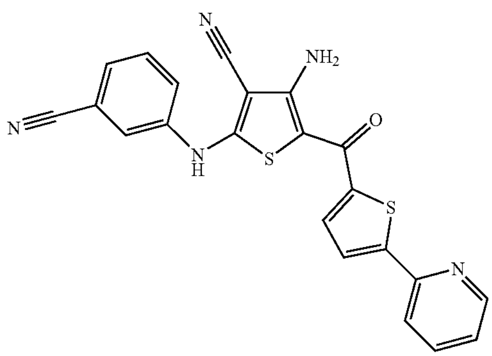 | 4-Amino-2-(3-cyano-phenylamino)-5-(5-pyridin-2-yl-thiophene-2-carbonyl)-thiophene-3-carbonitrile | 427.9 |
| 1-70 | 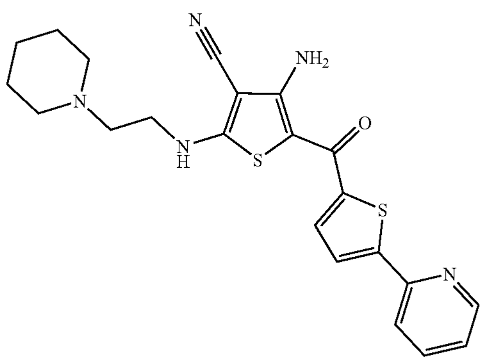 | 4-Amino-2-(2-piperidin-1-yl-ethylamino)-5-(5-pyridin-2-yl-thiophene-2-carbonyl)-thiophene-3-carbonitrile | 438.3 |
| 1-71 | 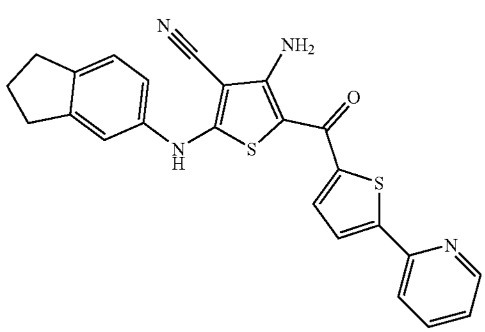 | 4-Amino-2-(indan-5-ylamino)-5-(5-pyridin-2-yl-thiophene-2-carbonyl)-thiophene-3-carbonitrile | 443.1 |

TABLE 1A-continued

Exemplary compounds of Formula I

| Cmpd number | Structure | Name | M + H |
|---|---|---|---|
| 1-72 | 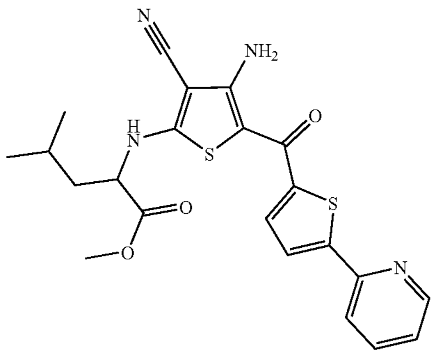 | 2-[4-Amino-3-cyano-5-(5-pyridin-2-yl-thiophene-2-carbonyl)-thiophen-2-ylamino]-4-methyl-pentanoic acid methyl ester | 455.1 |
| 1-73 | 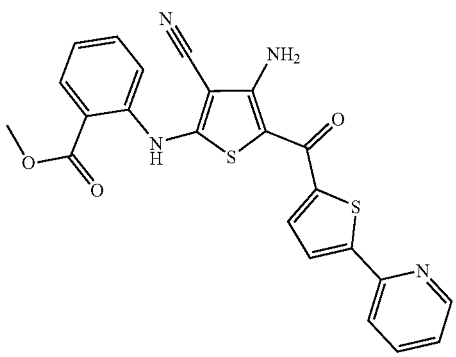 | 2-[4-Amino-3-cyano-5-(5-pyridin-2-yl-thiophene-2-carbonyl)-thiophen-2-ylamino]-benzoic acid methyl ester | 461.1 |
| 1-74 | 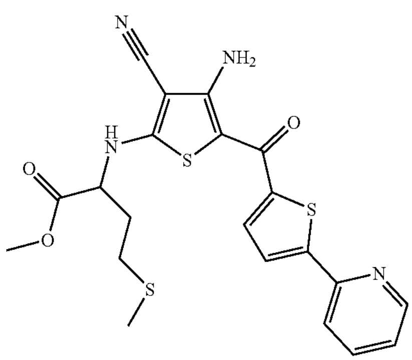 | 2-[4-Amino-3-cyano-5-(5-pyridin-2-yl-thiophene-2-carbonyl)-thiophen-2-ylamino]-4-methylsulfanyl-butyric acid methyl ester | 473.1 |
| 1-75 | 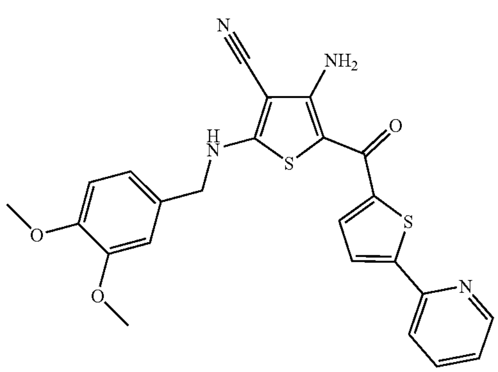 | 4-Amino-2-(3,4-dimethoxy-benzylamino)-5-(5-pyridin-2-yl-thiophene-2-carbonyl)-thiophene-3-carbonitrile | 477.1 |

TABLE 1A-continued

Exemplary compounds of Formula I

| Cmpd number | Structure | Name | M + H |
|---|---|---|---|
| 1-76 | 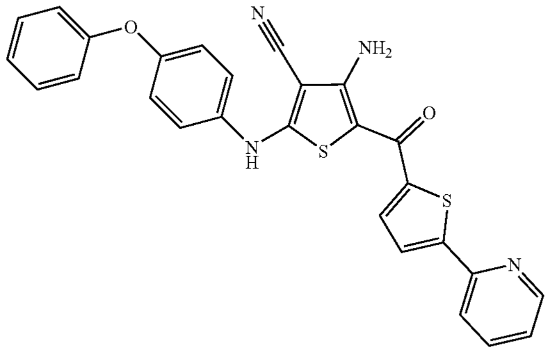 | 4-Amino-2-(4-phenoxy-phenylamino)-5-(5-pyridin-2-yl-thiophene-2-carbonyl)-thiophene-3-carbonitrile | 495.1 |
| 1-77 | 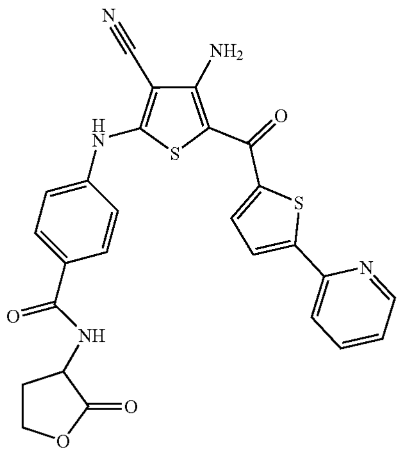 | 4-[4-Amino-3-cyano-5-(5-pyridin-2-yl-thiophene-2-carbonyl)-thiophen-2-ylamino]-N-(2-oxo-tetrahydro-furan-3-yl)-benzamide | 529.9 |
| 1-78 | 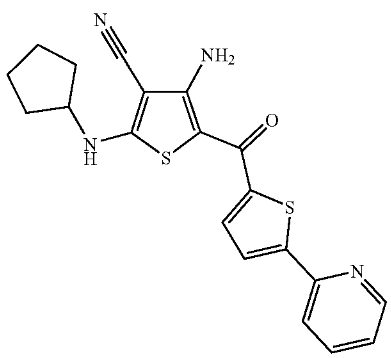 | 4-Amino-2-cyclopentylamino-5-(5-pyridin-2-yl-thiophene-2-carbonyl)-thiophene-3-carbonitrile | 395.1 |
| 1-79 | 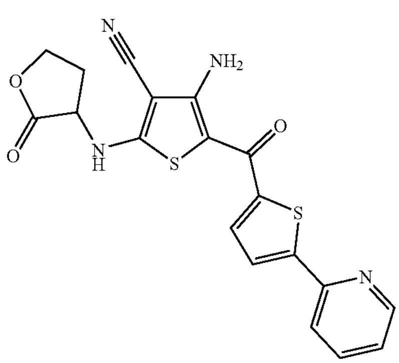 | 4-Amino-2-(2-oxo-tetrahydro-furan-3-ylamino)-5-(5-pyridin-2-yl-thiophene-2-carbonyl)-thiophene-3-carbonitrile | 411.1 |

TABLE 1A-continued

Exemplary compounds of Formula I

| Cmpd number | Structure | Name | M + H |
|---|---|---|---|
| 1-80 | 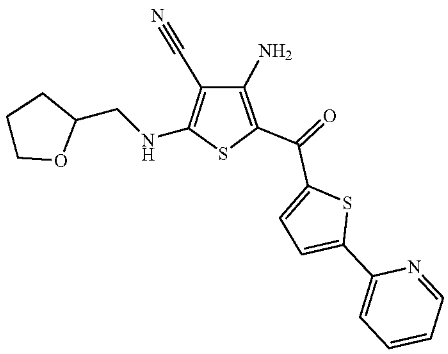 | 4-Amino-5-(5-pyridin-2-yl-thiophene-2-carbonyl)-2-[(tetrahydro-furan-2-ylmethyl)-amino]-thiophene-3-carbonitrile | 411.1 |
| 1-81 | 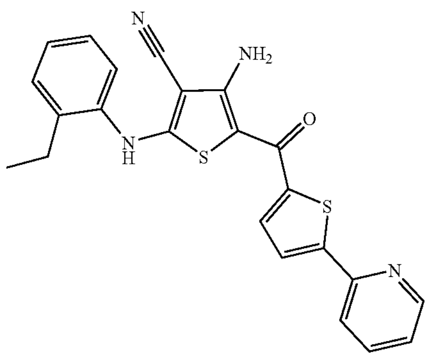 | 4-Amino-2-(2-ethyl-phenylamino)-5-(5-pyridin-2-yl-thiophene-2-carbonyl)-thiophene-3-carbonitrile | 431.1 |
| 1-82 | 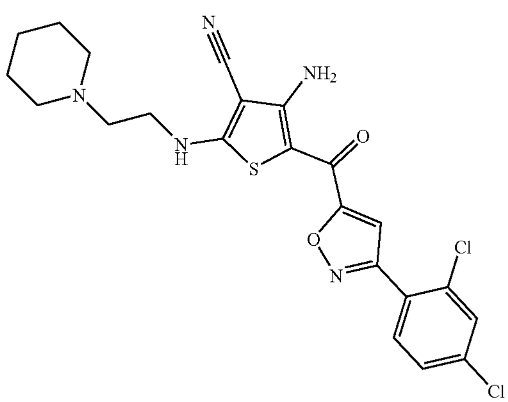 | 4-Amino-5-[3-(2,4-dichloro-phenyl)-isoxazole-5-carbonyl]-2-(2-piperidin-1-yl-ethylamino)-thiophene-3-carbonitrile | 490.3 |
| 1-83 | 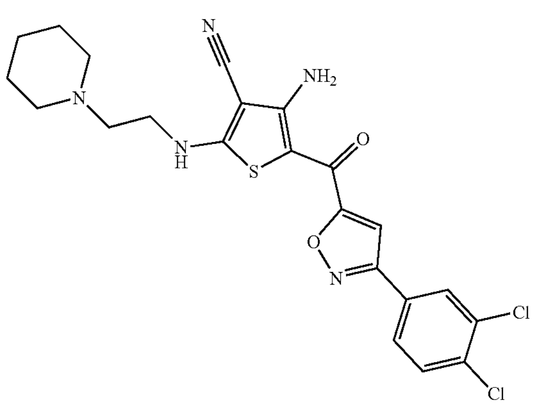 | 4-Amino-5-[3-(3,4-dichloro-phenyl)-isoxazole-5-carbonyl]-2-(2-piperidin-1-yl-ethylamino)-thiophene-3-carbonitrile | 490.3 |

TABLE 1A-continued

Exemplary compounds of Formula I

| Cmpd number | Structure | Name | M + H |
|---|---|---|---|
| 1-84 | 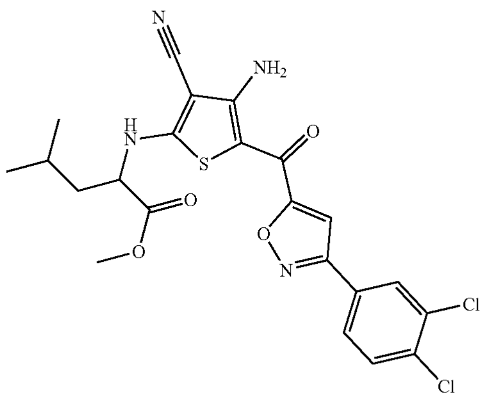 | 2-{4-Amino-3-cyano-5-[3-(3,4-dichloro-phenyl)-isoxazole-5-carbonyl]-thiophen-2-ylamino}-4-methyl-pentanoic acid methyl ester | 507.1 |
| 1-85 | 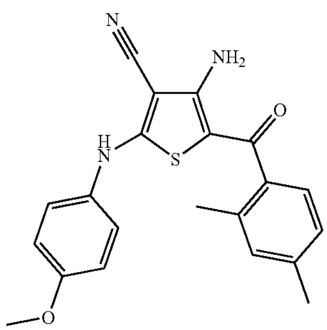 | 4-Amino-5-[3-(3,4-dimethyl-benzoyl)-2-(4-methoxy-phenylamino)-thiophene-3-carbonitrile | 378.3 |
| 1-86 | 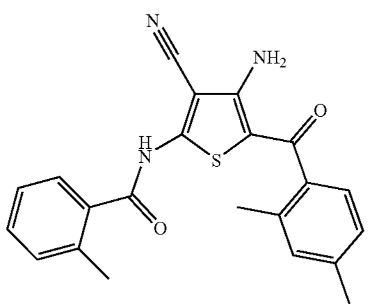 | N-[4-Amino-3-cyano-5-(2,4-dimethyl-benzoyl)-thiophen-2-yl]-2-methyl-benzamide | 390.3 |
| 1-87 | 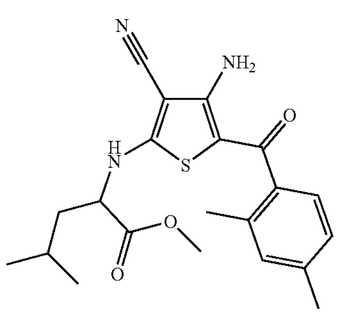 | 2-[4-Amino-3-cyano-5-(2,4-dimethyl-benzoyl)-thiophen-2-ylamino]-4-methyl-pentanoic acid methyl ester | 400.3 |

TABLE 1A-continued

Exemplary compounds of Formula I

| Cmpd number | Structure | Name | M + H |
|---|---|---|---|
| 1-88 | 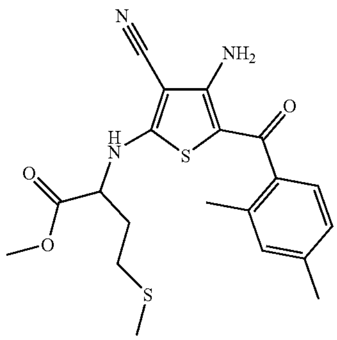 | 2-[4-Amino-3-cyano-5-(2,4-dimethyl-benzoyl)-thiophen-2-ylamino]-4-methylsulfanyl-butyric acid methyl ester | 418.3 |
| 1-89 | 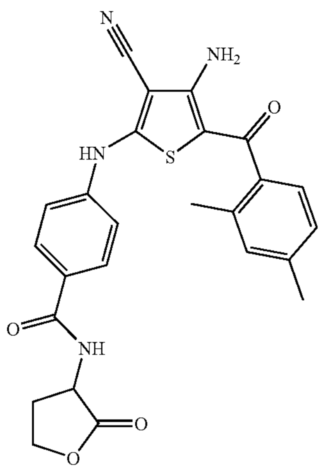 | 4-[4-Amino-3-cyano-5-(2,4-dimethyl-benzoyl)-thiophen-2-ylamino]-N-(2-oxo-tetrahydro-furan-3-yl)-benzamide | 475.1 |
| 1-90 | 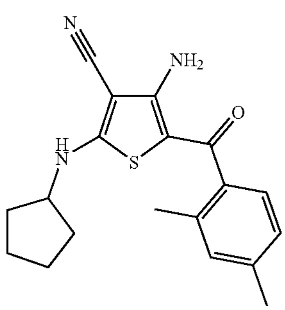 | 4-Amino-2-cyclopentylamino-5-(2,4-dimethyl-benzoyl)-thiophene-3-carbonitrile | 340.3 |
| 1-91 | 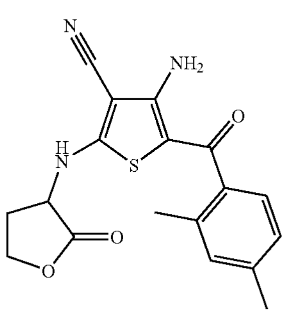 | 4-Amino-5-(2,4-dimethyl-benzoyl)-2-(2-oxo-tetrahydro-furan-3-ylamino)-thiophene-3-carbonitrile | 356.3 |

TABLE 1A-continued

Exemplary compounds of Formula I

| Cmpd number | Structure | Name | M + H |
|---|---|---|---|
| 1-92 | 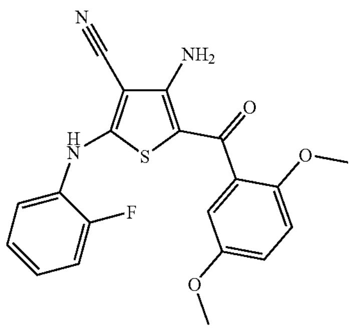 | 4-Amino-5-(2,5-dimethoxy-benzoyl)-2-(2-fluoro-phenylamino)-thiophene-3-carbonitrile | N/A |
| 1-93 | 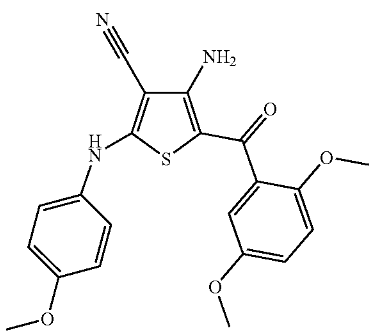 | 4-Amino-5-(2,5-dimethoxy-benzoyl)-2-(4-methoxy-phenylamino)-thiophene-3-carbonitrile | 410.3 |
| 1-94 | 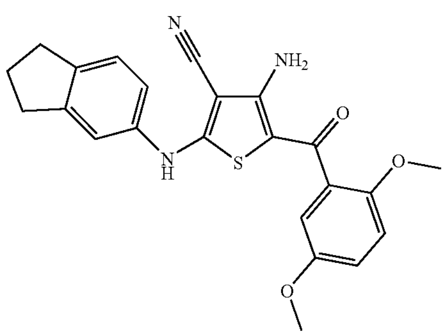 | 4-Amino-5-(2,5-dimethoxy-benzoyl)-2-(indan-5-ylamino)-thiophene-3-carbonitrile | 419.9 |
| 1-95 | 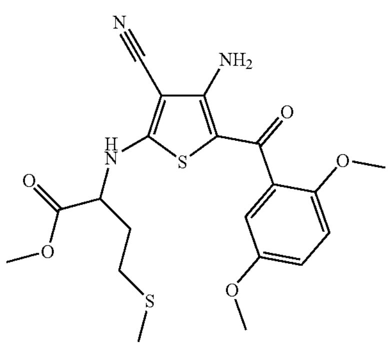 | 2-[4-Amino-3-cyano-5-(2,5-dimethoxy-benzoyl)-thiophen-2-ylamino]-4-methylsulfanyl-butyric acid methyl ester | 449.9 |

TABLE 1A-continued

Exemplary compounds of Formula I

| Cmpd number | Structure | Name | M + H |
|---|---|---|---|
| 1-96 | 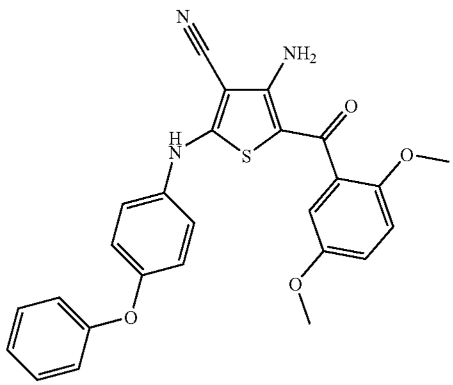 | 4-Amino-5-(2,5-dimethoxy-benzoyl)-2-(4-phenoxy-phenylamino)-thiophene-3-carbonitrile | 472.3 |
| 1-97 | 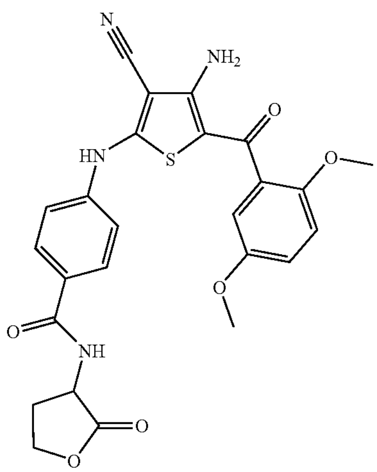 | 4-[4-Amino-3-cyano-5-(2,5-dimethoxy-benzoyl)-thiophen-2-ylamino]-N-(2-oxo-tetrahydro-furan-3-yl)-benzamide | 507.1 |
| 1-98 | 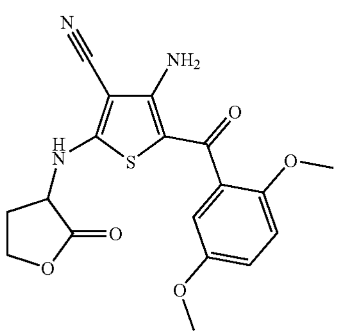 | 4-Amino-5-(2,5-dimethoxy-benzoyl)-2-(2-oxo-tetrahydro-furan-3-ylamino)-thiophene-3-carbonitrile | 388.3 |
| 1-99 | 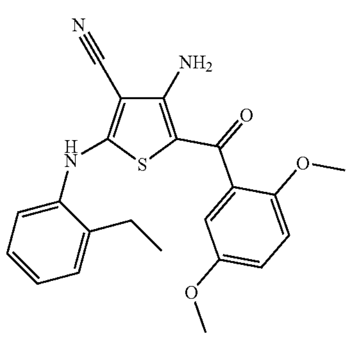 | 4-Amino-5-(2,5-dimethoxy-benzoyl)-2-(2-ethyl-phenylamino)-thiophene-3-carbonitrile | 408.3 |

TABLE 1A-continued

Exemplary compounds of Formula I

| Cmpd number | Structure | Name | M + H |
|---|---|---|---|
| 1-100 | 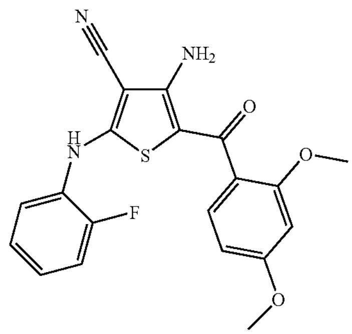 | 4-Amino-5-(2,4-dimethoxy-benzoyl)-2-(2-fluoro-phenylamino)-thiophene-3-carbonitrile | N/A |
| 1-101 | 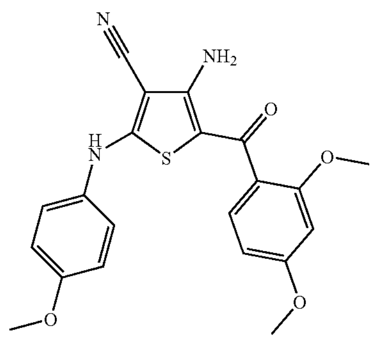 | 4-Amino-5-(2,4-dimethoxy-benzoyl)-2-(4-methoxy-phenylamino)-thiophene-3-carbonitrile | 410.3 |
| 1-102 | 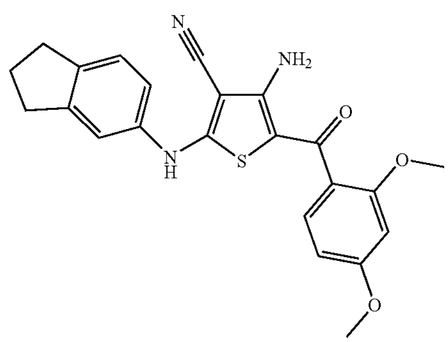 | 4-Amino-5-(2,4-dimethoxy-benzoyl)-2-(indan-5-ylamino)-thiophene-3-carbonitrile | N/A |
| 1-103 | 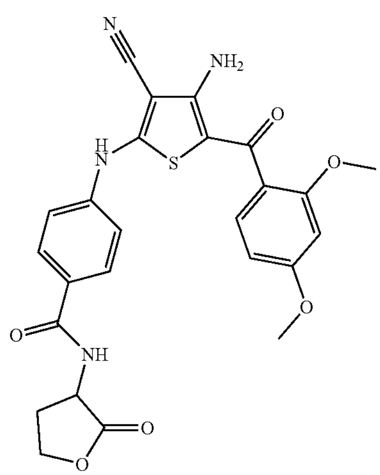 | 4-[4-Amino-3-cyano-5-(2,4-dimethoxy-benzoyl)-thiophen-2-ylamino]-N-(2-oxo-tetrahydro-furan-3-yl)-benzamide | 507.1 |

TABLE 1A-continued

Exemplary compounds of Formula I

| Cmpd number | Structure | Name | M + H |
|---|---|---|---|
| 1-104 | 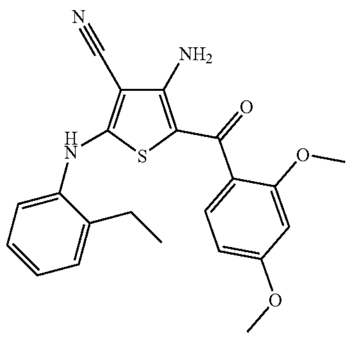 | 4-Amino-5-(2,4-dimethoxy-benzoyl)-2-(2-ethyl-phenylamino)-thiophene-3-carbonitrile | 408.3 |
| 1-105 | 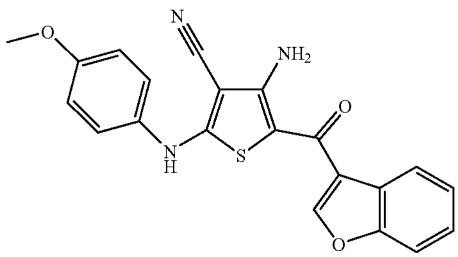 | 4-Amino-5-(benzofuran-3-carbonyl)-2-(4-methoxy-phenylamino)-thiophene-3-carbonitrile | N/A |
| 1-106 | 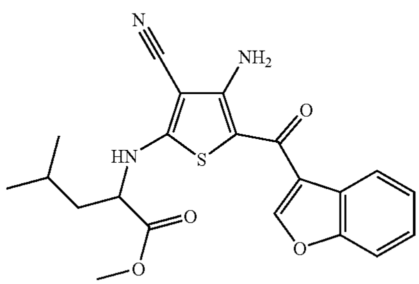 | 2-[4-Amino-5-(benzofuran-3-carbonyl)-3-cyano-thiophen-2-ylamino]-4-methyl-pentanoic acid methyl ester | 412.3 |
| 1-107 | 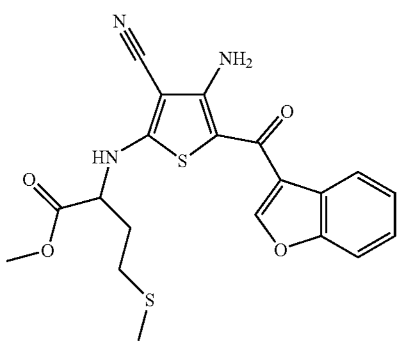 | 2-[4-Amino-5-(benzofuran-3-carbonyl)-3-cyano-thiophen-2-ylamino]-4-methylsulfanyl-butyric acid methyl ester | 430.3 |
| 1-108 | 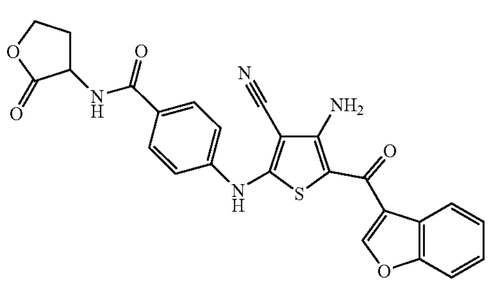 | 4-[4-Amino-5-(benzofuran-3-carbonyl)-3-cyano-thiophen-2-ylamino]-N-(2-oxo-tetrahydro-furan-3-yl)-benzamide | 487.1 |

TABLE 1A-continued

Exemplary compounds of Formula I

| Cmpd number | Structure | Name | M + H |
|---|---|---|---|
| 1-109 | 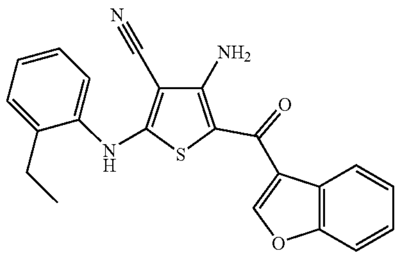 | 4-Amino-5-(benzofuran-3-carbonyl)-2-(2-ethyl-phenylamino)-thiophene-3-carbonitrile | N/A |
| 1-110 | 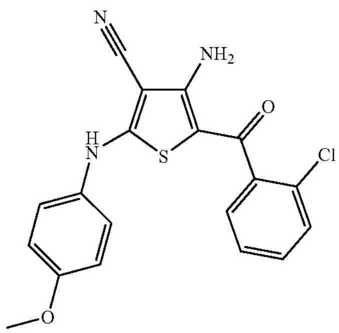 | 4-Amino-5-(2-chloro-benzoyl)-2-(4-methoxy-phenylamino)-thiophene-3-carbonitrile | 383.9 |
| 1-111 | 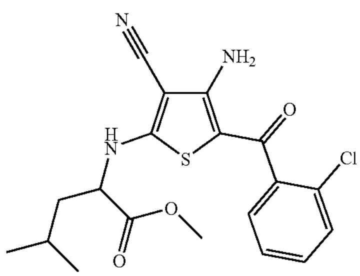 | 2-[4-Amino-5-(2-chloro-benzoyl)-3-cyano-thiophene-2-ylamino]-4-methyl-pentanoic acid methyl ester | 406.3 |
| 1-112 | 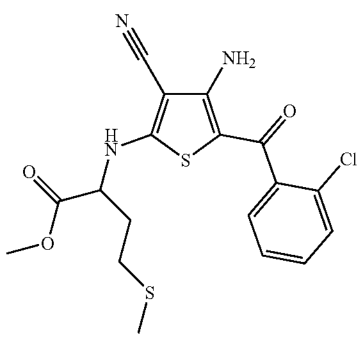 | 2-[4-Amino-5-(2-chloro-benzoyl)-3-cyano-thiophene-2-ylamino]-4-methylsulfanyl-butyric acid methyl ester | 423.9 |
| 1-113 | 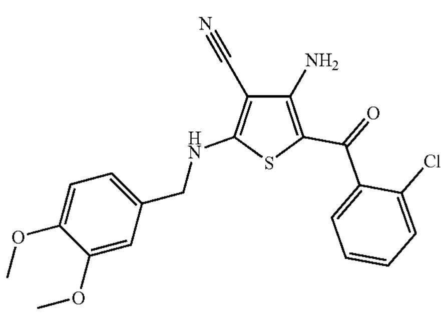 | 4-Amino-5-(2-chloro-benzoyl)-2-(3,4-dimethoxy-benzylamino)-thiophene-3-carbonitrile | 427.9 |

TABLE 1A-continued

Exemplary compounds of Formula I

| Cmpd number | Structure | Name | M + H |
|---|---|---|---|
| 1-114 | 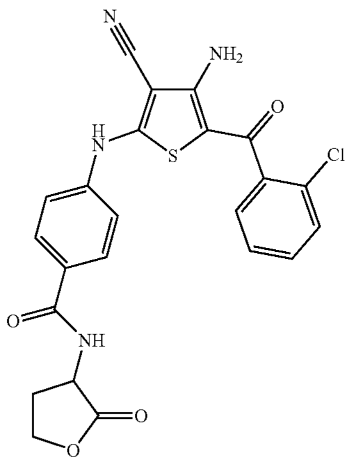 | 4-[4-Amino-5-(2-chloro-benzoyl)-3-cyano-thiophen-2-ylamino]-N-(2-oxo-tetrahydro-furan-3-yl)-benzamide | 481.1 |
| 1-115 | 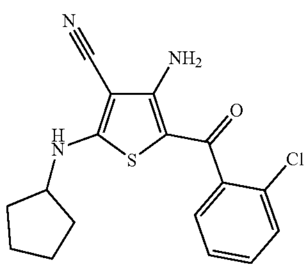 | 4-Amino-5-(2-chloro-benzoyl)-2-cyclopentylamino-thiophene-3-carbonitrile | 345.9 |
| 1-116 | 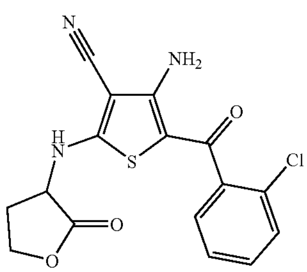 | 4-Amino-5-(2-chloro-benzoyl)-2-(2-oxo-tetrahydro-furan-3-ylamino)-thiophene-3-carbonitrile | 362.3 |
| 1-117 | 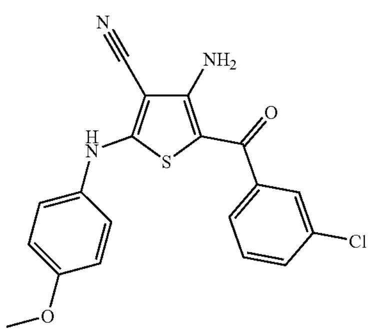 | 4-Amino-5-(3-chloro-benzoyl)-2-(4-methoxy-phenylamino)-thiophene-3-carbonitrile | N/A |

TABLE 1A-continued

Exemplary compounds of Formula I

| Cmpd number | Structure | Name | M + H |
|---|---|---|---|
| 1-118 | 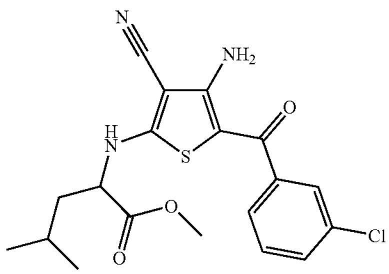 | 2-[4-Amino-5-(3-chloro-benzoyl)-3-cyano-thiophen-2-ylamino]-4-methyl-pentanoic acid methyl ester | 406.3 |
| 1-119 | 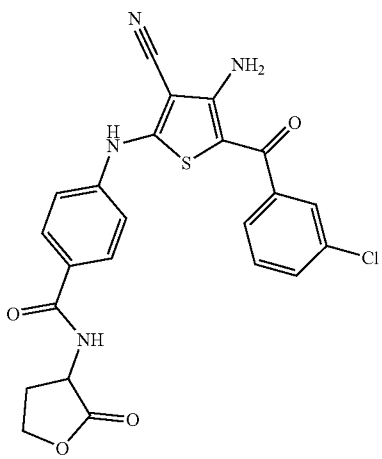 | 4-[4-Amino-5-(3-chloro-benzoyl)-3-cyano-thiophen-2-ylamino]-N-(2-oxo-tetrahydro-furan-3-yl)-benzamide | 481.1 |
| 1-120 | 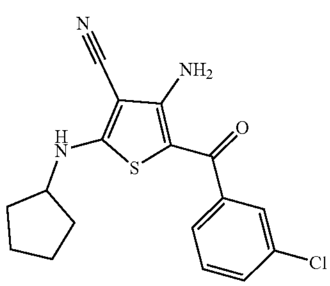 | 4-Amino-5-(3-chloro-benzoyl) 2-cyclopentylamino-thiophene-3-carbonitrile | 345.9 |
| 1-121 | 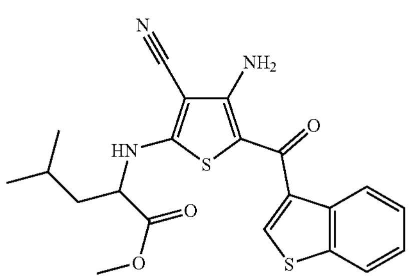 | 2-[4-Amino-5-(benzo[b]thiophene-3-carbonyl)-3-cyano-thiophen-2-ylamino]-4-methyl-pentanoic acid methyl ester | 427.9 |

TABLE 1A-continued

Exemplary compounds of Formula I

| Cmpd number | Structure | Name | M + H |
|---|---|---|---|
| 1-122 | 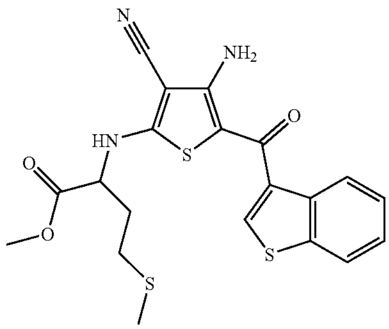 | 2-[4-Amino-5-(benzo[b]thiophene-3-carbonyl)-3-cyano-thiophen-2-ylamino]-4-methylsulfanyl-butyric acid methyl ester | 445.9 |
| 1-123 | 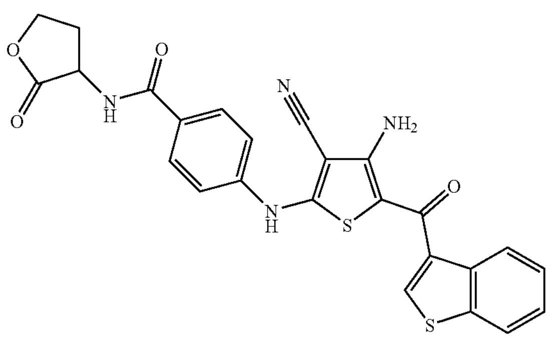 | 4-[4-Amino-5-(benzo[b]thiophene-3-carbonyl)-3-cyano-thiophen-2-ylamino]-N-(2-oxo-tetrahydro-furan-3-yl)-benzamide | 503.1 |
| 1-124 | 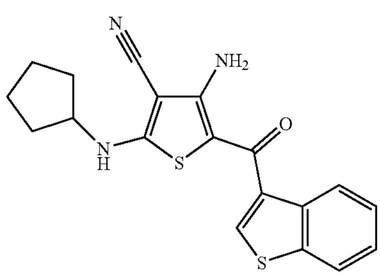 | 4-Amino-5-(benzo[b]thiophene-3-carbonyl)-2-cyclopentylamino-thiophene-3-carbonitrile | 367.9 |
| 1-125 | 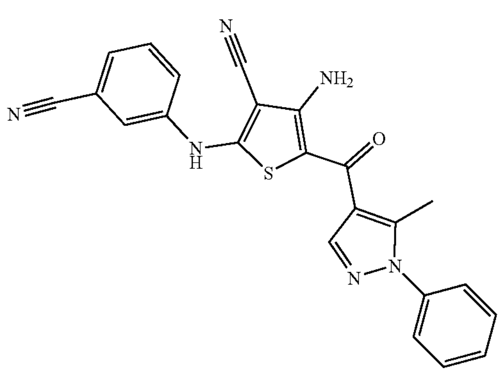 | 4-Amino-2-(3-cyano-phenylamino)-5-(5-methyl-1-phenyl-1H-pyrazole-4-carbonyl)-thiophene-3-carbonitrile | 425.1 |

TABLE 1A-continued

Exemplary compounds of Formula I

| Cmpd number | Structure | Name | M + H |
|---|---|---|---|
| 1-126 | 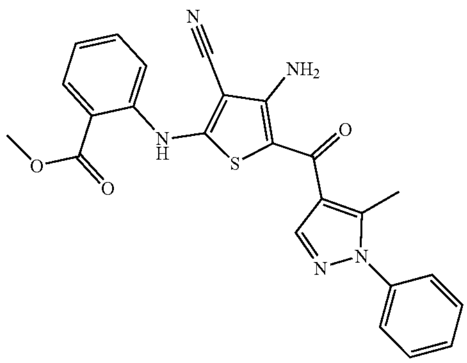 | 2-[4-Amino-3-cyano-5-(5-methyl-1-phenyl-1H-pyrazole-4-carbonyl)-thiophen-2-ylamino]-benzoic acid methyl ester | 458.3 |
| 1-127 | 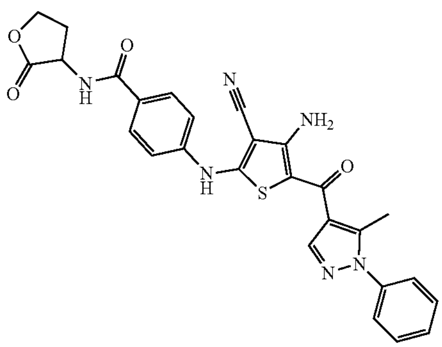 | 4-[4-Amino-3-cyano-5-(5-methyl-1-phenyl-1H-pyrazole-4-carbonyl)-thiophen-2-ylamino]-N-(2-oxo-tetrahydro-furan-3-yl)-benzamide | 527.1 |
| 1-128 | 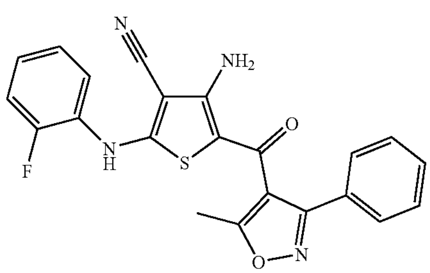 | 4-Amino-2-(2-fluoro-phenylamino)-5-(5-methyl-3-phenyl-isoxazole-4-carbonyl)-thiophene-3-carbonitrile | 419.1 |
| 1-129 | 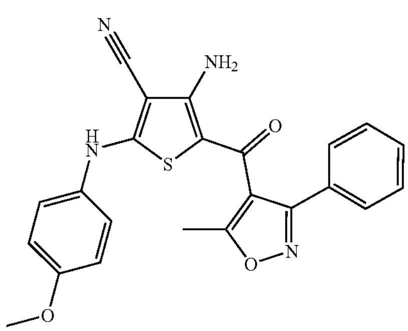 | 4-Amino-2-(4-methoxy-phenylamino)-5-(5-methyl-3-phenyl-isoxazole-4-carbonyl)-thiophene-3-carbonitrile | 431.5 |

TABLE 1A-continued

Exemplary compounds of Formula I

| Cmpd number | Structure | Name | M + H |
|---|---|---|---|
| 1-130 | 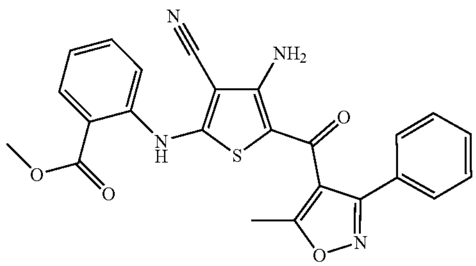 | 2-[4-Amino-3-cyano-5-(5-methyl-3-phenyl-isoxazole-4-carbonyl)-thiophen-2-ylamino]-benzoic acid methyl ester | 459.1 |
| 1-131 | 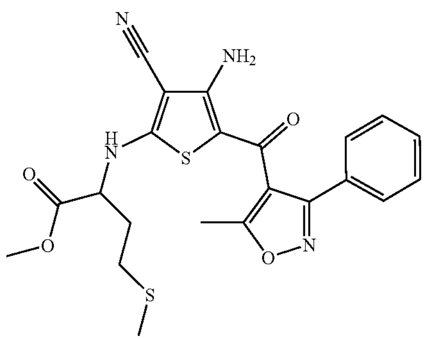 | 2-[4-Amino-3-cyano-5-(5-methyl-3-phenyl-isoxazole-4-carbonyl)-thiophen-2-ylamino]-4-methylsulfanyl-butyric acid methyl ester | 471.1 |
| 1-132 | 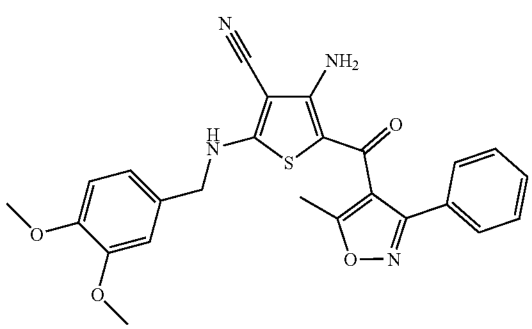 | 4-Amino-2-(3,4-dimethoxy-benzylamino)-5-(5-methyl-3-phenyl-isoxazole-4-carbonyl)-thiophene-3-carbonitrile | 475.1 |
| 1-133 | 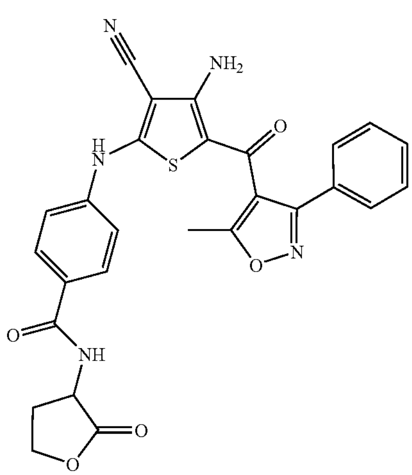 | 4-[4-Amino-3-cyano-5-(5-methyl-3-phenyl-isoxazole-4-carbonyl)-thiophen-2-ylamino]-N-(2-oxo-tetrahydro-furan-3-yl)-benzamide | 527.9 |

TABLE 1A-continued

Exemplary compounds of Formula I

| Cmpd number | Structure | Name | M + H |
|---|---|---|---|
| 1-134 | 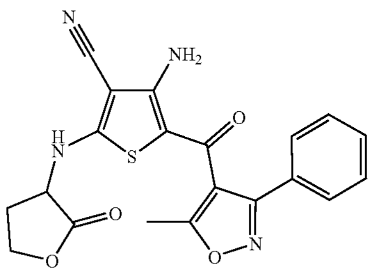 | 4-Amino-5-(5-methyl-3-phenyl-isoxazole-4-carbonyl)-2-(2-oxo-tetrahydro-furan-3-ylamino)-thiophene-3-carbonitrile | 409.1 |
| 1-135 | 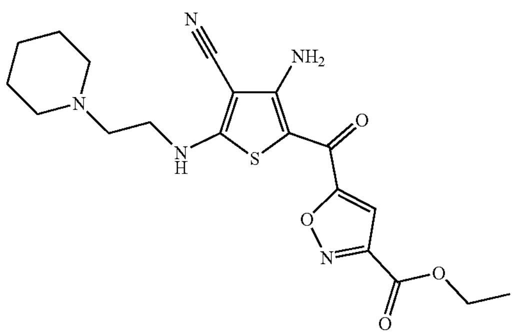 | 5-[3-Amino-4-cyano-5-(2-piperidin-1-yl-ethylamino)-thiophene-2-carbonyl]-isoxazole-3-carboxylic acid ethyl ester | 418.3 |
| 1-136 | 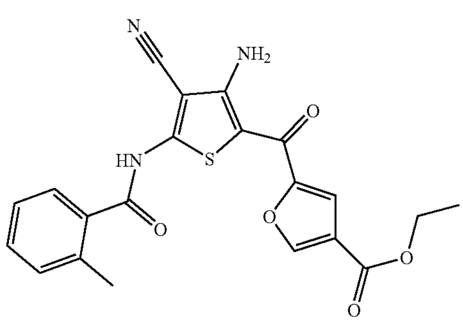 | 5-[3-Amino-4-cyano-5-(2-methyl-benzoylamino)-thiophene-2-carbonyl]-isoxazole-3-carboxylic acid ethyl ester | 425.1 |
| 1-137 | 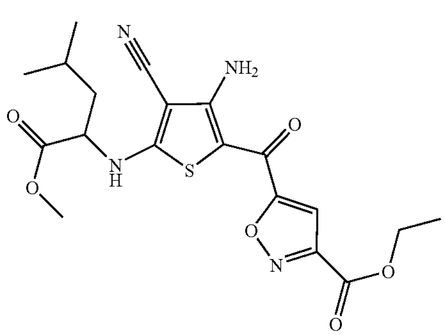 | 5-[3-Amino-4-cyano-5-(1-methoxycarbonyl-3-methyl-butylamino)-thiophene-2-carbonyl]-isoxazole-3-carboxylic acid ethyl ester | 435.1 |

TABLE 1A-continued

Exemplary compounds of Formula I

| Cmpd number | Structure | Name | M + H |
|---|---|---|---|
| 1-138 | 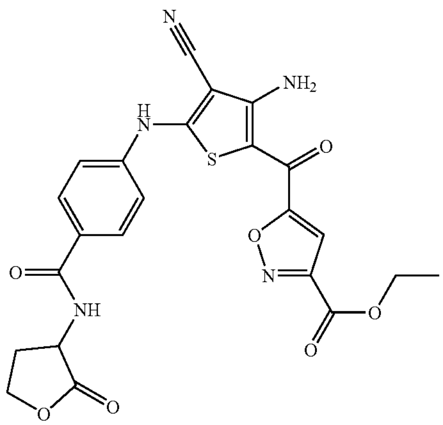 | 5-{3-Amino-4-cyano-5-[4-2-oxo-tetrahydro-furan-3-ylcarbamoyl)-phenylamino]-thiophene-2-carbonyl}-isoxazole-3-carboxylic acid ethyl ester | 509.9 |
| 1-139 | 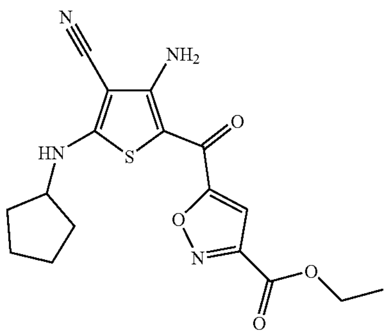 | 5-(3-Amino-4-cyano-5-cyclopentylamino-thiophene-2-carbonyl)-isoxazole-3-carboxylic acid ethyl ester | 375.1 |
| 1-140 | 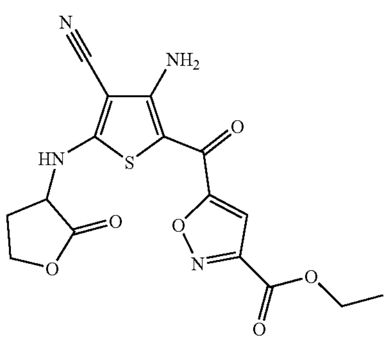 | 5-[3-Amino-4-cyano-5-(2-oxo-tetrahydro-furan-3-ylamino)-thiophene-2-carbonyl]-isoxazole-3-carboxylic acid ethyl ester | 391.1 |
| 1-141 | 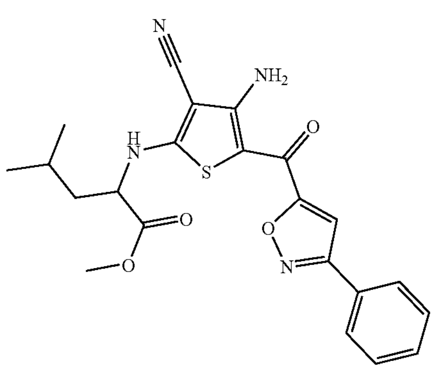 | 2-[4-Amino-3-cyano-5-(3-phenyl-isoxazole-5-carbonyl)-thiophen-2-ylamino]-4-methyl-pentanoic acid methyl ester | 439.1 |

TABLE 1A-continued

Exemplary compounds of Formula I

| Cmpd number | Structure | Name | M + H |
|---|---|---|---|
| 1-142 | 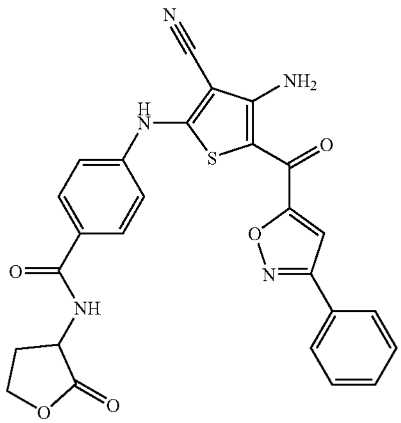 | 4-[4-Amino-3-cyano-5-(3-phenyl-isoxazole-5-carbonyl)-thiophen-2-ylamino]-N-(2-oxo-tetrahydro-furan-3-yl)-benzamide | 514.3 |
| 1-143 | 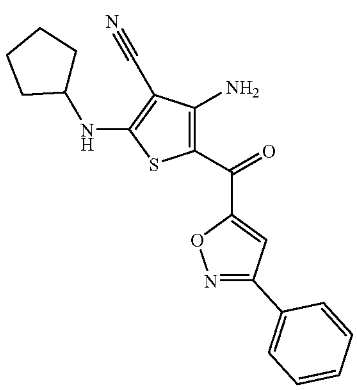 | 4-Amino-2-cyclopentylamino-5-(3-phenyl-isoxazole-5-carbonyl)-thiophene-3-carbonitrile | 378.99 |
| 1-144 | 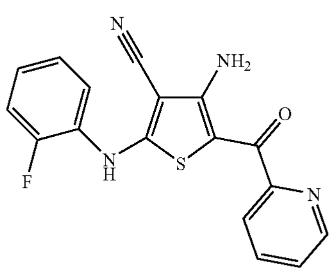 | 4-Amino-2-(2-fluoro-phenylamino)-5-(pyridine-2-carbonyl)-thiophene-3-carbonitrile | N/A |
| 1-145 | 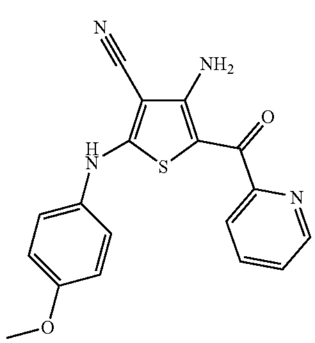 | 4-Amino-2-(4-methoxy-phenylamino)-5-(pyridine-2-carbonyl)-thiophene-3-carbonitrile | N/A |

TABLE 1A-continued

Exemplary compounds of Formula I

| Cmpd number | Structure | Name | M + H |
|---|---|---|---|
| 1-146 | 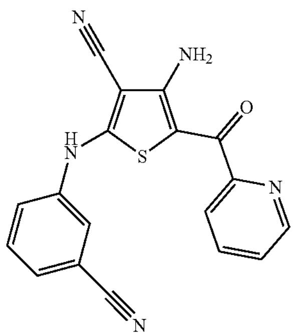 | 4-Amino-2-(3-cyano-phenylamino)-5-(pyridine-2-carbonyl)-thiophene-3-carbonitrile | N/A |
| 1-147 | 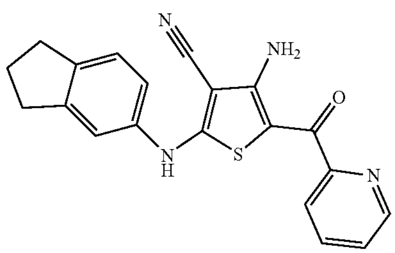 | 4-Amino-2-(indan-5-ylamino)-5-(pyridine-2-carbonyl)-thiophene-3-carbonitrile | N/A |
| 1-148 | 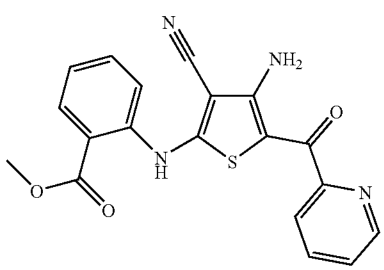 | 2-[4-Amino-3-cyano-5-(pyridine-2-carbonyl)-thiophen-2-ylamino]-benzoic acid methyl ester | N/A |
| 1-149 | 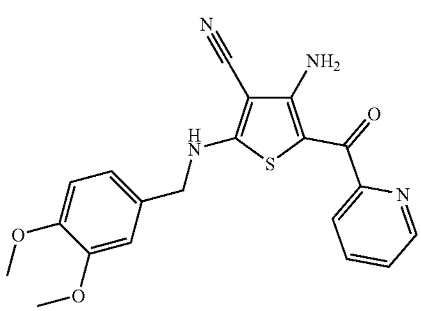 | 4-Amino-2-(3,4-dimethoxy-benzylamino)-5-(pyridine-2-carbonyl)-thiophene-3-carbonitrile | N/A |

TABLE 1A-continued

Exemplary compounds of Formula I

| Cmpd number | Structure | Name | M + H |
|---|---|---|---|
| 1-150 | 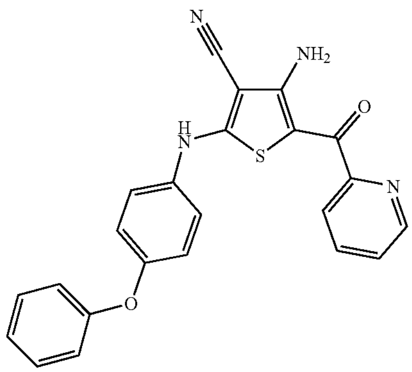 | 4-Amino-2-(4-phenoxy-phenylamino)-5-(pyridine-2-carbonyl)-thiophene-3-carbonitrile | N/A |
| 1-151 | 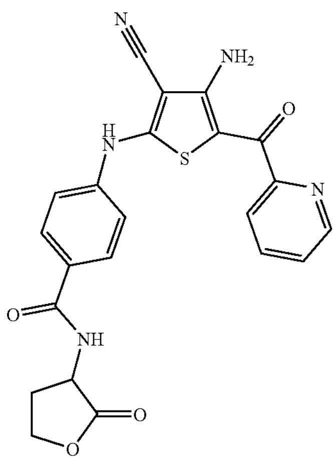 | 4-[4-Amino-3-cyano-5-(pyridine-2-carbonyl)-thiophen-2-ylamino]-N-(2-oxo-tetrahydro-furan-3-yl)-benzamide | 447.9 |
| 1-152 | 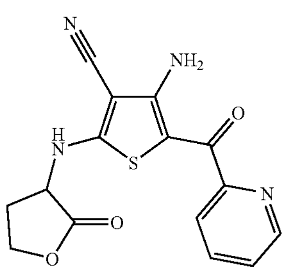 | 4-Amino-2-(2-oxo-tetrahydro-furan-3-ylamino)-5-(pyridine-2-carbonyl)-thiophene-3-carbonitrile | 329.1 |
| 1-153 | 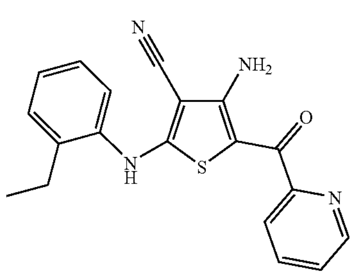 | 4-Amino-2-(2-ethyl-phenylamino)-5-(pyridine-2-carbonyl)-thiophene-3-carbonitrile | N/A |

TABLE 1A-continued

Exemplary compounds of Formula I

| Cmpd number | Structure | Name | M + H |
|---|---|---|---|
| 1-154 | 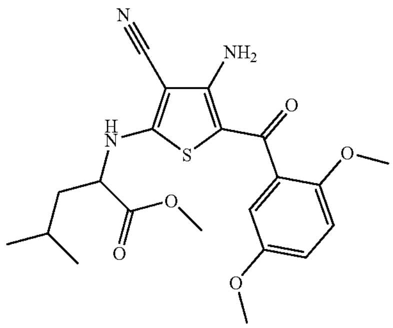 | 2-[4-Amino-3-cyano-5-(2,5-dimethoxy-benzoyl)-thiophen-2-ylamino]-4-methyl-pentanoic acid methyl ester | 432.3 |
| 1-155 | 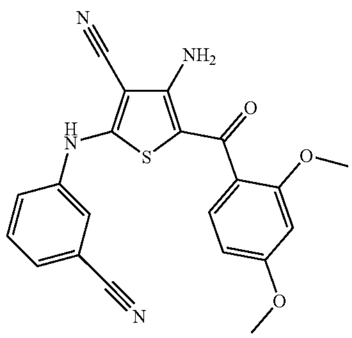 | 4-Amino-2-(3-cyano-phenylamino)-5-(2,4-dimethoxy-benzoyl)-thiophene-3-carbonitrile | 405.5 |
| 1-156 | 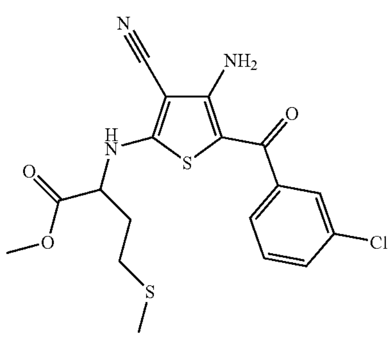 | 2-[4-(Amino-5-(3-chloro-benzoyl)-3-cyano-thiophen-2-ylamino]-4-methylsulfanyl-butyric acid methyl ester | 423.9 |
| 1-157 | 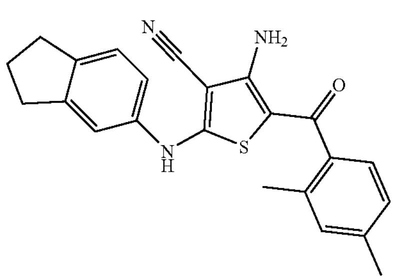 | 4-Amino-5-(2,4-dimethyl-benzoyl)-2-(indan-5-ylamino)-thiophene-3-carbonitrile | 388.3 |

TABLE 1A-continued

Exemplary compounds of Formula I

| Cmpd number | Structure | Name | M + H |
|---|---|---|---|
| 1-158 | 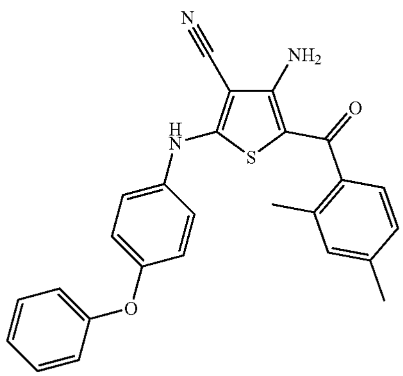 | 4-Amino-5-(2,4-dimethyl-benzoyl)-2-(4-phenoxy-phenylamino)-thiophene-3-carbonitrile | 440.3 |
| 1-159 | 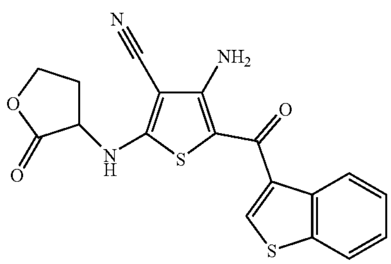 | 4-Amino-5-(benzo[b]thiophene-3-carbonyl)-2-(2-oxo-tetrahydro-furan-3-ylamino)-thiophene-3-carbonitrile | 383.9 |
| 1-160 | 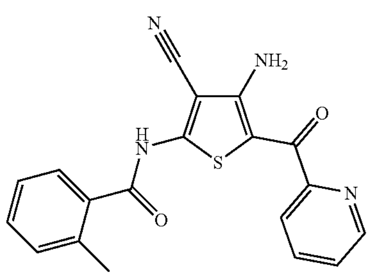 | N-[4-Amino-3-cyano-5-(pyridine-2-carbonyl)-thiophen-2-yl]-2-methyl-benzamide | 363.1 |
| 1-161 | 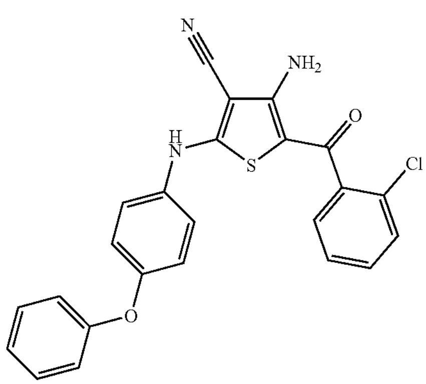 | 4-Amino-5-(2-chloro-benzoyl)-2-(4-phenoxy-phenylamino)-thiophene-3-carbonitrile | 445.9 |

TABLE 1A-continued

Exemplary compounds of Formula I

| Cmpd number | Structure | Name | M + H |
|---|---|---|---|
| 1-162 | 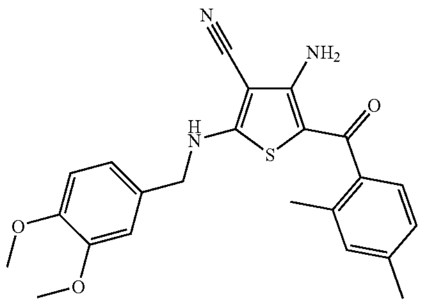 | 4-Amino-2-(3,4-dimethoxy-benzylamino)-5-(2,4-dimethyl-benzoyl)-thiophene-3-carbonitrile | 421.9 |
| 1-163 | 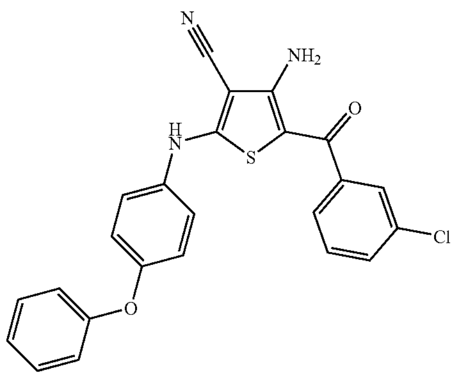 | 4-Amino-5-(3-chloro-benzoyl)-2-(4-phenoxy-phenylamino)-thiophene-3-carbonitrile | N/A |
| 1-164 | 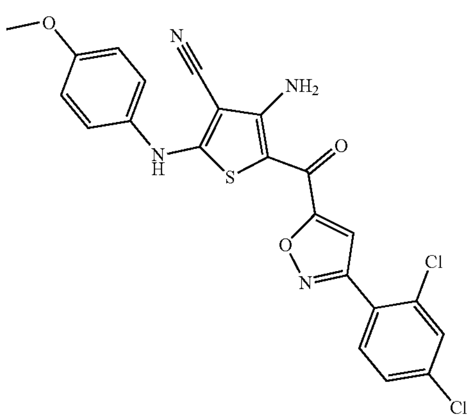 | 4-Amino-5-[3-(2,4-dichloro-phenyl)-isoxazole-5-carbonyl]-2-(4-methoxy-phenylamino)-thiophene-3-carbonitrile | N/A |
| 1-165 | 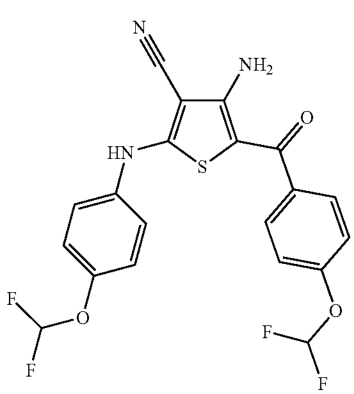 | 4-Amino-5-(4-difluoro-methoxy-benzoyl)-2-(4-difluoromethoxy-phenylamino)-thiophene-3-carbonitrile | 450 [M − H] |

TABLE 1A-continued

Exemplary compounds of Formula I

| Cmpd number | Structure | Name | M + H |
|---|---|---|---|
| 1-166 | 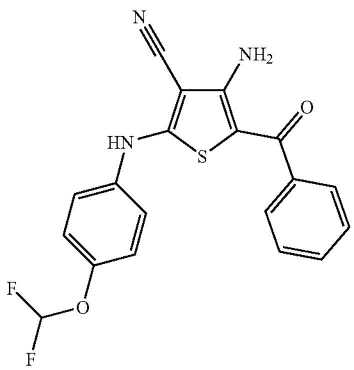 | 4-Amino-5-benzoyl-2-(4-difluoromethoxy-phenylamino)-thiophene-3-carbonitrile | 384 [M − H] |
| 1-167 | 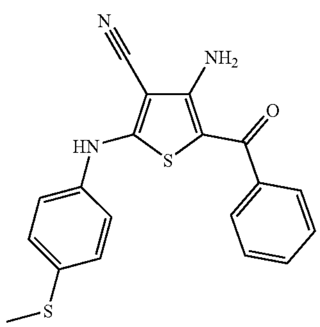 | 4-Amino-5-benzoyl-2-(4-methylsulfanyl-phenylamino)-thiophene-3-carbonitrile | 364 [M − H] |
| 1-168 | 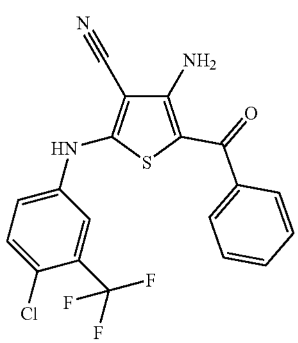 | 4-Amino-5-benzoyl-2-(4-chloro-3-trifluoromethyl-phenylamino)-thiophene-3-carbonitrile | 420 [M − H] |
| 1-169 | 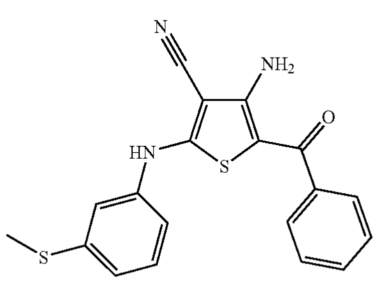 | 4-Amino-5-benzoyl-2-(3-methylsulfanyl-phenylamino)-thiophene-3-carbonitrile | 364 [M − H] |

TABLE 1A-continued

Exemplary compounds of Formula I

| Cmpd number | Structure | Name | M + H |
|---|---|---|---|
| 1-170 | 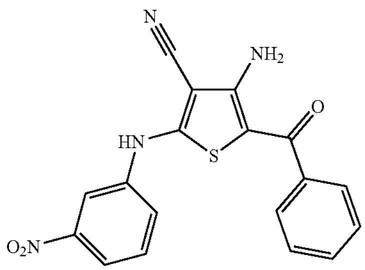 | 4-Amino-5-benzoyl-2-(3-nitro-phenylamino)-thiophene-3-carbonitrile | 365 [M − H] |
| 1-171 | 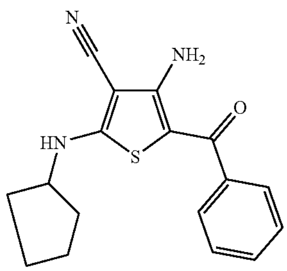 | 4-Amino-5-benzoyl-2-cyclopentylamino-thiophene-3-carbonitrile | 310 [M − H] |
| 1-172 | 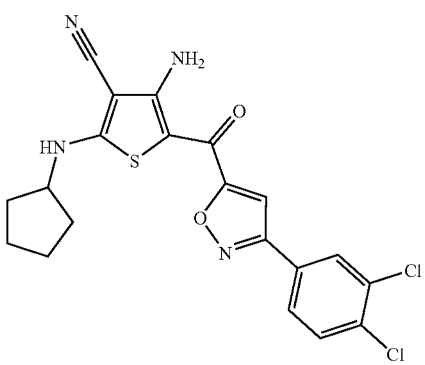 | 4-Amino-2-cyclopentylamino-5-[3-(3-4-dichloro-phenyl)-isoxazole-5-carbonyl]-thiophene-3-carbonitrile | 448.9 |
| 1-173 | 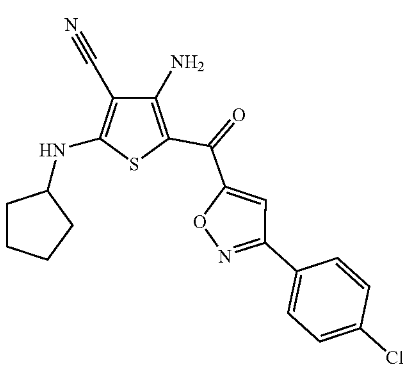 | 4-Amino-5-[3-(4-chloro-phenyl)-isoxazole-5-carbonyl]-2-cyclopentylamino-thiophene-3-carbonitrile | 411.0 [M − H] |

TABLE 1A-continued

Exemplary compounds of Formula I

| Cmpd number | Structure | Name | M + H |
|---|---|---|---|
| 1-174 | 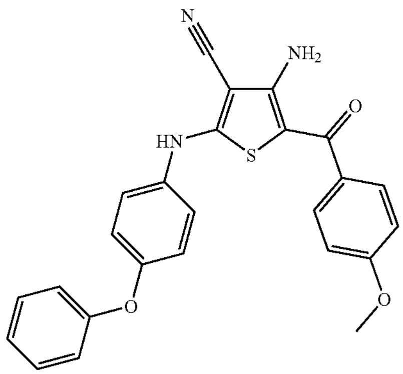 | 4-Amino-5-(4-methoxy-benzoyl)-2-(4-phenoxy)-phenylamino)-thiophene-3-carbonitrile | 440 [M − H] |
| 1-175 | 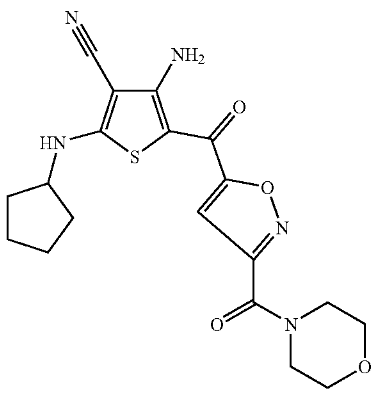 | 4-Amino-2-cyclopentylamino-5-[3-(morpholine-4-carbonyl)-isoxazole-5-carbonyl]-thiophene-3-carbonitrile | 414 [M − H] |
| 1-176 | 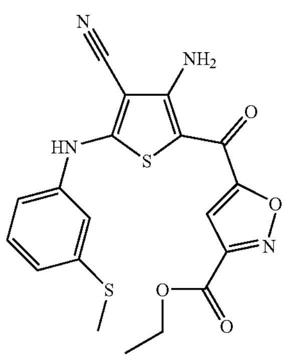 | 5-[3-Amino-4-cyano-5-(3-methylsulfanyl-phenylamino)-thiophene-2-carbonyl]-isoxazole-3-carboxylic acid ethyl ester | 427 [M − H] |
| 1-177 | 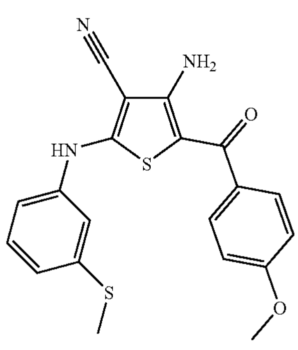 | 4-Amino-5-(4-methoxy-benzoyl)-2-(3-methylsulfanyl-phenylamino)-thiophene-3-carbonitrile | 394 [M − H] |

TABLE 1A-continued

Exemplary compounds of Formula I

| Cmpd number | Structure | Name | M + H |
|---|---|---|---|
| 1-178 | 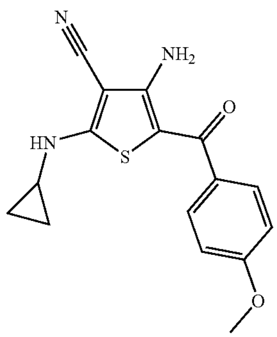 | 4-Amino-2-cyclopropylamino-5-(4-methoxy-benzoyl)-thiophene-3-carbonitrile | 312 [M − H] |
| 1-179 | 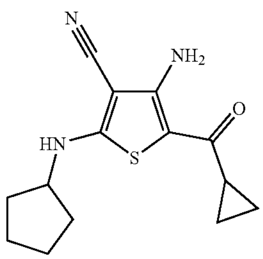 | 4-Amino-2-cyclopentylamino-5-cyclopropanecarbonyl-thiophene-3-carbonitrile | 276.13 |
| 1-180 | 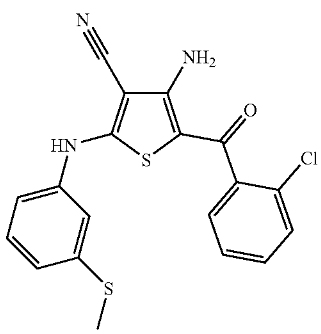 | 4-Amino-5-(2-chloro-benzoyl)-2-(3-methylsulfanyl-phenylamino)-thiophene-3-carbonitrile | 398 [M − H] |
| 1-181 | 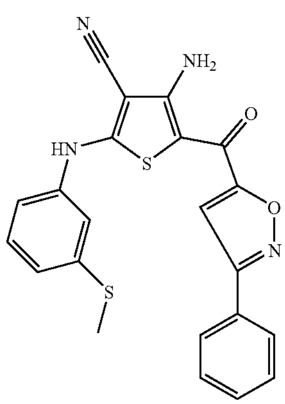 | 4-Amino-2-(3-methylsulfanyl-phenylamino)-5-(3-phenyl-isoxazole-5-carbonyl)-thiophene-3-carbonitrile | 431 [M − H] |
| 1-182 | 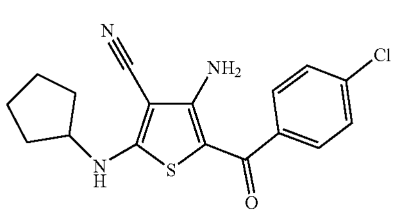 | 4-Amino-5-(4-chloro-benzoyl)-2-cyclopentylamino-thiophene-3-carbonitrile | 344.0 [M − H] |

TABLE 1A-continued

Exemplary compounds of Formula I

| Cmpd number | Structure | Name | M + H |
|---|---|---|---|
| 1-183 | 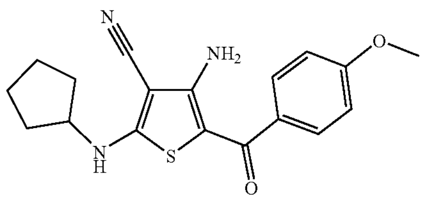 | 4-Amino-2-cyclopentylamino-5-(4-methoxy-benzoyl)-thiophene-3-carbonitrile | 340.1 [M − H] |
| 1-184 | 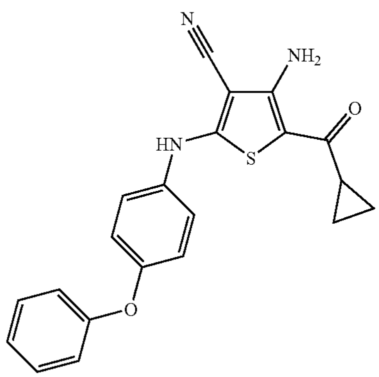 | 4-Amino-5-cyclopropanecarbonyl-2-(4-phenoxy-phenylamino)-thiophene-3-carbonitrile | 374.1 [M − H] |
| 1-185 | 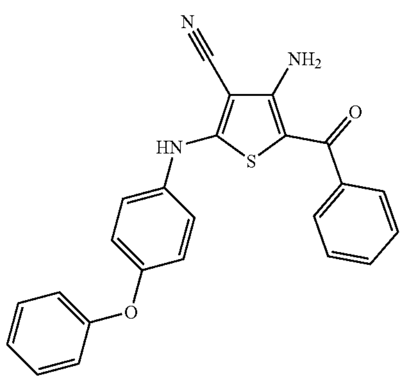 | 4-Amino-5-benzoyl-2-(4-phenoxy-phenylamino)-thiophene-3-carbonitrile | 410.1 [M − H] |
| 1-186 | 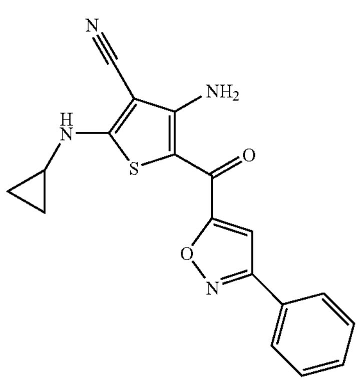 | 4-Amino-2-cyclopropylamino-5-(3-phenyl-isoxazole-5-carbonyl)-thiophene-3-carbonitrile | 349.1 [M − H] |

TABLE 1A-continued

Exemplary compounds of Formula I

| Cmpd number | Structure | Name | M + H |
|---|---|---|---|
| 1-187 | 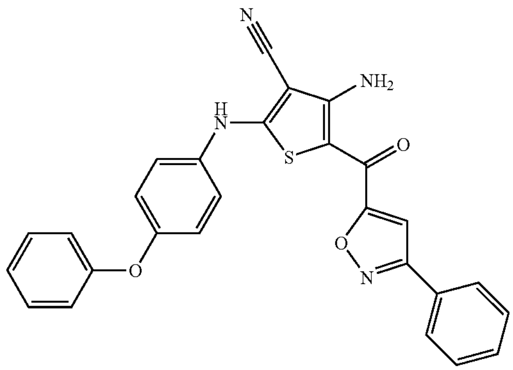 | 4-Amino-2-(4-phenoxy-phenylamino)-5-(3-phenyl-isoxazole-5-carbonyl)-thiophene-3-carbonitrile | 477.0 [M − H] |
| 1-188 | 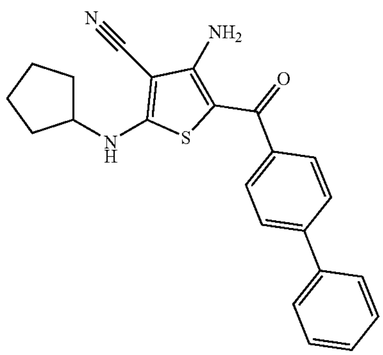 | 4-Amino-5-(biphenyl-4-carbonyl)-2-cyclopentylamino-thiophene-3-carbonitrile | N/A |
| 1-189 | 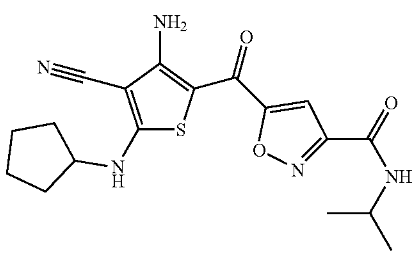 | 5-(3-Amino-4-cyano-5-cyclopentylamino-thiophene-2-carbonyl)-isoxazole-3-carboxylic acid isopropylamide | N/A |
| 1-190 | 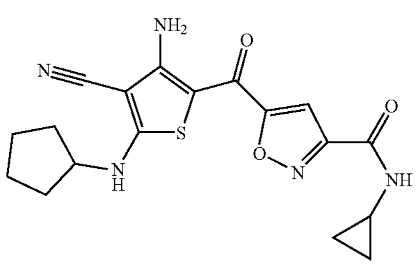 | 5-(3-Amino-4-cyano-5-cyclopentylamino-thiophene-2-carbonyl)-isoxazole-3-carboxylic acid cyclopropylamide | N/A |
| 1-191 | 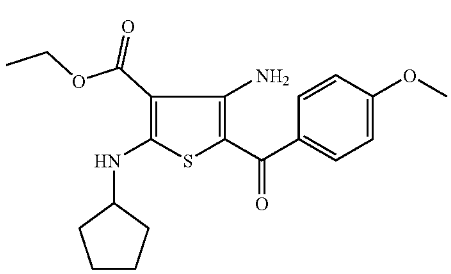 | 4-Amino-2-cyclopentylamino-5-(4-methoxy-benzoyl)-thiophene-3-carboxylic acid ethyl ester | 389 |

TABLE 1A-continued

Exemplary compounds of Formula I

| Cmpd number | Structure | Name | M + H |
|---|---|---|---|
| 1-192 | 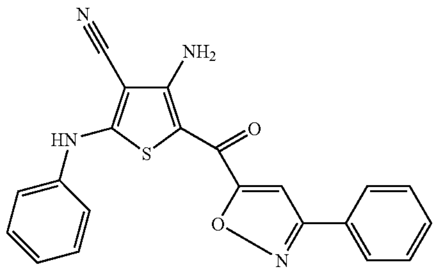 | 4-Amino-2-phenylamino-5-(3-phenyl-isoxazole-5-carbonyl)-thiophene-3-carbonitrile | 387 |
| 1-193 | 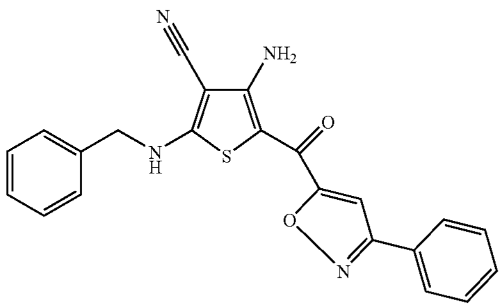 | 4-Amino-2-benzylamino-5-(3-phenyl-isoxazole-5-carbonyl)-thiophene-3-carbonitrile | 401.1 |
| 1-194 | 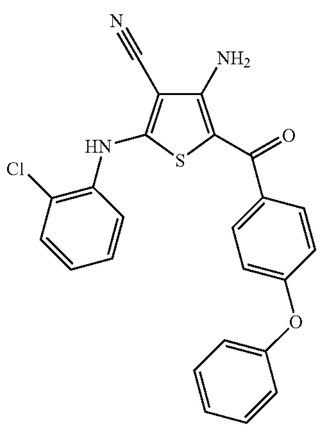 | 4-Amino-2-(2-chloro-phenylamino)-5-(4-phenoxy-benzoyl)-thiophene-3-carbonitrile | 444.0 [M − H] |
| 1-195 | 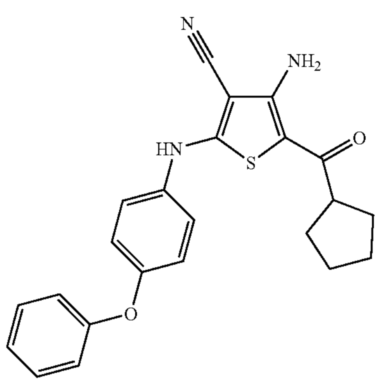 | 4-Amino-5-cyclopentanecarbonyl-2-(4-phenoxy-phenylamino)-thiophene-3-carbonitrile | 402.0 [M − H] |

TABLE 1A-continued

Exemplary compounds of Formula I

| Cmpd number | Structure | Name | M + H |
|---|---|---|---|
| 1-196 | 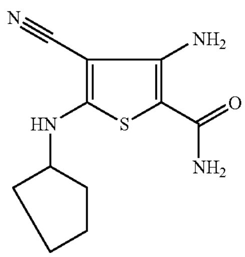 | 3-Amino-4-cyano-5-cyclopentylamino-thiophene-2-carboxylic acid amide | N/A |
| 1-197 | 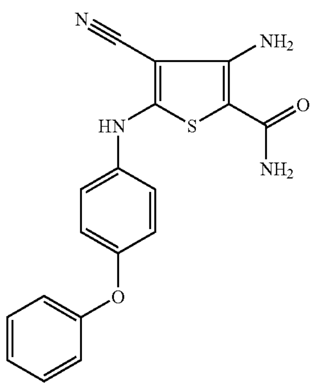 | 3-Amino-4-cyano-5-(4-phenoxy-phenyl amino)-thiophene-2-carboxylic acid amide | N/A |
| 1-198 | 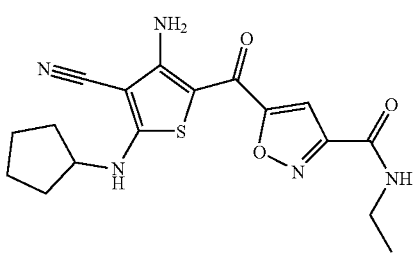 | 5-(3-Amino-4-cyano-5-cyclopentylamino-thiophene-2-carbonyl)-isoxazole-3-carboxylic acid ethylamide | N/A |
| 1-199 | 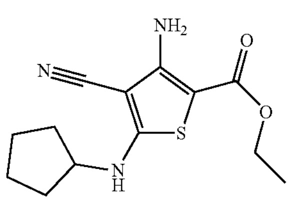 | 3-Amino-4-cyano-5-cyclopentylamino-thiophene-2-carboxylic acid ethyl ester | N/A |
| 1-200 | 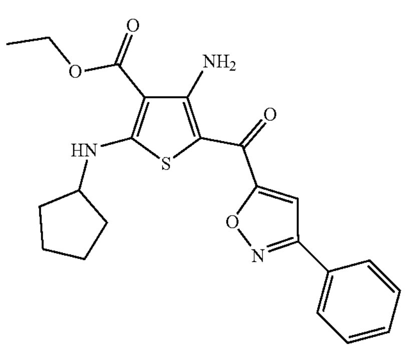 | 4-Amino-2-cyclopentylamino-5-(3-phenyl-isoxazole-5-carbonyl)-thiophene-3-carboxylic acid ethyl ester | N/A |

TABLE 1A-continued

Exemplary compounds of Formula I

| Cmpd number | Structure | Name | M + H |
|---|---|---|---|
| 1-201 | 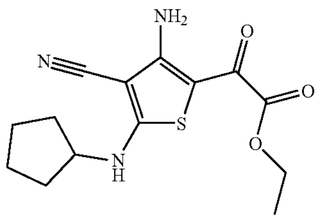 | (3-Amino-4-cyano-5-cyclopentylamino-thiophen-2-yl)-oxo-acetic acid ethyl ester | N/A |
| 1-202 | 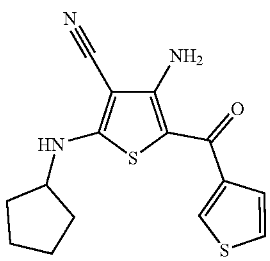 | 4-Amino-2-cyclopentylamino-5-(thiophene-3-carbonyl)-thiophene-3-carbonitrile | 318.1 |
| 1-203 | 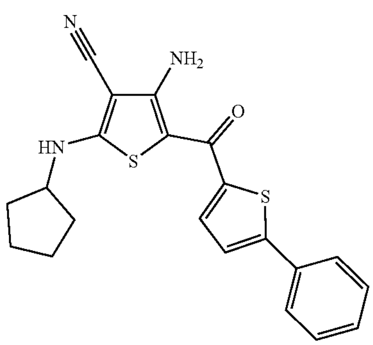 | 4-Amino-2-cyclopentylamino-5-(5-phenyl-thiophene-2-carbonyl)-thiophene-3-carbonitrile | 393.8 |
| 1-204 | 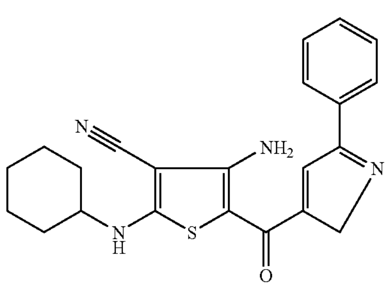 | 4-Amino-2-cyclohexylamino-5-(3-phenyl-isoxazole-5-carbonyl)-thiophene-3-carbonitrile | 393 |
| 1-205 | 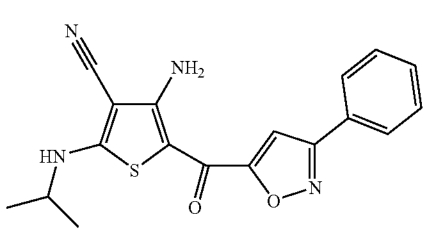 | 4-Amino-2-isopropylamino-5-(3-phenyl-isoxazole-5-carbonyl)-thiophene-3-carbonitrile | 353.1 |

TABLE 1A-continued

Exemplary compounds of Formula I

| Cmpd number | Structure | Name | M + H |
|---|---|---|---|
| 1-206 | 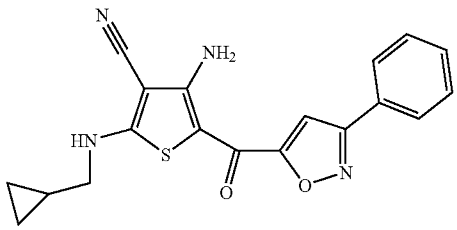 | 4-Amino-2-(cyclopropylmethyl-amino)-5-(3-phenyl-isoxazole-5-carbonyl)-thiophene-3-carbonitrile | 365.0 |
| 1-207 | 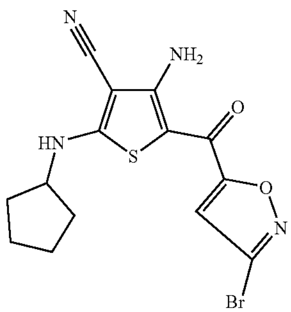 | 4-Amino-5-(3-bromo-isoxazole-5-carbonyl)-2-cyclopentylamino-thiophene-3-carbonitrile | 379 [M − H] |
| 1-208 | 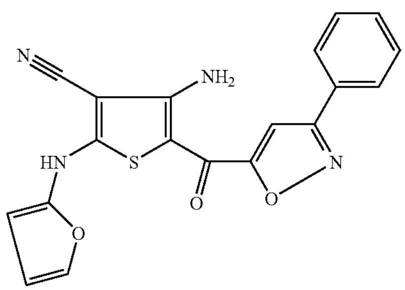 | 4-Amino-2-(furan-2-ylamino)-5-(3-phenyl-isoxazole-5-carbonyl)-thiophene-3-carbonitrile | 377.1 |
| 1-209 | 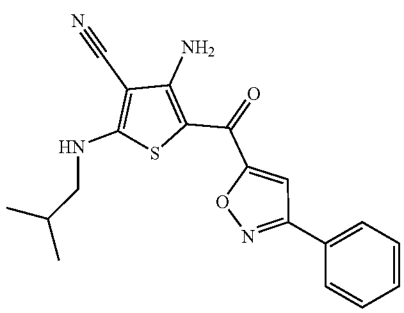 | 4-Amino-2-isobutylamino-5-(3-phenyl-isoxazole-5-carbonyl)-thiophene-3-carbonitrile | 367.2 |
| 1-210 | 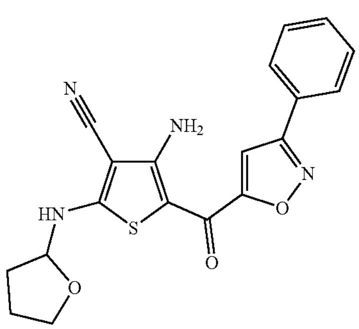 | 4-Amino-5-(3-phenyl-isoxazole-5-carbonyl)-2-(tetrahydro-furan-2-ylamino)-thiophene-3-carbonitrile | 381.1 |

TABLE 1A-continued

Exemplary compounds of Formula I

| Cmpd number | Structure | Name | M + H |
|---|---|---|---|
| 1-211 | 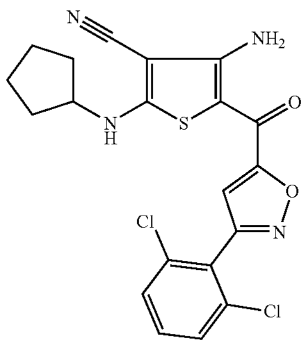 | 4-Amino-2-cyclopentylamino-5-[3-(2,6-dichloro-phenyl)-isoxazole-5-carbonyl]-thiophene-3-carbonitrile | 445 [M − H] |
| 1-212 | 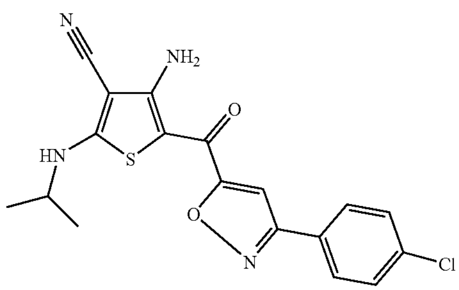 | 4-Amino-5-[3-(4-chloro-phenyl)-isoxazole-5-carbonyl]-2-isopropylamino-thiophene-3-carbonitrile | 385 [M − H] |
| 1-213 | 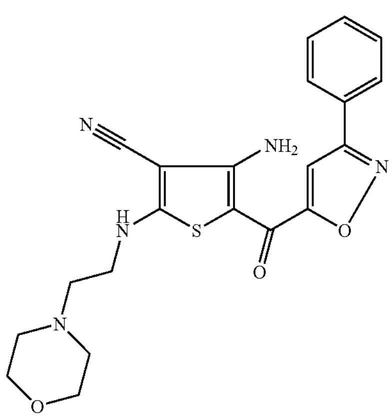 | 4-Amino-2-(2-morpholin-4-yl-ethylamino)-5-(3-phenyl-isoxazole-5-carbonyl)-thiophene-3-carbonitrile | 424.1 |
| 1-214 | 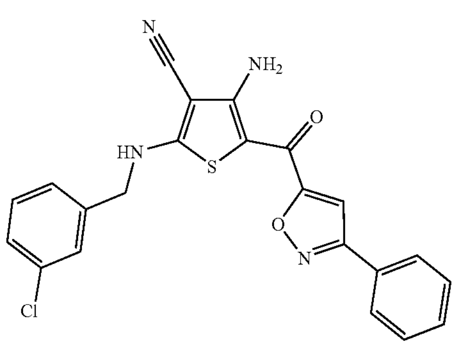 | 4-Amino-2-(3-chloro-benzylamino)-5-(3-phenyl-isoxazole-5-carbonyl)-thiophene-3-carbonitrile | 433.9 [M − H] |

TABLE 1A-continued

Exemplary compounds of Formula I

| Cmpd number | Structure | Name | M + H |
|---|---|---|---|
| 1-215 | 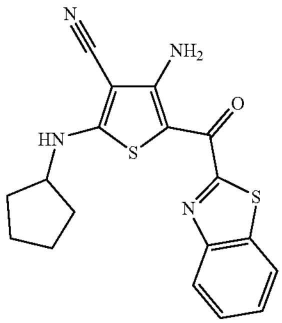 | 4-Amino-5-(benzothiazole-2-carbonyl)-2-cyclopentylamino-thiophene-3-carbonitrile | 369 |
| 1-216 | 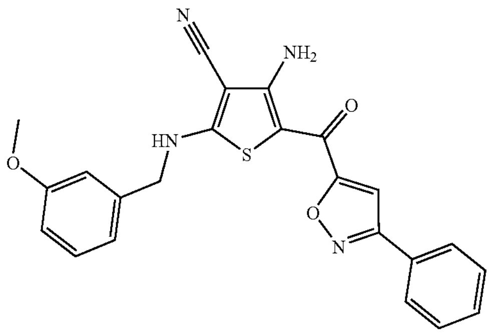 | 4-Amino-2-(3-methoxy-benzylamino)-5-(3-phenyl-isoxazole-5-carbonyl-thiophene-3-carbonitrile | 433.9 [M − H] |
| 1-217 | 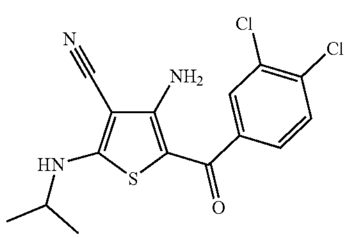 | 4-Amino-5-(3,4-dichloro-benzoyl)-2-isopropylamino-thiophene-3-carbonitrile | 355 |
| 1-218 | 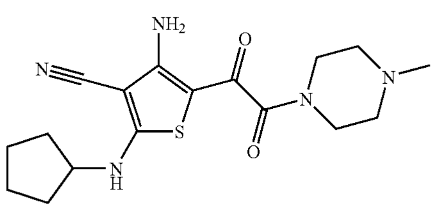 | 4-Amino-2-cyclopentylamino-5-[2-(4-methyl-piperazin-1-yl)-2-oxo-acetyl]-carbonitrile | N/A |
| 1-219 | 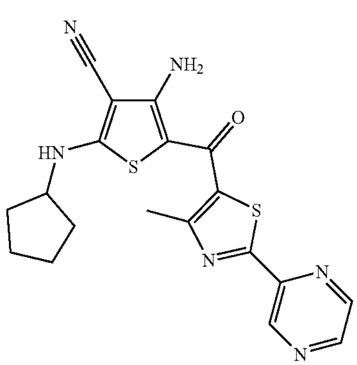 | 4-Amino-2-cyclopentylamino-5-(4-methyl-2-pyrazin-2-yl-thiazole-5-carbonyl)-thiophene-3-carbonitrile | 109.0 [M − H] |

TABLE 1A-continued

Exemplary compounds of Formula I

| Cmpd number | Structure | Name | M + H |
|---|---|---|---|
| 1-220 | 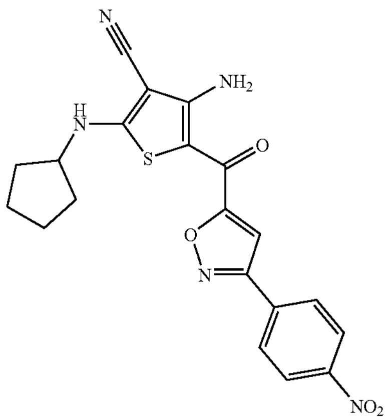 | 4-Amino-2-cyclopentylamino-5-[3-(4-nitro-phenyl)-isoxazole-5-carbonyl]-thiophene-3-carbonitrile | 422.0 [M − H] |
| 1-221 | 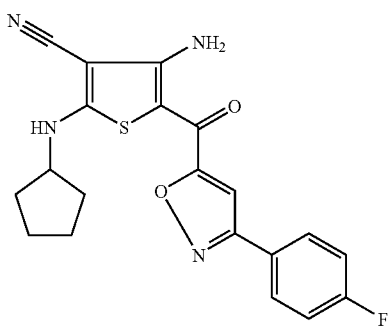 | 4-Amino-2-cyclopentylamino-5-[3-(4-fluoro-phenyl)-isoxazole-5-carbonyl]-thiophene-3-carbonitrile | 397 |
| 1-222 | 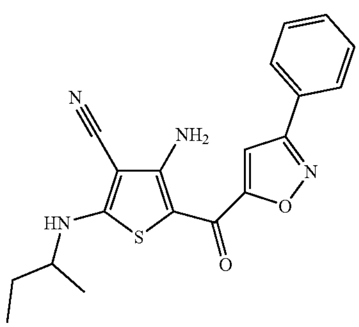 | 4-Amino-2-sec-butylamino-5-(3-phenyl-isoxazole-5-carbonyl)-thiophene-3-carbonitrile | 367.2 |
| 1-223 | 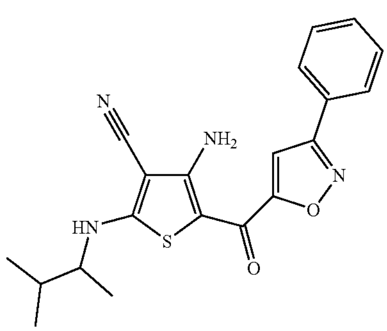 | 4-Amino-2-(1,2-dimethyl-propylamino)-5-(3-phenyl-isoxazoie-5-carbonyl)-thiophene-3-carbonitrile | 379.1 [M − H] |

TABLE 1A-continued

Exemplary compounds of Formula I

| Cmpd number | Structure | Name | M + H |
|---|---|---|---|
| 1-224 | 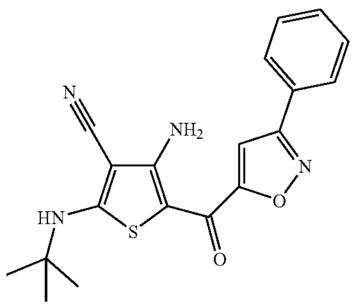 | 4-Amino-2-tert-butylamino-5-(3-phenyl-isoxazole-5-carbonyl)-thiophene-3-carbonitrile | 367.2 |
| 1-225 | 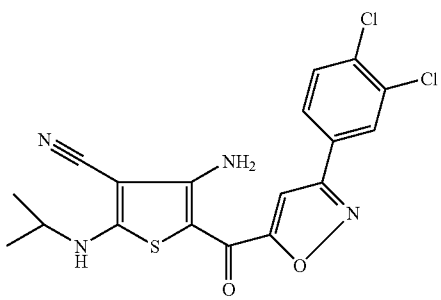 | 4-Amino-5-[3-(3,5-dichloro-isoxazole-5-carbonyl]-2-isopropylamino-thiophene-3-carbonitrile | 418.9 [M − H] |
| 1-226 | 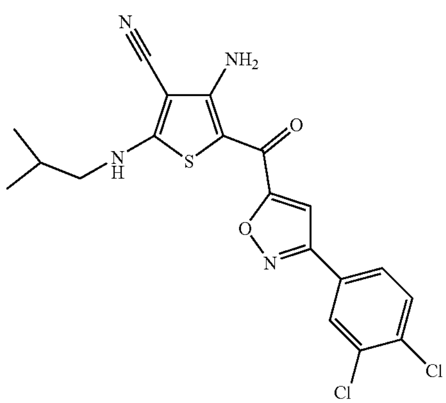 | 4-Amino-5-[3-(3,4-dichloro-phenyl)-isoxazole-5-carbonyl]-2-isobutylamino-thiophene-3-carbonitrile | 434.9 |
| 1-227 | 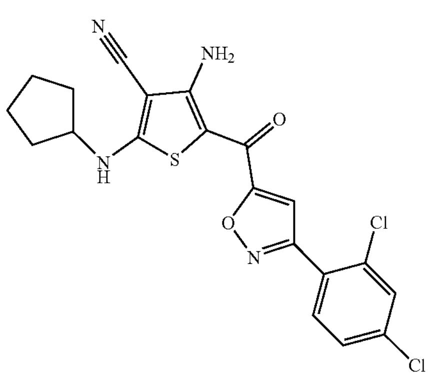 | 4-Amino-2-cyclopentylamino-5-[3-(2,4-dichloro-phenyl)-isoxazole-5-carbonyl]-thiophene-3-carbonitrile | N/A |

TABLE 1A-continued

Exemplary compounds of Formula I

| Cmpd number | Structure | Name | M + H |
|---|---|---|---|
| 1-228 | 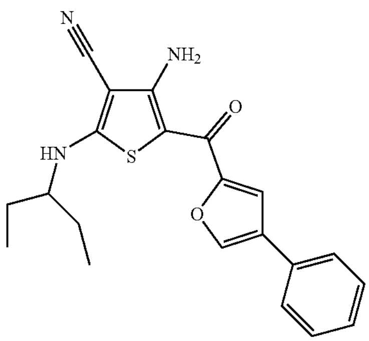 | 4-Amino-2-(1-ethyl-propylamino)-5-(3-phenyl-isoxazole-5-carbonyl)-thiophene-3-carbonitrile | 381.2 |
| 1-229 | 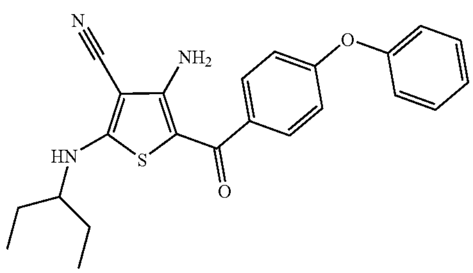 | 4-Amino-2-(1-ethyl-propylamino)-5-(4-phenoxy-benzoyl)-thiophene-3-carbonitrile | 406.2 |
| 1-230 | 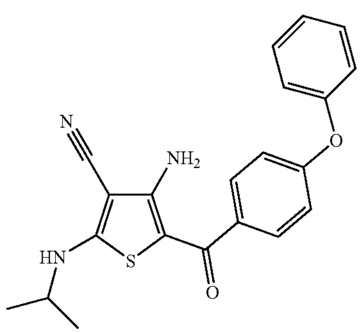 | 4-Amino-2-isopropylamino-5-(4-phenoxy-benzoyl)-thiophene-3-carbonitrile | 377.9 |
| 1-231 | 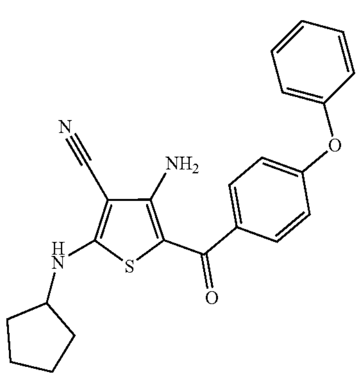 | 4-Amino-2-cyclopentylamino-5-(4-phenoxy-benzoyl)-thiophene-3-carbonitrile | 404.1 |

TABLE 1A-continued

Exemplary compounds of Formula I

| Cmpd number | Structure | Name | M + H |
|---|---|---|---|
| 1-232 | 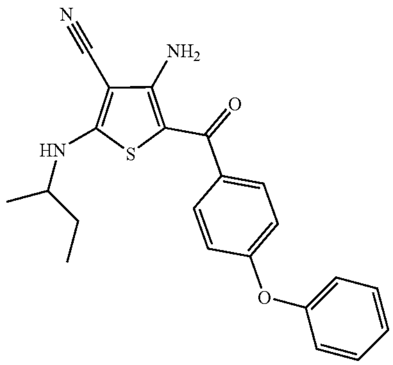 | 4-Amino-2-sec-butylamino-5-(4-phenoxy-benzoyl)-thiophene-3-carbonitrile | 392 |
| 1-233 | 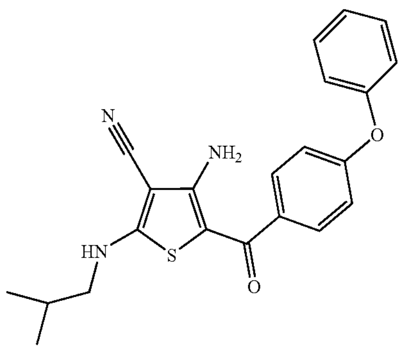 | 4-Amino-2-isobutylamino-5-(4-phenoxy-benzoyl)-thiophene-3-carbonitrile | 390.1 [M − H] |
| 1-234 | 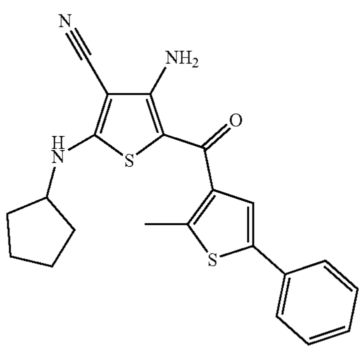 | 4-Amino-2-cyclopentylamino-5-(2-methyl-5-phenyl-thiophene-3-carbonyl)-thiophene-3-carbonitrile | 408.2 |
| 1-235 | 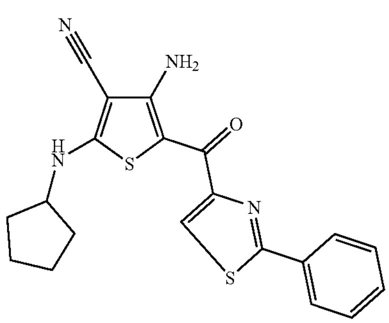 | 4-Amino-2-cyclopentylamino-5-(2-phenyl-thiazole-4-carbonyl)-thiophene-3-carbonitrile | 395 |

TABLE 1A-continued

Exemplary compounds of Formula I

| Cmpd number | Structure | Name | M + H |
|---|---|---|---|
| 1-236 | 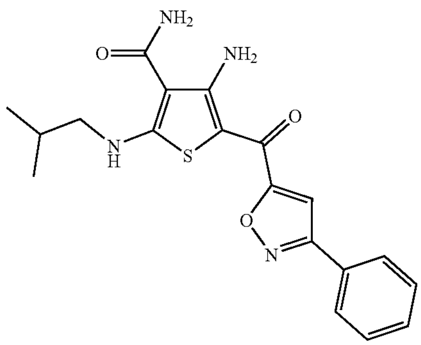 | 4-Amino-2-isobutylamino-5-(3-phenyl-isoxazole-5-carbonyl)-thiophene-3-carboxylic acid amide | 385.2 |
| 1-237 | 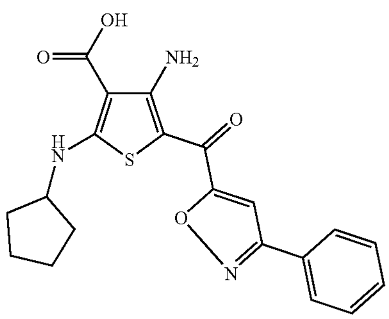 | 4-Amino-2-cyclopentylamino-5-(3-phenyl-isoxazole-5-carbonyl)-thiophene-3-carboxylic acid | N/A |
| 1-238 | 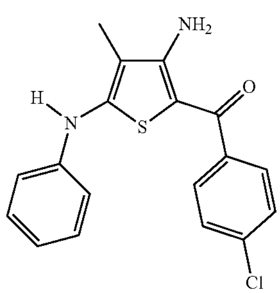 | (3-Amino-4-methyl-5-phenylamino-thiophen-2-yl)-(4-chloro-phenyl)-methanone | 343.0 |
| 1-239 | 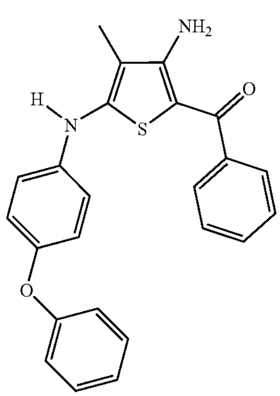 | [3-Amino-4-methyl-5-(4-phenoxy-phenylamino)-thiophen-2-yl]-phenyl-methanone | 401 |

TABLE 1A-continued

Exemplary compounds of Formula I

| Cmpd number | Structure | Name | M + H |
|---|---|---|---|
| 1-240 | 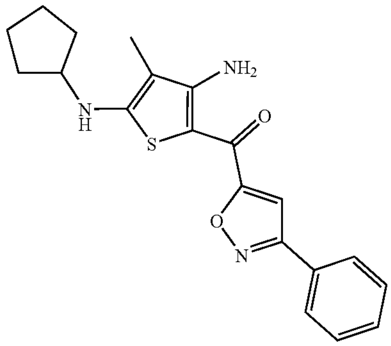 | (3-Amino-5-cyclopentylamino-4-methyl-thiophen-2-yl)-(3-phenyl-isoxazol-5-yl)-methanone | 368.1 |
| 1-241 | 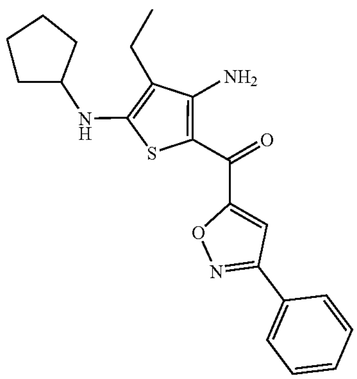 | (3-Amino-5-cyclopentylamino-4-ethyl-thiophen-2-yl)-(3-phenyl-isoxazole-5-yl)-methanone | 382.1 |
| 1-242 | 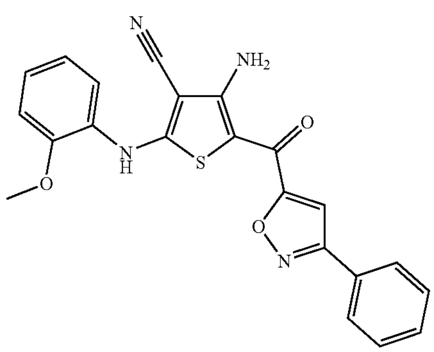 | 4-Amino-2-methoxy-phenylamino)-5-(3-phenyl-isoxazole-5-carbonyl)-thiophene-3-carbonitrile | N/A |
| 1-243 | 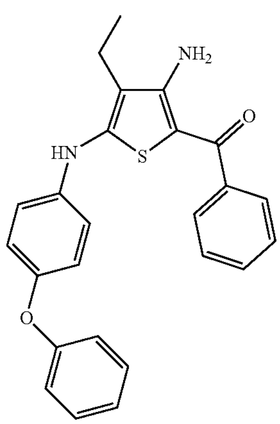 | [3-Amino-5-ethyl-5-(4-phenoxy-phenylamino)-thiophen-2-yl]-phenyl-methanone | 415 |

… TABLE 1A-continued

Exemplary compounds of Formula I

| Cmpd number | Structure | Name | M + H |
|---|---|---|---|
| 1-244 | 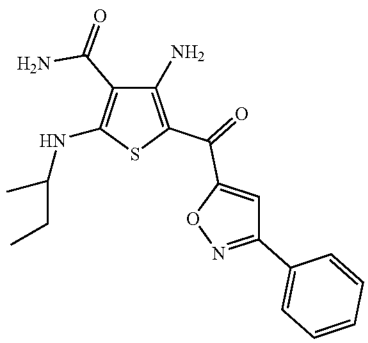 | 4-Amino-2-sec-butylamino-5-(3-phenyl-isoxazole-5-carbonyl)-thiophene-3-carboxylic acid amide | N/A |
| 1-245 | 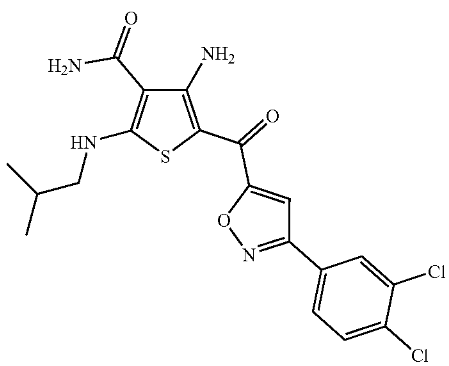 | 4-Amino-5-[3-(3,4-dichloro-phenyl)-isoxazole-5-carbonyl]-2-isobutylamino-thiophene-3-carboxylic acid amide | N/A |
| 1-246 | 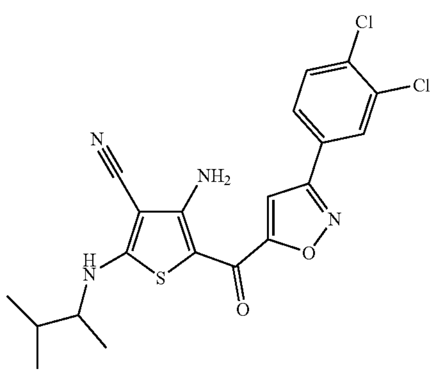 | 4-Amino-5-[3-(3,4-dichloro-phenyl)-isoxazole-5-carbonyl]-2-(1,2-dimethyl-propylamino)-thiophene-3-carbonitrile | 450 |
| 1-247 | 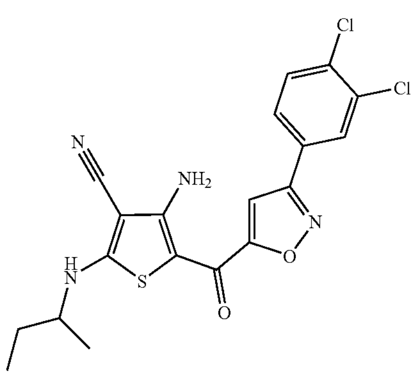 | 4-Amino-2-sec-butylamino-5-[3-(3,4-dichloro-phenyl)-isoxazole-5-carbonyl]-thiophene-3-carbonitrile | 436.1 |

TABLE 1A-continued

Exemplary compounds of Formula I

| Cmpd number | Structure | Name | M + H |
|---|---|---|---|
| 1-248 | 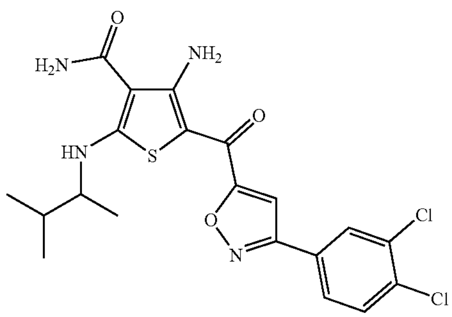 | 4-Amino-5-[3-(3,4-dichloro-phenyl)-isoxazole-5-carbonyl]-2-(1,2-dimethyl-propylamino)-thiophene-3-carboxylic acid amide | N/A |
| 1-249 | 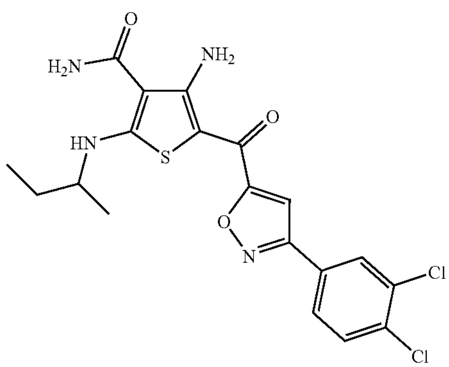 | 4-Amino-2-sec butylamino-5-[3-(3,4-dichloro-phenyl)-isoxazole-5-carbonyl]-thiophene-3-carboxylic acid amide | N/A |
| 1-250 | 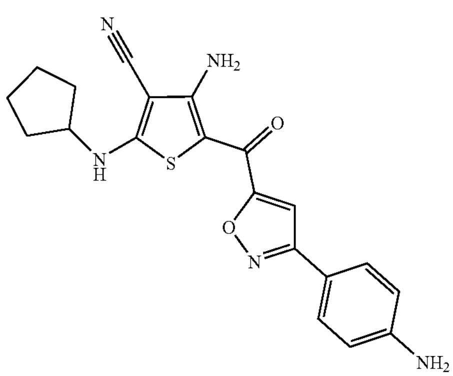 | 4-Amino-5-[3-(4-amino-phenyl)-isoxazole-5-carbonyl]-2-cyclopentylamino-thiophene-3-carbonitrile | N/A |
| 1-251 | 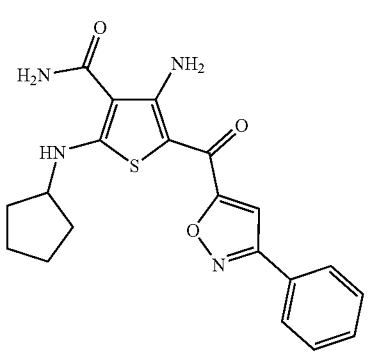 | 4-Amino-2-cyclopentylamino-5-(3-phenyl-isoxazole-5-carbonyl)-thiophene-3-carboxylic acid amide | 397.2 |

TABLE 1A-continued

Exemplary compounds of Formula I

| Cmpd number | Structure | Name | M + H |
|---|---|---|---|
| 1-252 | 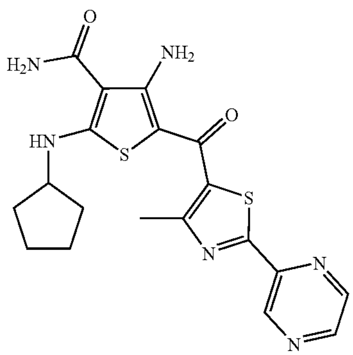 | 4-Amino-2-cyclopentylamino-5-(4-methyl-2-pyrazin-2-yl-thiazole-5-carbonyl)-thiophene-3-carboxylic acid amide | N/A |
| 1-253 | 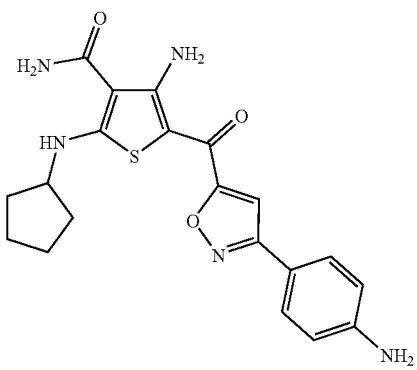 | 4-Amino-5-[3-(4-amino-phenyl)-isoxazole-5-carbonyl]-2-cyclopentylamino-thiophene-3-carboxylic acid amide | 412.41 |
| 1-254 | 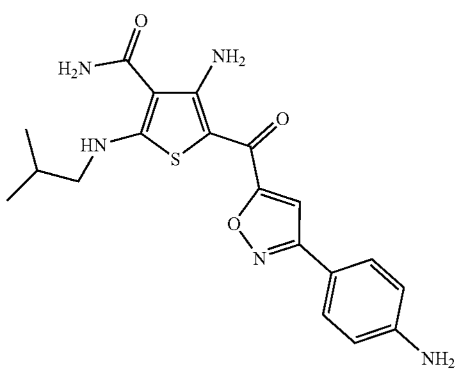 | 4-Amino-5-[3-(4-amino-phenyl)-isoxazole-5-carbonyl]-2-isobutylamino-thiophene-3-carboxylic acid amide | 400.44 |
| 1-255 | 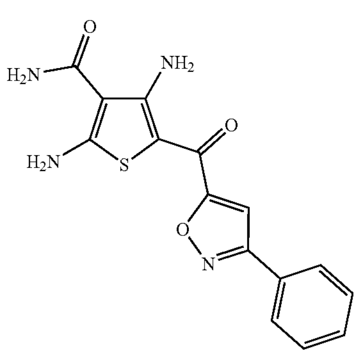 | 2,4-Diamino-5-(3-phenyl-isoxazole-5-carbonyl)-thiophene-3-carboxylic acid amide | N/A |

TABLE 1A-continued

Exemplary compounds of Formula I

| Cmpd number | Structure | Name | M + H |
|---|---|---|---|
| 1-256 | 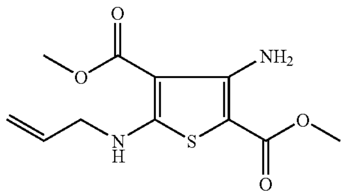 | 5-Allylamino-3-amino-thiophene-2,4-dicarboxylic acid dimethyl ester | N/A |
| 1-257 | 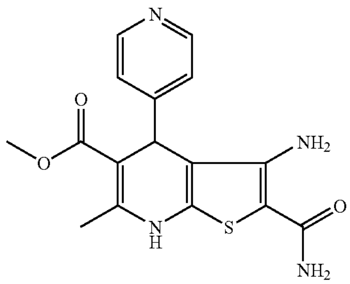 | 3-Amino-2-carbamoyl-6-methyl-4-pyridin-4-yl-4,7-dihydro-thieno[2,3-b]pyridine-5-carboxylic acid methyl ester | N/A |
| 1-258 | 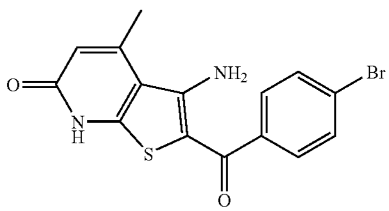 | 3-Amino-2-(4-bromo-benzoyl)-4-methyl-7H-thieno[2,3-b]pyridin-6-one | N/A |
| 1-259 | 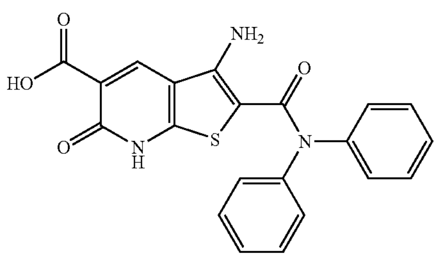 | 3-Amino-2-diphenylcarbamoyl-6-oxo-6,7-dihydro-thieno[2,3-b]pyridine-5-carboxylic acid | N/A |
| 1-260 | 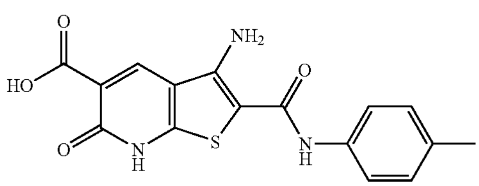 | 3-Amino-6-oxo-2-p-tolylcarbamoyl-6,7-dihydro-thieno[2,3-b]pyridine-5-carboxylic acid | N/A |

TABLE 1B

Formula I compound numbers and data.
For rat in vivo inhibition assay, + = >20%, − = <20%, blank = not assayed
100 mg/kg po, 2 hr challenge delay unless indicated otherwise.

| Comp number | % inhibition | | IC50 + = <10 mM/ − = >10 mM/ blank not assayed | | | |
|---|---|---|---|---|---|---|
| | r TNFα | h TNFα | PDE4B | PDE4B2 | PDE4D | PDE4D5 |
| 1-1 | | | + | + | + | + |
| 1-2 | | | + | + | + | + |
| 1-3 | | | − | | | |
| 1-4 | | | − | | − | |

TABLE 1B-continued

Formula I compound numbers and data.
For rat in vivo inhibition assay, + = >20%, − = <20%,
blank = not assayed
100 mg/kg po, 2 hr challenge delay unless indicated otherwise.

| Comp number | % inhibition r TNFα | h TNFα | PDE4B | PDE4B2 | PDE4D | PDE4D5 |
|---|---|---|---|---|---|---|
| 1-5 | | | + | | | |
| 1-6 | | | − | | | |
| 1-7 | | | − | | | |
| 1-8 | | | + | | | |
| 1-9 | | | + | | | |
| 1-10 | | | − | | | |
| 1-11 | | | − | | | |
| 1-12 | | | − | − | − | − |
| 1-13 | | | + | | | |
| 1-14 | | | + | | | |
| 1-15 | | | | | | |
| 1-16 | | | + | − | − | − |
| 1-17 | | | + | + | + | + |
| 1-18 | | | + | + | + | + |
| 1-19 | | | + | | + | |
| 1-20 | | + | + | + | + | + |
| 1-21 | | | + | + | + | + |
| 1-22 | | | + | + | + | + |
| 1-23 | | | − | | − | |
| 1-24 | | | − | | − | |
| 1-25 | | | + | | + | |
| 1-26 | | | + | | + | |
| 1-27 | | | | | − | |
| 1-28 | − | + | + | + | + | + |
| 1-29 | + (1 hr ip) | | + | + | + | + |
| 1-30 | + | | + | + | + | + |
| 1-31 | − (200 mg 1 hr) + (100 mg 2 hr) | + | + | + | + | + |
| 1-32 | − | | + | + | + | + |
| 1-33 | + | | + | + | + | + |
| 1-34 | + | | + | + | + | + |
| 1-35 | − | | + | + | + | + |
| 1-36 | − (1 hr) | | + | + | + | + |
| 1-37 | − (1 hr) | | + | + | + | + |
| 1-38 | | | − | | − | |
| 1-39 | | | − | | − | |
| 1-40 | | − | + | + | + | + |
| 1-41 | | | − | | − | |
| 1-42 | | | + | | − | |
| 1-43 | | | + | + | + | + |
| 1-44 | | | + | − | + | |
| 1-45 | | | − | | − | |
| 1-46 | | | − | | − | |
| 1-47 | | | − | | − | |
| 1-48 | | | − | | − | |
| 1-49 | | | + | | + | |
| 1-50 | | | + | + | + | + |
| 1-51 | | | + | | − | |
| 1-52 | | | + | | − | |
| 1-53 | | | − | | − | |
| 1-54 | | | + | | + | |
| 1-55 | | | + | + | + | + |
| 1-56 | | | + | | − | |
| 1-57 | | | − | − | + | − |
| 1-58 | | | + | | + | |
| 1-59 | | | − | | − | |
| 1-60 | | | + | | − | |
| 1-61 | | | + | + | + | + |
| 1-62 | | | − | − | − | − |
| 1-63 | | | − | | − | |
| 1-64 | | | + | | − | |
| 1-65 | | | − | | − | |
| 1-66 | | | + | + | + | + |
| 1-67 | | | + | + | + | + |
| 1-68 | | | + | − | + | − |
| 1-69 | | | + | + | + | + |
| 1-70 | | | + | | + | |
| 1-71 | | | + | + | + | − |
| 1-72 | | | + | | + | |
| 1-73 | | | + | | + | |
| 1-74 | | | + | + | + | + |
| 1-75 | | | + | + | + | + |
| 1-76 | | | + | | − | |
| 1-77 | | | + | + | + | + |
| 1-78 | | | + | + | + | + |
| 1-79 | | | + | | + | |
| 1-80 | | | + | | + | |
| 1-81 | | | + | − | + | − |
| 1-82 | | | − | − | − | − |
| 1-83 | | | − | − | − | − |
| 1-84 | | | | | | |
| 1-85 | | | + | + | + | + |
| 1-86 | | | + | − | + | − |
| 1-87 | | | − | | − | |
| 1-88 | | | + | | − | |
| 1-89 | | | + | | + | |
| 1-90 | | | + | + | + | + |
| 1-91 | | | + | | − | |
| 1-92 | | | + | | + | |
| 1-93 | | | + | | + | |
| 1-94 | | | + | | + | |
| 1-95 | | | + | | − | |
| 1-96 | | | + | | − | |
| 1-97 | | | − | | + | |
| 1-98 | | | + | | − | |
| 1-99 | | | + | + | + | + |
| 1-100 | | | + | | + | |
| 1-101 | | | + | | + | |
| 1-102 | | | + | | + | |
| 1-103 | | | − | | − | |
| 1-104 | | | + | | + | |
| 1-105 | | | + | | + | |
| 1-106 | | | + | | − | |
| 1-107 | | | + | | + | |
| 1-108 | | | + | | + | |
| 1-109 | | | + | | + | |
| 1-110 | | + | + | + | + | + |
| 1-111 | | | + | | + | |
| 1-112 | | | + | | + | |
| 1-113 | | | + | | + | |
| 1-114 | | | + | | + | |
| 1-115 | | | + | | + | |
| 1-116 | | | − | | − | |
| 1-117 | | | + | | + | |
| 1-118 | | | + | | − | |
| 1-119 | | | + | | + | |
| 1-120 | | | + | | + | |
| 1-121 | | | + | | + | |
| 1-122 | | | + | | + | |
| 1-123 | | | + | | + | |
| 1-124 | | | + | | − | |
| 1-125 | | | + | + | + | + |
| 1-126 | | | + | | + | |
| 1-127 | | | + | | + | |
| 1-128 | | | + | | + | |
| 1-129 | | | + | + | + | + |
| 1-130 | | | + | + | + | + |
| 1-131 | | | + | | + | |
| 1-132 | | | + | | + | |
| 1-133 | | | + | | + | |
| 1-134 | | | + | | + | |
| 1-135 | | | + | | + | |
| 1-136 | | | − | | − | |
| 1-137 | | | + | | − | |
| 1-138 | | | + | | + | |
| 1-139 | | | + | + | + | + |

TABLE 1B-continued

Formula I compound numbers and data.
For rat in vivo inhibition assay, + = >20%, − = <20%,
blank = not assayed
100 mg/kg po, 2 hr challenge delay unless indicated otherwise.

| Comp number | % inhibition r TNFα | h TNFα | IC50 + = <10 mM/− = >10 mM/ blank not assayed | | | |
|---|---|---|---|---|---|---|
| | | | PDE4B | PDE4B2 | PDE4D | PDE4D5 |
| 1-140 | | | + | | − | |
| 1-141 | | | + | | + | |
| 1-142 | | | + | + | + | |
| 1-143 | −/+ <br> − (80 mg) <br> + (ip) <br> + (50 mg, ip) | | + | + | + | + |
| 1-144 | | | + | | + | |
| 1-145 | | | − | | − | |
| 1-146 | | | + | | − | |
| 1-147 | | | + | | + | |
| 1-148 | | | + | | + | |
| 1-149 | | | + | | + | |
| 1-150 | | | + | | − | |
| 1-151 | | | + | | − | |
| 1-152 | | | − | | − | |
| 1-153 | | | + | | − | |
| 1-154 | | | + | | − | |
| 1-155 | | | + | + | + | + |
| 1-156 | | | + | | + | |
| 1-157 | | | + | | + | |
| 1-158 | | | + | | − | |
| 1-159 | | | + | | + | |
| 1-160 | | | + | | − | |
| 1-161 | + (90 mg, ip) <br> − (90 mg, po) | | + | + | − | + |
| 1-162 | | | + | | + | |
| 1-163 | | | + | | − | |
| 1-164 | | | + | | + | − |
| 1-165 | | | + | | + | |
| 1-166 | − | | + | | + | |
| 1-167 | − | | + | | + | |
| 1-168 | | | + | | + | |
| 1-169 | + (70 mg) | | + | + | + | + |
| 1-170 | | | + | | + | |
| 1-171 | − | | + | + | + | + |
| 1-172 | | | + | + | − | − |
| 1-173 | − | | + | + | − | − |
| 1-174 | | | + | | | |
| 1-175 | | | + | | | |
| 1-176 | | | + | | + | |
| 1-177 | − | | + | | + | |
| 1-178 | | | + | | + | |
| 1-179 | | | + | | + | |
| 1-180 | | | + | + | + | + |
| 1-181 | − | | + | + | + | + |
| 1-182 | | | + | | − | |
| 1-183 | | | + | | + | |
| 1-184 | | | + | | + | |
| 1-185 | | | + | | + | |
| 1-186 | − | | + | + | − | + |
| 1-187 | | | − | − | − | − |
| 1-188 | | | + | | | |
| 1-189 | | | + | | + | + |
| 1-190 | | | + | | + | + |
| 1-191 | − (50 mg) | − | + | + | + | + |
| 1-192 | − (50 mg) | + | + | + | + | + |
| 1-193 | − | | + | | − | |
| 1-194 | | | + | | | |
| 1-195 | | | + | | | + |
| 1-196 | | | − | | − | |
| 1-197 | | | − | | − | |
| 1-198 | | | + | − | + | − |
| 1-199 | | | + | | + | |
| 1-200 | | | − | − | + | − |
| 1-201 | | | + | | + | |
| 1-202 | | | + | | + | |
| 1-203 | | | + | | + | |
| 1-204 | | | − | − | − | − |
| 1-205 | − | − | + | − | + | |
| 1-206 | | | − | − | − | |
| 1-207 | | | + | | + | |
| 1-208 | | | − | + | − | − |
| 1-209 | − | | + | + | + | + |
| 1-210 | | | + | + | + | + |
| 1-211 | | | + | + | + | + |
| 1-212 | + (90 mg) | − | + | + | − | − |
| 1-213 | | | + | − | + | |
| 1-214 | | | − | − | − | − |
| 1-215 | | | + | + | + | + |
| 1-216 | | | − | − | − | − |
| 1-217 | | | + | | + | |
| 1-218 | | | − | | − | |
| 1-219 | | + | + | + | + | + |
| 1-220 | − | | + | + | − | − |
| 1-221 | − (50 mg) | | + | + | − | − |
| 1-222 | | − | + | + | + | − |
| 1-223 | | − | + | + | − | − |
| 1-224 | | | + | + | + | + |
| 1-225 | − | | + | + | − | − |
| 1-226 | | | − | − | − | − |
| 1-227 | | | + | − | + | − |
| 1-228 | | | + | | + | − |
| 1-229 | | | + | | + | |
| 1-230 | | | + | | + | |
| 1-231 | | | + | | + | |
| 1-232 | | | + | | + | |
| 1-233 | | | + | + | + | + |
| 1-234 | | | + | | + | |
| 1-235 | | | + | | + | |
| 1-236 | + (50 mg) <br> + (50 mg, ip) | − | + | + | + | + |
| 1-237 | | | + | + | | + |
| 1-238 | | | + | + | | + |
| 1-239 | | | + | − | | − |
| 1-240 | | + | + | + | | + |
| 1-241 | | − | + | + | | − |
| 1-242 | | + | + | + | | + |
| 1-243 | | | + | + | | − |
| 1-244 | | + | + | + | + | + |
| 1-245 | | + | + | + | + | + |
| 1-246 | | | + | + | − | − |
| 1-247 | − | | + | + | − | − |
| 1-248 | | | + | + | + | − |
| 1-249 | − | | + | | + | − |
| 1-250 | − | | + | + | + | + |
| 1-251 | + (50 mg) | − | + | + | + | + |
| 1-252 | | − | + | + | + | + |
| 1-253 | − | | + | + | + | + |
| 1-254 | | + | + | + | + | + |
| 1-255 | − | | − | − | − | − |

TABLE 3C

Additional compounds of Formula I

| Cmpd. | Structure | Name |
|---|---|---|
| 3 | 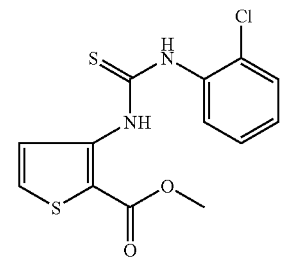 | 3-[3-(2-Chloro-phenyl)-thioureido]-thiophene-2-carboxylic acid methyl ester |
| 4 | 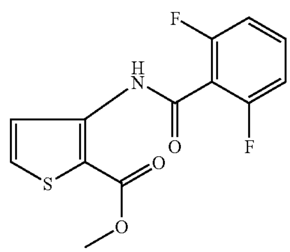 | 3-(2,6-Difluoro-benzoylamino)-thiophene-2-carboxylic acid methyl ester |
| 5 | 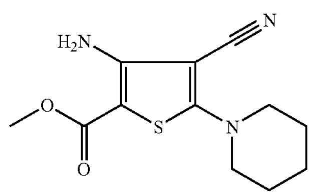 | 3-Amino-4-cyano-5-piperidin-1-yl-thiophene-2-carboxylic acid methyl ester |
| 6 | 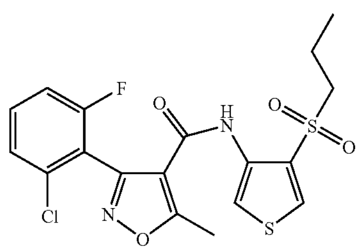 | 3-(2-Chloro-6-fluoro-phenyl)-5-methyl-isoxazole-4-carboxylic acid [4-(propane-1-sulfonyl)-thiophen-3-yl]-amide |
| 8 | 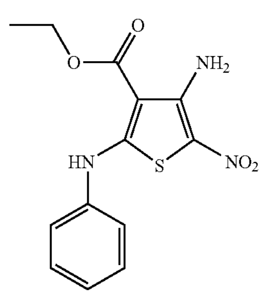 | 4-Amino-5-nitro-2-phenylamino-thiophene-3-carboxylic acid ethyl ester |
| 12 | 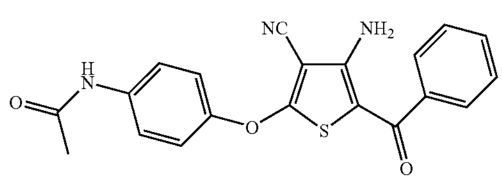 | N-{4-[(4-amino-5-benzoyl-3-cyano-2-thienyl)oxy]phenyl}acetamide |

TABLE 3C-continued

Additional compounds of Formula I

| Cmpd. | Structure | Name |
|---|---|---|
| 14 | 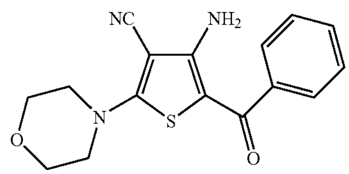 | 4-amino-5-benzoyl-2-morpholino-3-thiophenecarbonitrile |
| 16 | 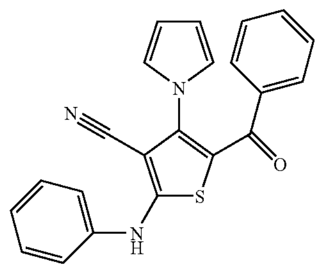 | 2-anilino-5-benzoyl-4-(1H-pyrrol-1-yl)-3-thiophenecarbonitrile |
| 21 | 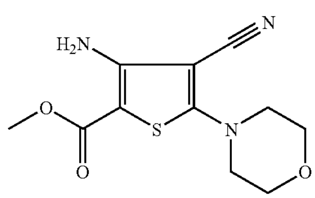 | 3-Amino-4-cyano-5-morpholin-4-yl-thiophene-2-carboxylic acid methyl ester |

TABLE 2A

Formula II compounds:

| Cmpd number | Structure | Name | M + H |
|---|---|---|---|
| 2-1 | 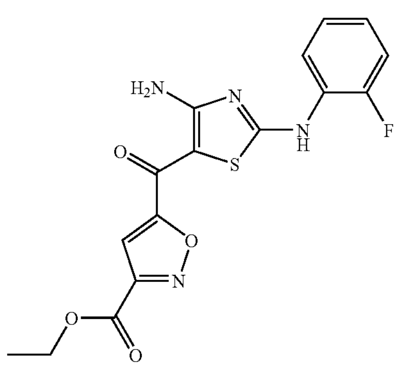 | 5-[4-Amino-2-(2-fluoro-phenylamino)-thiazole-5-carbonyl]-isoxazole-3-carboxylic acid ethyl ester | 377.1 |

TABLE 2A-continued

Formula II compounds:

| Cmpd number | Structure | Name | M + H |
|---|---|---|---|
| 2-2 | 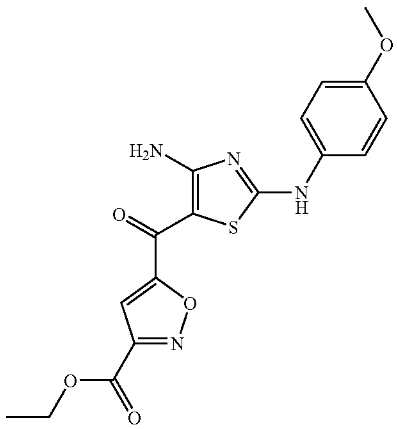 | 5-[4-Amino-2-(4-methoxy-phenylamino)-thiazole-5-carbonyl]-isoxazole-3-carboxylic acid ethyl ester | 389.1 |
| 2-3 | 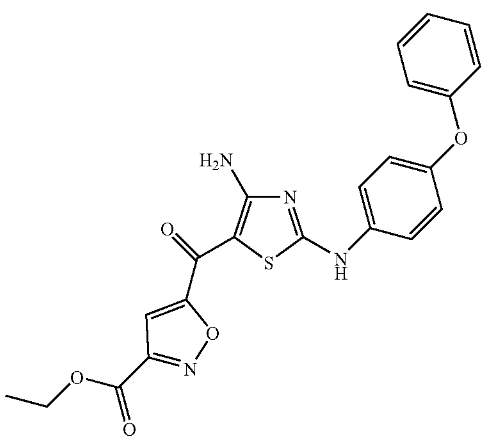 | 5-[4-Amino-2-(4-phenoxy-phenylamino)-thiazole-5-carbonyl]-isoxazole-3-carboxylic acid ethyl ester | 451.1 |
| 2-4 | 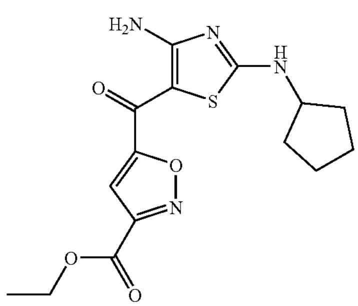 | 5-(4-Amino-2-cyclopentylamino-thiazole-5-carbonyl)-isoxazole-3-carboxylic acid ethyl ester | 351.1 |
| 2-5 | 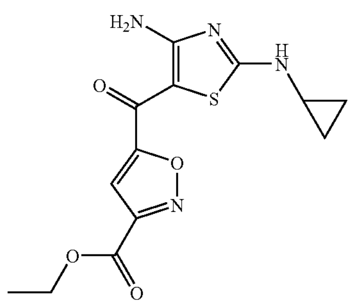 | 5-(4-Amino-2-cyclopropylamino-thiazole-5-carbonyl)-isoxazole-3-carboxylic acid ethyl ester | 323.1 |

TABLE 2A-continued

Formula II compounds:

| Cmpd number | Structure | Name | M + H |
|---|---|---|---|
| 2-6 | 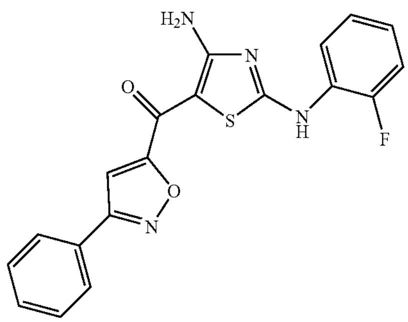 | [4-Amino-2-(2-fluoro-phenylamino)-thiazol-5-yl]-(3-phenyl-isoxazol-5-yl)-methanone | 389.1 |
| 2-7 | 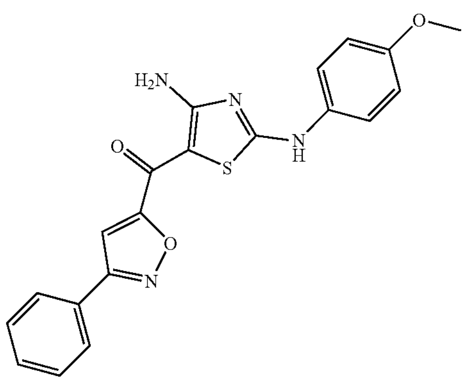 | [4-Amino-2-(4-methoxy-phenylamino)-thiazol-5-yl]-(3-phenyl-isoxazol-5-yl)-methanone | 393.1 |
| 2-8 | 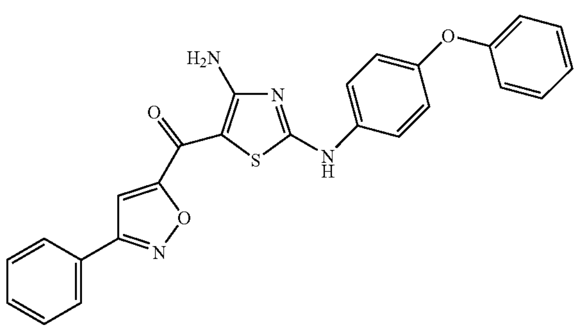 | [4-Amino-2-(4-phenoxy-phenylamino)-thiazol-5-yl]-(3-phenyl-isoxazol-5-yl)-methanone | 455.1 |
| 2-9 | 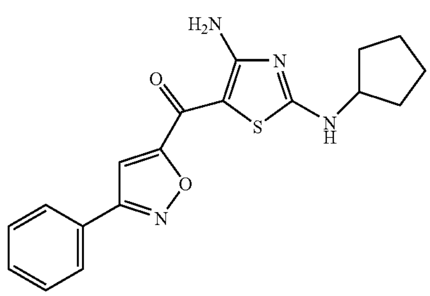 | (4-Amino-2-cyclopentylamino-thiazol-5-yl)-(3-phenyl-isoxazol-5-yl)-methanone | 355.1 |

TABLE 2A-continued

Formula II compounds:

| Cmpd number | Structure | Name | M + H |
|---|---|---|---|
| 2-10 | 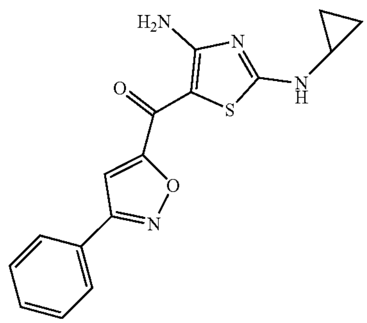 | (4-Amino-2-cyclopropylamino-thiazol-5-yl)-(3-phenyl-isoxazol-5-yl)-methanone | 327.1 |
| 2-11 | 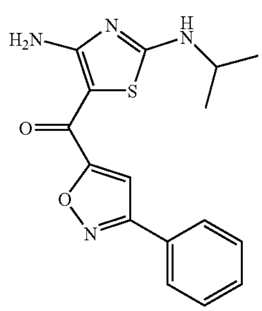 | (4-Amino-2-isopropylamino-thiazol-5-yl)-(3-phenyl-isoxazol-5-yl)-methanone | 329.02 |
| 2-12 | 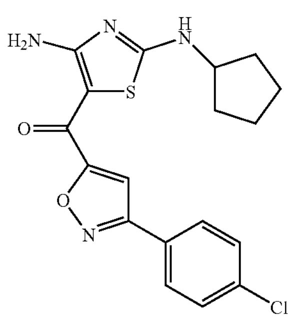 | (4-Amino-2-cyclopentylamino-thiazol-5-yl)-[3-(4-chloro-phenyl)-isoxazol-5-yl]-methanone | 390.39 |
| 2-13 | 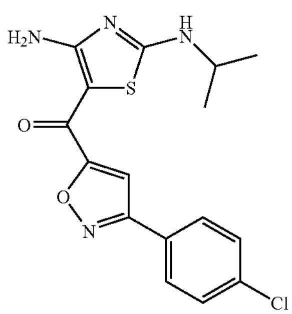 | (4-Amino-2-isopropylamino-thiazol-5-yl)-[3-(4-chloro-phenyl)-isoxazol-5-yl]-methanone | 363.18 |

TABLE 2A-continued

Formula II compounds:

| Cmpd number | Structure | Name | M + H |
|---|---|---|---|
| 2-14 | 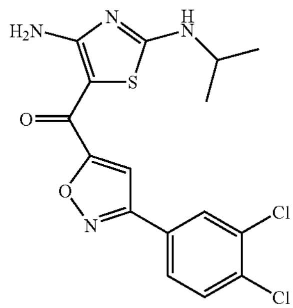 | (4-Amino-2-isopropylamino-thiazol-5-yl)-[3-(3,4-dichloro-phenyl)-isoxazol-5-yl]-methanone | 398.56 |
| 2-15 | 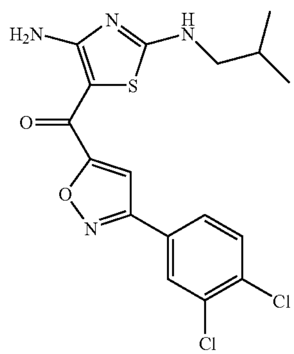 | (4-Amino-2-isobutylamino-thiazol-5-yl)-[3-(3,4-dichloro-phenyl)-isoxazol-5-yl]-methanone | 410.92 |
| 2-16 | 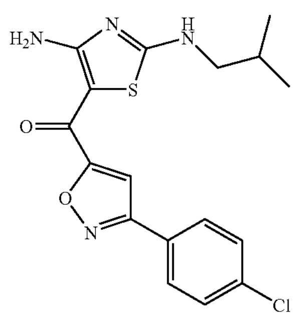 | (4-Amino-2-isobutylamino-thiazol-5-yl)-[3-(4-chloro-phenyl)-isoxazol-5-yl]-methanone | 377.01 |
| 2-17 | 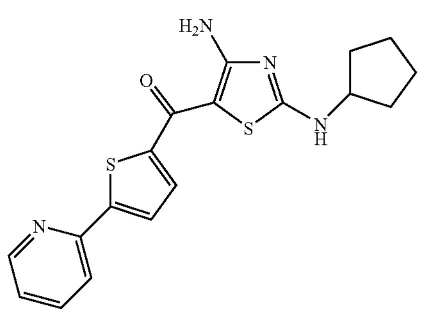 | (4-Amino-2-cyclopentylamino-thiazol-5-yl)-(5-pyridin-2-yl-thiophen-2-yl)-methanone | 371 |

TABLE 2A-continued

Formula II compounds:

| Cmpd number | Structure | Name | M + H |
|---|---|---|---|
| 2-18 | 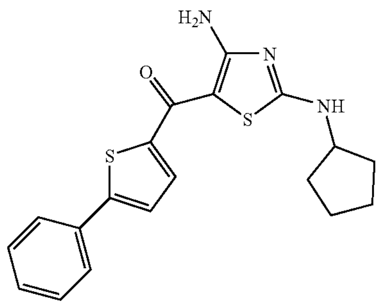 | (4-Amino-2-cyclopentylamino-thiazol-5-yl)-(5-phenyl-thiophen-2-yl)-methanone | 370.2 |
| 2-19 | 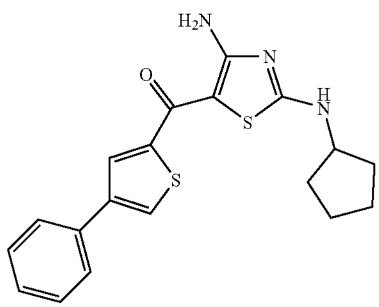 | (4-Amino-2-cyclopentylamino-thiazol-5-yl)-(4-phenyl-thiophen-2yl)-methanone | 371.7 |
| 2-20 | 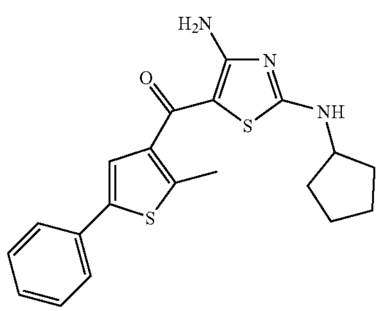 | (4-Amino-2-cyclopentylamino-thiazol-5-yl)-(2-methyl-5-phenyl-thiophen-3-yl)-methanone | |
| 2-21 | 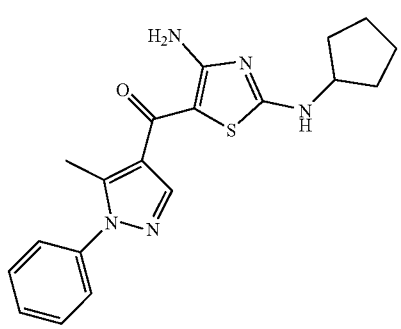 | (4-Amino-2-cyclopentylamino-thiazol-5-yl)-(5-methyl-1-phenyl-1H-pyrazol-4-yl)-methanone | 368.1 |

TABLE 2A-continued

Formula II compounds:

| Cmpd number | Structure | Name | M + H |
|---|---|---|---|
| 2-22 | 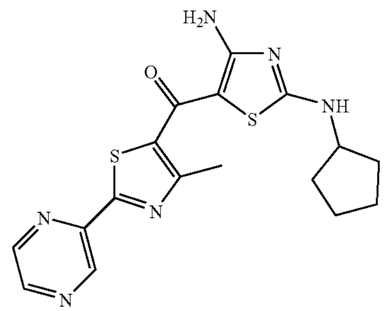 | (4-Amino-2-cyclopentylamino-thiazol-5-yl)-(4-methyl-2-pyrazin-2-yl-thiazol-5-yl)-methanone | 387 |
| 2-23 | 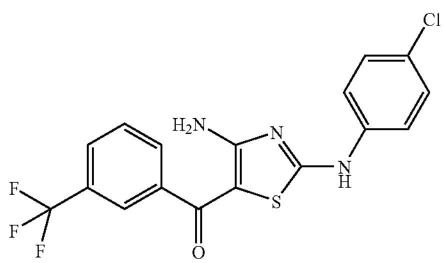 | [4-Amino-2-(4-chloro-phenylamino)-thiazol-5-yl]-(3-trifluoromethyl-phenyl)-methanone | 395.9 |
| 2-24 | 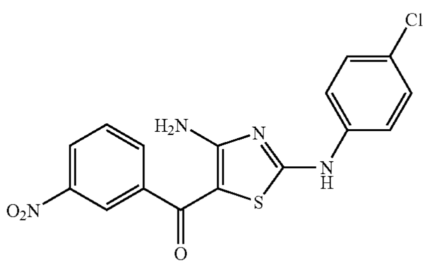 | [4-Amino-2-(4-chloro-phenylamino)-thiazol-5-yl]-(3-nitro-phenyl)-methanone | |
| 2-25 | 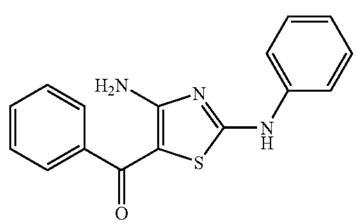 | (4-Amino-2-phenylamino-thiazol-5-yl)-phenyl-methanone | 296 |
| 2-26 | 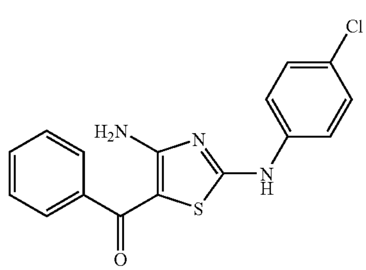 | [4-Amino-2-(4-chloro-phenylamino)-thiazol-5-yl]-phenyl-methanone | 328.1 |

TABLE 2A-continued

Formula II compounds:

| Cmpd number | Structure | Name | M + H |
|---|---|---|---|
| 2-27 | 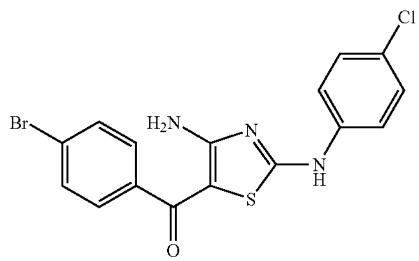 | [4-Amino-2-(4-chloro-phenylamino)-thiazol-5-yl]-(4-bromo-phenyl)-methanone | |
| 2-28 | 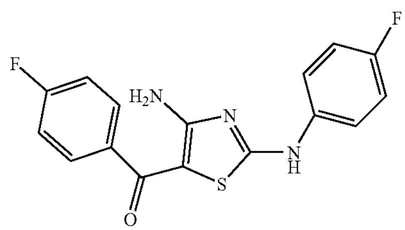 | [4-Amino-2-(4-fluoro-phenylamino)-thiazol-5-yl]-(4-fluoro-phenyl)-methanone | |
| 2-29 | 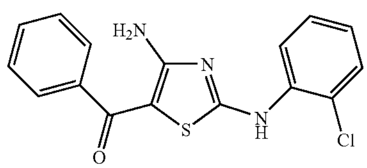 | [4-Amino-2-(2-chloro-phenylamino)-thiazol-5-yl]-phenyl-methanone | 328.1 |
| 2-30 | 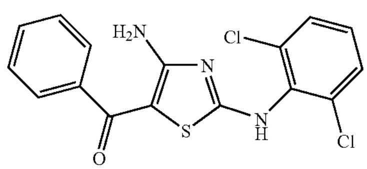 | [4-Amino-2-(2,6-dichloro-phenylamino)-thiazol-5-yl]-phenyl-methanone | 365.1 |
| 2-31 | 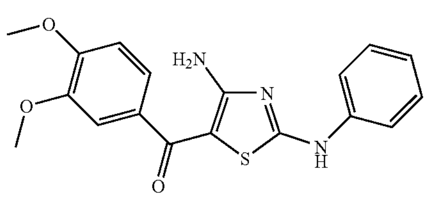 | (4-Amino-2-phenylamino-thiazol-5-yl)-(3,4-dimethoxy-phenyl)-methanone | 354.1 |
| 2-32 | 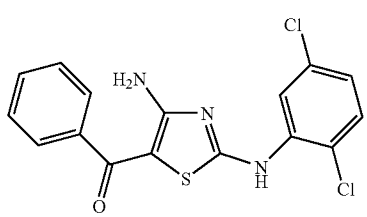 | [4-Amino-2-(2,5-dichloro-phenylamino)-thiazol-5-yl]-phenyl-methanone | 362.0 |

TABLE 2A-continued

Formula II compounds:

| Cmpd number | Structure | Name | M + H |
|---|---|---|---|
| 2-33 | 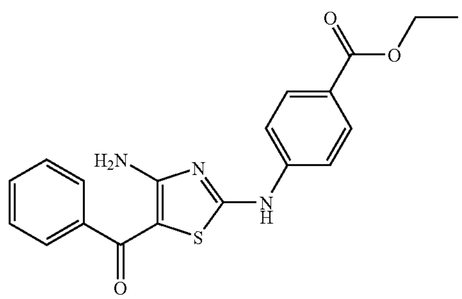 | 4-(4-Amino-5-benzoyl-thiazol-2-ylamino)-benzoic acid ethyl ester | 366.1 |
| 2-34 | 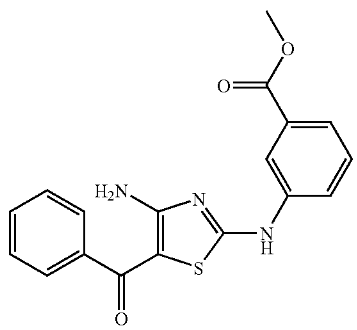 | 3-(4-Amino-5-benzoyl-thiazol-2-ylamino)-benzoic acid methyl ester | 352.0 |
| 2-35 | 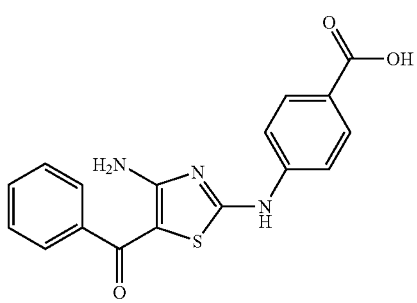 | 4-(4-Amino-5-benzoyl-thiazol-2-ylamino)-benzoic acid | 338.1 |
| 2-36 | 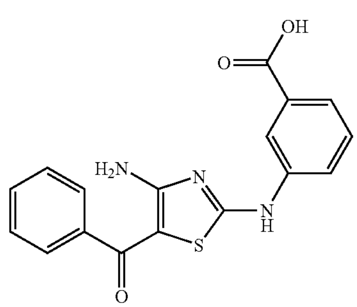 | 3-(4-Amino-5-benzoyl-thiazol-2-ylamino)-benzoic acid | 338.1 |
| 2-37 | 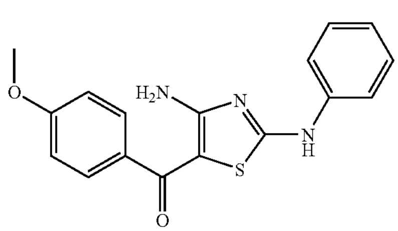 | (4-Amino-2-phenylamino-thiazol-5-yl)-(4-methoxy-phenyl)-methanone | 324.1 |

TABLE 2A-continued

Formula II compounds:

| Cmpd number | Structure | Name | M + H |
|---|---|---|---|
| 2-38 | 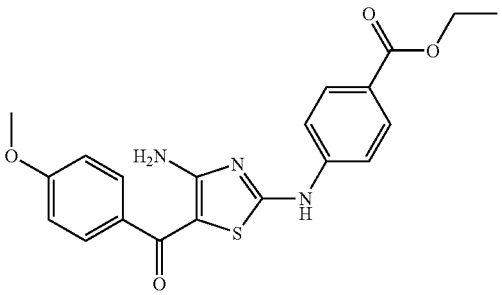 | 4-[4-Amino-5-(4-methoxy-benzoyl)-thiazol-2-ylamino]-benzoic acid ethyl ester | 396.0 |
| 2-39 | 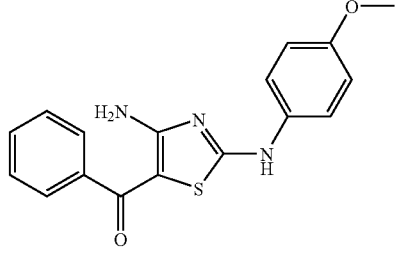 | [4-Amino-2-(4-methoxy-phenylamino)-thiazol-5-yl]-phenyl-methanone | |
| 2-40 | 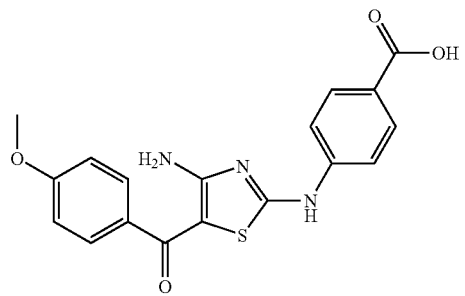 | 4-[4-Amino-5-(4-methoxy-benzoyl)-thiazol-2-ylamino]-benzoic acid | 368.0 |
| 2-41 | 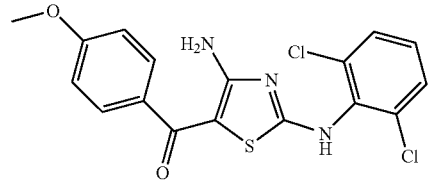 | [4-Amino-2-(2,6-dichloro-phenylamino)-thiazol-5-yl]-(4-methoxy-phenyl)-methanone | 393.9 |
| 2-42 | 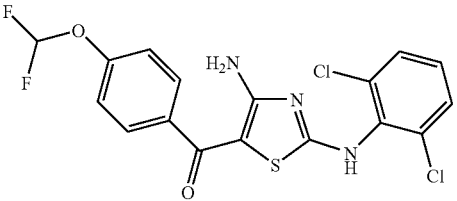 | [4-Amino-2-(2,6-dichloro-phenylamino)-thiazol-5-yl]-(4-difluoromethoxy-phenyl)-methanone | 429.9 |

TABLE 2A-continued

Formula II compounds:

| Cmpd number | Structure | Name | M + H |
|---|---|---|---|
| 2-43 | 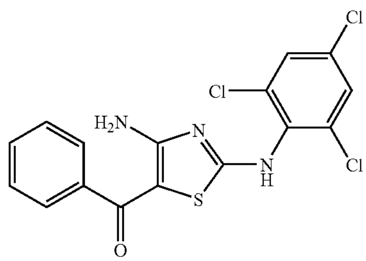 | [4-Amino-2-(2,4,6-trichloro-phenylamino)-thiazol-5-yl]-phenyl-methanone | 397.9 |
| 2-44 | 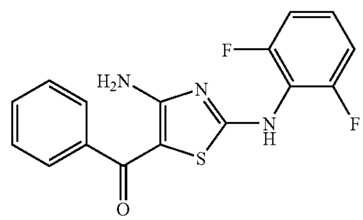 | [4-Amino-2-(2,6-difluoro-phenylamino)-thiazol-5-yl]-phenyl-methanone | 330.1 |
| 2-45 | 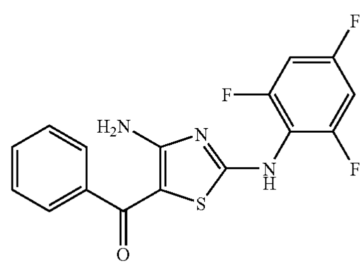 | [4-Amino-2-(2,4,6-trifluoro-phenylamino)-thiazol-5-yl]-phenyl-methanone | 348.0 |
| 2-46 | 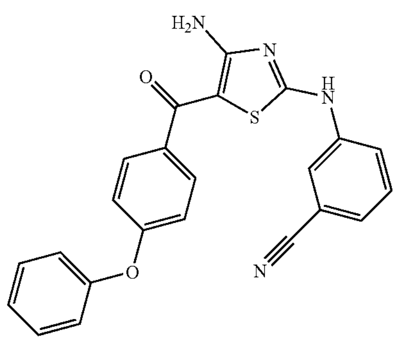 | 3-[4-Amino-5-(4-phenoxy-benzoyl)-thiazol-2-ylamino]-benzonitrile | 413.1 |
| 2-47 | 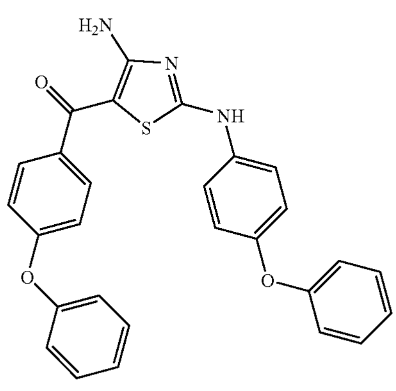 | [4-Amino-2-(4-phenoxy-phenylamino)-thiazol-5-yl]-(4-phenoxy-phenyl)-methanone | 479.9 |

TABLE 2A-continued

Formula II compounds:

| Cmpd number | Structure | Name | M + H |
|---|---|---|---|
| 2-48 | 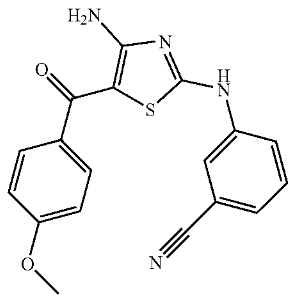 | 3-[4-Amino-5-(4-methoxy-benzoyl)-thiazol-2-ylamino]-benzonitrile | 351.1 |
| 2-49 | 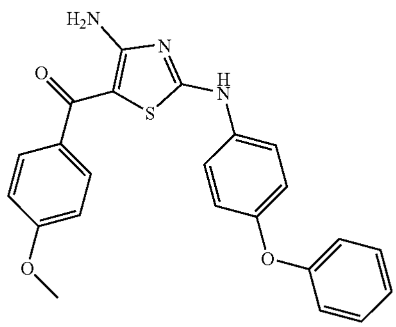 | [4-Amino-2-(4-phenoxy-phenylamino)-thiazol-5-yl]-(4-methoxy-phenyl)-methanone | 418.3 |
| 2-50 | 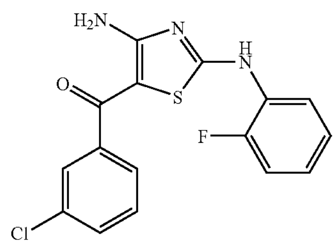 | [4-Amino-2-(2-fluoro-phenylamino)-thiazol-5-yl]-(3-chloro-phenyl)-methanone | 357.9 |
| 2-51 | 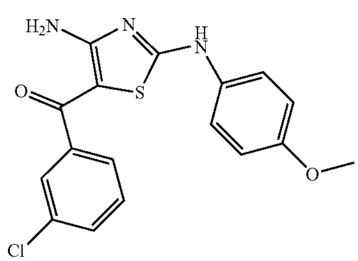 | [4-Amino-2-(4-methoxy-phenylamino)-thiazol-5-yl]-(3-chloro-phenyl)-methanone | 360.3 |
| 2-52 | 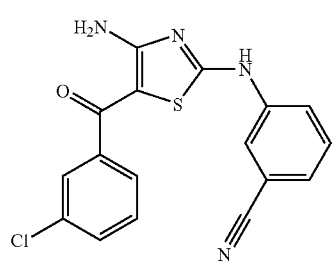 | 3-[4-Amino-5-(3-chloro-benzoyl)-thiazol-2-ylamino]-benzonitrile | 355.1 |

TABLE 2A-continued

Formula II compounds:

| Cmpd number | Structure | Name | M + H |
|---|---|---|---|
| 2-53 | 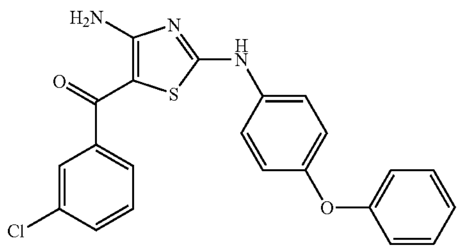 | [4-Amino-2-(4-phenoxy-phenylamino)-thiazol-5-yl]-(3-chloro-phenyl)-methanone | 421.9 |
| 2-54 | 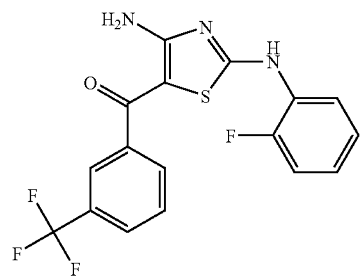 | [4-Amino-2-(2-fluoro-phenylamino)-thiazol-5-yl]-(3-trifluoromethyl-phenyl)-methanone | 381.9 |
| 2-55 | 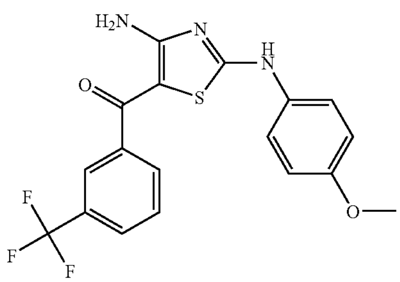 | [4-Amino-2-(4-methoxy-phenylamino)-thiazol-5-yl]-(3-trifluoromethyl-phenyl)-methanone | 393.9 |
| 2-56 | 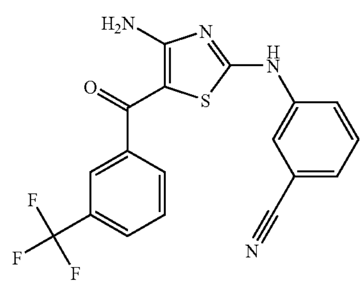 | 3-[4-Amino-5-(3-trifluoromethyl-benzoyl)-thiazol-2-ylamino]-benzonitrile | 389.1 |
| 2-57 | 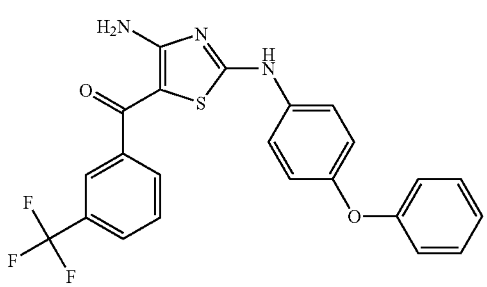 | [4-Amino-2-(4-phenoxy-phenylamino)-thiazol-5-yl]-(3-trifluoromethyl-phenyl)-methanone | 456.3 |

TABLE 2A-continued

Formula II compounds:

| Cmpd number | Structure | Name | M + H |
|---|---|---|---|
| 2-58 | 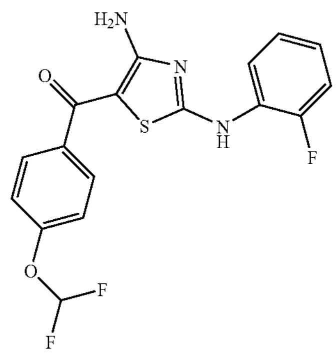 | [4-Amino-2-(2-fluoro-phenylamino)-thiazol-5-yl]-(4-difluoromethoxy-phenyl)-methanone | 379.9 |
| 2-59 | 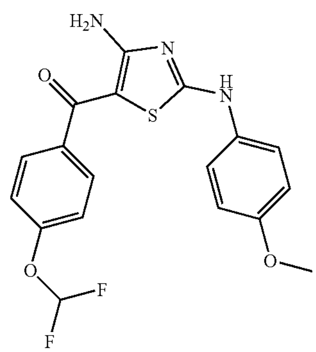 | [4-Amino-2-(4-methoxy-phenylamino)-thiazol-5-yl]-(4-difluoromethoxy-phenyl)-methanone | 391.9 |
| 2-60 | 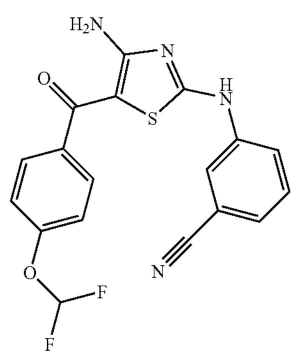 | 3-[4-Amino-5-(4-difluoromethoxy-benzoyl)-thiazol-2-ylamino]-benzonitrile | 387.1 |
| 2-61 | 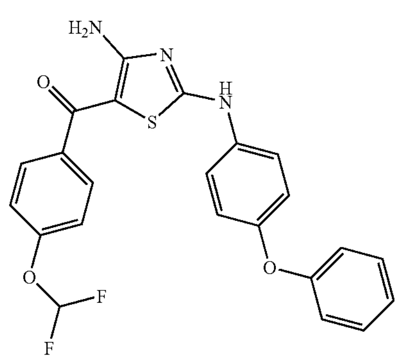 | [4-Amino-2-(4-phenoxy-phenylamino)-thiazol-5-yl]-(4-difluoromethoxy-phenyl)-methanone | 453.9 |

TABLE 2A-continued

Formula II compounds:

| Cmpd number | Structure | Name | M + H |
|---|---|---|---|
| 2-62 | 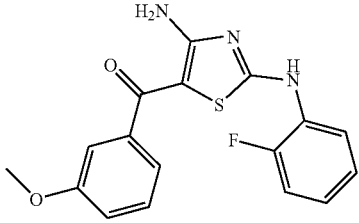 | [4-Amino-2-(2-fluoro-phenylamino)-thiazol-5-yl]-(3-methoxy-phenyl)-methanone | 343.9 |
| 2-63 | 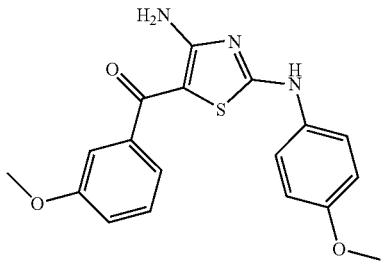 | [4-Amino-2-(4-methoxy-phenylamino)-thiazol-5-yl]-(3-methoxy-phenyl)-methanone | 356.3 |
| 2-64 | 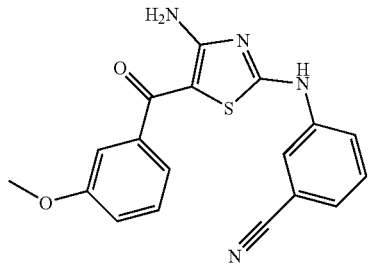 | 3-[4-Amino-5-(3-methoxy-benzoyl)-thiazol-2-ylamino]-benzonitrile | 351.5 |
| 2-65 | 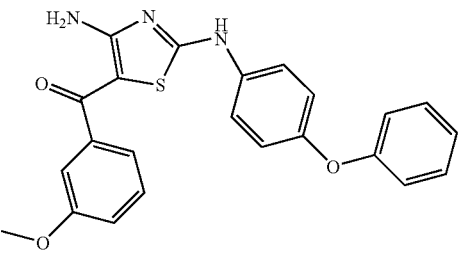 | [4-Amino-2-(4-phenoxy-phenylamino)-thiazol-5-yl]-(3-methoxy-phenyl)-methanone | 418.3 |
| 2-66 | 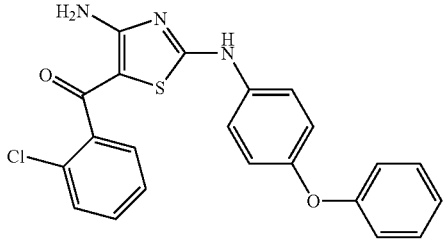 | [4-Amino-2-(4-phenoxy-phenylamino)-thiazol-5-yl]-(2-chloro-phenyl)-methanone | 421.9 |

TABLE 2A-continued

Formula II compounds:

| Cmpd number | Structure | Name | M + H |
|---|---|---|---|
| 2-67 | 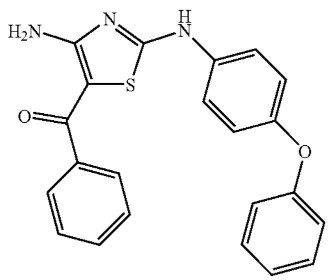 | [4-Amino-2-(4-phenoxy-phenylamino)-thiazol-5-yl]-phenyl-methanone | 388.3 |
| 2-68 | 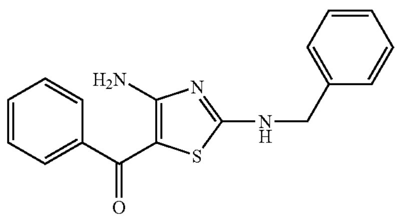 | (4-Amino-2-benzylamino-thiazol-5-yl)-phenyl-methanone | 308.1 |
| 2-69 | 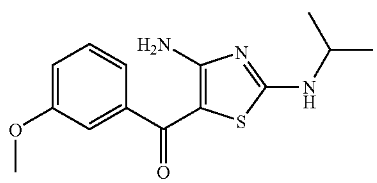 | (4-Amino-2-isopropylamino-thiazol-5-yl)-(3-methoxy-phenyl)-methanone | |
| 2-70 | 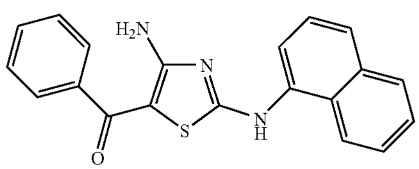 | [4-Amino-2-(naphthalen-1-ylamino)-thiazol-5-yl]-phenyl-methanone | 344.1 |
| 2-71 | 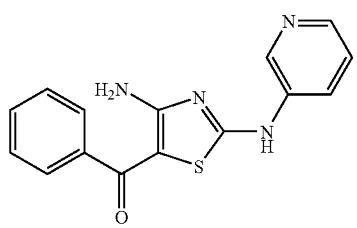 | [4-Amino-2-(pyridin-3-ylamino)-thiazol-5-yl]-phenyl-methanone | 295.1 |
| 2-72 | 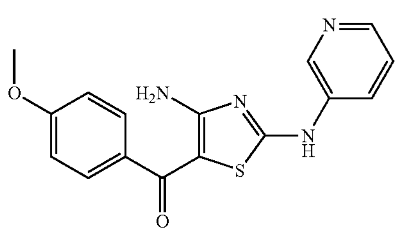 | [4-Amino-2-(pyridin-3-ylamino)-thiazol-5-yl]-(4-methoxy-phenyl)-methanone | 325.1 |

TABLE 2A-continued

Formula II compounds:

| Cmpd number | Structure | Name | M + H |
|---|---|---|---|
| 2-73 | 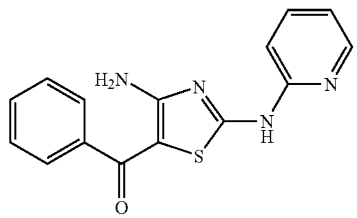 | [4-Amino-2-(pyridin-2-ylamino)-thiazol-5-yl]-phenyl-methanone | 297.2 |
| 2-74 | 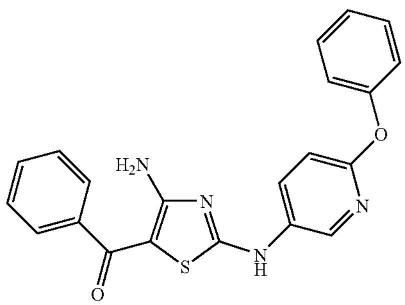 | [4-Amino-2-(6-phenoxy-pyridin-3-ylamino)-thiazol-5-yl]-phenyl-methanone | 387.1 |
| 2-75 | 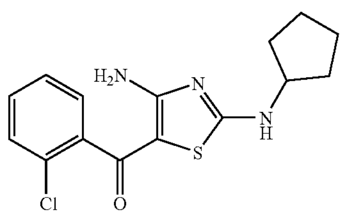 | (4-Amino-2-cyclopentylamino-thiazol-5-yl)-(2-chloro-phenyl)-methanone | 320.1 |
| 2-76 | 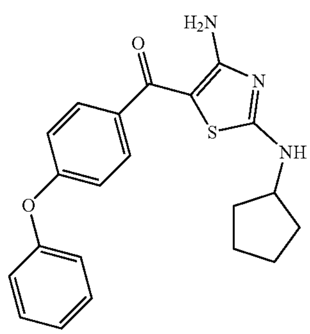 | (4-Amino-2-cyclopentylamino-thiazol-5-yl)-(4-phenoxy-phenyl)-methanone | 380.3 |
| 2-77 | 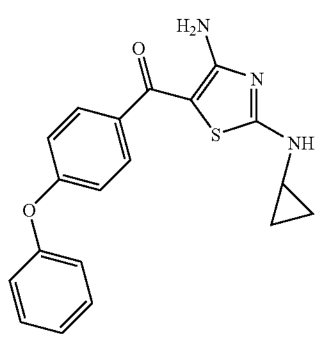 | (4-Amino-2-cyclopropylamino-thiazol-5-yl)-(4-phenoxy-phenyl)-methanone | 352.3 |

TABLE 2A-continued

Formula II compounds:

| Cmpd number | Structure | Name | M + H |
|---|---|---|---|
| 2-78 | 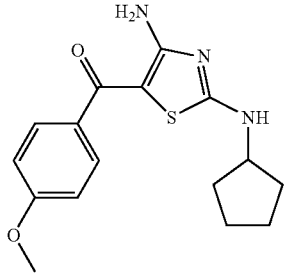 | (4-Amino-2-cyclopentylamino-thiazol-5-yl)-(4-methoxy-phenyl)-methanone | 318.3 |
| 2-79 | 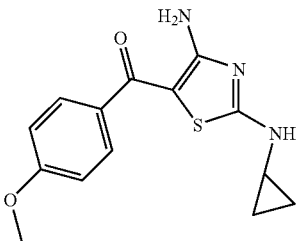 | (4-Amino-2-cyclopropylamino-thiazol-5-yl)-(4-methoxy-phenyl)-methanone | 290.3 |
| 2-80 | 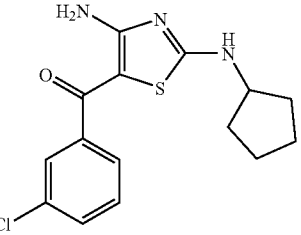 | (4-Amino-2-cyclopentylamino-thiazol-5-yl)-(3-chloro-phenyl)-methanone | 322.3 |
| 2-81 | 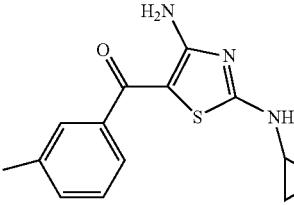 | (4-Amino-2-cyclopropylamino-thiazol-5-yl)-(3-chloro-phenyl)-methanone | 293.9 |
| 2-82 | 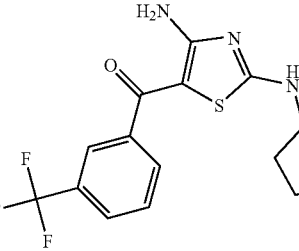 | (4-Amino-2-cyclopentylamino-thiazol-5-yl)-(3-trifluoromethyl-phenyl)-methanone | 356.3 |
| 2-83 | 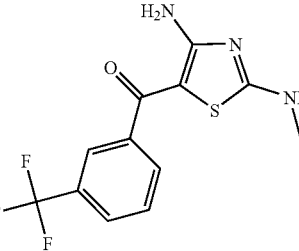 | (4-Amino-2-cyclopropylamino-thiazol-5-yl)-(3-trifluoromethyl-phenyl)-methanone | 328.3 |

TABLE 2A-continued

Formula II compounds:

| Cmpd number | Structure | Name | M + H |
|---|---|---|---|
| 2-84 | 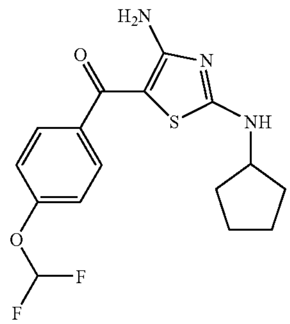 | (4-Amino-2-cyclopentylamino-thiazol-5-yl)-(4-difluoromethoxy-phenyl)-methanone | 354.3 |
| 2-85 | 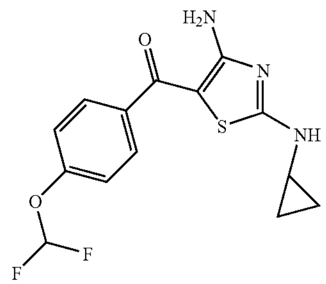 | (4-Amino-2-thiazol-5-yl)-(4-difluoromethoxy-phenyl)-methanone | 326.3 |
| 2-86 | 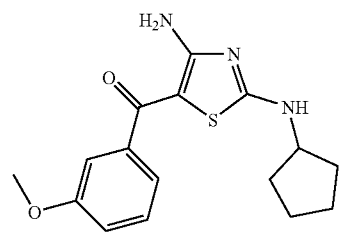 | (4-Amino-2-cyclopentylamino-thiazol-5-yl)-(3-methoxy-phenyl)-methanone | 317.9 |
| 2-87 | 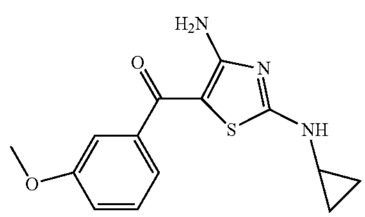 | (4-Amino-2-cyclopropylamino-thiazol-5-yl)-(3-methoxy-phenyl)-methanone | 290.3 |
| 2-88 | 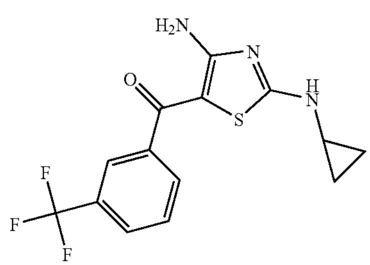 | (4-Amino-2-cyclopropylamino-thiazol-5-yl)-(3-trifluoromethyl-phenyl)-methanone | 328.3 |
| 2-89 | 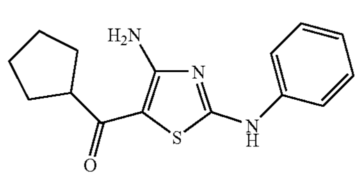 | (4-Amino-2-phenylamino-thiazol-5-yl)-cyclopentyl-methanone | 286.2 |

TABLE 2A-continued

Formula II compounds:

| Cmpd number | Structure | Name | M + H |
|---|---|---|---|
| 2-90 | 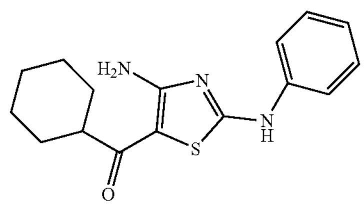 | (4-Amino-2-phenylamino-thiazol-5-yl)-cyclohexyl-methanone | 300.2 |
| 2-91 | 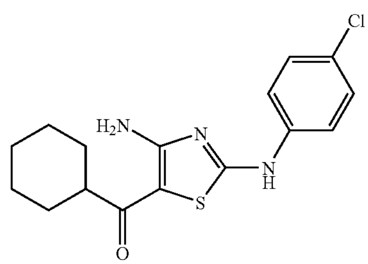 | [4-Amino-2-(4-chloro-phenylamino)-thiazol-5-yl]-cyclohexyl-methanone | 334.1 |
| 2-92 | 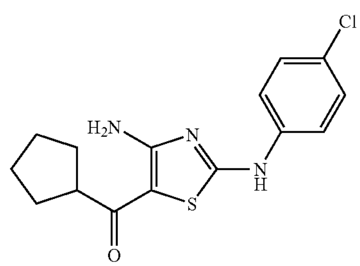 | [4-Amino-2-(4-chloro-phenylamino)-thiazol-5-yl]-cyclopentyl-methanone | 320.1 |
| 2-93 | 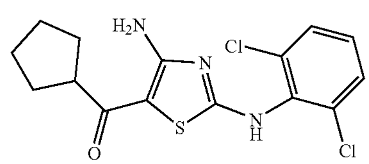 | [4-Amino-2-(2,6-dichloro-phenylamino)-thiazol-5-yl]-cyclopentyl-methanone | 354.0 |
| 2-94 | 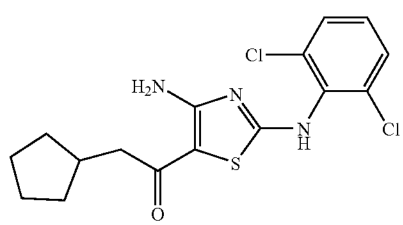 | 1-[4-Amino-2-(2,6-dichloro-phenylamino)-thiazol-5-yl]-2-cyclopentyl-ethanone | 368.1 |
| 2-95 | 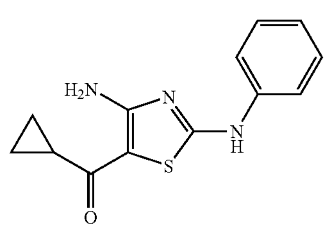 | (4-Amino-2-phenylamino-thiazol-5-yl)-cyclopropyl-methanone | 258.2 |

TABLE 2A-continued

Formula II compounds:

| Cmpd number | Structure | Name | M + H |
|---|---|---|---|
| 2-96 | 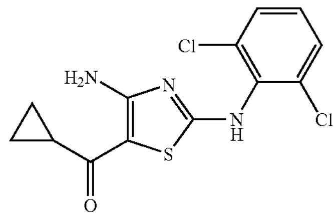 | [4-Amino-2-(2,6-dichloro-phenylamino)-thiazol-5-yl]-cyclopropyl-methanone | 328.0 |
| 2-97 | 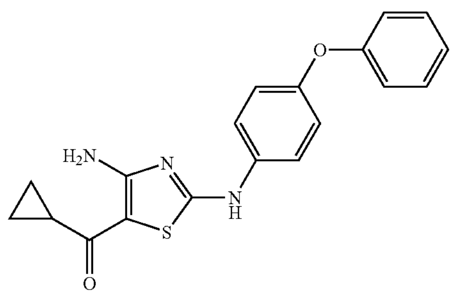 | [4-Amino-2-(4-phenoxy-phenylamino)-thiazol-5-yl]-cyclopropyl-methanone | 350.1 |
| 2-98 | 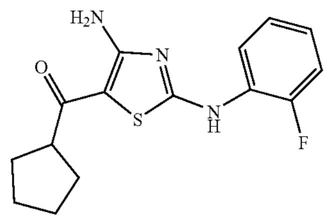 | [4-Amino-2-(2-fluoro-phenylamino)-thiazol-5-yl]-cyclopentyl-methanone | 306.3 |
| 2-99 | 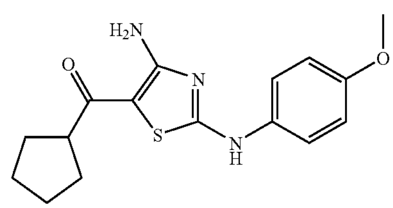 | [4-Amino-2-(4-methoxy-phenylamino)-thiazol-5-yl]-cyclopentyl-methanone | 317.9 |
| 2-100 | 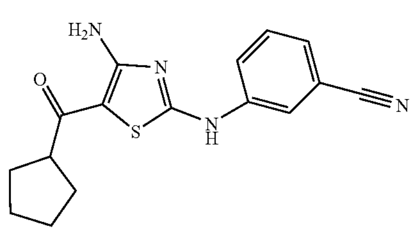 | 3-(4-Amino-5-cyclopentanecarbonyl-thiazol-2-ylamino)-benzonitrile | 313.1 |
| 2-101 | 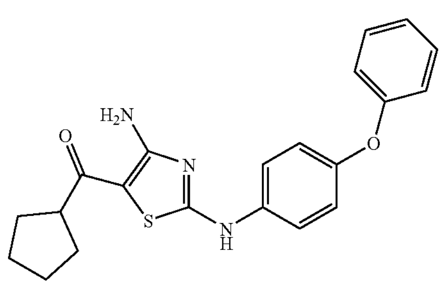 | [4-Amino-2-(4-phenoxy-phenylamino)-thiazol-5-yl]-cyclopentyl-methanone | 380.3 |

TABLE 2A-continued

Formula II compounds:

| Cmpd number | Structure | Name | M + H |
|---|---|---|---|
| 2-102 | (structure) | (4-Amino-2-cyclopentylamino-thiazol-5-yl)-thiophen-3-yl-methanone | 294.1 |
| 2-103 | (structure) | (4-Amino-2-cyclopentylamino-thiazol-5-yl)-benzothiazol-2-yl-methanone | 345 |

TABLE 2B

Formula II activity data r TNF is rat in vivo data, inhibition assay, + = >20%, − = <20%, blank = not assayed

| Compound | % inhibition r TNFα | IC 50 vs. indicated assay + = <10 μM/− = >10 μM/blank = not assayed | | | | |
|---|---|---|---|---|---|---|
| | | h TNFα | PDE4B | PDE4B2 | PDE4D | PDE4D5 |
| 2-1 | − | | + | | + | |
| 2-2 | | | + | | + | |
| 2-3 | | | − | | − | |
| 2-4 | | | + | | + | |
| 2-5 | | | + | | + | |
| 2-6 | + | − | + | + | + | + |
| 2-7 | | | + | | + | |
| 2-8 | | | | | − | |
| 2-9 | + | | + | + | + | + |
| 2-10 | | | + | | + | |
| 2-11 | | | + | | + | |
| 2-12 | | | + | | + | |
| 2-13 | | | + | | + | |
| 2-14 | | | + | | + | |
| 2-15 | | | + | | + | |
| 2-16 | | | + | | + | |
| 2-17 | | | + | | + | |
| 2-18 | | | + | | + | |
| 2-19 | | + | + | + | | + |
| 2-20 | | | + | | + | |
| 2-21 | | | + | | + | |
| 2-22 | | | + | | + | |

For inhibition assay, + = >20%, − = <20%, blank = not assayed
100 mg/kg po, 2 hr challenge delay unless indicated otherwise

| Compound number | % inhibition r TNFα | IC 50 vs. indicated assay + = <10 μM/− = >10 μM/blank = not assayed | | | | |
|---|---|---|---|---|---|---|
| | | h TNFα | h TNFα | h TNFα | h TNFα | h TNFα |
| 2-23 | − | − | + | + | + | + |
| 2-24 | | | + | | + | |
| 2-25 | | | + | | + | |
| 2-26 | | | + | | + | |
| 2-27 | | | + | | + | |
| 2-28 | | | + | | + | |
| 2-29 | | | + | | + | |
| 2-30 | | | + | + | + | + |
| 2-31 | | | + | | + | |
| 2-32 | | | + | | + | |
| 2-33 | + | | + | | − | |
| 2-34 | − | | + | | + | |
| 2-35 | | − | + | + | + | + |
| 2-36 | | | + | | + | |
| 2-37 | | | + | | + | |
| 2-38 | − 1 hr | | + | | + | |
| 2-39 | | | + | | + | |
| 2-40 | − 1 hr | | + | | + | |
| 2-41 | − | | + | | + | |
| 2-42 | | | + | | + | |
| 2-43 | | | + | | − | |
| 2-44 | | | + | | | |
| 2-45 | | | | | | |
| 2-46 | | | + | | + | |
| 2-47 | | | + | | − | |
| 2-48 | | | + | | + | |
| 2-49 | | | + | | + | |
| 2-50 | | | + | | + | |
| 2-51 | | | + | | + | |
| 2-52 | | | + | | + | |
| 2-53 | | | + | | + | |
| 2-54 | | | + | | + | |
| 2-55 | | | + | | + | |
| 2-56 | | | + | | + | |
| 2-57 | | | + | | − | |
| 2-58 | | | + | | + | |
| 2-59 | | | + | | + | |
| 2-60 | | | + | | − | |
| 2-61 | | | | | | |
| 2-62 | | | + | | + | |
| 2-63 | | | + | | + | |
| 2-64 | | | + | | − | |
| 2-65 | | | + | | + | |

TABLE 2B-continued

Formula II activity data

| | | | | | | |
|---|---|---|---|---|---|---|
| 2-66 | | | + | − | | |
| 2-67 | | | + | + | | + |
| 2-68 | | | + | + | | |
| 2-69 | | | + | − | | |
| 2-70 | | | + | + | | |
| 2-71 | | | + | + | | |
| 2-72 | | | + | + | | |
| 2-73 | | | + | − | | |
| 2-74 | | | − | + | | |
| 2-75 | | | − | − | | |
| 2-76 | | − | + | + | + | + |
| 2-77 | | | + | + | | |
| 2-78 | | | + | + | | |
| 2-79 | | | + | + | | |
| 2-80 | + | + | + | + | + | + |
| 2-81 | | | + | + | | |
| 2-82 | | | + | + | | |
| 2-83 | | | + | + | | |
| 2-84 | | | + | + | | |
| 2-85 | | | + | − | | |
| 2-86 | | | + | + | | |
| 2-87 | | | + | + | | |
| 2-88 | | | + | + | | |
| 2-89 | | | + | + | | |
| 2-90 | | | + | + | | |
| 2-91 | | | + | − | | |
| 2-92 | | | + | + | + | + |
| 2-93 | − 1 hr | | + | + | | |
| 2-94 | | | − | − | | |
| 2-95 | | | + | − | | |
| 2-96 | | | + | + | | |
| 2-97 | | | + | + | | |
| 2-98 | | | + | + | | |
| 2-99 | | | − | − | | |
| 2-100 | | | + | + | | |
| 2-101 | | | − | − | | |
| 2-102 | | | + | + | | |
| 2-103 | | | + | + | | |

TABLE 3A

Formula III compounds, names and activity data $IC_{50}$
+ = <10 μM
− = >10 μM
blank not assayed

| Comp number | Structure | PDE4B | PDE4D | M + H |
|---|---|---|---|---|
| 3-1 | 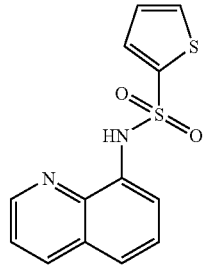<br>Thiophene-2-sulfonic acid quinolin-8-ylamide | − | − | 291 |
| 3-2 | 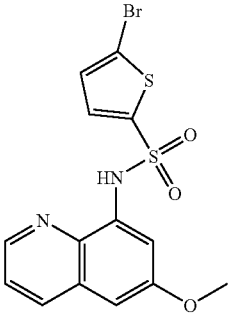<br>5-Bromo-thiophene-2-sulfonic acid (6-methoxy-quinolin-8-yl)-amide | − | − | 399 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-3 | 5-Chloro-thiophene-2-sulfonic acid (7-methyl-quinolin-8-yl)-amide | − | − | 339 |
| 3-4 | 5-Bromo-thiophene-2-sulfonic acid quinolin-8-ylamide | − | − | 369 |
| 3-5 | Thiophene-2-sulfonic acid (7-methyl-quinolin-8-yl)-amide | − | − | 305 |
| 3-6 | 5-Bromo-thiophene-2-sulfonic acid (7-methyl-quinolin-8-yl)-amide | − | − | 383 |

TABLE 3A-continued

Formula III compounds, names and activity data

IC$_{50}$
+ = <10 µM
− = >10 µM
blank not assayed

| Comp number | Structure | PDE4B | PDE4D | M + H |
|---|---|---|---|---|
| 3-7 | 5-Chloro-thiophene-2-sulfonic acid quinolin-8-ylamide | − | − | 325 |
| 3-8 | 4,5-Dichloro-thiophene-2-sulfonic acid (7-methyl-quinolin-8-yl)-amide | − | − | 373 |
| 3-9 | 4,5-Dichloro-thiophene-2-sulfonic acid (6-methoxy-quinolin-8-yl)-amide | − | − | 389 |
| 3-10 | 4,5-Dichloro-thiophene-2-sulfonic acid quinolin-8-ylamide | − | − | 359 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-11 | 2,5-Dichloro-thiophene-3-sulfonic acid (7-methyl-quinolin-8-yl)-amide | − | − | 371 [M − H] |
| 3-12 | 5-Chloro-thiophene-2-sulfonic acid (6-methoxy-quinolin-8-yl)-amide | − | − | 355 |
| 3-13 | Thiophene-2-sulfonic acid (6-methoxy-quinolin-8-yl)-amide | − | − | 321 |
| 3-14 | 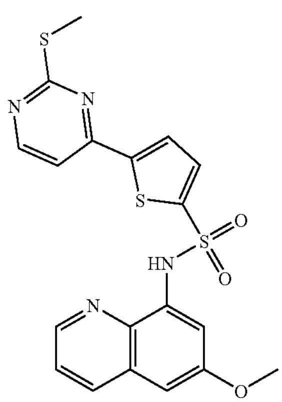 | + | + | 445 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| | 5-(2-Methylsulfanyl-pyrimidin-4-yl)-thiophene-2-sulfonic acid (6-methoxy-quinolin-8-yl)-amide | | | |
| 3-15 | 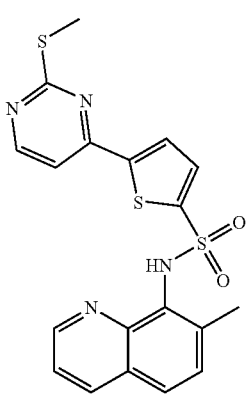<br>5-(2-Methylsulfanyl-pyrimidin-4-yl)-thiophene-2-sulfonic acid (7-methyl-quinolin-8-yl)-amide | − | − | 427 [M − H] |
| 3-16 | 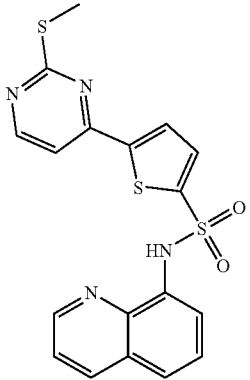<br>5-(2-Methylsulfanyl-pyrimidin-4-yl)-thiophene-2-sulfonic acid quinolin-8-ylamide | + | + | 415 |
| 3-17 | 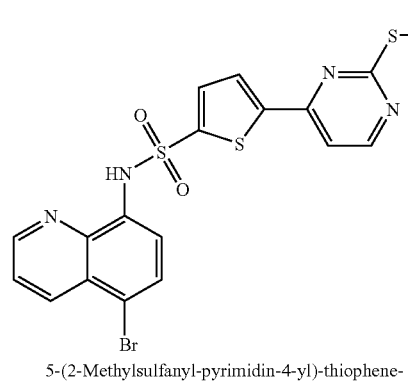<br>5-(2-Methylsulfanyl-pyrimidin-4-yl)-thiophene-2-sulfonic acid (5-bromo-quinolin-8-yl)-amide | + | | 493.1 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-18 | 5-(2-Methylsulfanyl-pyrimidin-4-yl)-thiophene-2-sulfonic acid (5-methoxy-quinolin-8-yl)-amide | + | | 445.1 |
| 3-19 | 5-(2-Methylsulfanyl-pyrimidin-5-yl)-thiophene-2-sulfonic acid methyl-quinolin-8-yl-amide | + | | N/A |
| 3-20 | 5-(1-Methyl-5-trifluoromethyl-1H-pyrazol-3-yl)-thiophene-2-sulfonic acid quinolin-8-ylamide | − | − | 439 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-21 | 5-(1-Methyl-5-trifluoromethyl-1H-pyrazol-3-yl)-thiophene-2-sulfonic acid (6-methoxy-quinolin-8-yl)-amide | − | − | 469 |
| 3-22 | 5-(1-Methyl-5-trifluoromethyl-1H-pyrazol-3-yl)-thiophene-2-sulfonic acid (7-methyl-quinolin-8-yl)-amide | − | − | 453 |
| 3-23 | 5-Isoxazol-3-yl-thiophene-2-sulfonic acid quinolin-8-ylamide | − | − | 358 |

TABLE 3A-continued
Formula III compounds, names and activity data
IC$_{50}$
+ = <10 μM
− = >10 μM
blank not assayed
| Comp number | Structure | PDE4B | PDE4D | M + H |
|---|---|---|---|---|
| 3-24 | 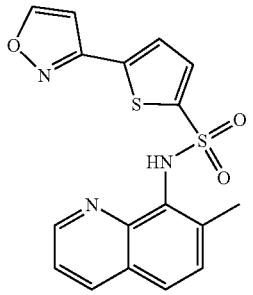 5-Isoxazol-3-yl-thiophene-2-sulfonic acid (7-methyl-quinolin-8-yl)-amide | − | − | 372 |
| 3-25 | 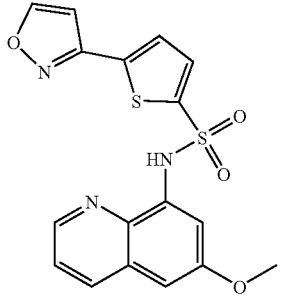 5-Isoxazol-3-yl-thiophene-2-sulfonic acid (6-methoxy-quinolin-8-yl)-amide | − | − | 388 |
| 3-26 | 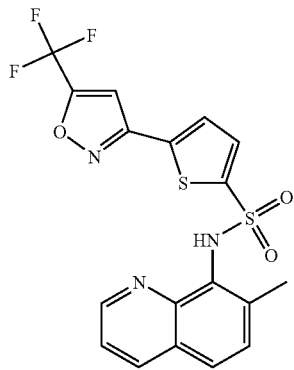 5-(5-Trifluoromethyl-isoxazol-3-yl)-thiophene-2-sulfonic acid (7-methyl-quinolin-8-yl)-amide | − | − | 440 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-27 | 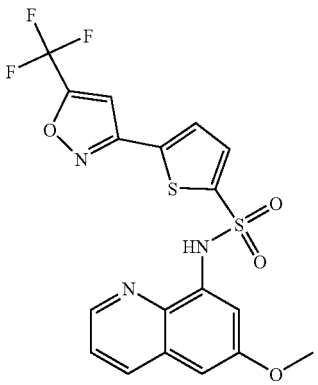 5-(5-Trifluoromethyl-isoxazol-3-yl)-thiophene-2-sulfonic acid (6-methoxy-quinolin-8-yl)-amide | − | − | 454 |
| 3-28 | 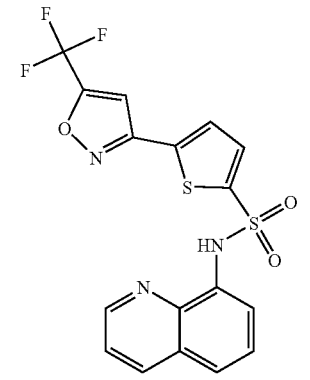 5-(5-Trifluoromethyl-isoxazol-3-yl)-thiophene-2-sulfonic acid quinolin-8-ylamide | − | − | 424 [M − H] |
| 3-29 | 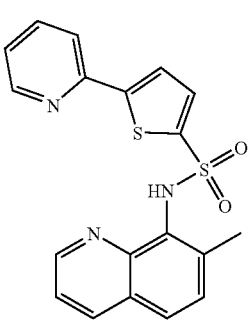 5-Pyridin-2-yl-thiophene-2-sulfonic acid (7-methyl-quinolin-8-yl)-amide | − | − | 382 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-30 | 5-Pyridin-2-yl-thiophene-2-sulfonic acid quinolin-8-ylamide | − | − | 366 [M − H] |
| 3-31 | 5-Pyridin-2-yl-thiophene-2-sulfonic acid (6-methoxy-quinolin-8-yl)-amide | + | − | 398 |
| 3-32 | N-[5-(Quinolin-8-ylsulfamoyl)-thiophen-2-ylmethyl]-benzamide | − | − | 424 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-33 | 5-(2-Methyl-thiazol-4-yl)-thiophene-2-sulfonic acid quinolin-8-ylamide | + | + | 388 |
| 3-34 | 5-Oxazol-5-yl-thiophene-2-sulfonic acid quinolin-8-ylamide | + | + | 357.9 |
| 3-35 | 5-Oxazol-5-yl-thiophene-2-sulfonic acid (5-bromo-quinolin-8-yl)-amide | + | | 438.3 |
| 3-36 | 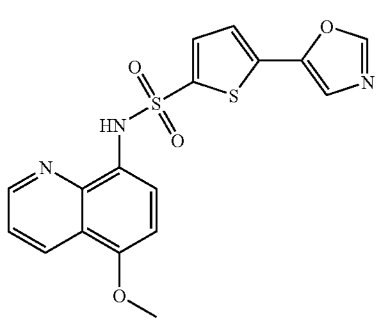 | + | | 388.3 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|

5-Oxazol-5-yl-thiophene-2-sulfonic acid (5-methoxy-quinolin-8-yl)-amide 3-37

4-Benzenesulfonyl-thiophene-2-sulfonic acid quinolin-8-ylamide

− − 431

3-38

5-Benzenesulfonyl-thiophene-2-sulfonic acid (7-methyl-quinolin-8-yl)-amide

− − 443 [M − H]

3-39

4-Benzenesulfonyl-thiophene-2-sulfonic acid (7-methyl-quinolin-8-yl)-amide

− − 443 [M − H]

3-40

− − 431

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-41 | 5-Benzenesulfonyl-thiophene-2-sulfonic acid quinolin-8-ylamide | + | − | 461 |
| 3-42 | 5-Benzenesulfonyl-thiophene-2-sulfonic acid (6-methoxy-quinolin-8-yl)-amide | − | − | 595.6 |
| 3-43 | 5-(7-Methyl-quinolin-8-ylsulfamoyl)-furan-2-carboxylic acid methyl ester | − | − | 345 [M − H] |
| 3-44 | | − | − | 333 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-45 | 5-(Quinolin-8-ylsulfamoyl)-furan-2-carboxylic acid methyl ester | − | − | 363 |
| | 5-(6-Methoxy-quinolin-8-ylsulfamoyl)-furan-2-carboxylic acid methyl ester | | | |
| 3-46 | 4-Methyl-N-quinolin-8-yl-benzenesulfonamide | − | − | N/A |
| 3-47 | N-(5-Bromo-quinolin-8-yl)-4-methyl-benzenesulfonamide | − | − | N/A |
| 3-48 | N-(6-Methoxy-quinolin-8-yl)-4-methyl-benzenesulfonamide | − | − | N/A |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-49 | 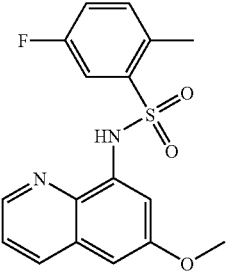<br>5-Fluoro-N-(6-methoxy-quinolin-8-yl)-2-methyl-benzenesulfonamide | − | − | 347 |
| 3-50 | 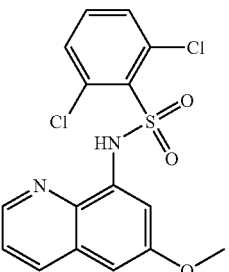<br>2,6-Dichloro-N-(6-methoxy-quinolin-8-yl)-benzenesulfonamide | | − | 383 |
| 3-51 | 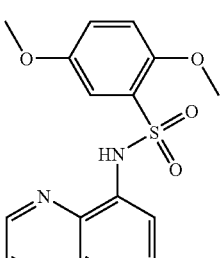<br>2,5-Dimethoxy-N-(6-methoxy-quinolin-8-yl)-benzenesulfonamide | − | − | 375 |
| 3-52 | 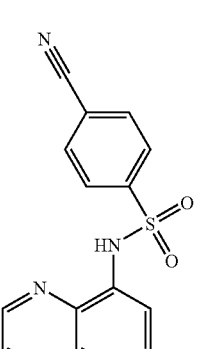<br>4-Cyano-N-(6-methoxy-quinolin-8-yl)-benzenesulfonamide | − | − | 340 |

TABLE 3A-continued
Formula III compounds, names and activity data
IC$_{50}$
+ = <10 μM
− = >10 μM
blank not assayed
| Comp number | Structure | PDE4B | PDE4D | M + H |
|---|---|---|---|---|
| 3-53 | 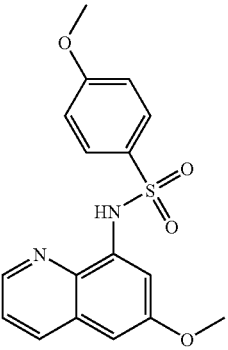 4-Methoxy-N-(6-methoxy-quinolin-8-yl)-benzenesulfonamide | − | − | 345 |
| 3-54 | 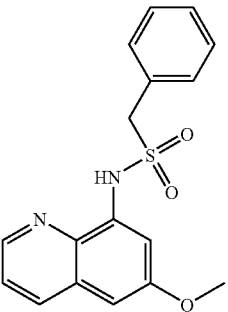 N-(6-Methoxy-quinolin-8-yl)-C-phenyl-methanesulfonamide | − | − | 329 |
| 3-55 | 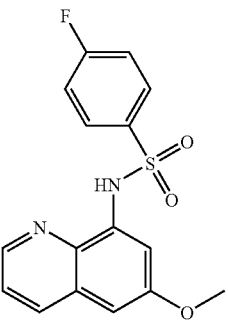 4-Fluoro-N-(6-methoxy-quinolin-8-yl)-benzenesulfonamide | − | − | 333 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-56 | 3-Fluoro-N-(6-methoxy-quinolin-8-yl)-benzenesulfonamide | − | − | 333 |
| 3-57 | N-(6-Methoxy-quinolin-8-yl)-2-methyl-benzenesulfonamide | − | − | 329 |
| 3-58 | 2-Methoxy-N-(6-methoxy-quinolin-8-yl)-5-methyl-benzenesulfonamide | − | − | 359 |
| 3-59 | 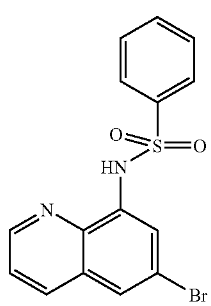 | − | | 363.1<br>365.1 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| | N-(6-Bromo-quinolin-8-yl)-benzenesulfonamide | | | |
| 3-60 | 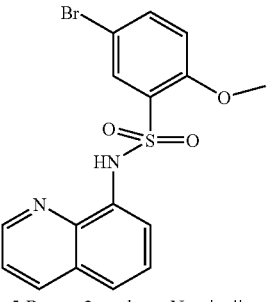<br>5-Bromo-2-methoxy-N-quinolin-8-yl-benzenesulfonamide | − | | 393.1<br>395.1 |
| 3-61 | 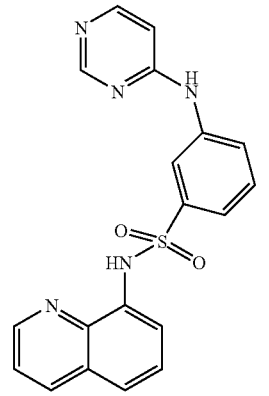<br>3-(Pyrimidin-4-ylamino)-N-quinolin-8-yl-benzenesulfonamide | + | | 378 |
| 3-62 | 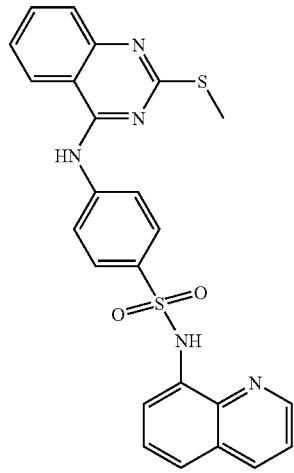<br>4-(2-Methylsulfanyl-quinazolin-4-yl amino)-N-quinolin-8-yl-benzenesulfonamide | + | | 474.2 |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-63 | 3-(2-Methylsulfanyl-quinazolin-4-yl amino)-N-quinolin-8-yl-benzenesulfonamide | + | | 474.2 |
| 3-64 | 4-(Pyridine-4-carbonyl)-N-quinolin-8-yl-benzenesulfonamide | + | | 389.95 |
| 3-65 | 4-Morpholin-4-yl-N-quinolin-8-yl-benzenesulfonamide | + | | N/A |

TABLE 3A-continued

Formula III compounds, names and activity data

IC$_{50}$
+ = <10 μM
− = >10 μM
blank not assayed

| Comp number | Structure | PDE4B | PDE4D | M + H |
|---|---|---|---|---|
| 3-66 | 3-(2-Methyl-pyrimidin-4-yl)-N-quinolin-8-yl-benzenesulfonamide | + | + | 377.1 |
| 3-67 | N-(5-Bromo-quinolin-8-yl)-3-(2-methyl-pyrimidin-4-yl)-benzenesulfonamide | − | | 457.1 |
| 3-68 | N-(5-Methoxy-quinolin-8-yl)-3-(2-methyl-pyrimidin-4-yl)-benzenesulfonamide | + | | 407.1 |

TABLE 3A-continued
Formula III compounds, names and activity data
IC$_{50}$
+ = <10 μM
− = >10 μM
blank not assayed
| Comp number | Structure | PDE4B | PDE4D | M + H |
|---|---|---|---|---|
| 3-69 | 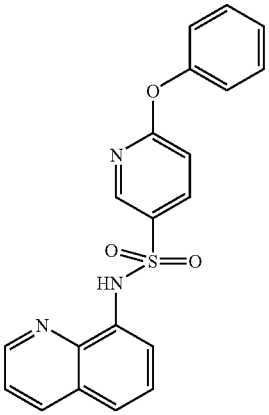 6-Phenoxy-pyridine-3-sulfonic acid quinolin-8-ylamide | | − | 377.96 |
TABLE 3B
Additional Sulfonamide compounds of Formula III
| Cmpd # PLX # | | MW |
|---|---|---|
| 49 | 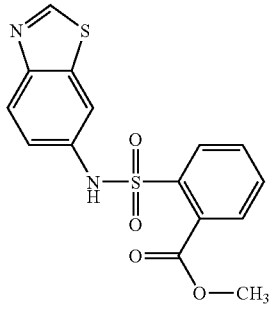 | 348.402 |
| 51 | 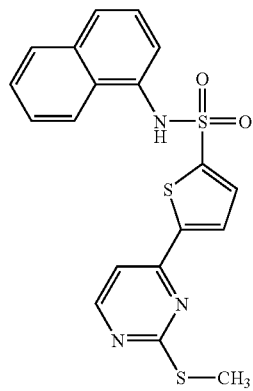 | 413.545 |

TABLE 3B-continued

Additional Sulfonamide compounds of Formula III

| Cmpd # PLX # | | MW |
|---|---|---|
| 52 | | 442.480 |
| 53 | | 523.535 |
| 54 | | 383.447 |
| 55 | | 411.429 |
| 56 | | 499.479 |

TABLE 3B-continued
Additional Sulfonamide compounds of Formula III
| Cmpd # PLX # | | MW |
|---|---|---|
| 57 | 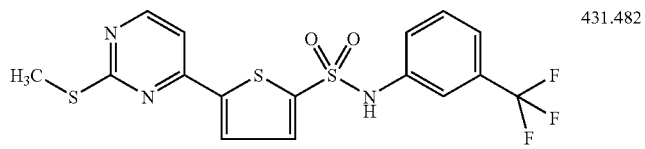 | 431.482 |
| 58 | 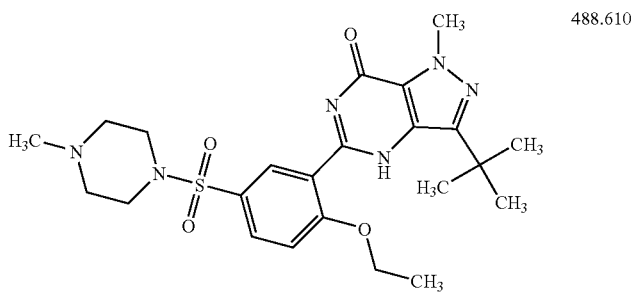 | 488.610 |
| 59 | 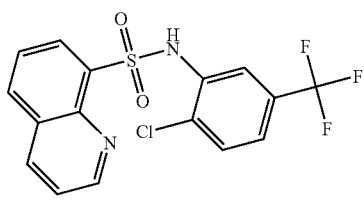 | 386.780 |
| 60 | 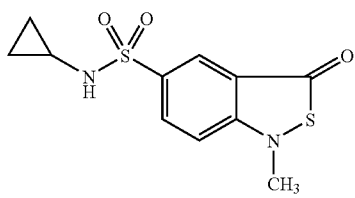 | 284.359 |
| 61 | 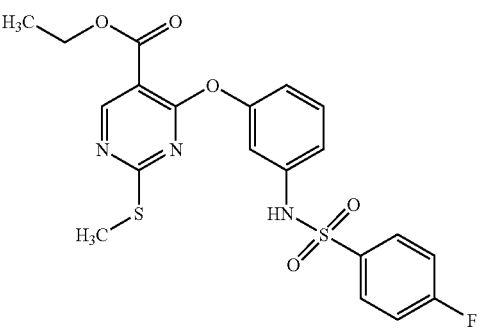 | 463.508 |

TABLE 3B-continued

Additional Sulfonamide compounds of Formula III

| Cmpd #<br>PLX # | Structure | MW |
|---|---|---|
| 64 | | 411.917 |
| 65 | | 296.345 |
| 66 | | 507.637 |
| 67 | | 402.476 |
| 69 | | 413.545 |

TABLE 3B-continued

Additional Sulfonamide compounds of Formula III

| Cmpd #<br>PLX # | | MW |
|---|---|---|
| 70 | | 366.483 |
| 71 | | 414.533 |

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for PDE4B proteins and/or various phosphodiesterase domain sequences can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure

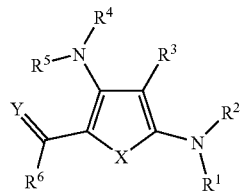

Formula I or a salt thereof,
wherein:

X is selected from the group consisting of O and S;

$R^3$ is selected from the group consisting of cyano, nitro, —C(Z)$R^8$, —S($O_2$)NR$^9$R$^{10}$, —S($O_2$)$R^{11}$, and optionally substituted lower alkyl;

$R^1$, $R^2$, $R^4$, $R^5$, $R^7$, $R^9$ and $R^{10}$ are independently selected from the group consisting of hydrogen, acyl, optionally substituted lower alkyl, optionally substituted lower alkenyl, optionally substituted lower alkynyl, optionally substituted cycloalkyl, optionally substituted heterocycle, optionally substituted heterocycloalkyl, optionally substituted aryl, optionally substituted aralkyl, optionally substituted heteroaryl, and optionally substituted heteroaralkyl, provided, however, that $R^1$ and $R^2$, or $R^4$ and $R^5$, or $R^9$ and $R^{10}$, or $R^2$ and $R^3$ can combine to form an optionally substituted heterocycle;

Y and Z are independently selected from the group consisting of O and S;

$R^8$ is selected from the group consisting of, hydroxy, alkoxy, thioalkoxy, optionally substituted amine, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, optionally substituted heteroaralkyl, and optionally substituted heterocycle; and $R^{11}$ is selected from the group consisting of hydroxy, alkoxy, thioalkoxy, optionally substituted lower alkyl, optionally substituted lower alkenyl, optionally substituted lower alkynyl, optionally substituted cycloalkyl, optionally substituted heterocycloalkyl, optionally substituted aryl, optionally substituted aralkyl, optionally substituted heteroaryl, and optionally substituted heteroaralkyl;

$R^6$ is

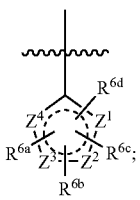

$Z^1$, $Z^2$, $Z^3$, and $Z^4$ are independently selected from the group consisting of —O—, —S—, —$CR^{6a}$—, —$CR^{6b}$—, —$CR^{6c}$—, and —$NR^{6d}$—, wherein:
at least one of $Z^1$, $Z^2$, $Z^3$, and $Z^4$ is a heteroatom; and
$Z^1$, $Z^2$, $Z^3$, and $Z^4$ are selected to produce a stable compound;

$R^{6a}$, $R^{6b}$, and $R^{6c}$ are independently selected from the group consisting of hydrogen, halo hydroxy, alkoxy, alkylthio, alkylsulfinyl, alkylsulfonyl, acyloxy, optionally substituted aryl, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl, optionally substituted alkenyl, and optionally substituted alkynyl, attached at any available point to produce a stable compound; or $R^{6a}$, $R^{6b}$, and $R^{6c}$ can, in combination with the five-membered ring comprising $Z^1$, $Z^2$, $Z^3$, and $Z^4$, combine to form an optionally substituted fused heterocyclic ring system; and $R^{6d}$ is optionally present, and when present is selected from the group consisting of hydrogen, optionally substituted lower alkyl, optionally substituted aryl, optionally substituted heterocycle, optionally substituted heteroaryl, acyl, sulfonyl, amido, thioamido, and sulfonamido;

provided, however, that
when $R^6$ is thiophen-2-yl, then $R^1$ and $R^2$ are not selected from the group consisting of phenyl, lower alkyl, and lower alkenyl;
when $R^6$ is furan-2-yl, then $R^1$ and $R^2$ are not selected from the group consisting of optionally substituted phenyl and optionally substituted phenylalkyl; and
when $R^1$ or $R^2$ is furan-2-yl-methylene or furan-2-yl-ethylene, then $R^6$ is not optionally substituted phenyl.

2. The compound of claim 1 wherein:
X is S, and
Y is O.

3. The compound of claim 2 wherein:
$R^1$ is selected from the group consisting of optionally substituted lower alkyl, optionally substituted lower alkenyl, optionally substituted lower alkynyl, acyl, optionally substituted cycloalkyl, optionally substituted heterocycle, optionally substituted heterocycloalkyl, optionally substituted aryl, optionally substituted aralkyl, optionally substituted heteroaryl, and optionally substituted heteroaralkyl; and
$R^2$, $R^4$ and $R^5$ are hydrogen.

4. The compound of claim 1 wherein: $R^6$ is selected from the group consisting of

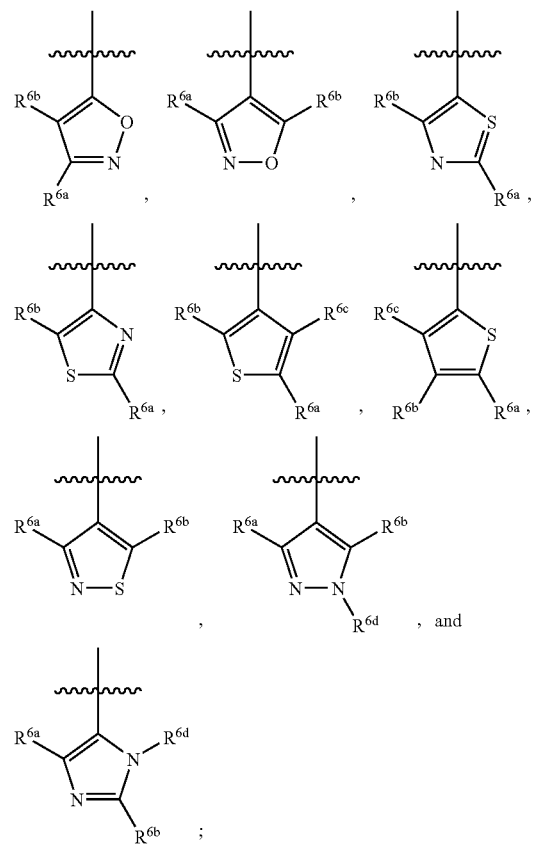

$R^{6a}$, $R^{6b}$, and $R^{6c}$ are independently selected from the group consisting of hydrogen, halo, hydroxy, alkoxy, alkylthio, alkylsulfinyl, alkylsulfonyl, acyloxy, optionally substituted aryl, amino, amido, amidino urea optionally substituted with alkyl, aryl, heteroaryl or heterocyclyl groups, aminosulfonyl optionally N-mono- or N,N-di-substituted with alkyl aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano, thiol, sulfonamido, optionally substituted alkyl optionally substituted alkenyl, and optionally substituted alkynyl, attached at any available point to produce a stable compound; and $R^{6d}$ is selected from the group consisting of hydrogen, optionally substituted lower alkyl, optionally substituted aryl, optionally substituted heterocycle, optionally substituted heteroaryl, acyl, sulfonyl, amido, thioamido and sulfonamido;

provided, however, that
when $R^6$ is thiophenc-2-yl, then $R^{6a}$ is not hydrogen or halo.

5. The compound of claim 4 wherein:

$R^6$ is selected from the group consisting of

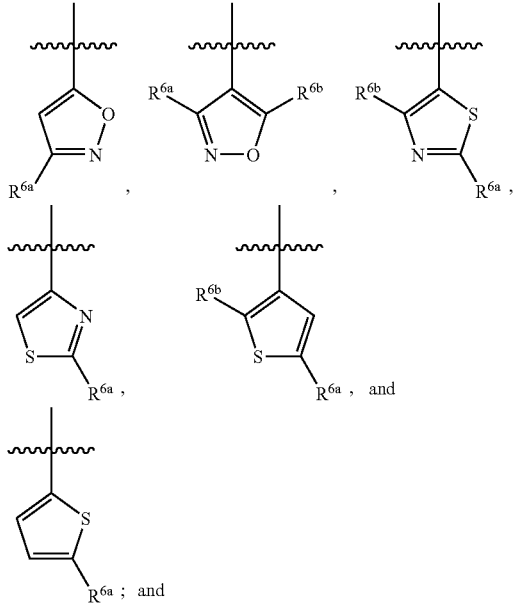

$R^{6a}$ and $R^{6b}$ are independently selected from the group consisting of hydrogen, halo, hydroxy, alkoxy, alkylthio, alkylsulfinyl, alkylsulfonyl, acyloxy, optionally substituted aryl, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl, nitro, cyano thiol, sulfonamido, optionally substituted alkyl, optionally substituted alkenyl, and optionally substituted alkynyl, attached at any available point to produce stable compound, provided, however, that when $R^6$ is thiophene-2-yl, then $R^{6a}$ is not hydrogen or halo.

6. The compound of claim 1 wherein at least one of $R^1$ and $R^2$ is selected from the group consisting of optionally substituted cycloalkyl, optionally substituted heterocycle, and optionally substituted heterocycloalkyl.

7. The compound of claim 1 having structure

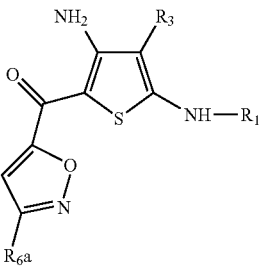

wherein:

$R^1$ is selected from the group consisting of hydrogen, acyl, optionally substituted lower alkyl, optionally substituted lower alkenyl, optionally substituted lower alkynyl, optionally substituted cycloalkyl optionally substituted heterocycle, optionally substituted heterocycloalkyl, optionally substituted aryl, optionally substituted aralkyl, optionally substituted heteroaryl and optionally substituted heteroaralkyl;

$R^3$ is selected from the group consisting of cyano, nitro, —C(Z)R$^8$, —S(O$_2$)NR$^9$R$^{10}$, —S(O$_2$)R$^{11}$, and optionally substituted lower alkyl; and $R^{6a}$ is selected from the group consisting of hydrogen, halo, hydroxy, alkoxy, alkylthio, alkylsulfinyl, alkylsulfonyl, acyloxy, optionally substituted aryl, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, carboxyl, optionally substituted heterocycle, optionally substituted hetaryl nitro, cyano, thiol, sulfonamido, optionally substituted alkyl, optionally substituted alkenyl, and optionally substituted alkynyl, attached at any available point to produce a stable compound.

8. A composition comprising
a compound according to claim 1 and
a pharmaceutically acceptable carrier.

9. A method for treating a human patient suffering from or at risk of a disease or condition for which PDE4B modulation provides a therapeutic benefit, said method comprising administering to said patient an effective amount of a compound according to claim 1, wherein said disease or condition is selected from the group consisting of asthma, chronic obstructive pulmonary disease (COPD), Alzheimer's disease, diffuse large-cell B cell lymphoma, and chronic lymphocytic leukemia.

* * * * *

UNITED STATES PATENT AND TRADEMARK OFFICE
CERTIFICATE OF CORRECTION

| | | |
|---|---|---|
| PATENT NO. | : 7,585,859 B2 | Page 1 of 1 |
| APPLICATION NO. | : 11/123893 | |
| DATED | : September 8, 2009 | |
| INVENTOR(S) | : Ibrahim et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (592) days Delete the phrase "by 592 days" and insert -- by 1082 days --

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO.        : 7,585,859 B2                                    Page 1 of 1
APPLICATION NO.   : 11/123893
DATED             : September 8, 2009
INVENTOR(S)       : Prabha N. Ibrahim et al.

It is certified that error appears in the above-identified patent and that said Letters Patent is hereby corrected as shown below:

On the Title Page

Item "(73)   Assignee:  Plexxikon, Inc., Berkeley, CA (US)"

Should read

Item --(73)   Assignee:  Plexxikon Inc., Berkeley, CA (US)--

Signed and Sealed this
Twenty-ninth Day of May, 2012

David J. Kappos
*Director of the United States Patent and Trademark Office*